(12) United States Patent
Kyotani et al.

(10) Patent No.: US 7,211,577 B2
(45) Date of Patent: *May 1, 2007

(54) WATER-SOLUBLE PHENYLPYRIDAZINE DERIVATIVE AND MEDICINE CONTAINING THE SAME

(75) Inventors: Yoshinori Kyotani, Tokyo (JP); Tomoyuki Koshi, Saitama (JP); Hiromichi Shigyo, Tokyo (JP); Hideo Yoshizaki, Saitama (JP); Takahiro Kitamura, Tokyo (JP); Shunji Takemura, Tokyo (JP); Kyoko Yasuoka, Tokyo (JP); Junko Totsuka, Tokyo (JP); Seiichi Sato, Tokyo (JP)

(73) Assignee: Kowa Co., Ltd., Nagoya-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/544,881

(22) PCT Filed: Mar. 16, 2004

(86) PCT No.: PCT/JP2004/003487

§ 371 (c)(1),
(2), (4) Date: Aug. 8, 2005

(87) PCT Pub. No.: WO2004/083188

PCT Pub. Date: Sep. 30, 2004

(65) Prior Publication Data

US 2006/0142292 A1    Jun. 29, 2006

(30) Foreign Application Priority Data

Mar. 18, 2003    (JP) .............................. 2003-073403

(51) Int. Cl.
*C07D 237/04*    (2006.01)
*C07D 403/06*    (2006.01)
*A61K 31/50*    (2006.01)
*A61K 31/51*    (2006.01)

(52) U.S. Cl. .............. 514/236.5; 514/247; 514/252.02; 514/252.03; 544/114; 544/238; 544/239

(58) Field of Classification Search ................ 544/114, 544/238, 239; 514/236.5, 247, 252.02, 252.03
See application file for complete search history.

(56) References Cited

U.S. PATENT DOCUMENTS

| | | |
|---|---|---|
| 4,954,518 A | 9/1990 | Takano et al. |
| 6,348,468 B1 | 2/2002 | Ohkuchi et al. |
| 6,403,586 B1 | 6/2002 | Ohkuchi et al. |
| 6,664,256 B1 | 12/2003 | Ohkuchi et al. |
| 6,680,316 B1 | 1/2004 | Ohkuchi et al. |
| 6,861,428 B2 * | 3/2005 | Kyotani et al. ............. 514/247 |
| 6,869,954 B2 * | 3/2005 | Kyotani et al. ............. 514/247 |
| 2002/0123496 A1 | 9/2002 | Ohkuchi et al. |
| 2004/0147516 A1 | 7/2004 | Ohkuchi et al. |
| 2005/0065155 A1 | 3/2005 | Ohkuchi et al. |
| 2005/0085480 A1 | 4/2005 | Kyotani et al. |

FOREIGN PATENT DOCUMENTS

| | | |
|---|---|---|
| DE | 2 333 643 | 1/1974 |
| EP | 0 376 288 | 7/1990 |
| JP | 07-069894 | 3/1995 |
| JP | 7-503017 | 3/1995 |
| WO | 97/05878 | 2/1997 |
| WO | 98/41511 | 9/1998 |
| WO | 99/10331 | 3/1999 |
| WO | 99/10332 | 3/1999 |
| WO | 99/25697 | 5/1999 |
| WO | 99/44995 | 9/1999 |
| WO | 00/24719 | 5/2000 |
| WO | 00/50408 | 8/2000 |
| WO | 02/04427 | 1/2002 |
| WO | 03/027077 | 4/2003 |
| WO | 2004/078751 | 9/2004 |

OTHER PUBLICATIONS

Chalmers (TiPS vol. 17, pp. 166-172 Apr. 1996).*

(Continued)

*Primary Examiner*—Kahsay Habte
(74) *Attorney, Agent, or Firm*—Oblon, Spivak, McClelland, Maier & Neustadt, P.C.

(57) ABSTRACT

A phenylpyridazine derivative represented by the formula (1):

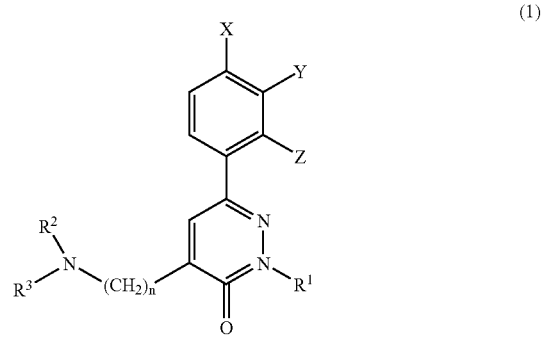

(1)

Wherein, R1, R2, R3, X, Y, Z and n have the same meaning as defined in the specification; or a salt thereof, or a medicine containing the compound. The present invention provides water-soluble phenylpyridazine derivatives and medicines containing them, which have excellent inhibitory activity against interleukin-β production, high water solubility and high oral absorbability.

10 Claims, 5 Drawing Sheets

OTHER PUBLICATIONS

Chang et al. Am. J. Respir. Crit. Care Med, vol. 156, 1230-1234 (1997).*
Assuma et al. J. Immuno. 169:403-409 (1998).*
Wilson, et al. J. Antimicrobial Chemotherapy 41, Suppl. A:51-63 (1998).*
Chernow et al. Chest 112(6) 1997.*
Li et al. Cell 80:401-411 (1995).*
Molina et al. J. Clin. Inves. 84:733-737.*
Arend et al. Arthritis and Rheumatism, 38(2):151-160 (1995).*
Rossenwasser J. Alergy Clin. Immuno., 102(3) Sep. 1998.*
Romas et al. Osteopros Int (1997), 7(Suppl. 3):S47-S53.*
Ohzeki et al. "Antirheumatic activities of KE-298, having an effect on IL-1 (1st Report)", The Japan Inflammation Academy, 11th session, with English translation 1990.

Casini-Raggi et al. "Anti-inflammatory Effects of CGP 47969A, a Novel Inhibitor of Proinflammatory Cytokine Synthesis, in Rabbit Immune Colitis", Gastroenterology, vol. 109, pp. 812-818 1995.
Tanaka et al. "Hydroxyindole derivatives as inhibitors of IL-1 generation. II. Synthesis and pharmacological activities of (E)-3-(7-hydroxy-6-methoxyindole-4-yl)-2-methylpropenoic acid derivatives", Eur J Med Chem, vol. 31, pp. 187-198 1996.
Ku et al. "Interleukin-1beta Converting Enzyme Inhibition Blocks Progression of Type II Collagen-induced Arthritis in Mice", Cytokine, vol. 8, No. 5, pp. 377-386 1996.
Nannini et al. "Synthesis and pharmacological activity of some 5, 6-diphenyl-pyridazines", Eur J Med Chem, vol. 14, pp. 53-60 1979.

* cited by examiner

WATER-SOLUBLE PHENYLPYRIDAZINE DERIVATIVE AND MEDICINE CONTAINING THE SAME

TECHNICAL FIELD

This invention relates to water-soluble phenylpyridazine derivatives, which exhibit excellent inhibitory activity against interleukin-1β production, have high water solubility and oral absorbability, and are useful for the prevention and treatment of immune system diseases, inflammatory diseases, and ischemic diseases, for example, and also to medicines containing them as active ingredients.

BACKGROUND ART

In many diseases, for example, rheumatism, arthritis, osteoporosis, inflammatory colitis, immune deficiency syndrome, ichorrhemia, hepatitis, nephritis, ischemic diseases, insulin-dependent diabetes mellitus, arterial sclerosis, Parkinson's disease, Alzheimer's disease, and leukemia, an increased production of interleukin-1β, which is an inflammatory cytokine, is observed. This interleukin-1β serves to induce synthesis of an enzyme which is considered to take part in inflammation—like collagenase and PLA2- and, when intra-articularly injected to animals, causes multiarticular damage highly resembling rheumatoid arthritis. In a healthy body, on the other hand, the activity of interleukin-1β is controlled by interleukin-1 receptor, soluble interleukin-1 receptor and interleukin-1 receptor antagonist.

From research conducted using recombinant bioactivity-inhibiting substances, anti-interleukin-1β antibodies and anti-receptor antibodies against various disease models and also from research performed using knockout mice, interleukin-1β has been found to play an important role in the body, leading to an increasing potential of substances having interleukin-1β inhibitory activity as therapeutics for such diseases.

For example, immunosuppressors and steroids, which are used for the treatment of rheumatism among these many diseases, have been reported to inhibit production of interleukin-1β. Among compounds currently under development, KE298, a benzoylpropionic acid derivative [*The Japanese Society of Inflammation* (11th), 1990], for example, has been reported to also exhibit inhibitory activity against interleukin-1β production although it is an immunoregulator. Inhibitory activity against interleukin-1β production is also observed in a group of compounds which are called "COX-2 selective inhibitors", for example, nimesulide as a phenoxysulfonanilide derivative (DE Publication No. 2333643), T-614 as a phenoxybenzopyran derivative (U.S. Pat. No. 4,954,518), and tenidap (oxyindole derivative) as a dual inhibitor (COX-1/5-LO).

However, interleukin-1β production inhibitory activity is not the primary action or effect of any of these compounds so that the inhibitory activity against interleukin-1β production is less than the primary action thereof.

More recently, increased synthetic research has been conducted emphasizing inhibitory activity against interleukin-1β production. Production inhibitors can be classified into a group of compounds which inhibit the transfer process and an inflammatory signal to a cell nucleus, the transcription or translation stage, and another group of compounds which inhibit the enzyme ICE that functions in the processing of a precursor of interleukin-1β. Known examples of compounds presumed to have the former action include SB203580 [JP-A-1995-503017], FR167653 (*Eur. J. Pharm.*, 327, 169–175, 1997), E-5090 (EP Patent Publication No. 376288), CGP47969A (*Gastroenterology*, 109, 812–818, 1995), hydroxyindole derivatives (*Eur. J. Med. Chem.* 31, 187–198, 1996), and triarylpyrrole derivatives (WO 9705878), while known examples of compounds presumed to have the latter action include VE-13,045 which is a peptide compound (*Cytokine*, 8(5), 377–386, 1996).

None of these compounds, however, exhibit sufficient inhibitory activity against interleukin-1β production.

On the other hand, it is known that 5,6-diphenyl-pyridazine derivatives exhibit analgesic and anti-inflammatory action (*Eur. J. Med. Chem.*, 14, 53–60, 1979). Further, 6-phenylpyridazinones have been reported to be useful as cardiotovics (U.S. Pat. No. 4,404,203). Nothing has been reported, however, with respect to inhibitory activity of these pyridazine compounds against interleukin-1β production.

The present inventors previously reported in WO 99/44995 that high inhibitory activity against interleukin-1β production was observed on phenylpyridazine derivatives. Recently, certain phenylpyridazine derivatives having inhibitory activity against interleukin-1β production have been reported (JP 7-69894 A, WO 98/41511, WO 99/10331, WO 99/10332, WO99/25697, WO00/50408). These reported compounds, however, are different in chemical structure from the compounds of the present invention.

DISCLOSURE OF THE INVENTION

The compounds disclosed in WO 99/44995 exhibit strong inhibitory activity against interleukin-1β production. However, the water solubility of these compounds is so low that formulating them into pharmaceutical preparations, such as tablets, required further investigations. In the course of a further investigation, the present inventors discovered that the introduction of a substituted or unsubstituted aminoalkyl group to the 4-position of 6-phenylpyridazin-3-one affords a compound useful as a preventive or therapeutic for immune system diseases, inflammatory diseases, and ischemic diseases, for example, due to its significantly improved water solubility, good oral absorbability and excellent inhibitory activity against interleukin-1β production, leading to the completion of the present invention.

Thus, in one aspect of the present invention, there is provided a phenylpyridazine derivative represented by the formula (1):

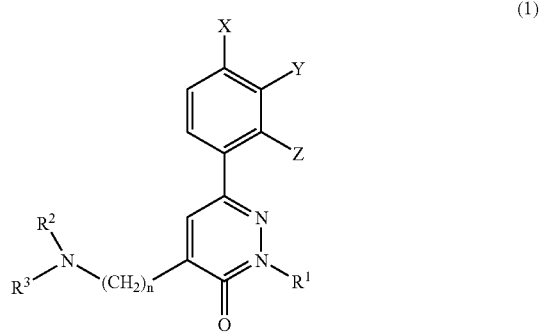

(1)

wherein:

R¹ is optionally substituted alkyl, or optionally substituted alkenyl;

R² and R³ each independently represents hydrogen or alkyl, hydroxyalkyl, dihydroxyalkyl or alkynyl, or R² and R³ are fused together with the adjacent nitrogen atom to form an optionally substituted, nitrogen-containing saturated heterocyclic group;

X, Y and Z each independently represents hydrogen, halogen, optionally substituted alkyl, alkoxy, alkylthio, alkylsulfinyl or alkylsulfonyl, or optionally substituted aryl; and n stands for a number of from 1 to 5;

with the proviso that R² and R³ are not hydrogen atoms or the same $C_1$–$C_3$ alkyl groups at the same time when R¹ is a benzyl group or a $C_1$–$C_3$ alkyl group; or a salt thereof.

In another aspect of the present invention, there is also provided a medicine comprising the phenylpyridazine derivative or the salt thereof as an active ingredient.

In a further aspect of the present invention, there is also provided a pharmaceutical composition comprising the phenylpyridazine derivative (1) or the salt thereof and a pharmacologically acceptable carrier.

In a still further aspect of the present invention, there is also provided use of the phenylpyridazine derivative (1) or the salt thereof for the production of a medicine.

In a yet further aspect of the present invention, there is also provided a method for treating a disease caused by increased production of interleukin-1β production, which comprises administering the phenylpyridazine derivative (1) or the salt thereof.

BEST MODES FOR CARRYING OUT THE INVENTION

Figure 1:
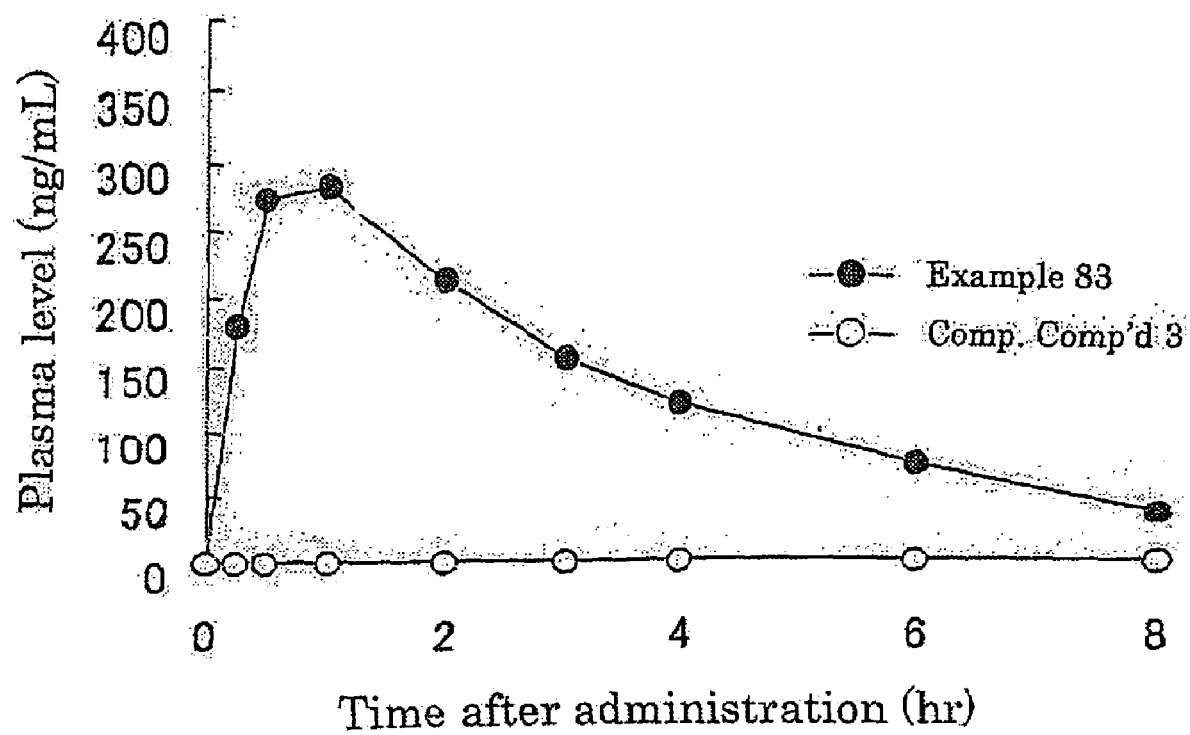
FIG. 1 is a graphic representation of the oral absorbability of a compound according to the present invention (Example 83) and a comparative compound 3.
Figure 2:
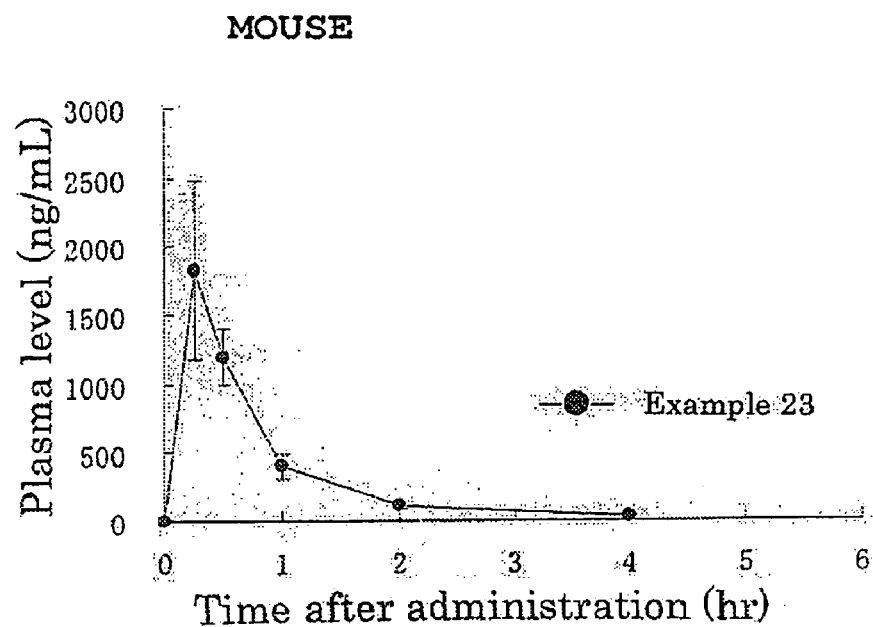
FIG. 2 is graphic representations of the oral absorbability of a compound according to the present invention (Example 23)
Figure 2:
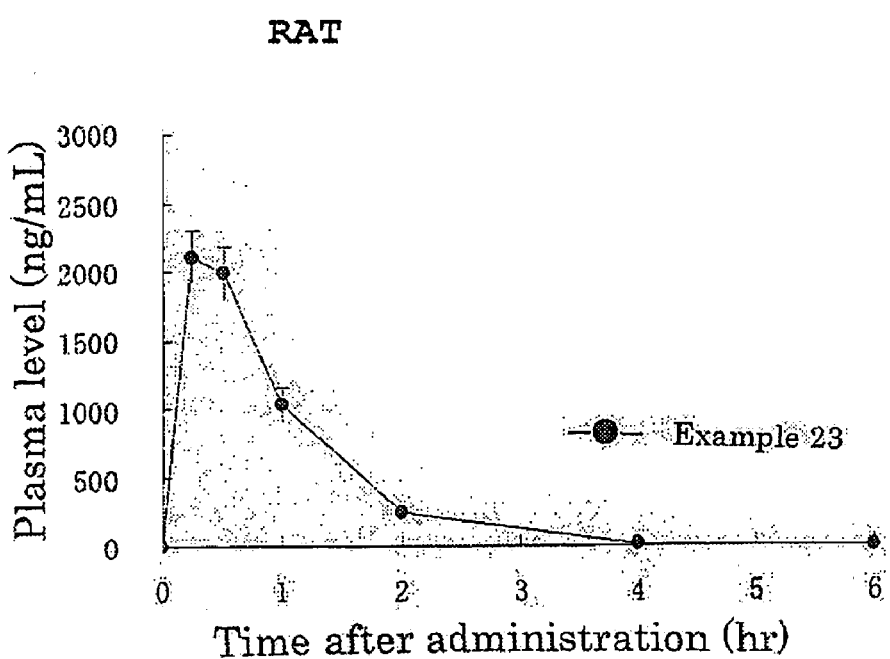
Figure 3:
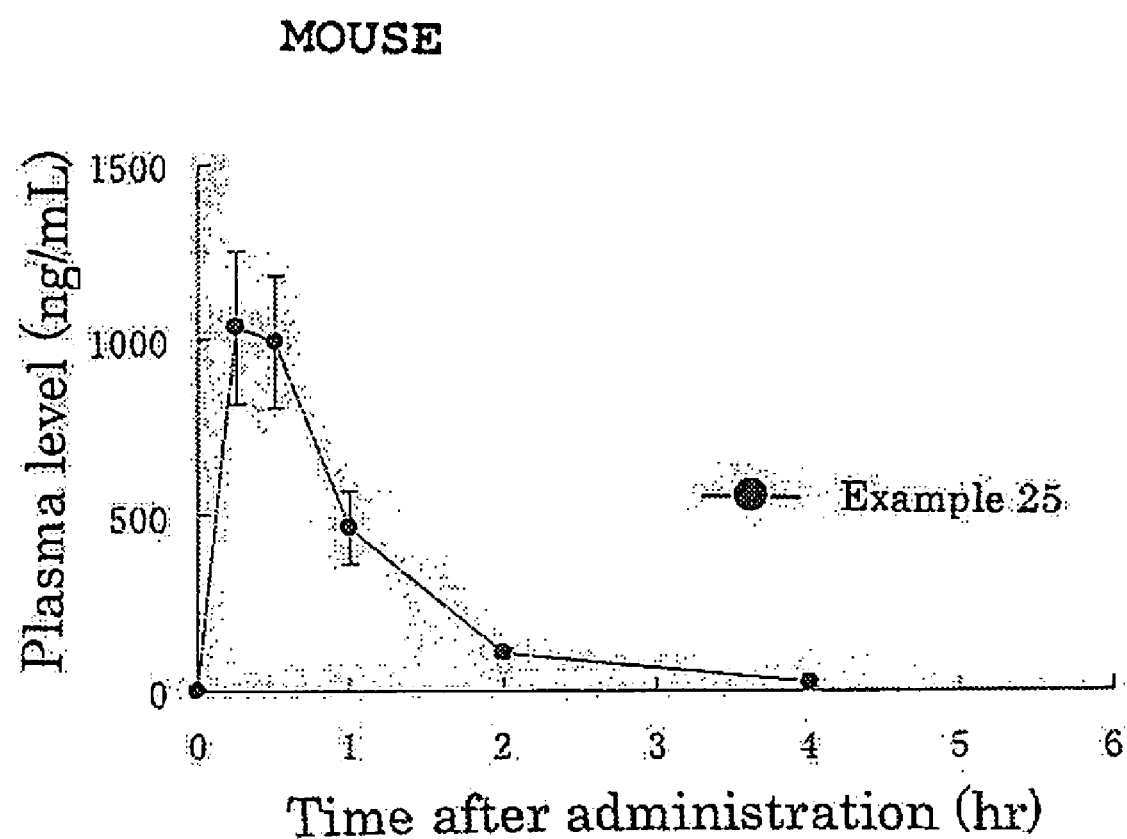
FIG. 3 is graphic representations of the oral absorbability of a compound according to the present invention (Example 25)
Figure 4:
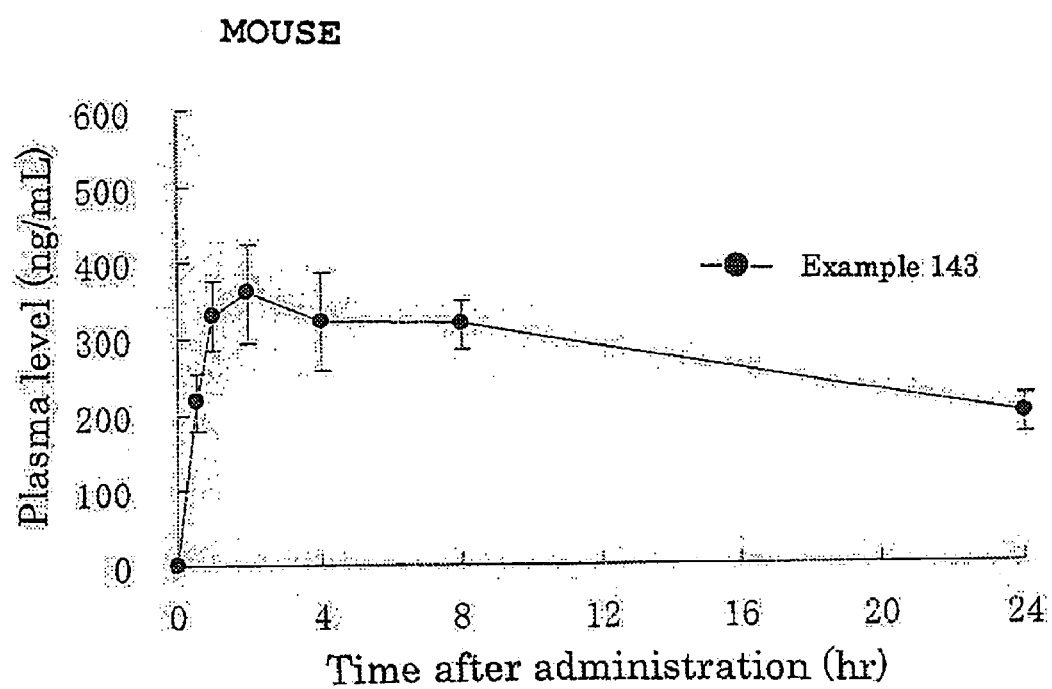
FIG. 4 is graphic representations of the oral absorbability of a further compound according to the present invention (Example 143)
Figure 5:
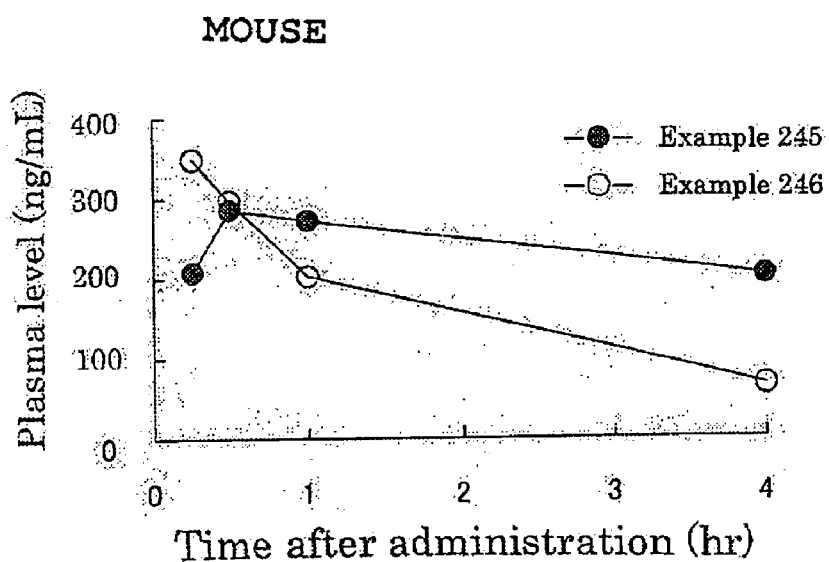
FIG. 5 is graphic representations of the oral absorbability of compounds according to the present invention (Example 245 and Example 246)
Figure 6:
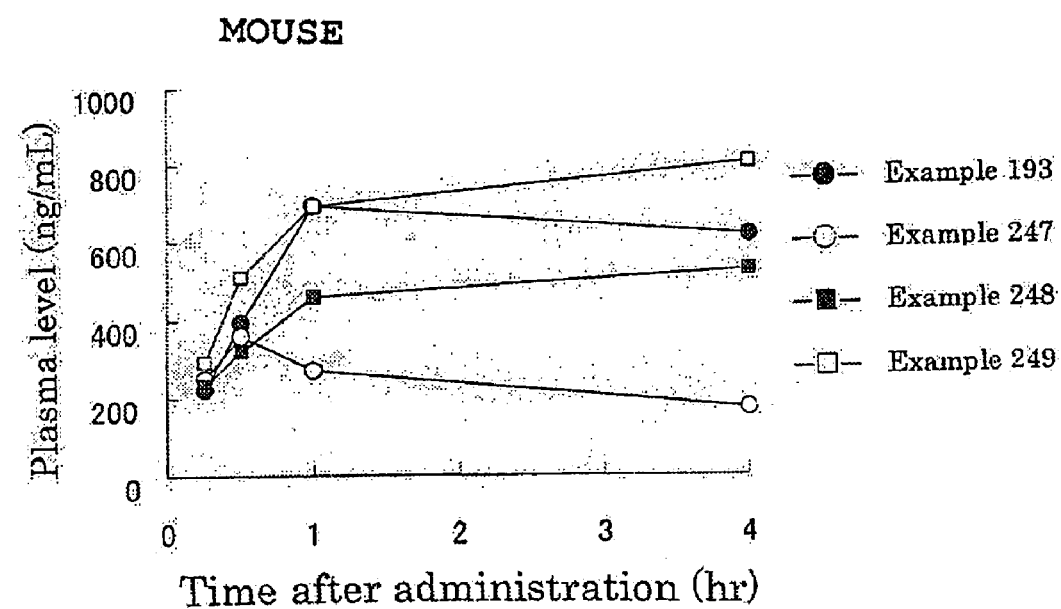
FIG. 6 is graphic representations of the oral absorbability of compounds according to the present invention (Example 193, Example 247, Example 248 and Example 249).

In the above formula (1), the alkyl moieties in the alkyl, hydroxyalkyl, dihydroxyalkyl, alkoxy, alkylthio, alkylsulfinyl and alkylsulfonyl represent those having 1 to 12 carbon atoms, more preferably 1 to 7 carbon atoms. These alkyl moieties include linear, branched, cyclic as well as alkyl groups having cyclic structures, for example, methyl, ethyl, n-propyl, isopropyl, n-butyl, isobutyl, cyclopropyl, cyclobutyl, cyclopentyl, cyclohexyl, cyclopropylmethyl, cyclopropylethyl, cyclobutylmethyl, cyclopentylmethyl and cyclohexylmethyl.

In the above formula (1), the alkyl represented by R¹ has preferably 1 to 12 carbon atoms, more preferably 1 to 7 carbon atoms, notably 4 to 7 carbon atoms. Illustrative of such alkyl groups are linear, branched, cyclic as well as alkyl groups having cyclic structures. Preferred examples include methyl, ethyl, propyl, isobutyl, cyclobutyl, cyclopentyl, cyclohexyl, cyclopropylmethyl, cyclopropylethyl, cyclobutylmethyl, cyclopentylmethyl and cyclohexylmethyl, with methyl, ethyl, isobutyl, cyclopropylmethyl and cyclopentylmethyl being particularly preferred.

The alkenyl represented by R¹ preferably has 2 to 12 carbon atoms, with 2 to 7 carbon atoms being particularly preferred. Illustrative of such alkenyl groups are linear and branched alkenyl groups, for example, vinyl, propenyl, butenyl and pentenyl.

Illustrative of group(s) which the alkyl or alkenyl group represented by R¹ may contain as substituent (s) are optionally substituted aryl groups and optionally substituted heteroaryl groups. Examples of the aryl groups include aryl groups having 6 to 14 carbon atoms, for example, phenyl and naphthyl, with phenyl being particularly preferred. Examples of the heteroaryl groups, on the other hand, include 5- or 6-membered cyclic heteroaryl groups having 1 to 3 nitrogen atoms, for example, pyrrolyl, imidazolyl, pyrazolyl, pyridyl, pyrimidyl, pyrazinyl and pyridazinyl, with pyridyl being particularly preferred.

These aryl or heteroaryl groups may contain 1 to 3 substituents such as halogen atoms, alkyl groups or alkoxy groups. Examples of the halogen atoms include fluorine, chlorine, bromine and iodine, with fluorine and chlorine being particularly preferred. These alkyl and alkoxy groups preferably have 1 to 12 carbon atoms, with 1 to 7 carbon atoms being particularly preferred.

The alkyl, hydroxyalkyl and dihydroxyalkyl represented by R² and R³ preferably have 1 to 12 carbon atoms, with 1 to 7 carbon atoms being particularly preferred. These groups may preferably be linear or branched. Specific examples include methyl, ethyl, n-propyl, isopropyl, n-butyl, isobutyl, hydroxyethyl, hydroxypropyl, hydroxybutyl, dihydroxypropyl and dihydroxybutyl.

The alkynyls represented by R² and R³ preferably have 3 to 12 carbon atoms, with 3 to 7 carbon atoms being particularly preferred. Illustrative is propargyl (2-propynyl).

Illustrative of the nitrogen-containing, saturated heterocyclic group which may be formed as a result of fusion of R² and R³ with the adjacent nitrogen atom are 5- to 7-membered saturated heterocyclic groups, for example, pyrrolidinyl, piperidino, piperazinyl, homopiperazinyl and morpholino, with pyrrolidinyl, piperazinyl, piperidino and morpholino being particularly preferred.

Illustrative of group(s) which these heterocyclic groups may contain as substituent (s) are halogen atoms, alkyl groups, alkoxycarbonyl groups and aralkyl groups. Examples of the halogen atoms include fluorine, chlorine, bromine and iodine. The alkyl groups can contain 1 to 12 carbon atoms, preferably 1 to 7 carbon atoms. Illustrative of the alkoxycarbonyl groups are $C_1$–$C_{12}$ alkyloxycarbonyl groups, with $C_1$–$C_7$ alkyloxycarbonyl groups being preferred. Illustrative of the aralkyl groups are phenyl ($C_1$–$C_7$ alkyl) groups, with benzyl being particularly preferred.

Illustrative of the halogens represented by X, Y and Z are fluorine, chlorine, bromine, and iodine. The alkyl groups can contain 1 to 12 carbon atoms, with 1 to 7 carbon atoms being particularly preferred. Among these alkyl groups, linear or branched ones are particularly preferred. Illustrative of group(s) which the alkyl group may contain as substituent(s) are halogen atoms and alkoxy groups. The alkoxy, alkylthio, alkylsulfinyl and alkylsulfonyl groups can contain 1 to 12 carbon atoms, with 1 to 7 carbon atoms being particularly preferred. Among these alkoxy, alkylthio, alkylsulfinyl and alkylsulfonyl groups, linear or branched ones are particularly preferred. Specific examples include methoxy, ethoxy, propoxy, isopropoxy, butoxy, methylthio, ethylthio, propylthio, isopropylthio, butylthio, methylsulfinyl, ethylsulfinyl, propylsulfinyl, isopropylsulfinyl, butylsulfinyl, methylsulfonyl, ethylsulfonyl, propylsulfonyl, isopropylsulfonyl, and butylsulfonyl. Illustrative of the aryl are aryl groups having 6 to 14 carbon atoms, for example, phenyl and naphthyl, with phenyl being particularly preferred. Illustrative of group(s) which the aryl may contain as substituent (s) are halogen atoms, alkyl groups, and alkoxy groups.

n stands for a number of from 1 to 5, with 1 to 3 being more preferred, and with 1 or 3 being particularly preferred.

When $R^1$ is a benzyl group or a $C_1$–$C_3$ alkyl group, $R^2$ and $R^3$ are not hydrogen atoms or the same $C_1$–$C_3$ alkyl groups at the same time.

In the formula (1), particularly preferred as $R^1$ are isobutyl, cyclopropylmethyl, cyclopentylmethyl, cinnamyl, halogenocinnamyl, benzyl, halogenobenzyl, dihalogenobenzyl, (halogenophenyl)ethyl, (dihalogenophenyl)ethyl, (halogenophenyl)propyl, and (dihalogenophenyl)propy. Specifically, chlorobenzyl, dichlorobenzyl, fluorobenzyl, difluorobenzyl, (chlorophenyl)ethyl, (dichlorophenyl)ethyl, (fluorophenyl)ethyl, (difluorophenyl)ethyl, (chlorophenyl) propyl, (dichlorophenyl)propyl, (fluorophenyl) propyl and (difluorophenyl) propyl are preferred in particular. Preferred as $R^2$ and $R^3$ are hydrogen, $C_{1-7}$ alkyl, $C_{1-7}$ hydroxyalkyl, and propargyl. Preferred as the heterocyclic group formed by $R^2$ and $R^3$ are piperazinyl, piperidino, pyrrolidinyl and morpholino, each of which may optionally be substituted by one or more $C_{1-7}$ alkyl or benzyl groups. Preferred as X are methyl, methoxy, methylthio, and halogens. Preferred as Y are hydrogen, methyl and halogens. Preferred as Z is hydrogen. Preferred as n are 1 and 3.

In the present invention, still more preferred are compounds of the formula (1) in which $R^1$ is a group selected from halogenobenzyl, dihalogenobenzyl, (halogenophenyl) ethyl, (dihalogenophenyl)ethyl, (halogenophenyl)propyl or (dihalogenophenyl)propyl; $R^2(R^3)N$— is a group selected from amino, dimethylamino, piperazinyl or N-methylpiperazinyl; X is halogen or methoxy; Y is methyl or halogen; Z is hydrogen; and n stands for 1 or 3.

Particularly preferred are compounds of the formula (1) in which $R^1$ is a group selected from chlorobenzyl, dichlorobenzyl, fluorobenzyl, difluorobenzyl, (chlorophenyl)ethyl, (dichlorophenyl)ethyl, (chlrorophenyl)propyl or (dichlorophenyl)propyl; $R^2(R^3)N$— is a group selected from amino, dimethylamino, piperazinyl or N-methylpiperazinyl; X is halogen or methoxy; Y is methyl or halogen; Z is hydrogen; and n stands for 1 or 3.

Among these, the following compounds are preferred:

4-dimethylaminomethyl-6-(3-fluoro-4-methylphenyl)-2-isobutyl-2H-pyridazin-3-one,
2-cyclopropylmethyl-4-dimethylaminomethyl-6-(3-fluoro-4-methoxyphenyl)-2H-pyridazin-3-one,
2-cyclopropylmethyl-6-(3-fluoro-4-methoxyphenyl)-4-(4-benzyl-1-piperazinyl)methyl-2H-pyridazin-3-one,
2-cyclopropylmethyl-6-(3-fluoro-4-methoxyphenyl)-4-(1-piperazinyl)methyl-2H-pyridazin-3-one,
4-N,N-bis(2-hydroxyethyl)aminomethyl-2-cyclopropylmethyl-6-(3-fluoro-4-methoxyphenyl)-2H-pyridazin-3-one,
4-aminomethyl-2-cyclopropylmethyl-6-(3-fluoro-4-methoxyphenyl)-2H-pyridazin-3-one,
4-dimethylaminomethyl-2-isobutyl-6-(4-methylphenyl)-2H-pyridazin-3-one,
4-diethylaminomethyl-2-isobutyl-6-(4-methylphenyl)-2H-pyridazin-3-one,
4-N,N-bis(2-hydroxyethyl)aminomethyl-6-(4-methylphenyl)-2-isobutyl-2H-pyridazin-3-one,
6-(4-fluoro-3-methylphenyl)-2-isobutyl-4-(4-methyl-1-piperazinyl)methyl-2H-pyridazin-3-one,
4-dimethylaminomethyl-6-(4-fluoro-3-methylphenyl)-2-isobutyl-2H-pyridazin-3-one,
4-N,N-bis(2-hydroxyethyl)aminomethyl-6-(3,4-difluorophenyl)-2-isobutyl-2H-pyridazin-3-one,
2-(4-chlorocinnamyl)-6-(4-fluoro-3-methylphenyl)-4-(4-methyl-1-piperazinyl)methyl-2H-pyridazin-3-one,
2-cyclopropylmethyl-4-(4-methyl-1-piperazinyl)methyl-6-[4-(methylthio)phenyl]-2H-pyridazin-3-one,
4-N,N-bis(2-hydroxyethyl)aminomethyl-2-cyclopropylmethyl-6-[4-(methylthio)phenyl]-2H-pyridazin-3-one,
2-cyclopropylmethyl-4-dimethylaminomethyl-6-[4-(methylthio)phenyl]-2H-pyridazin-3-one,
2-isobutyl-6-[4-(methylthio)phenyl]-4-propargylaminomethyl-2H-pyridazin-3-one,
4-dimethylaminomethyl-2-isobutyl-6-[4-(methylthio)phenyl]-2H-pyridazin-3-one,
2-(4-chlorobenzyl)-4-dimethylaminomethyl-6-(3-fluoro-4-methoxyphenyl)-2H-pyridazin-3-one,
2-cyclopentylmethyl-6-(3-fluoro-4-methoxyphenyl)-4-(4-methyl-1-piperazinyl)methyl-2H-pyridazin-3-one,
2-cyclopentylmethyl-4-dimethylaminomethyl-6-(3-fluoro-4-methoxyphenyl)-2H-pyridazin-3-one,
2-cyclopentylmethyl-6-(3-fluoro-4-methoxyphenyl)-4-(1-piperazinyl)methyl-2H-pyridazin-3-one,
4-aminomethyl-2-cyclopentylmethyl-6-(3-fluoro-4-methoxyphenyl)-2H-pyridazin-3-one,
2-(4-fluorobenzyl)-6-(3-fluoro-4-methoxyphenyl)-4-(4-methyl-1-piperazinyl)methyl-2H-pyridazin-3-one,
4-dimethylaminomethyl-2-(4-fluorobenzyl)-6-(3-fluoro-4-methoxyphenyl)-2H-pyridazin-3-one,
2-(4-fluorobenzyl)-6-(3-fluoro-4-methoxyphenyl)-4-(1-piperazinyl)methyl-2H-pyridazin-3-one,
4-aminomethyl-2-(4-fluorobenzyl)-6-(3-fluoro-4-methoxyphenyl)-2H-pyridazin-3-one,
4-aminomethyl-2-(4-chlorobenzyl)-6-(3-fluoro-4-methoxyphenyl)-2H-pyridazin-3-one,
2-(3,4-difluorobenzyl)-6-(3-fluoro-4-methoxyphenyl)-4-(4-methyl-1-piperazinyl)methyl-2H-pyridazin-3-one,
2-(3,4-difluorobenzyl)-4-dimethylaminomethyl-6-(3-fluoro-4-methoxyphenyl)-2H-pyridazin-3-one,
6-(3-fluoro-4-methoxyphenyl)-2-[3-(4-fluorophenyl)propyl]-4-(4-methyl-1-piperazinyl)methyl-2H-pyridazin-3-one,
4-dimethylaminomethyl-6-(3-fluoro-4-methoxyphenyl)-2-[3-(4-fluorophenyl)propyl]-2H-pyridazin-3-one,
4-N,N-bis(2-hydroxyethyl)aminomethyl-6-(3-fluoro-4-methoxyphenyl)-2-[3-(4-fluorophenyl)propyl]-2H-pyridazin-3-one,
6-(3-fluoro-4-methoxyphenyl)-2-[3-(4-fluorophenyl)propyl]-4-(1-piperazinyl)methyl-2H-pyridazin-3-one,
4-aminomethyl-6-(3-fluoro-4-methoxyphenyl)-2-[3-(4-fluorophenyl)propyl]-2H-pyridazin-3-one,
2-(4-chlorocinnamyl)-6-(3-fluoro-4-methoxyphenyl)-4-[4-(2-hydroxyethyl)-1-piperazinyl]methyl-2H-pyridazin-3-one,
2-(4-chlorocinnamyl)-6-(3-fluoro-4-methoxyphenyl)-4-(4-methyl-1-piperazinyl)methyl-2H-pyridazin-3-one,
2-cyclopropylmethyl-6-(3-fluoro-4-methoxyphenyl)-4-[3-(4-methyl-1-piperazinyl)propyl]-2H-pyridazin-3-one, 2-cyclopropylmethyl-4-(3-dimethylaminopropyl)-6-(3-fluoro-4-methoxyphenyl)-2H-pyridazin-3-one,
2-cyclopropylmethyl-6-(3-fluoro-4-methoxyphenyl)-4-[3-(1-piperazinyl)propyl]-2H-pyridazin-3-one, and
4-(3-aminopropyl)-2-cyclopropylmethyl-6-(3-fluoro-4-methoxyphenyl)-2H-pyridazin-3-one.

Further, the following compounds are especially preferred:
2-[3-(4-chlorophenyl)propyl]-6-(4-fluoro-3-methylphenyl)-4-(4-methyl-1-piperazinyl)methyl-2H-pyridazin-3-one,
2-[3-(2-chlorophenyl)propyl]-6-(4-fluoro-3-methylphenyl)-4-(4-methyl-1-piperazinyl)methyl-2H-pyridazin-3-one,
2-[3-(3-chlorophenyl)propyl]-6-(4-fluoro-3-methylphenyl)-4-(4-methyl-1-piperazinyl)methyl-2H-pyridazin-3-one,
2-(4-chlorobenzyl)-6-(4-fluoro-3-methylphenyl)-4-(4-methyl-1-piperazinyl)methyl-2H-pyridazin-3-one,
2-(2-chlorobenzyl)-6-(4-fluoro-3-methylphenyl)-4-(4-methyl-1-piperazinyl)methyl-2H-pyridazin-3-one,
2-(2-chlorobenzyl)-6-(4-fluoro-3-methylphenyl)-4-[3-(4-methyl-1-piperazinyl)propyl]-2H-pyridazin-3-one,
4-(3-aminopropyl)-2-(2-chlorobenzyl)-6-(4-fluoro-3-methylphenyl)-2H-pyridazin-3-one,
2-[2-(2-chlorophenyl)ethyl]-6-(4-fluoro-3-methylphenyl)-4-(4-methyl-1-piperazinyl)methyl-2H-pyridazin-3-one,
2-[2-(4-chlorophenyl)ethyl]-6-(4-fluoro-3-methylphenyl)-4-(4-methyl-1-piperazinyl)methyl-2H-pyridazin-3-one,
2-(2,6-dichlorobenzyl)-6-(4-fluoro-3-methylphenyl)-4-(4-methyl-1-piperazinyl)methyl-2H-pyridazin-3-one,
2-(2,6-dichlorobenzyl)-6-(4-fluoro-3-methylphenyl)-4-(1-piperazinyl)methyl-2H-pyridazin-3-one,
4-aminomethyl-2-(2,6-dichlorobenzyl)-6-(4-fluoro-3-methylphenyl)-2H-pyridazin-3-one,
2-[3-(2,6-dichlorophenyl)propyl]-6-(4-fluoro-3-methylphenyl)-4-(4-methyl-1-piperazinyl)methyl-2H-pyridazin-3-one,
2-(3,4-difluorobenzyl)-6-(4-fluoro-3-methylphenyl)-4-(4-methyl-1-piperazinyl)methyl-2H-pyridazin-3-one,
4-aminomethyl-2-(2-chlorobenzyl)-6-(4-fluoro-3-methylphenyl)-2H-pyridazin-3-one,
2-(4-fluorobenzyl)-6-(3-fluoro-4-methoxylphenyl)-4-[3-(4-methyl-1-piperazinyl)propyl]-2H-pyridazin-3-one,
2-(4-fluorobenzyl)-6-(3-fluoro-4-methoxylphenyl)-4-[3-(1-piperazinyl)propyl]-2H-pyridazin-3-one,
2-[3-(2-chlorophenyl)propyl]-6-(3-fluoro-4-methoxylphenyl)-4-(4-methyl-1-piperazinyl)methyl-2H-pyridazin-3-one
2-[3-(4-chlorophenyl)propyl]-6-(3-fluoro-4-methoxylphenyl)-4-(4-methyl-1-piperazinyl)methyl-2H-pyridazin-3-one
4-aminomethyl-2-[3-(2-chlorophenyl)propyl]-6-(3-fluoro-4-methoxylphenyl)-2H-pyridazin-3-one,
4-aminomethyl-2-[3-(4-chlorophenyl)propyl]-6-(3-fluoro-4-methoxylphenyl)-2H-pyridazin-3-one,
2-cyclopropylmethyl-6-(3-fluoro-4-methoxylphenyl)-4-[3-(1-piperazinyl)propyl]-2H-pyridazin-3-one,
4-(3-aminopropyl)-2-cyclopropylmethyl-6-(3-fluoro-4-methoxylphenyl)-2H-pyridazin-3-one,
2-(4-fluorobenzyl)-6-(3-fluoro-4-methoxylphenyl)-4-(4-methyl-1-piperazinyl)methyl-2H-pyridazin-3-one,
2-(4-fluorobenzyl)-6-(3-fluoro-4-methoxylphenyl)-4-(1-piperazinyl)methyl-2H-pyridazin-3-one,
2-(3,4-difluorobenzyl)-6-(3-fluoro-4-methoxylphenyl)-4-(4-methyl-1-piperazinyl)methyl-2H-pyridazin-3-one,
2-(3,4-difluorobenzyl)-4-dimethylaminomethyl-6-(3-fluoro-4-methoxylphenyl)-2H-pyridazin-3-one,
2-(4-chlorocinnamyl)-6-(3-fluoro-4-methoxylphenyl)-4-(4-methyl-1-piperazinyl)methyl-2H-pyridazin-3-one,
2-(4-chlorocinnamyl)-6-(3-fluoro-4-methoxylphenyl)-4-[4-(2-hydroxyethyl)-1-piperazinyl]methyl-2H-pyridazin-3-one,
4-N,N-bis(2-hydroxyethyl)aminomethyl-2-cyclopropylmethyl-6-(3-fluoro-4-methoxylphenyl)-2H-pyridazin-3-one,
4-aminomethyl-2-cyclopropylmethyl-6-(3-fluoro-4-methoxylphenyl)-2H-pyridazin-3-one, and
2-(4-chlorocinnamyl)-6-(4-fluoro-3-methylphenyl)-4-(4-methyl-1-piperazinyl)methyl-2H-pyridazin-3-one.

In particular, the following compounds are preferred:
2-[3-(4-chlorophenyl)propyl]-6-(4-fluoro-3-methylphenyl)-4-(4-methyl-1-piperazinyl)methyl-2H-pyridazin-3-one,
2-(4-chlorobenzyl)-6-(4-fluoro-3-methylphenyl)-4-(4-methyl-1-piperazinyl)methyl-2H-pyridazin-3-one,
4-(3-aminopropyl)-2-(2-chlorobenzyl)-6-(4-fluoro-3-methylphenyl)-2H-pyridazin-3-one,
2-[2-(4-chlorophenyl)ethyl]-6-(4-fluoro-3-methylphenyl)-4-(4-methyl-1-piperazinyl)methyl-2H-pyridazin-3-one,
2-(2,6-dichlorobenzyl)-6-(4-fluoro-3-methylphenyl)-4-(4-methyl-1-piperazinyl)methyl-2H-pyridazin-3-one,
2-[3-(2-chlorophenyl)propyl]-6-(3-fluoro-4-methoxylphenyl)-4-(4-methyl-1-piperazinyl)methyl-2H-pyridazin-3-one,
2-[3-(4-chlorophenyl)propyl]-6-(3-fluoro-4-methoxylphenyl)-4-(4-methyl-1-piperazinyl)methyl-2H-pyridazin-3-one,
2-cyclopropylmethyl-6-(3-fluoro-4-methoxylphenyl)-4-[3-(1-piperazinyl)propyl]-2H-pyridazin-3-one,
4-(3-aminopropyl)-2-cyclopropylmethyl-6-(3-fluoro-4-methoxylphenyl)-2H-pyridazin-3-one,
2-(4-fluorobenzyl)-6-(3-fluoro-4-methoxylphenyl)-4-(4-methyl-1-piperazinyl)methyl-2H-pyridazin-3-one,
2-(4-fluorobenzyl)-6-(3-fluoro-4-methoxylphenyl)-4-(1-piperazinyl)methyl-2H-pyridazin-3-one,
2-(3,4-difluorobenzyl)-6-(3-fluoro-4-methoxylphenyl)-4-(4-methyl-1-piperazinyl)methyl-2H-pyridazin-3-one,
2-(3,4-difluorobenzyl)-4-dimethylaminomethyl-6-(3-fluoro-4-methoxylphenyl)-2H-pyridazin-3-one,
2-(4-chlorocinnamyl)-6-(3-fluoro-4-methoxylphenyl)-4-(4-methyl-1-piperazinyl)methyl-2H-pyridazin-3-one,
2-(4-chlorocinnamyl)-6-(3-fluoro-4-methoxylphenyl)-4-[4-(2-hydroxyethyl)-1-piperazinyl]methyl-2H-pyridazin-3-one,
4-N,N-bis(2-hydroxyethyl)aminomethyl-2-cyclopropylmethyl-6-(3-fluoro-4-methoxylphenyl)-2H-pyridazin-3-one,
4-aminomethyl-2-cyclopropylmethyl-6-(3-fluoro-4-methoxylphenyl)-2H-pyridazin-3-one, and
2-(4-chlorocinnamyl)-6-(4-fluoro-3-methylphenyl)-4-(4-methyl-1-piperazinyl)methyl-2H-pyridazin-3-one.

Specifically, the following compounds are preferred from the standpoint of water solubility and oral absorbability:
2-(3,4-difluorobenzyl)-4-dimethylaminomethyl-6-(3-fluoro-4-methoxyphenyl)-2H-pyridazin-3-one,
2-(4-chlorocinnamyl)-6-(4-fluoro-3-methylphenyl)-4-(4-methyl-1-piperazinyl)methyl-2H-pyridazin-3-one,
2-(4-fluorobenzyl)-6-(3-fluoro-4-methoxyphenyl)-4-(1-piperazinyl)methyl-2H-pyridazin-3-one,
2-[3-(4-chlorophenyl)propyl]-6-(4-fluoro-3-methylphenyl)-4-(4-methyl-1-piperazinyl)methyl-2H-pyridazin-3-one,
2-(4-chlorocinnamyl)-6-(3-fluoro-4-methoxyphenyl)-4-(4-methyl-1-piperazinyl)methyl-2H-pyridazin-3-one, or
2-(4-chlorocinnamyl)-6-(3-fluoro-4-methoxyphenyl)-4-[4-(2-hydroxyethyl)-1-piperazinyl]methyl-2H-pyridazin-3-one; or a salt thereof.

As the salt of the compound (1) of the present invention, an acid addition salt is preferred. Examples of the acid addition salt include inorganic acid salts, such as the hydrochloride, sulfate, nitrate and phosphate, and organic acid salts, such as the methanesulfonate, maleate, fumarate, citrate and oxalate.

Further, the compound according to the present invention may exist in the form of solvates and a keto-enol tautomer. Such solvates and tautomer are encompassed by the present invention. Illustrative of the solvates are those formed as a result of addition of solvents used upon production, for example, water and alcohols. No particular limitation is imposed on the solvents insofar as they do not adversely affect the inhibitory activity or the like of the compound according to the present invention against interleukin-1β production. As a solvate, the hydrate is preferred.

The phenylpyridazine compound (1) according to the present invention can be prepared, for example, by the following preparation processes (a) to (d).

(a) Preparation Process of Compounds Having the Formula (1) in which n=1

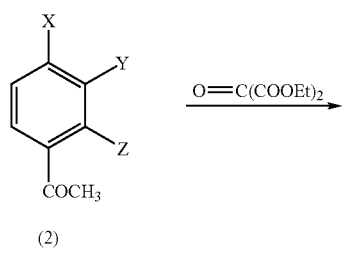
(2)

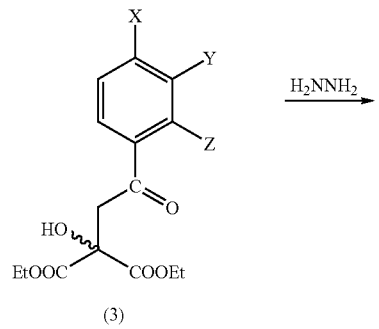
(3)

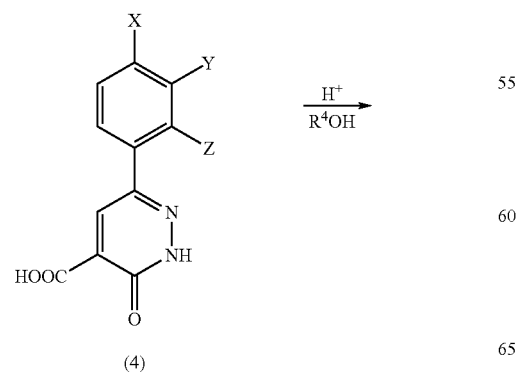
(4)

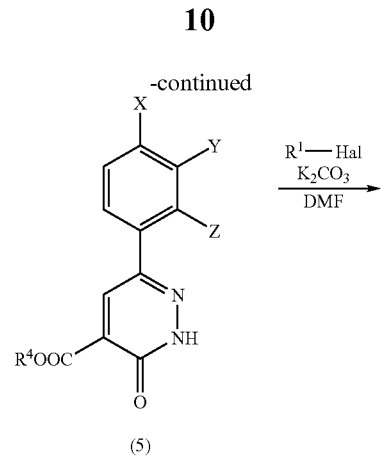
(5)

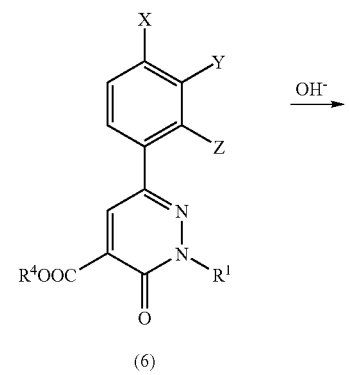
(6)

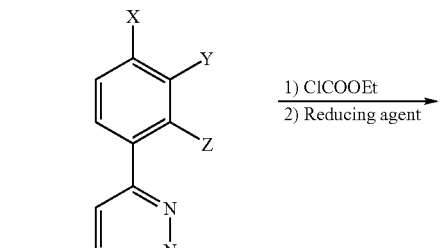
(7)

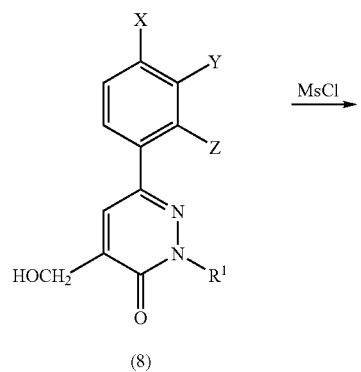
(8)

-continued

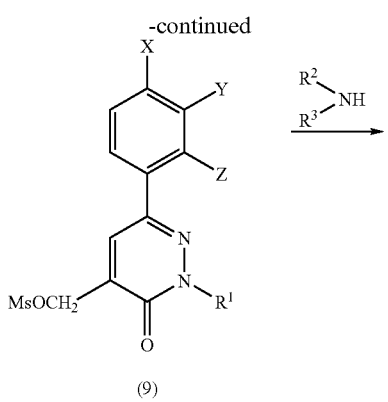

(9)

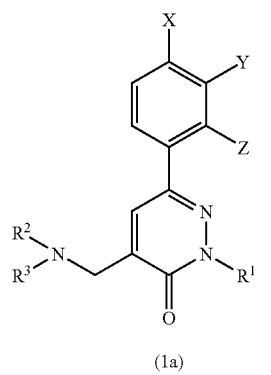

(1a)

wherein R⁴ represents alkyl, Hal represents halogen, Ms represents methanesulfonyl, and $R^1$, $R^2$, $R^3$, X, Y and Z have the same meanings as described above.

A description will hereinafter be made about the individual reaction steps.

In the steps from an acetophenone (2) to a compound (5), the acetophenone (2) and diethyl ketomalonate are heated under stirring to yield a compound (3). Hydrazine is caused to act on the compound to carry out a ring-closing reaction, and the reaction product is then treated with an alkali, for example, sodium hydroxide or the like to afford a compound (4). The compound (4) is next reacted with an alcohol such as methanol to give the compound (5).

$R^1$-Hal is reacted to the compound (5) in the presence of an alkali such as potassium carbonate to provide a compound (6). The compound (6) is hydrolyzed into a compound (7). After ethyl chlorocarbonate is caused to act on the compound (7) to convert it into an acid anhydride, the acid anhydride is reduced with a reducing agent such as sodium borohydride to afford a compound (8). A reaction of methanesulfonyl chloride with the compound (8) in the presence of a base such as triethylamine provides a compound (9), a key intermediate in this reaction scheme.

A reaction of a desired amine [$R^2(R^3)$NH] with the compound (9) yields the target compound (1a). It is preferred to carry out this reaction, for example, in a polar solvent such as dimethylformamide in the presence or absence of an alkali such as potassium carbonate. Incidentally, if an amino group is contained in the group $R^2$ or $R^3$ in the amine, a reaction may be carried out using a raw material protected with an appropriate protecting group, for example, an alkoxycarbonyl group, followed by the removal of the protecting group.

To obtain a compound (1a) in which $R^2$ and $R^3$ are hydrogen atoms, potassium phthalimide is reacted with the compound (9), and the reaction product is reacted further with hydrazine or the like.

A compound (1a) in which X, Y and/or Z is methylsulfinyl or methylsulfonyl can be obtained by oxidizing a corresponding compound, in which X, Y and/or Z is methylthio, with a peracid, for example, perbenzoic acid. This methylsulfination or methylsulfonation may be carried out at the stage of the intermediate (9).

(b) Preparation Process of Compounds Having the Formula (1) in which n=3

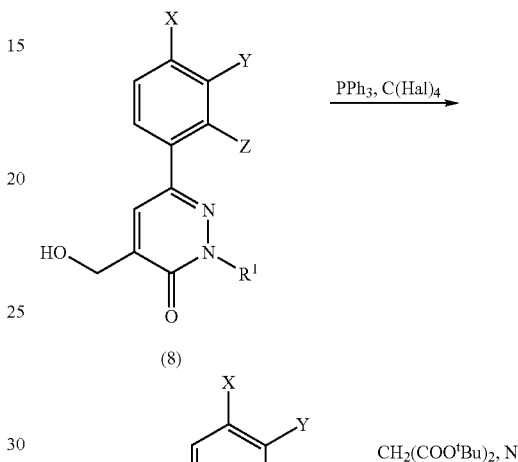

(8)

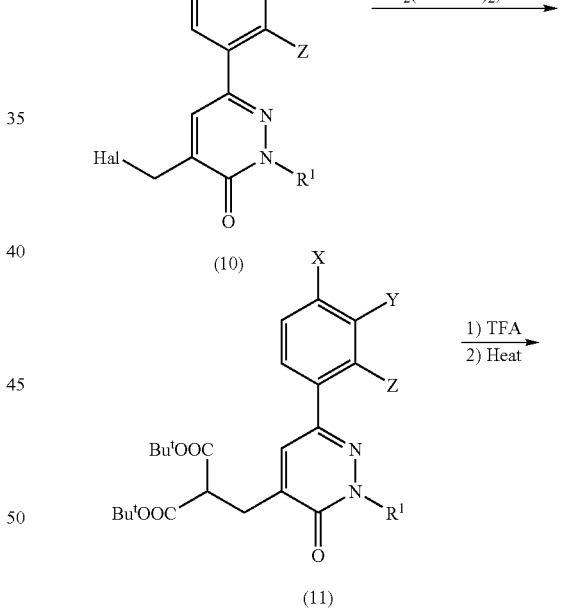

(10)

(11)

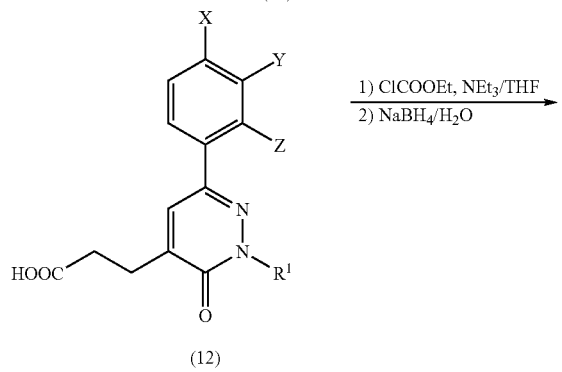

(12)

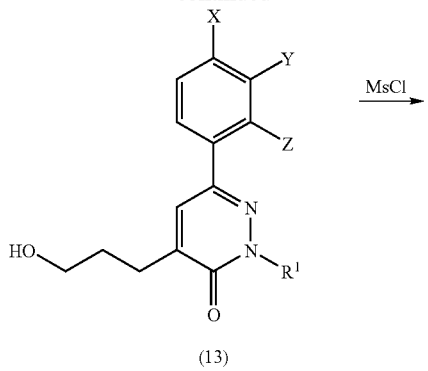

(13)

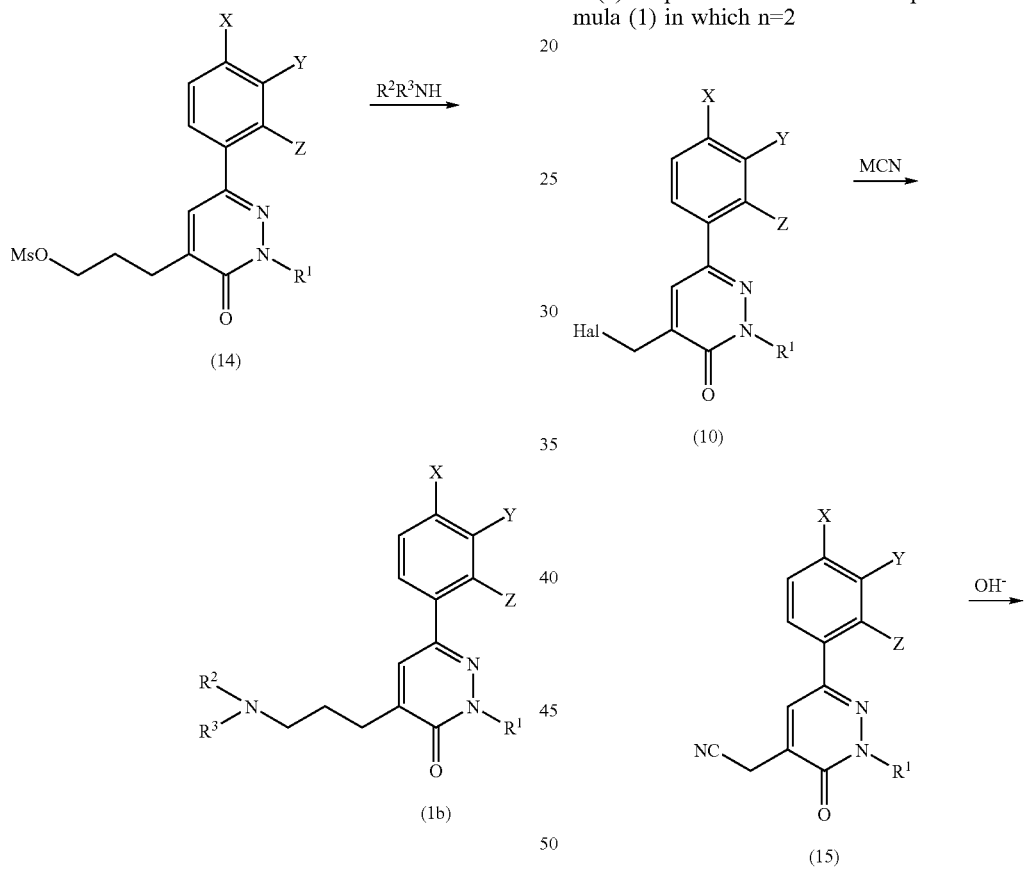

(14)

(1b)

(10)

(15)

(16)

wherein Hal, Ms, $R^1$, $R^2$, $R^3$, X, Y and Z have the same meanings as defined above.

According to the preparation process (b), a carbon tetrahalide such as carbon tetrabromide is firstly reacted with the compound (8) in the presence of triphenylphosphine to obtain a halide (10), with which a malonate is then reacted in the presence of sodium hydride to yield a compound (11). An acid such as trifluoroacetic acid is reacted with the compound (11) to convert it into a dicarboxylic acid, followed by heating to yield a compound (12). Ethyl chlorocarbonate is caused to act on the compound (12) to convert it into an acid anhydride, which is then reduced with a reducing agent such as sodium borohydride to yield a compound (13). Methanesulfonylchloride is reacted with the compound (13) in the presence of a base such as triethylamine to yield a compound (14), a key intermediate in the process according to the present invention.

A target compound (1b) can be obtained by reacting a corresponding amine ($R^2R^3NH$) with the compound (14). This reaction may preferably be conducted, for example, in the presence or absence of an alkali such as potassium carbonate in a polar solvent such as dimethylformamide. When an amino group is contained in the group $R^2$ or $R^3$ of the amine, a reaction may be conducted using a raw material in which the amino group has been protected with an appropriate protecting group (for example, an alkoxycarbonyl group), followed by deprotection of the protecting group.

To yield a compound (1b) in which $R^2$ and $R^3$ are both hydrogen atoms, the compound can be obtained by reacting potassium phthalimide with the compound (14) and then reacting hydrazine or the like.

(c) Preparation Process of Compounds Having the Formula (1) in which n=2

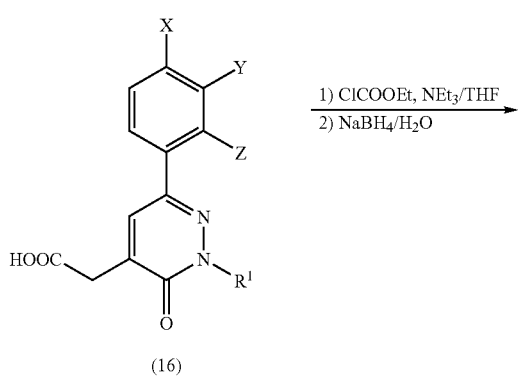

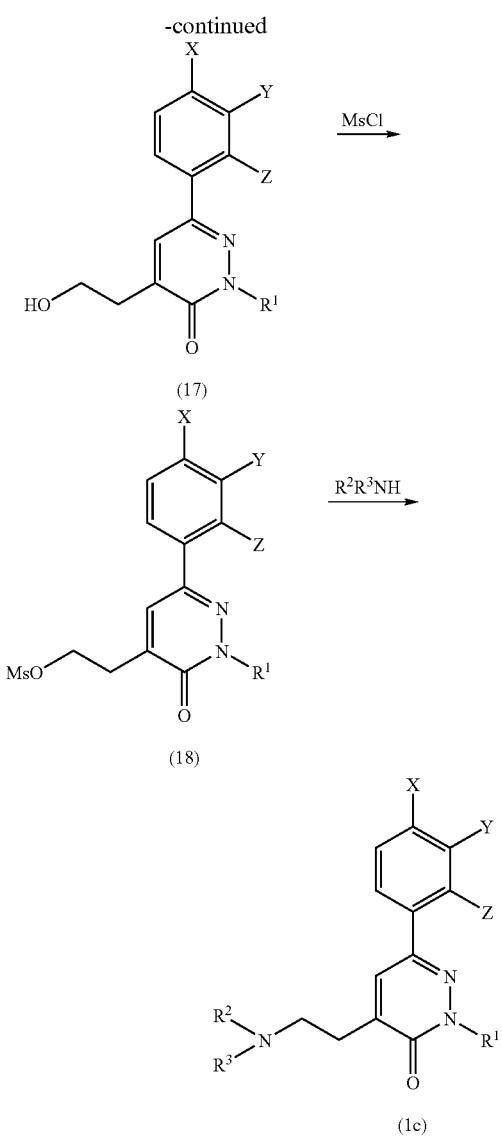

wherein M represents a metal atom, and Hal, Ms, $R^1$, $R^2$, $R^3$, X, Y and Z have the same meanings as defined above.

According to the preparation process (c), a cyanide such as sodium cyanide is reacted with a halide (10) to convert it into a nitrile derivative (15), which is then hydrolyzed to yield a compound (16). From the compound (16), a target compound (1c) can be obtained via an alcohol derivative (17) and a mesyloxy derivative (18) by a similar procedure as in the preparation of compounds containing three methylene groups.

(d) Preparation Process of Compounds Having the Formula (1) in which n=4 or 5

These compounds can be obtained by combining the synthesis processes (b) and (c).

The salt of the compound (1) according to the present invention can be obtained by causing an organic acid or inorganic acid to act in a manner known per se in the art.

The compound (1) according to the present invention can be isolated and purified by subjecting it to purification procedures commonly employed in organic synthesis chemistry, for example, filtration, extraction, washing, drying, concentration, recrystallization, various chromatographic procedures, and/or the like. Each intermediate can be subjected to the subsequent reaction without bothering to purify it. The compound (1) may be provided as a solvate with a solvent such as a reaction solvent or recrystallization solvent, especially as the hydrate.

The compound (1) according to the present invention is excellent in water solubility, is also good in oral absorbability and has inhibitory activity against interleukin-1β production, and therefore, is useful as a preventive or therapeutic for immune system diseases, inflammatory diseases, ischemic diseases, osteoporosis, ichorrhemia and the like. Examples of ischemic diseases include ischemic heart diseases, ischemic encephalopathy, ischemic nephritis, and ischemic hepatitis.

The pharmaceutical composition of the present invention contains the compound (1) or the salt thereof as an active ingredient. Using the active ingredient alone or together with a pharmacologically acceptable carrier such as a solubilizer, excipient, binder or extender, it can be formed into pharmaceutical preparation forms such as tablets, capsules, granules, powders, injections and suppositories. These pharmaceutical preparations can be produced by known methods. For example, oral preparations can be produced by suitably formulating the compound (1) or the salt in combination with solubilizers such as tragacanth gum, gumarabic, sucrose esters, lecithin, olive oil, soybean oil and PEG400; excipients such as starch, mannitol and lactose; binders such as carboxymethylcellulose sodium and hydroxypropylcellulose; disintegrators such as crystalline cellulose and carboxymethylcellulose calcium; lubricants such as talc and magnesium stearate; anticaking agents such as light anhydrous silicic acid. The pharmaceutical composition according to the present invention is administered orally or parenterally.

The administered dosage of the pharmaceutical composition according to the present invention varies depending on the body weight, age, sex, conditions and the like of each patient. In general, however, it is preferred to administer to an adult in an amount of about 0.01 to 1,000 mg, preferably 0.1 to 100 mg, of the present pharmaceutical composition in terms of the compound (1) per day in 1 to 3 portions.

EXAMPLES

The present invention will now be further described by reference to the following Examples. The Examples are provided solely for purposes of illustration and are not intended to be limitative.

Example 1

Preparation of 4-(4-tert-butoxycarbonyl-1-piperazinyl)methyl-6-(3-fluoro-4-methylphenyl)-2-isobutyl-2H-pyridazin-3-one 1) Preparation of 4-(1-hydroxyethyl)-2-fluorotoluene To an ice-cold solution of 3-fluoro-4-methylbenzaldehyde (50 mg, 0.36 mmol) in THF (0.5 mL) was added dropwise a 0.93 M solution (0.47 mL) of methylmagnesium bromide (0.44 mmol) in THF. The temperature of the reaction mixture was allowed to rise back to room temperature, at which the reaction mixture was stirred for 1 hour. Then, 2 mol/L hydrochloric acid was added, and the mixture was extracted with ethyl acetate. The extract was washed with brine and dried over anhydrous sodium sulfate. The solvent was distilled off under reduced pressure to yield title compound as a pale yellow oil (55.8 mg, quantitative).

$^1$H NMR(400 MHz, CDCl$_3$)δ: 1.46(3H, d, J=6.4 Hz), 2.26(3H, d, J=1.8 Hz), 4.85(1H, q, J=6.4 Hz), 6.99–7.06(2H, m), 7.14(1H, dd, J=7.8, 7.8 Hz).

2) Preparation of 3'-fluoro-4'-methylacetophenone

To a solution of 4-(1-hydroxyethyl)-2-fluorotoluene (55.8 mg, 0.36 mmol) in methylene chloride (1 mL) were added molecular sieve 4A (56.0 mg) and PCC 94.0 mg (0.43 mmol), and the mixture was stirred at room temperature for 1 hour. The reaction mixture was filtered through Celite, and the filtrate was concentrated under reduced pressure. The residue was purified by column chromatography on silica gel [silica gel 5 g, hexane/ethyl acetate (10/1)] to yield the title compound as a pale yellow oil (47.5 mg, 86.0%).

$^1$H NMR(400 MHz, CDCl$_3$)δ: 2.32(3H, d, J=1.8 Hz), 2.56(3H, s), 7.26(1H, dd, J=7.6, 7.6 Hz), 7.56(1H, dd, J=1.6, 10.4 Hz), 7.62(1H, dd, J=1.6, 7.8 Hz).

3) Preparation of ethyl 2-ethoxycarbonyl-4-(3-fluoro-4-methylphenyl)-2-hydroxy-4-oxobutanoate A mixture of 3'-fluoro-4'-methylacetophenone (4.92 g, 32.3 mmol) and diethyl ketomalonate (6.19 g, 35.6 mmol) was stirred at 120° C. for 48 hours. The temperature of the reaction mixture was allowed to drop back to room temperature, and the mixture was purified by column chromatography on silica gel [silica gel 100 g, chloroform/ethyl acetate (10/1)] to yield the title compound as yellow crystals (8.41 g, 79.3%).

Melting point: 68.7–69.0° C. $^1$H NMR(400 MHz, CDCl$_3$) δ: 1.30(6H, t, J=7.1 Hz), 2.34(3H, s), 3.78(2H, s), 4.25(1H, s), 4.31(4H, q, J=7.1 Hz), 7.29(1H, dd, J=7.6 Hz), 7.59(1H, d, J=10.2 Hz), 7.65(1H, dd, J=1.5, 7.8 Hz). IR(KBr) cm$^{-1}$: 3485, 1740, 1684, 1253, 856, 577.

4) Preparation of 4-carboxy-6-(3-fluoro-4-methylphenyl)-2H-pyridazin-3-one

To a solution of ethyl 2-ethoxycarbonyl-4-(3-fluoro-4-methylphenyl)-2-hydroxy-4-oxobutanoate (8.41 g, 25.8 mmol) in isopropanol (100 mL) was added hydrazine monohydrate (2.84 g, 56.8 mmol), and the mixture was heated under stirring at 100° C. for 6 hours. Then, 2 mol/L sodium hydroxide was added, and the mixture was stirred further at the same temperature for 4 hours. The reaction mixture was ice-cooled, and concentrated hydrochloric acid was added to acidify the system. The precipitate was collected by filtration, thoroughly washed with water and dried to yield the title compound as a slightly yellow crystalline powder (5.67 g, 87.7%).

Melting point: 281.3–282.0° C. (dec.) $^1$H NMR(400 MHz, DMSO-d$_6$)δ: 2.28(3H, d, J=1.0 Hz), 7.41(1H, dd, J=8.1, 8.1 Hz), 7.67–7.73(2H, m), 8.49(1H, s), 14.09(1H, br). IR(KBr) cm$^{-1}$: 1736, 1641, 1441, 1125, 926, 806.

5) Preparation of 6-(3-fluoro-4-methylphenyl)-4-methoxycarbonyl-2H-pyridazin-3-one To an ice-cold suspension of 4-carboxy-6-(3-fluoro-4-methylphenyl)-2H-pyridazin-3-one (5.50 g, 22.2 mmol) in methanol (100 mL) was added dropwise thionyl chloride (2.72 g, 24.4 mmol), and the mixture was stirred at 80° C. for 8 hours. The temperature of the reaction mixture was allowed to drop back to room temperature, and the solvent was distilled off under reduced pressure. Water was added to the ice-cold residue. The precipitate was collected by filtration, washed with water and dried to yield the title compound as pale yellow fine-needles (5.43 g, 92.7%).

Melting point: 206.0–207.3° C. $^1$H NMR(400 MHz, CDCl$_3$)δ: 2.33(3H, d, J=1.7 Hz), 4.00(3H, s), 7.29(1H, dd, J=7.9, 7.9 Hz), 7.46–7.53(2H, m), 8.32(1H, s), 11.61(1H, s). IR(KBr) cm$^{-1}$: 1715, 1671, 1266, 1177, 1091, 812.

6) Preparation of 6-(3-fluoro-4-methylphenyl)-2-isobutyl-4-methoxycarbonyl-2H-pyridazin-3-one To a solution of 6-(3-fluoro-4-methylphenyl)-4-methoxycarbonyl-2H-pyridazin-3-one (5.28 g, 20.0 mmol) in N,N-dimethylformamide (40 mL) were added potassium carbonate (5.53 g, 40.0 mmol) and isobutyl bromide (3.29 g, 24.0 mmol), and the mixture was stirred at 80° C. for 1 hour. The temperature of the reaction mixture was allowed to drop back to room temperature. A saturated aqueous solution of sodium hydrogencarbonate was added, and the mixture was extracted with ethyl acetate. The extract was washed with brine, and dried over anhydrous sodium sulfate. The solvent was distilled off under reduced pressure. The residue was purified by column chromatography on silica gel [silica gel 100 g, chloroform/methanol (100/1→50/1)) to yield the title compound as an orange oil (5.41 g, 84.9%).

$^1$H NMR(400 MHz, CDCl$_3$)δ: 0.99(6H, d, J=6.6 Hz), 2.32–2.42(1H, m), 2.33(3H, s), 3.98(3H, s), 4.12(2H, d, J=7.4 Hz), 7.28(1H, dd, J=7.8, 7.8 Hz), 7.46(1H, dd, J=1.6, 7.8 Hz), 7.50(1H, dd, J=1.6, 10.7 Hz), 8.21(1H, s).

7) Preparation of 4-carboxy-6-(3-fluoro-4-methylphenyl)-2-isobutyl-2H-pyridazin-3-one To a suspension of 6-(3-fluoro-4-methylphenyl)-2-isobutyl-4-methoxycarbonyl-2H-pyridazin-3-one (5.27 g, 16.6 mmol) in methanol (50 mL) was added a 2 mol/L aqueous sodium hydroxide (50 mL), and the mixture was stirred at 60° C. for 15 minutes. The temperature of the reaction mixture was allowed to drop back to room temperature, and then, water was added. After the system was acidified with concentrated hydrochloric acid, the mixture was extracted with ethyl acetate. The extract was washed with brine, and dried over anhydrous sodium sulfate. The solvent was distilled off under reduced pressure, and the residue was recrystallized from chloroform-hexane to yield the title compound as colorless fine-needles (4.73 g, 93.8%).

Melting point: 159.0–159.5° C. $^1$H NMR(400 MHz, CDCl$_3$)δ: 1.02(6H, d, J=6.7 Hz), 2.33–2.42(1H, m), 2.35 (3H, d, J=1.6 Hz), 4.21 (2H, d, J=7.4 Hz), 7.32 (1H, dd, J=7.8, 7.8 Hz), 7.52 (1H, dd, J=1.8, 8.0 Hz), 7.55(1H, dd, J=1.8, 10.6 Hz), 8.63(1H, s), 14.13(1H, s). IR(KBr) cm$^{-1}$: 2960, 1742, 1633, 1574, 1425, 1101, 820.

8) Preparation of 6-(3-fluoro-4-methylphenyl)-4-hydroxymethyl-2-isobutyl-2H-pyridazin-3-one To a solution of 4-carboxy-6-(3-fluoro-4-methyl-phenyl)-2-isobutyl-2H-pyridazin-3-one (4.53 g, 14.9 mmol) in THF (40 mL) was added triethylamine (1.66 g, 16.4 mmol). To the ice-cooled mixture was added dropwise a solution of ethyl chlorocarbonate (1.78 g, 16.4 mmol) in THF (5 mL), and the mixture was stirred for 30 minutes. Triethylamine hydrochloride was filtered off. An ice-cold solution of sodium borohydride (564 mg, 14.9 mmol) in water (1 mL) was added to the filtrate, and then, the mixture was stirred at room temperature for 10 minutes. Thereafter, 2 mol/L hydrochloric acid was added to the reaction mixture, and the mixture was extracted with ethyl acetate. The organic layer was washed with brine, and dried over anhydrous sodium sulfate. The solvent was distilled off under reduced pressure. The residue was purified by column chromatography on silica gel [silica gel 300 g, chloroform/methanol (100/1→50/1)) to yield the title compound as a colorless crystalline powder (1.08 g, 25.0%).

Melting point: 147.3–147.5° C. $^1$H NMR(400 MHz, CDCl$_3$)δ: 0.99(6H, d, J=6.6 Hz), 2.29–2.39(1H, m), 2.32 (3H, d, J=1.8 Hz), 3.05(1H, t, J=6.0 Hz), 4.08(2H, d, J=7.4 Hz), 4.71(2H, dd, J=1.2, 6.0 Hz), 7.26(1H, dd, J=7.8 Hz), 7.46(1H, dd, J=7.8, 7.8 Hz), 7.50(1H, dd, J=1.8, 10.8 Hz), 7.65(1H, s). IR(KBr) cm$^{-1}$: 3330, 1644, 1596, 1514, 1226, 1087, 824.

9) Preparation of 6-(3-fluoro-4-methylphenyl)-2-isobutyl-4-methanesulfonyloxymethyl-2H-pyridazin-3-one To an ice-cold solution of 6-(3-fluoro-4-methyl-phenyl)-4-hydroxymethyl-2-isobutyl-2H-pyridazin-3-one (1.08 g, 3.73 mmol) in methylene chloride (20 mL) were added triethylamine (491 mg, 4.85 mmol) and methanesulfonyl chloride (513 mg, 4.48 mmol), and the mixture was stirred for 1 hour. A saturated aqueous solution of sodium hydrogencarbonate was added to the reaction mixture, and then, the mixture was extracted with ethyl acetate. The extract was washed with brine and dried over anhydrous sodium sulfate. The solvent was distilled off under reduced pressure, and the residue was recrystallized from chloroform-hexane to yield the title compound as a colorless crystalline powder (964 mg, 70.4%).

Melting point: 142.7–143.4° C. $^1$H NMR(400 MHz, CDCl$_3$)δ: 0.99(6H, d, J=6.8 Hz), 2.30–2.34(1H, m), 2.33 (3H, d, J=1.8 Hz), 3.17(3H, s), 4.08(2H, d, J=7.4 Hz), 5.27(2H, d, J=1.4 Hz), 7.27(1H, dd, J=7.8, 7.8 Hz), 7.45(1H, dd, J=1.8, 8.0 Hz), 7.50(1H, dd, J=1.8, 10.9 Hz), 7.76(1H, t, J=1.4 Hz). IR(KBr) cm$^{-1}$: 3435, 2964, 1658, 1610, 1354, 1165, 875.

10) Preparation of 4-(4-tert-butoxycarbonyl-1-piperazinyl)-methyl-6-(3-fluoro-4-methylphenyl)-2-isobutyl-2H-pyridazin-3-one To a solution of 6-(3-fluoro-4-methylphenyl)-2-isobutyl-4-methanesulfonyloxymethyl-2H-pyridazin-3-one (100 mg, 0.27 mmol) in acetonitrile (1 mL) were added potassium carbonate (56.3 mg, 0.41 mmol) and tert-butyl 1-piperazinecarboxylate (60.7 mg, 0.33 mmol), and the mixture was stirred at 80° C. for 2 hours. The temperature of the reaction mixture was allowed to drop back to room temperature, and then, water was added. The mixture was extracted with chloroform. The extract was dried over anhydrous sodium sulfate. The solvent was distilled off under reduced pressure, and the residue was purified by column chromatography on silica gel [chloroform/methanol (40/1)] to yield the title compound as a yellow oil (115 mg, 92.4%).

$^1$H NMR(400 MHz, CDCl$_3$)δ: 0.98(6H, d, J=3.4 Hz), 1.47(9H, s), 2.28–2.40(1H, m), 2.33(3H, s), 2.52(4H, t, J=4.7 Hz), 3.51(4H, t, J=4.7 Hz), 3.58(2H, s), 4.07 (2H, d, 4.1 Hz), 7.27 (1H, dd, J=7.6, 7.6 Hz), 7.44–7.52 (2H, m), 7.77(1H, s).

Example 2

Preparation of 6-(3-fluoro-4-methylphenyl)-2-isobutyl-4-(1-piperazinyl)methyl-2H-pyridazin-3-one dihydrochloride To a solution of 4-(4-tert-butoxycarbonyl-1-piperazinyl)methyl-6-(3-fluoro-4-methylphenyl)-2-isobutyl-2H-pyridazin-3-one (115 mg, 0.25 mmol) in ethyl acetate (2 mL) was added a 4 mol/L solution (2 mL) of hydrochloric acid in ethyl acetate, and the mixture was stirred at 50° C. for 1 hour. The temperature of the reaction mixture was allowed to drop back to room temperature, and then, diethyl ether was added. The precipitate was collected to yield the title compound as a colorless crystalline powder (81.1 mg, 75.0%).

Melting point: 186.2–195.0° C. (dec.) $^1$H NMR(400 MHz, DMSO-d$_6$)δ: 0.95(6H, d, J=6.8 Hz), 2.22–2.33(1H, m), 2.29(3H, d, J=2.0 Hz), 3.15(4H, br), 3.32(4H, t, J=5.2 Hz), 3.93(2H, s), 4.02(2H, d, J=7.1 Hz), 7.40(1H, dd, J=8.1, 8.1 Hz), 7.59–7.66(2H, m), 8.21(1H, s). IR(KBr) cm$^{-1}$: 1656, 1610, 1425, 1306, 956. Mass m/z: 358(M$^+$)

Example 3

Preparation of 6-(3-fluoro-4-methylphenyl)-2-isobutyl-4-(4-methyl-1-piperazinyl)methyl-2H-pyridazin-3-one Following the procedure of Example 1(10), 6-(3-fluoro-4-methylphenyl)-2-isobutyl-4-methanesulfonyloxymethyl-2H-pyridazin-3-one and 1-methylpiperazine were reacted to yield the title compound as a yellow oil (yield: 93.4%).

$^1$H NMR(400 MHz, CDCl$_3$)δ: 0.98(6H, d, J=6.8 Hz), 2.28–2.40(1H, m), 2.33(6H, s), 2.52(4H, br), 2.62(4H, br), 3.58(2H, s), 4.07(2H, d, J=7.4 Hz), 7.27(1H, dd, J=7.9, 7.9 Hz), 7.46–7.52(2H, m), 7.75(1H, d, J=1.0 Hz).

Example 4

Preparation of 6-(3-fluoro-4-methylphenyl)-2-isobutyl-4-(4-methyl-1-piperazinyl)methyl-2H-pyridazin-3-one dihydrochloride To a solution of 6-(3-fluoro-4-methylphenyl)-2-isobutyl-4-(4-methyl-1-piperazinyl)methyl-2H-pyridazin-3-one (94.4 mg, 0.25 mmol) in methanol (1 mL) was added dropwise at room temperature under stirring a 4 mol/L solution (0.15 mL) of hydrochloric acid in ethyl acetate. The solvent was distilled off under reduced pressure. The residue was recrystallized from methanol-ether to yield the title compound as a colorless crystalline powder (71.9 mg, 63.7%).

Melting point: 248.5–252.0° C. (dec.) $^1$H NMR(400 MHz, DMSO-d$_6$)δ: 0.94(6H, d, J=6.8 Hz), 2.29(3H, d, J=1.8 Hz), 2.22–2.33(1H, m), 2.77(3H, s), 3.18(4H, br), 3.38(4H, br), 3.91(2H, s), 4.02(2H, d, J=7.0 Hz), 7.40(1H, dd, J=8.0, 8.0 Hz), 7.59–7.65(2H, m), 8.16(1H, s). IR(KBr) cm$^{-1}$: 1653, 1609, 1451, 1425, 951. Mass m/z: 372(M$^+$)

Example 5

Preparation of 4-N,N-bis(2-hydroxyethyl)aminomethyl-6-(3-fluoro-4-methylphenyl)-2-isobutyl-2H-pyridazin-3-one Following the procedure of Example 1(10), 6-(3-fluoro-4-methylphenyl)-2-isobutyl-4-methanesulfonyloxymethyl-2H-pyridazin-3-one and diethanolamine were reacted to yield the title compound as a yellow oil (yield: 84.8%).

$^1$H NMR(400 MHz, CDCl$_3$)δ: 0.96(6H, d, J=6.6 Hz), 2.27–2.38(1H, m), 2.30(3H, s), 2.70(4H, t, J=5.0 Hz), 3.66 (4H, t, J=5.2 Hz), 3.69(2H, s), 4.06(2H, d, J=7.2 Hz), 7.23(1H, dd, J=7.9, 7.9 Hz), 7.46–7.52(2H, m), 7.79(1H, s).

Example 6

Preparation of 4-N,N-bis(2-hydroxyethyl)aminomethyl-6-(3-fluoro-4-methylphenyl)-2-isobutyl-2H-pyridazin-3-one hydrochloride Following the procedure of Example 4, 4-N,N-bis(2-hydroxyethyl)aminomethyl-6-(3-fluoro-4-methylphenyl)-2-isobutyl-2H-pyridazin-3-one was reacted to yield the title compound as a colorless crystalline powder (yield: 85.9%).

Melting point: 159.7–160.7° C. $^1$H NMR(400 MHz, DMSO-d$_6$)δ: 0.96(6H, d, J=6.6 Hz), 2.20–2.34(1H, m), 2.30(3H, d, J=1.7 Hz), 3.35(4H, t, J=5.1 Hz), 3.84(4H, t, J=5.1 Hz), 4.05(2H, d, J=7.0 Hz), 4.45(2H, s), 7.42(1H, dd, J=8.2, 8.2 Hz), 7.62–7.68(2H, m), 8.47(1H, s). IR(KBr) cm$^{-1}$: 1663, 1613, 1427, 1087, 1052, 821. Mass m/z: 359 (M$^+$—H$_2$O)

Example 7

Preparation of 4-dimethylaminomethyl-6-(3-fluoro-4-methylphenyl)-2-isobutyl-2H-pyridazin-3-one To 6-(3-fluoro-4-methylphenyl)-2-isobutyl-4-methanesulfonyloxymethyl-2H-pyridazin-3-one (100 mg, 0.27 mmol) was added a 40% aqueous dimethylamine (1 mL), and the mixture was stirred at 80° C. for 2 hours. The temperature of the reaction mixture was allowed to drop back to room temperature, and then, water was added. The mixture was extracted with chloroform. The extract was dried over anhydrous sodium sulfate. The solvent was distilled off under reduced pressure, and the residue was purified by column chromatography on silica gel [chloroform/methanol (40/1)] to yield the title compound as a yellow oil (69.7 mg, 80.9%).

$^1$H NMR(400 MHz, CDCl$_3$)δ: 0.98(6H, d, J=6.8 Hz), 2.23–2.41(1H, m), 2.31(3H, s), 2.35(6H, s), 3.50(2H, d, J=1.2 Hz), 4.08(2H, d, J=7.4 Hz), 7.26(1H, dd, J=7.9, 7.9 Hz), 7.47–7.54(2H, m), 7.76(1H, d, J=1.4 Hz).

Example 8

Preparation of 4-dimethylaminomethyl-6-(3-fluoro-4-methylphenyl)-2-isobutyl-2H-pyridazin-3-one hydrochloride Following the procedure of Example 4, 4-dimethyl-aminomethyl-6-(3-fluoro-4-methylphenyl)-2-isobutyl-2H-pyridazin-3-one was reacted to yield the title compound as a colorless crystalline powder (yield: 85.4%).

Melting point: 246.5–248.5° C. $^1$H NMR(400 MHz, DMSO-d$_6$)δ: 0.96(6H, d, J=6.6 Hz), 2.23–2.34(1H, m), 2.30(3H, s), 2.81(6H, s), 4.05(2H, d, J=7.0 Hz), 4.27(2H, s), 7.41(1H, dd, J=8.0, 8.0 Hz), 7.22–7.68(2H, m), 8.52(1H, s). IR(KBr) cm$^{-1}$: 1648, 1607, 1422, 1227, 1110, 1051. Mass m/z: 317(M$^+$)

Example 9

Preparation of 2-cyclopropylmethyl-6-(3-fluoro-4-methoxyphenyl)-4-methylaminomethyl-2H-pyridazin-3-one 1) Preparation of 4-carboxy-2-cyclopropylmethyl-6-(3-fluoro-4-methoxyphenyl)-2H-pyridazin-3-one Following the procedure of Example 1(7), 2-cyclopropylmethyl-6-(3-fluoro-4-methoxyphenyl)-4-methoxycarbonyl-2H-pyridazin-3-one was reacted to yield the title compound as yellow crystals (yield: 98.9%).

Melting point: 169.1–170.7° C. $^1$H NMR(400 MHz, CDCl$_3$)δ: 0.50–0.67(4H, m), 1.40–1.50(1H, m), 3.97(3H, s), 4.23(2H, d, J=7.3 Hz), 7.07(1H, dd, J=8.5, 8.5 Hz), 7.57(1H, ddd, J=1.2, 2.2, 8.5 Hz), 7.85(1H, dd, J=2.2, 12.2 Hz), 8.63(1H, s), 14.20(1H, s). IR(KBr) cm$^{-1}$: 1761, 1629, 1521, 1476, 1461. Mass m/z: 318(M$^+$)

2) Preparation of 2-cyclopropylmethyl-6-(3-fluoro-4-methoxyphenyl)-4-hydroxymethyl-2H-pyridazin-3-one Following the procedure of Example 1(8), 4-carboxy-2-cyclopropylmethyl-6-(3-fluoro-4-methoxyphenyl)-2H-pyridazin-3-one was reacted to yield the title compound as slightly yellow fine-needles (yield: 21.3%).

Melting point: 119.4–122.6° C. $^1$H NMR(400 MHz, CDCl$_3$)δ: 0.45–0.60(4H, m), 1.36–1.47(1H, m), 3.12(1H, t, J=6.0 Hz), 3.95(3H, s), 4.10(2H, d, J=7.3 Hz), 4.72(2H, dd, J=1.2, 5.9 Hz), 7.03(1H, dd, J=8.5, 8.5 Hz), 7.51(1H, ddd, J=1.2, 2.2, 8.5 Hz), 7.62(1H, dd, J=2.2, 12.4 Hz), 7.65(1H, t, J=1.2 Hz). IR(KBr) cm$^{-1}$: 3431, 1652, 1604, 1524. Mass m/z: 304(M$^+$).

3) Preparation of 2-cyclopropylmethyl-6-(3-fluoro-4-methoxyphenyl)-4-methanesulfonyloxymethyl-2H-pyridazin-3-one Following the procedure of Example 1(9), 2-cyclopropylmethyl-6-(3-fluoro-4-methoxyphenyl)-4-hydroxymethyl-2H-pyridazin-3-one was reacted to yield the title compound as slightly yellow needles (yield: 80.4%).

Melting point: 156.9–158.4° C. $^1$H NMR(400 MHz, CDCl$_3$)δ: 0.45–0.61(4H, m), 1.36–1.46(1H, m), 3.18(3H, s), 3.95(3H, s), 4.10(2H, d, J=7.3 Hz), 5.28(2H, d, J=1.2 Hz), 7.03(1H, dd, J=8.5, 8.5 Hz), 7.51(1H, ddd, J=1.2, 2.2, 8.5 Hz), 7.62(1H, dd, J=2.2, 12.2 Hz), 7.76(1H, t, J=1.2 Hz). IR(KBr) cm$^{-1}$: 1656, 1612, 1523, 1358, 1177. Mass m/z: 382(M$^+$).

4) Preparation of 2-cyclopropylmethyl-6-(3-fluoro-4-methoxyphenyl)-4-methylaminomethyl-2H-pyridazin-3-one A solution of 2-cyclopropylmethyl-6-(3-fluoro-4-methoxyphenyl)-4-methanesulfonyloxymethyl-2H-pyridazin-3-one (160 mg, 0.42 mmol) in 30% methylamine/ethanol (5 mL) was stirred at 80° C. for 4 hours in a sealed tube. The solvent was distilled off under reduced pressure, and the residue was purified by preparative thin-layer chromatography on silica gel [developing solvent: chloroform/methanol (10/1)] to yield title compound as a slightly yellow oil (87 mg, 65.5%).

$^1$H NMR(400 MHz, CDCl$_3$)δ: 0.45–0.59(4H, m), 1.36–1.47(1H, m), 1.85(1H, br), 2.52(3H, s), 3.80(2H, d, J=1.2 Hz), 3.95(3H, s), 4.10(2H, d, J=7.3 Hz), 7.01(1H, dd, J=8.5, 8.5 Hz), 7.52(1H, ddd, J=1.2, 2.2, 8.5 Hz), 7.62(1H, dd, J=2.2, 12.4 Hz), 7.66(1H, t, J=1.2 Hz). Mass m/z: 317(M$^+$).

Example 10

Preparation of 2-cyclopropylmethyl-6-(3-fluoro-4-methoxyphenyl)-4-methylaminomethyl-2H-pyridazin-3-one hydrochloride Following the procedure of Example 4, 2-cyclopropylmethyl-6-(3-fluoro-4-methoxyphenyl)-4-methylaminomethyl-2H-pyridazin-3-one was reacted to yield the title compound as slightly yellow needles (yield: 93.8%).

Melting point: 220.8–224.3° C. (dec.) $^1$H NMR(400 MHz, DMSO-d$_6$)δ: 0.44–0.54(4H, m), 1.29–1.40(1H, m), 2.66(3H, s), 3.91(3H, s), 4.05(2H, d, J=7.3 Hz), 4.12(2H, s), 7.33(1H, dd, J=8.5, 8.5 Hz), 7.70–7.79(2H, m), 8.39 (1H, s). IR(KBr) cm$^{-1}$: 1645, 1599, 1521, 1437.

Example 11

Preparation of 2-cyclopropylmethyl-6-(3-fluoro-4-methoxyphenyl)-4-(4-methyl-1-piperazinyl)methyl-2H-pyridazin-3-one Following the procedure of Example 1(10), 2-cyclopropylmethyl-6-(3-fluoro-4-methoxyphenyl)-4-methanesulfonyloxymethyl-2H-pyridazin-3-one and N-methylpiperazine were reacted to yield the title compound as a yellow oil (yield: 73.8%).

$^1$H NMR(400 MHz, CDCl$_3$)δ: 0.45–0.59(4H, m), 1.36–1.47(1H, m), 2.33(3H, s), 2.52(4H, br), 2.62(4H, br), 3.80(2H, d, J=1.2 Hz), 3.58(2H, d, J=1.0 Hz), 3.95(3H, s), 4.09(2H, d, J=7.3 Hz), 7.04(1H, dd, J=8.5, 8.5 Hz), 7.53(1H, ddd, J=1.2, 2.2, 8.5 Hz), 7.61(1H, dd, J=2.2, 12.4 Hz), 7.74(1H, t, J=1.2 Hz). IR(Neat) cm$^{-1}$: 1652, 1608, 1520, 1456, 1440. Mass m/z: 386(M$^+$).

Example 12

Preparation of 2-cyclopropylmethyl-6-(3-fluoro-4-methoxyphenyl)-4-(4-methyl-1-piperazinyl)methyl-2H-pyridazin-3-one dihydrochloride Following the procedure of Example 4, 2-cyclopropylmethyl-6-(3-fluoro-4-methoxyphenyl)-4-(4-methyl-1-piperazinyl)methyl-2H-pyridazin-3-one was reacted to yield the title compound as pale yellow needles (yield: 81.0%).

Melting point: 237.4–238.4° C. (dec.) $^1$H NMR(400 MHz, DMSO-d$_6$)δ: 0.47–0.58(4H, m), 1.31–1.41(1H, m), 2.33(3H, s), 2.52(4H, br), 2.62(4H, br), 2.90–3.85(10H, m), 3.91(3H, s), 4.03(2H, d, J=7.3 Hz), 7.30(1H, dd, J=8.5, 8.5 Hz), 7.70–7.78(2H, m), 8.28(1H, brs). IR(KBr) cm$^{-1}$: 1653, 1608, 1523, 1438.

Example 13

Preparation of 2-cyclopropylmethyl-4-dimethylaminomethyl-6-(3-fluoro-4-methoxyphenyl)-2H-pyridazin-3-one Following the procedure of Example 7, 2-cyclopropylmethyl-6-(3-fluoro-4-methoxyphenyl)-4-methanesulfonyloxymethyl-2H-pyridazin-3-one and dimethylamine were reacted to yield the title compound as a yellow oil (yield: 88.1%).

$^1$H NMR(400 MHz, CDCl$_3$)δ: 0.45–0.59(4H, m), 1.37–1.48(1H, m), 2.36(6H, s), 3.51(2H, s), 3.95(3H, s), 4.10(2H, d, J=7.3 Hz), 7.02(1H, dd, J=8.5, 8.5 Hz), 7.53–7.57(1H, m), 7.64(1H, dd, J=2.2, 12.7 Hz), 7.75(1H, s). IR(Neat) cm$^{-1}$: 1652, 1608, 1523, 1456, 1438. Mass m/z: 331(M$^+$).

Example 14

Preparation of 2-cyclopropylmethyl-4-dimethylaminomethyl-6-(3-fluoro-4-methoxyphenyl)-2H-pyridazin-3-one hydrochloride Following the procedure of Example 4, 2-cyclopropylmethyl-4-dimethylaminomethyl-6-(3-fluoro-4-methoxyphenyl)-2H-pyridazin-3-one was reacted to yield the title compound as slightly yellow needles (yield: 89.0%).

Melting point: 233.6–235.0° C. (dec.) $^1$H NMR(400 MHz, DMSO-d$_6$)δ: 0.41–0.54(4H, m), 1.27–1.37 (1H, m), 2.83(6H, s), 3.92(3H, s), 4.06(2H, d, J=7.3 Hz), 4.30(2H, s), 7.33(1H, dd, J=8.8, 8.8 Hz), 7.69–7.77(2H, m), 8.51(1H, s). IR(KBr) cm$^{-1}$: 1648, 1584, 1522, 1439.

Example 15

Preparation of 2-cyclopropylmethyl-6-(3-fluoro-4-methoxyphenyl)-4-(2-hydroxyethyl)aminomethyl-2H-pyridazin-3-one Following the procedure of Example 9(4), 2-cyclopropylmethyl-6-(3-fluoro-4-methoxyphenyl)-4-methanesulfonyloxymethyl-2H-pyridazin-3-one and 2-aminoethanol were reacted to yield the title compound as a yellow oil (yield: 72.1%).

$^1$H NMR(400 MHz, CDCl$_3$)δ: 0.44–0.59(4H, m), 1.36–1.47(1H, m), 2.86(2H, t, J=5.1 Hz), 3.73(2H, t, J=5.1 Hz), 3.84(2H, d, J=1.0 Hz), 3.94(3H, s), 4.10(2H, d, J=7.3 Hz), 7.02(1H, dd, J=8.5, 8.5 Hz), 7.50–7.54(1H, m), 7.62 (1H, dd, J=2.2, 12.7 Hz), 7.67(1H, s). IR(Neat) cm$^{-1}$: 3411, 1651, 1605, 1523, 1439. Mass m/z: 347(M$^+$).

Example 16

Preparation of 2-cyclopropylmethyl-6-(3-fluoro-4-methoxyphenyl)-4-(2-hydroxyethyl)aminomethyl-2H-pyridazin-3-one hydrochloride Following the procedure of Example 4, 2-cyclopropylmethyl-6-(3-fluoro-4-methoxyphenyl)-4-(2-hydroxyethyl)aminomethyl-2H-pyridazin-3-one was reacted to yield the title compound as pale brown needles (yield: 79.2%).

Melting point: 166.8–169.3° C. (dec.) $^1$H NMR(400 MHz, CDCl$_3$)δ: 0.40–0.54(4H, m), 1.27–1.37(1H, m), 3.13 (2H, m), 3.28(2H, br), 3.74(3H, s), 4.05(2H, d, J=7.1 Hz), 4.18(2H, s), 5.31(1H, br), 7.33(1H, dd, J=8.8, 8.8 Hz), 7.69–7.79(2H, m), 8.40(1H, s). IR(KBr) cm$^{-1}$: 3334, 1654, 1616, 1604, 1523, 1441.

Example 17

Preparation of 4-(4-benzyl-1-piperazinyl)methyl-2-cyclopropylmethyl-6-(3-fluoro-4-methoxyphenyl)-2H-pyridazin-3-one Following the procedure of Example 1(10), 2-cyclopropylmethyl-6-(3-fluoro-4-methoxyphenyl)-4-methanesulfonyloxymethyl-2H-pyridazin-3-one and 1-benzylpiperazine were reacted to yield the title compound as a yellow oil (yield: 97.7%).

$^1$H NMR(400 MHz, CDCl$_3$)δ: 0.44–0.58(4H, m), 1.36–1.46(1H, m), 2.56(4H, br), 2.62(4H, br), 3.56(2H, s), 3.58(2H, d, J=1.0 Hz), 3.95(3H, s), 4.09(2H, d, J=7.1 Hz), 7.04(1H, dd, J=8.5, 8.5 Hz), 7.23–7.36(5H, m), 7.50–7.55 (1H, m), 7.61(1H, dd, J=2.2, 12.7 Hz), 7.75(1H, s). IR(Neat) cm$^{-1}$: 1652, 1608, 1522, 1438, 1289, 1237. Mass m/z: 462(M$^+$).

Example 18

Preparation of 4-(4-benzyl-1-piperazinyl)methyl-2-cyclopropylmethyl-6-(3-fluoro-4-methoxyphenyl)-2H-pyridazin-3-one dihydrochloride Following the procedure of Example 4, 4-(4-benzyl-1-piperazinyl)methyl-2-cyclopropylmethyl-6-(3-fluoro-4-methoxyphenyl)-2H-pyridazin-3-one was reacted to yield the title compound as slightly yellow prisms (yield: 85.7%).

Melting point: 253.0–257.9° C. (dec.) $^1$H NMR(400 MHz, DMSO-d$_6$)δ: 0.41–0.55(4H, m), 1.27–1.38(1H, m), 3.06–3.49(10H, br), 3.56(2H, s), 3.91(3H, s), 4.02(2H, d, J=7.3 Hz), 4.39(2H, brs), 7.30(1H, dd, J=8.5, 8.5 Hz), 7.44–7.48(3H, m), 7.59–7.64(2H, m), 7.69–7.77(2H, m), 8.30(1H, brs). IR(KBr) cm$^{-1}$: 1656, 1616, 1523, 1439, 1292, 1271.

Example 19

Preparation of 4-(4-tert-butoxycarbonyl-1-piperazinyl)methyl-2-cyclopropylmethyl-6-(3-fluoro-4-methoxyphenyl)-2H-pyridazin-3-one Following the procedure of Example 1(10), 2-cyclopropylmethyl-6-(3-fluoro-4-methoxyphenyl)-4-methanesulfonyloxymethyl-2H-pyridazin-3-one and tert-butyl 1-piperazinecarboxylate were reacted to yield the title compound as a pale brown oil (yield: 98.9%).

$^1$H NMR(400 MHz, CDCl$_3$)δ: 0.44–0.59(4H, m), 1.47 (9H, s), 1.38–1.46(1H, m), 2.53(4H, t, J=4.9 Hz), 3.51(4H, t, J=4.9 Hz), 3.58(2H, d, J=1.2 Hz), 3.95(3H, s), 4.10(2H, d, J=7.3 Hz), 7.03(1H, dd, J=8.5, 8.5 Hz), 7.51(1H, ddd, J=1.2, 2.2, 8.5 Hz), 7.61(1H, dd, J=2.2, 12.7 Hz), 7.76(1H, s). IR(Neat) cm$^{-1}$: 1698, 1653, 1609, 1523, 1438, 1427. Mass m/z: 472(M$^+$).

Example 20

Preparation of 2-cyclopropylmethyl-6-(3-fluoro-4-methoxyphenyl)-4-(1-piperazinyl)methyl-2H-pyridazin-3-one 4-(4-tert-Butoxycarbonyl-1-piperazinyl)methyl-2-cyclopropylmethyl-6-(3-fluoro-4-methoxyphenyl)-2H-pyridazine-3-one (220 mg, 0.47 mmol) was dissolved in ice-cold trifluoroacetic acid (2 mL), and at the same temperature, the mixture was stirred for 15 minutes. Water (10 mL) was added to the reaction mixture. The mixture was alkalinized with potassium carbonate and extracted twice with chloroform (20 mL). The extracts were washed with brine (20 mL) and dried over anhydrous sodium sulfate. The solvent was distilled off under reduced pressure. The residue was recrystallized from chloroform-hexane to yield the title compound as pale yellow prisms (120 mg, 69.2%).

Melting point: 111.5–118.0° C. $^1$H NMR(400 MHz, CDCl$_3$)δ: 0.45–0.59(4H, m), 1.36–1.47(1H, m), 2.55(4H, br), 2.96(4H, t, J=4.9 Hz), 3.56(2H, d, J=1.5 Hz), 3.95(3H, s), 4.09(2H, d, J=7.3 Hz), 7.04(1H, dd, J=8.5, 8.5 Hz), 7.53(1H, ddd, J=1.2, 2.2, 8.5 Hz), 7.62(1H, dd, J=2.2, 12.7 Hz), 7.76(1H, t, J=1.5 Hz). IR(KBr) cm$^{-1}$: 3328, 1648, 1605, 1520, 1437. Mass m/z: 372(M$^+$).

Example 21

Preparation of 2-cyclopropylmethyl-6-(3-fluoro-4-methoxyphenyl)-4-(1-piperazinyl)methyl-2H-pyridazin-3-one dihydrochloride Following the procedure of Example 4, 2-cyclopropylmethyl-6-(3-fluoro-4-methoxyphenyl)-4-(1-piperazinyl)methyl-2H-pyridazin-3-one was reacted to yield the title compound as slightly yellow prisms (yield: 94.5%).

Melting point: 139.1–142.4° C. $^1$H NMR(400 MHz, DMSO-d$_6$)δ: 0.42–0.56(4H, m), 1.29–1.39(1H, m), 3.40 (4H, br), 3.70(4H, br), 3.91(3H, s), 4.16(2H, d, J=7.3 Hz), 4.16(2H, brs), 7.31(1H, dd, J=8.5, 8.5 Hz), 7.71–7.73(2H, m), 8.41(1H, brs). IR(KBr) cm$^{-1}$: 3435, 1660, 1610, 1526, 1440, 1291.

Example 22

Preparation of 4-N,N-bis(2-hydroxyethyl)aminomethyl-2-cyclopropylmethyl-6-(3-fluoro-4-methoxyphenyl)-2H-pyridazin-3-one Following the procedure of Example 1(10), 2-cyclopropylmethyl-6-(3-fluoro-4-methoxyphenyl)-4-methanesulfonyloxymethyl-2H-pyridazin-3-one and diethanolamine were reacted to yield the title compound as a pale brown oil (yield: 83.0%).

$^1$H NMR(400 MHz, CDCl$_3$)δ: 0.43–0.58(4H, m), 1.35–1.46(1H, m), 2.71 (4H, t, J=4.9 Hz), 3.67(4H, t, J=4.9 Hz), 3.71(2H, s), 3.85(2H, br), 3.94(3H, s), 4.10(2H, d, J=7.3 Hz), 7.01(1H, dd, J=8.5, 8.5 Hz), 7.51–7.56(1H, m), 7.61(1H, dd, J=2.2, 12.4 Hz), 7.73(1H, t, J=1.5 Hz). IR(Neat) cm$^{-1}$: 3616, 3476, 3275, 1648, 1601, 1529. Mass m/z: 391(M$^+$).

Example 23

Preparation of 4-N,N-bis(2-hydroxyethyl)aminomethyl-2-cyclopropylmethyl-6-(3-fluoro-4-methoxyphenyl)-2H-pyridazin-3-one hydrochloride Following the procedure of Example 4, 4-N,N-bis(2-hydroxyethyl)aminomethyl-2-cyclopropylmethyl-6-(3-fluoro-4-methoxyphenyl)-2H-pyridazin-3-one was reacted to yield the title compound as pale yellow prisms (yield: 75.9%).

Melting point: 175.2–176.8° C. $^1$H NMR(400 MHz, DMSO-d$_6$)δ: 0.42–0.55(4H, m), 1.28–1.39(1H, m), 3.36 (4H, br), 3.82(4H, br), 3.92(3H, s), 4.06(2H, d, J=7.3 Hz), 4.49(2H, brs), 7.33(1H, dd, J=8.5, 8.5 Hz), 7.71–7.79(2H, m), 8.47(1H, brs). IR(KBr) cm$^{-1}$: 3162, 1652, 1604, 1531.

Example 24

Preparation of 4-aminomethyl-2-cyclopropylmethyl-6-(3-fluoro-4-methoxyphenyl)-2H-pyridazin-3-one

1) Preparation of 2-cyclopropylmethyl-6-(3-fluoro-4-methoxyphenyl)-4-phthalimidomethyl-2H-pyridazin-3-one To a solution of 2-cyclopropylmethyl-6-(3-fluoro-4-methoxyphenyl)-4-methanesulfonyloxymethyl-2H-pyridazin-3-one (220 mg, 0.57 mmol) in N,N-dimethylformamide (5 mL) was added potassium phthalimide (160 mg, 0.87 mmol), and the mixture was stirred at 80° C. for 2 hours. Water (30 mL) was added to the reaction mixture. After stirring under cooling over ice water, precipitated crystals were collected by filtration, dried in air, and recrystallized from chloroform-hexane to yield the title compound as colorless needles (202 mg, 81.0%).

Melting point: 241.7–243.6° C. $^1$H NMR(400 MHz, CDCl$_3$)δ: 0.45–0.59(4H, m), 1.37–1.47(1H, m), 3.90(3H, s), 4.10(2H, d, J=7.1 Hz), 4.91 (2H, d, J=1.2 Hz), 6.95(1H, dd, J=8.5, 8.5 Hz), 7.29(1H, t, J=1.2 Hz), 7.38(1H, ddd, J=1.2, 2.2, 8.5 Hz), 7.48(1H, dd, J=2.2, 12.4 Hz), 7.76–7.81(2H, m), 7.90–7.95(2H, m). IR(KBr) cm$^{-1}$: 1712, 1653, 1614, 1524. Mass m/z: 433(M$^+$).

2) Preparation of 4-aminomethyl-2-cyclopropylmethyl-6-(3-fluoro-4-methoxyphenyl)-2H-pyridazin-3-one To a solution of 2-cyclopropylmethyl-6-(3-fluoro-4-methoxyphenyl)-4-phthalimidomethyl-2H-pyridazin-3-one (190 mg, 0.43 mmol) in methanol (5 mL) was added hydrazine monohydrate (110 mg, 2.20 mmol), and the mixture was heated under reflux for 2 hours. Methanol was distilled off under reduced pressure, and chloroform (20 mL) was added to the residue. The mixture was successively washed with water (10 mL) and brine (10 mL) in this order, and was then dried over anhydrous sodium sulfate. The solvent was distilled off under reduced pressure. The residue was purified by preparative thin-layer chromatography on silica gel [developing solvent: chloroform/10% w/v solution of methanol in ammonia (20/1)] to yield the title compound as pale yellow crystals (130 mg, 97.8%).

$^1$H NMR(400 MHz, CDCl$_3$)δ: 0.45–0.59(4H, m), 1.37–1.47(1H, m), 1.51(2H, br), 3.89(2H, d, J=1.2 Hz), 3.95(3H, s), 4.11(2H, d, J=7.1 Hz), 7.02(1H, dd, J=8.5, 8.5 Hz), 7.53(1H, ddd, J=1.2, 2.4, 8.5 Hz), 7.63(1H, dd, J=2.2, 12.7 Hz), 7.68(1H, s). IR(KBr) cm$^{-1}$: 3393, 1651, 1606, 1523, 1438, 1293. Mass m/z: 303(M$^+$).

Example 25

Preparation of 4-aminomethyl-2-cyclopropylmethyl-6-(3-fluoro-4-methoxyphenyl)-2H-pyridazin-3-one hydrochloride Following the procedure of Example 4, 4-aminomethyl-2-cyclopropylmethyl-6-(3-fluoro-4-methoxyphenyl)-2H-pyridazin-3-one was reacted to yield the title compound as pale yellow needles (81.0%).

Melting point: 188.2–194.2° C. (dec.) $^1$H NMR(400 MHz, DMSO-d$_6$)δ: 0.42–0.55(4H, m), 1.29–1.39(1H, m), 3.92(3H, s), 4.01(2H, s), 4.06(2H, d, J=7.1 Hz), 7.34(1H, dd, J=8.5, 8.5 Hz), 7.71–7.78(2H, m), 8.31(1H, s). IR(KBr) cm$^{-1}$: 3507, 3440, 1644, 1581, 1522, 1438.

Example 26

Preparation of 4-(4-tert-butoxycarbonyl-1-piperazinyl)methyl-6-(3-fluoro-4-methoxyphenyl)-2-isobutyl-2H-pyridazin-3-one Following the procedure of Example 1(10), 6-(3-fluoro-4-methoxyphenyl)-2-isobutyl-4-methanesulfonyloxymethyl-2H-pyridazin-3-one and tert-butyl 1-piperazinecarboxylate were reacted to yield the title compound as a yellow oil (yield: 94.3%).

$^1$H NMR(400 MHz, CDCl$_3$)δ: 0.98(6H, d, J=6.6 Hz), 1.46(9H, s), 2.27–2.40(1H, m), 2.52(4H, t, J=5.2 Hz), 3.50 (4H, t, J=5.2 Hz), 3.57(2H, s), 3.95(3H, s), 4.06(2H, d, J=7.4 Hz), 7.03(1H, dd, J=8.6, 8.6 Hz), 7.51(1H, dd, J=1.2, 8.4 Hz), 7.60(1H, dd, J=2.2, 12.5 Hz), 7.75(1H, s).

Example 27

Preparation of 6-(3-fluoro-4-methoxyphenyl)-2-isobutyl-4-(1-piperazinyl)methyl-2H-pyridazin-3-one dihydrochloride Following the procedure of Example 2, 4-(4-tert-butoxycarbonyl-1-piperazinyl)methyl-6-(3-fluoro-4-methoxyphenyl)-2-isobutyl-2H-pyridazin-3-one was reacted to yield the title compound as a colorless crystalline powder (yield: 58.5%).

Melting point: 163.0–177.0° C. (dec.) $^1$H NMR(400 MHz, DMSO-d$_6$)δ: 0.94(6H, d, J=6.8 Hz), 2.22–2.33(1H, m), 3.17(4H, br), 3.33(4H, t, J=5.3 Hz), 3.92(3H, s), 3.96 (2H, s), 4.01(2H, d, J=7.1 Hz), 7.27(1H, dd, J=8.9, 8.9 Hz), 7.67–7.72(2H, m), 8.22(1H, s). IR(KBr) cm$^{-1}$: 1656, 1608, 1522, 1440, 1291, 1113. Mass m/z: 374(M$^+$).

Example 28

Preparation of 6-(3-fluoro-4-methoxyphenyl)-2-isobutyl-4-(4-methyl-1-piperazinyl)methyl-2H-pyridazin-3-one Following the procedure of Example 1(10), 6-(3-fluoro-4-methoxyphenyl)-2-isobutyl-4-methanesulfonyloxymethyl-2H-pyridazin-3-one and 1-methylpiperazine were reacted to yield the title compound as a yellow oil (yield: 80.9%).

$^1$H NMR(400 MHz, CDCl$_3$)δ: 0.98(6H, d, J=6.8 Hz), 2.28–2.40(1H, m), 2.34(3H, s), 2.55(4H, br), 2.63(4H, br), 3.58(2H, d, J=1.4 Hz), 3.95(3H, s), 4.06(2H, d, J=7.4 Hz), 7.04(1H, dd, J=8.6, 8.6 Hz), 7.53(1H, dd, J=1.2, 8.6 Hz), 7.61 (1H, dd, J=2.2, 12.5 Hz), 7.73(1H, s).

Example 29

Preparation of 6-(3-fluoro-4-methoxyphenyl)-2-isobutyl-4-(4-methyl-1-piperazinyl)methyl-2H-pyridazin-3-one dihydrochloride Following the procedure of Example 4, 6-(3-fluoro-4-methoxyphenyl)-2-isobutyl-4-(4-methyl-1-piperazinyl)methyl-2H-pyridazin-3-one was reacted to yield the title compound as a colorless crystalline powder (yield: 73.3%).

Melting point: 236.9–237.0° C. $^1$H NMR(400 MHz, DMSO-d$_6$)δ: 0.94(6H, d, J=6.8 Hz), 2.21–2.32(1H, m), 2.77(3H, s), 3.14(4H, br), 3.36(4H, br), 3.87(2H, s), 3.91 (3H, s), 4.00(2H, d, J=7.1 Hz), 7.26(1H, dd, J=8.5, 8.5 Hz), 7.66–7.71(2H, m), 8.12(1H, s). IR(KBr) cm$^{-1}$: 1655, 1606, 1524, 1440, 1291, 1113, 1022. Mass m/z: 388(M$^+$)

Example 30

Preparation of 4-N,N-bis(2-hydroxyethyl)aminomethyl-6-(3-fluoro-4-methoxyphenyl)-2-isobutyl-2H-pyridazin-3-one Following the procedure of Example 1(10), 6-(3-fluoro-4-methoxyphenyl)-2-isobutyl-4-methanesulfonyloxymethyl-2H-pyridazin-3-one and diethanolamine were reacted to yield the title compound as a yellow oil (yield: 87.2%).

$^1$H NMR(400 MHz, CDCl$_3$)δ: 0.96(6H, d, J=6.8 Hz), 2.27–2.39(1H, m), 2.71(4H, t, J=5.0 Hz), 3.67(4H, t, J=5.0 Hz), 3.70(2H, s), 3.93(3H, s), 4.07(2H, d, J=7.4 Hz), 7.01 (1H, dd, J=8.6, 8.6 Hz), 7.53(1H, dd, J=1.4, 8.4 Hz), 7.61(1H, dd, J=2.2, 12.5 Hz), 7.72(1H, s).

Example 31

Preparation of 4-N,N-bis(2-hydroxyethyl)aminomethyl-6-(3-fluoro-4-methoxyphenyl)-2-isobutyl-2H-pyridazin-3-one hydrochloride Following the procedure of Example 4, 4-N,N-bis(2-hydroxyethyl)aminomethyl-6-(3-fluoro-4-methoxyphenyl)-2-isobutyl-2H-pyridazin-3-one was reacted to yield the title compound as colorless flakes (yield: 89.0%).

Melting point: 129.8–133.1° C. $^1$H NMR(400 MHz, DMSO-d$_6$)δ: 0.95(6H, d, J=6.8 Hz), 2.23–2.34(1H, m), 3.34(4H, t, J=5.1 Hz), 3.83(4H, t, J=5.2 Hz), 3.92(3H, s), 4.03(2H, d, J=7.0 Hz), 4.44(2H, s), 7.29(1H, dd, J=8.7, 8.7 Hz), 7.69–7.75(2H, m), 8.46(1H, s). IR(KBr) cm$^{-1}$: 1652, 1601, 1525, 1440, 1277. Mass m/z: 362(M$^+$—CH$_2$OH)

Example 32

Preparation of 4-dimethylaminomethyl-6-(3-fluoro-4-methoxyphenyl)-2-isobutyl-2H-pyridazin-3-one Following the procedure of Example 7, 6-(3-fluoro-4-methoxyphenyl)-2-isobutyl-4-methanesulfonyloxymethyl-2H-pyridazin-3-one and dimethylamine were reacted to yield the title compound as a yellow oil (yield: 88.6%).

$^1$H NMR(400 MHz, CDCl$_3$)δ: 0.98(6H, d, J=6.8 Hz), 2.30–2.40(1H, m), 2.36(6H, s), 3.50(2H, s), 3.93(3H, s), 4.07(2H, d, J=7.2 Hz), 7.02(1H, dd, J=8.6, 8.6 Hz), 7.55(1H, d, J=8.6 Hz), 7.63(1H, dd, J=2.1, 12.5 Hz), 7.75(1H, s).

Example 33

Preparation of 4-dimethylaminomethyl-6-(3-fluoro-4-methoxyphenyl)-2-isobutyl-2H-pyridazin-3-one hydrochloride Following the procedure of Example 4, 4-dimethylaminomethyl-6-(3-fluoro-4-methoxyphenyl)-2-isobutyl-2H-pyridazin-3-one was reacted to yield the title compound as colorless needles (yield: 81.0%).

Melting point: 212.4–212.8° C. $^1$H NMR(400 MHz, DMSO-d$_6$)δ: 0.95(6H, d, J=6.8 Hz), 2.23–2.33(1H, m), 2.81(6H, s), 3.92(3H, s), 4.04(2H, s, J=7.1 Hz), 4.27(2H, s), 7.29(1H, dd, J=8.1, 8.1 Hz), 7.70–7.75(2H, m), 8.51(1H, s). IR(KBr) cm$^{-1}$: 1652, 1607, 1522, 1439, 1292, 1112. Mass m/z: 333(M$^+$)

Example 34

Preparation of 4-(4-tert-butoxycarbonyl-1-piperazinyl)methyl-2-isobutyl-6-phenyl-2H-pyridazin-3-one

1) Preparation of 4-methoxycarbonyl-6-phenyl-2H-pyridazin-3-one

Following the procedure of Example 1(5), 4-carboxy-6-phenyl-2H-pyridazin-3-one was reacted to yield the title compound as pale yellow crystals (yield: 98.9%).

Melting point: 202.5–206.2° C. (dec.) $^1$H NMR(400 MHz, CDCl$_3$)δ: 4.01(3H, s), 7.45–7.54(3H, m), 7.78–7.85 (2H, m), 8.38(1H, s), 11.86(1H, br) IR(KBr) cm$^{-1}$: 1717, 1670, 1443, 1259. Mass m/z: 230(M$^+$).

2) Preparation of 2-isobutyl-4-methoxycarbonyl-6-phenyl-2H-pyridazin-3-one

Following the procedure of Example 1(6), 4-methoxycarbonyl-6-phenyl-2H-pyridazin-3-one was reacted to yield the title compound as a yellow oil (yield: 94.1%).

$^1$H NMR(400 MHz, CDCl$_3$)δ: 1.00(6H, d, J=6.6 Hz), 2.33–2.44(1H, m), 3.98(3H, s), 4.14(2H, d, J=7.4 Hz), 7.42–7.51(3H, m), 7.79–7.83(2H, m), 8.27(1H, s).

3) Preparation of 4-carboxy-2-isobutyl-6-phenyl-2H-pyridazin-3-one

Following the procedure of Example 1(7), 2-isobutyl-4-methoxycarbonyl-6-phenyl-2H-pyridazin-3-one was reacted to yield the title compound as colorless fine-needles (yield: 82.5%).

Melting point: 120.5–121.0° C. $^1$H NMR(400 MHz, CDCl$_3$)δ: 1.03(6H, d, J=6.6 Hz), 2.34–2.45(1H, m), 4.23 (2H, d, J=7.4 Hz) 7.49–7.54 (3H,m), 7.84–7.89 (2H,m), 8.69 (1H,s), 14.20 (1H, s). IR(KBr) cm$^{-1}$: 3448, 2956, 1741, 1636, 1418, 1116. Mass m/z: 272(M$^+$)

4) Preparation of 4-hydroxymethyl-2-isobutyl-6-phenyl-2H-pyridazin-3-one

Following the procedure of Example 1(8), 4-carboxy-2-isobutyl-6-phenyl-2H-pyridazin-3-one was reacted to yield the title compound as colorless fine-needles (yield: 22.3%).

$^1$H NMR(400 MHz, CDCl$_3$)δ: 0.98(6H, d, J=6.6 Hz), 2.29–2.40(1H, m), 3.67(1H, br), 4.08(2H, d, J=7.4 Hz), 4.72(2H, d, J=3.9 Hz), 7.39–7.49(3H, m), 7.76(1H, t, J=1.4 Hz), 7.79–7.84(2H, m).

5) Preparation of 2-isobutyl-4-methanesulfonyloxymethyl-6-phenyl-2H-pyridazin-3-one Following the procedure of Example 1(9), 4-hydroxymethyl-2-isobutyl-6-phenyl-2H-pyridazin-3-one was reacted to yield the title compound as colorless fine-needles (yield: 68.4%).

Melting point: 129.7° C. $^1$H NMR(400 MHz, CDCl$_3$)δ: 0.99(6H, d, J=6.6 Hz), 2.30–2.41(1H, m), 3.17(3H, s), 4.10(2H, d, J=7.2 Hz), 5.28(2H, d, J=1.2 Hz), 7.43–7.52(3H, m), 7.79–7.82(3H, m). IR(KBr) cm$^{-1}$: 3442, 2963, 1658, 1611, 1355, 1165, 872. Mass m/z: 336(M$^+$)

6) Preparation of 4-(4-tert-butoxycarbonyl-1-piperazinyl)-methyl-2-isobutyl-6-phenyl-2H-pyridazin-3-one Following the procedure of Example 1(10), 2-isobutyl-4-methanesulfonyloxymethyl-6-phenyl-2H-pyridazin-3-one and tert-butyl 1-piperazinecarboxylate were reacted in N,N-dimethylformamide as a solvent to yield the title compound as a yellow oil (yield: 83.5%).

$^1$H NMR(400 MHz, CDCl$_3$)δ: 0.99(6H, d, J=6.8 Hz), 1.47(9H, s), 2.53(4H, t, J=4.9 Hz), 3.50(4H, t, J=4.9 Hz), 3.59(2H, d, J=1.0 Hz), 4.09(2H, d, J=7.2 Hz), 7.40–7.50(3H, m), 7.80–7.84(3H, m).

Example 35

Preparation of 2-isobutyl-6-phenyl-4-(1-piperazinyl)-methyl-2H-pyridazin-3-one dihydrochloride Following the procedure of Example 2, 4-(4-tert-butoxycarbonyl-1-piperazinyl)methyl-2-isobutyl-6-phenyl-2H-pyridazin-3-one was reacted to yield the title compound as a white solid (yield: 67.9%).

Melting point: 154.3–159.5° C. $^1$H NMR(400 MHz, CDCl$_3$)δ: 0.94(6H, d, J=6.8 Hz), 2.20–2.32(1H,m), 2.86(4H, br), 3.21(4H, br), 3.71(2H, s), 4.01(2H, d, J=7.2 Hz), 7.42–7.53(3H, m), 7.84–7.89(2H, m), 7.96(1H, s). IR(KBr) cm$^{-1}$: 1656, 1610, 1445, 694. Mass m/z: 326(M$^+$)

Example 36

Preparation of 2-isobutyl-4-(4-methyl-1-piperazinyl)methyl-6-phenyl-2H-pyridazin-3-one Following the procedure of Example 1(10), 2-isobutyl-4-methanesulfonyloxymethyl-6-phenyl-2H-pyridazin-3-one and N-methylpiperazine were reacted to yield the title compound as a yellow oil (yield: 77.1%).

$^1$H NMR(400 MHz, CDCl$_3$)δ: 0.99(6H, d, J=6.8 Hz), 2.30–2.40(1H, m), 2.34(3H, s), 2.55(4H, br), 2.64(4H, br), 3.59(2H, d, J=1.4 Hz), 4.08(2H, d, J=7.2 Hz), 7.40–7.50(3H, m), 7.78–7.84(3H, m).

Example 37

Preparation of 2-isobutyl-4-(4-methyl-1-piperazinyl)methyl-6-phenyl-2H-pyridazin-3-one dihydrochloride Following the procedure of Example 4, 2-isobutyl-4-(4-methyl-1-piperazinyl)methyl-6-phenyl-2H-pyridazin-3-one was reacted to yield the title compound as a colorless crystalline powder (yield: 66.3%).

Melting point: 243.8–244.3° C. $^1$H NMR(400 MHz, DMSO-d$_6$)δ: 0.95(6H, d, J=6.8 Hz), 2.22–2.34(1H, m), 2.76(3H, s), 3.01(4H, br), 3.30(4H, br), 3.77(2H, s), 4.02(2H, d, J=7.2 Hz), 7.43–7.53(3H, m), 7.85–7.89(2H, m), 8.02(1H, s). IR(KBr) cm$^{-1}$: 2960, 1653, 1610, 1446. Mass m/z: 340(M$^+$)

Example 38

Preparation of 4-N,N-bis(2-hydroxyethyl)aminomethyl-2-isobutyl-6-phenyl-2H-pyridazin-3-one Following the procedure of Example 1(10), 2-isobutyl-4-methanesulfonyloxymethyl-6-phenyl-2H-pyridazin-3-one and diethanolamine were reacted to yield the title compound as a yellow oil (yield: 38.7%).

$^1$H NMR(400 MHz, CDCl$_3$)δ: 0.97(6H, d, J=6.6 Hz), 2.29–2.40(1H, m), 2.79(4H, br), 3.70(4H, br), 3.80(2H, s), 4.09(2H, d, J=7.4 Hz), 7.39–7.48(3H, m), 7.81–7.87(3H, m)

Example 39

Preparation of 4-N,N-bis(2-hydroxyethyl)aminomethyl-2-isobutyl-6-phenyl-2H-pyridazin-3-one hydrochloride Following the procedure of Example 4, 4-N,N-bis(2-hydroxyethyl)aminomethyl-2-isobutyl-6-phenyl-2H-pyridazin-3-one was reacted to yield the title compound as colorless flakes (yield: 68.4%).

Melting point: 131.6–132.0° C. $^1$H NMR(400 MHz, DMSO-d$_6$)δ: 0.96(6H, d, J=6.6 Hz), 2.25–2.35(1H, m), 3.35(4H, t, J=5.1 Hz), 3.84(4H, t, J=5.4 Hz), 4.06(2H, d, J=7.1 Hz), 4.47(2H, s), 7.45–7.54(3H, m), 7.90–7.94(2H, m), 8.48(1H, s). IR(KBr) cm$^{-1}$: 1655, 1610, 1421, 1053. Mass m/z: 314(M$^+$—CH$_2$OH)

Example 40

Preparation of 4-dimethylaminomethyl-2-isobutyl-6-phenyl-2H-pyridazin-3-one

Following the procedure of Example 7, 2-isobutyl-4-methanesulfonyloxymethyl-6-phenyl-2H-pyridazin-3-one and dimethylamine were reacted to yield the title compound as a yellow oil (yield: 81.1%).

$^1$H NMR(400 MHz, CDCl$_3$)δ: 0.99(6H, d, J=6.8 Hz), 2.32–2.41(1H, m), 2.35(6H, s), 3.51(2H, d, J=1.2 Hz), 4.09(2H, d, J=7.2 Hz), 7.38–7.48(3H, m), 7.80–7.87(3H, m).

Example 41

Preparation of 4-dimethylaminomethyl-2-isobutyl-6-phenyl-2H-pyridazin-3-one hydrochloride Following the procedure of Example 4, 4-dimethylaminomethyl-2-isobutyl-6-phenyl-2H-pyridazin-3-one was reacted to yield the title compound as pale yellow flakes (yield: 71.5%).

Melting point: 221.7–222.3° C. $^1$H NMR(400 MHz, DMSO-d$_6$)δ: 0.96(6H, d, J=6.8 Hz), 2.24–2.35(1H, m), 2.82(6H, s), 4.06(2H, d, J=7.1 Hz), 4.29(2H, s), 7.44–7.54 (3H, m), 7.90–7.94(2H, m), 8.54(1H, s). IR(KBr) cm$^{-1}$: 1648, 1610, 1460, 1052. Mass m/z: 285(M$^+$)

Example 42

Preparation of 4-(4-benzyl-1-piperazinyl)methyl-2-isobutyl-6-(4-methylphenyl)-2H-pyridazin-3-one 1) Preparation of 2-isobutyl-4-methoxycarbonyl-6-(4-methylphenyl)-2H-pyridazin-3-one Following the procedure of Example 1(6), 4-methoxycarbonyl-6-(4-methylphenyl)-2H-pyridazin-3-one was reacted to yield the title compound as slightly yellow needles (yield: 91.6%).

Melting point: 67.0–70.1° C. $^1$H NMR(400 MHz, CDCl$_3$) δ: 0.99(6H, d, J=6.6 Hz), 2.32–2.43(1H, m), 2.41(3H, s), 3.98(3H, s), 4.13(2H, d, J=7.3 Hz), 7.28(2H, d, J=8.3 Hz), 7.70(2H, d, J=8.3 Hz), 8.24(1H, s). IR(KBr) cm$^{-1}$: 1718, 1663, 1605. Mass m/z: 300(M$^+$)

2) Preparation of 4-carboxy-2-isobutyl-6-(4-methylphenyl)-2H-pyridazin-3-one

Following the procedure of Example 1(7), 2-isobutyl-4-methoxycarbonyl-6-(4-methylphenyl)-2H-pyridazin-3-one was reacted to yield the title compound as slightly yellow needles (yield: 86.7%).

Melting point: 162.1–165.4° C. $^1$H NMR(400 MHz, CDCl$_3$)δ: 1.02(6H, d, J=6.8 Hz), 2.34–2.44(1H, m), 2.47 (3H, s), 4.21(2H, d, J=7.3 Hz), 7.31 (2H, d, J=8.3 Hz), 7.75 (2H, d, J=8.3 Hz), 8.66(1H, s), 14.26(1H, s). IR(KBr) cm$^{-1}$: 1740, 1633, 1571, 1425. Mass m/z: 286(M$^+$).

3) Preparation of 4-hydroxymethyl-2-isobutyl-6-(4-methylphenyl)-2H-pyridazin-3-one Following the procedure of Example 1(8), 4-carboxy-2-isobutyl-6-(4-methylphenyl)-2H-pyridazin-3-one was reacted to yield the title compound as slightly yellow needles (yield: 46.0%).

Melting point: 121.9–123.5° C. $^1$H NMR(400 MHz, CDCl$_3$)δ: 0.99(6H, d, J=6.8 Hz), 2.30–2.40(1H, m), 2.40 (3H, s), 3.22(1H, br), 4.08(2H, d, J=7.3 Hz), 4.71(2H, s), 7.27(2H, d, J=8.3 Hz), 7.77(1H, s), 7.70(2H, d, J=8.3 Hz). IR(KBr) cm$^{-1}$: 3334, 1645, 1596, 1522. Mass m/z: 272(M$^+$).

4) Preparation of 2-isobutyl-4-methanesulfonyloxymethyl-6-(4-methylphenyl)-2H-pyridazin-3-one Following the procedure of Example 1(9), 4-hydroxymethyl-2-isobutyl-6-(4-methylphenyl)-2H-pyridazin-3-one was reacted to yield the title compound as slightly yellow needles (yield: 87.4%).

Melting point: 132.0–135.5° C. $^1$H NMR(400 MHz, CDCl$_3$)δ: 0.99(6H, d, J=6.6 Hz), 2.29–2.39(1H, m), 2.41 (3H, s), 3.17 (3H, s), 4.08(2H, d, J=7.6 Hz), 5.27(2H, t, J=1.5 Hz), 7.27(2H, d, J=8.3 Hz), 7.72(2H, d, J=8.3 Hz), 7.79(1H, t, J=11.5 Hz). IR(KBr) cm$^{-1}$: 1656, 1609, 1355, 1166. Mass m/z: 350(M$^+$).

5) Preparation of 4-(4-benzyl-1-piperazinyl)methyl-2-isobutyl-6-(4-methylphenyl)-2H-pyridazin-3-one Following the procedure of Example 1(10), 2-isobutyl-4-methanesulfonyloxymethyl-6-(4-methylphenyl)-2H-pyridazin-3-one and 1-benzylpiperazine were reacted to yield the title compound as a pale yellow oil (yield: 97.7%).

$^1$H NMR(400 MHz, CDCl$_3$)δ: 0.97(6H, d, J=6.8 Hz), 2.29–2.39(1H, m), 2.41(3H, s), 2.55(4H, br), 2.61 (4H, br), 3.54 (2H, s), 3.57 (2H, d, J=1.5 Hz), 4.07 (2H, d, J=7.3 Hz), 7.22–7.36(7H, m), 7.70(2H, d, J=8.3 Hz), 7.77(1H, t, J=1.5 Hz). IR(Neat) cm$^{-1}$: 1657, 1652, 1518, 1455. Mass m/z: 430(M$^+$).

Example 43

Preparation of 4-(4-benzyl-1-piperazinyl)methyl-2-isobutyl-6-(4-methylphenyl)-2H-pyridazin-3-one dihydrochloride Following the procedure of Example 4, 4-(4-benzyl-1-piperazinyl)methyl-2-isobutyl-6-(4-methylphenyl)-2H-pyridazin-3-one was reacted to yield the title compound as colorless needles (yield: 91.8%).

Melting point: 253.5–260.1° C. (dec.) $^1$H NMR(400 MHz, DMSO-d$_6$)δ: 0.92(6H, d, J=6.6 Hz), 2.18–2.28 (1H, m), 2.34(3H, s), 3.43(10H, br), 3.99(2H, d, J=7.3 Hz), 4.36(2H, brs), 7.22(2H, d, J=8.1 Hz), 7.43–7.49(3H, m), 7.58–7.65(2H, m), 7.78(2H, d, J=8.1 Hz), 8.30(1H, brs). IR(KBr) cm$^{-1}$: 1660, 1617, 1452.

Example 44

Preparation of 4-dimethylaminomethyl-2-isobutyl-6-(4-methylphenyl)-2H-pyridazin-3-one Following the procedure of Example 7, 2-isobutyl-4-methanesulfonyloxymethyl-6-(4-methylphenyl)-2H-pyridazin-3-one and dimethylamine were reacted to yield the title compound as a slightly yellow oil (yield: 96.6%).

$^1$H NMR(400 MHz, CDCl$_3$)δ: 0.98(6H, d, J=6.8 Hz), 2.38–2.41(1H, m), 2.35(6H, s), 2.40(3H, s), 3.50(2H, d, J=1.5 Hz), 4.08(2H, d, J=7.3 Hz), 7.26(2H, d, J=8.1 Hz), 7.73(2H, d, J=8.1 Hz), 7.78(1H, t, J=1.5 Hz). IR(Neat) cm$^{-1}$: 1652, 1609, 1518, 1455. Mass m/z: 299(M$^+$).

Example 45

Preparation of 4-dimethylaminomethyl-2-isobutyl-6-(4-methylphenyl)-2H-pyridazin-3-one hydrochloride Following the procedure of Example 4, 4-dimethylaminomethyl-2-isobutyl-6-(4-methylphenyl)-2H-pyridazin-3-one was reacted to yield the title compound as colorless needles (yield: 91.8%).

Melting point: 237.6–239.6° C. $^1$H NMR(400 MHz, DMSO-d$_6$)δ: 0.94(6H, d, J=6.8 Hz), 2.19–2.30(1H, m), 2.37(3H, s), 2.81(6H, s), 4.02(2H, d, J=7.0 Hz), 4.30(2H, s), 7.34(2H, d, J=8.1 Hz), 7.81(2H, d, J=8.1 Hz), 8.46(1H, s). IR(KBr) cm$^{-1}$: 1648, 1605, 1460, 1421.

Example 46

Preparation of 4-diethylaminomethyl-2-isobutyl-6-(4-methylphenyl)-2H-pyridazin-3-one Following the procedure of Example 9(4), 2-isobutyl-4-methanesulfonyloxymethyl-6-(4-methylphenyl)-2H-pyridazin-3-one and diethylamine were reacted to yield the title compound as a pale yellow oil (yield: 95.0%).

$^1$H NMR(400 MHz, CDCl$_3$)δ: 0.98 (6H, d, J=6.8 Hz), 1.07 (6H, t, J=7.1 Hz), 2.30–2.42 (1H, m), 2.40(3H, s), 2.60(4H, q, J=7.1 Hz), 3.60(2H, d, J=1.5 Hz), 4.08(2H, d, J=7.3 Hz), 7.26(2H, d, J=8.1 Hz), 7.73(2H, d, J=8.1 Hz), 7.89(1H, t, J=1.5 Hz). IR(Neat) cm$^{-1}$: 1652, 1609, 1518, 1465, 1455. Mass m/z: 327(M$^+$).

Example 47

Preparation of 4-diethylaminomethyl-2-isobutyl-6-(4-methylphenyl)-2H-pyridazin-3-one hydrochloride Following the procedure of Example 4, 4-diethylaminomethyl-2-isobutyl-6-(4-methylphenyl)-2H-pyridazin-3-one was reacted to yield the title compound as slightly yellow needles (yield: 93.8%).

Melting point: 203.9–207.0° C. $^1$H NMR(400 MHz, DMSO-d$_6$)δ: 0.94(6H, d, J=6.6 Hz), 1.27(6H, t, J=7.2 Hz), 2.20–2.30(1H, m), 2.37(3H, s), 3.09–3.24(4H, m), 4.03(2H, d, J=7.1 Hz), 4.28(2H, d, J=5.4 Hz), 7.34(2H, d, J=8.1 Hz), 7.82(2H, d, J=8.1 Hz), 8.55(1H, s). IR(KBr) cm$^{-1}$: 1652, 1610, 1523, 1481, 1468.

Example 48

Preparation of 4-N,N-bis(2-hydroxyethyl)aminomethyl-6-(4-methylphenyl)-2-isobutyl-2H-pyridazin-3-one Following the procedure of Example 1(10), 2-isobutyl-4-methanesulfonyloxymethyl-6-(4-methylphenyl)-2H-pyridazin-3-one and diethanolamine were reacted to yield the title compound as a pale yellow oil (yield: 95.0%).

$^1$H NMR(400 MHz, CDCl$_3$)δ: 0.97(6H, d, J=6.6 Hz), 2.28–2.41(1H, m), 2.40(3H, s), 2.71(4H, t, J=5.0 Hz), 3.66 (4H, t, J=5.0 Hz), 3.70(2H, s), 3.78(2H, br), 4.09(2H, d, J=7.6 Hz), 7.26(2H, d, J=8.1 Hz), 7.68(1H, s), 7.70(2H, d, J=8.1 Hz). IR(Neat) cm$^{-1}$: 3392, 1645, 1600, 1520. Mass m/z: 341 (M$^+$—H$_2$O)

Example 49

Preparation of 4-N,N-bis(2-hydroxyethyl)aminomethyl-6-(4-methylphenyl)-2-isobutyl-2H-pyridazin-3-one hydrochloride Following the procedure of Example 4, 4-N,N-bis(2-hydroxyethyl)aminomethyl-6-(4-methylphenyl)-2-isobutyl-2H-pyridazin-3-one was reacted to yield the title compound as slightly yellow needles (yield: 86.4%).

Melting point: 158.9–161.5° C. (dec.) $^1$H NMR(400 MHz, DMSO-d$_6$)δ: 0.94(6H, d, J=6.6 Hz), 2.19–2.30(1H, m), 2.37(3H, s), 3.27–3.46(4H, m), 3.77–3.85(4H, m), 4.02 (2H, d, J=7.3 Hz), 4.50(2H, brs), 5.35(2H, br), 7.34(2H, d, J=8.1 Hz), 7.81(2H, d, J=8.1 Hz), 8.46(1H, s). IR(KBr) cm$^{-1}$: 3292, 1664, 1615, 1423.

Example 50

Preparation of 4-aminomethyl-2-isobutyl-6-(4-methylphenyl)-2H-pyridazin-3-one

1) Preparation of 2-isobutyl-6-(4-methylphenyl)-4-phthalimidomethyl-2H-pyridazin-3-one Following the procedure of Example 24(1), 2-isobutyl-4-methanesulfonyloxymethyl-6-(4-methylphenyl)-2H-pyridazin-3-one was reacted to yield the title compound as colorless needles (yield: 98.2%).

Melting point: 221.6–223.8° C. $^1$H NMR(400 MHz, CDCl$_3$)δ: 0.98(6H, d, J=6.6 Hz), 2.27–2.41(1H, m), 2.36 (3H, s), 4.08(2H, d, J=7.3 Hz), 4.91 (2H, d, J=1.5 Hz), 7.20(2H, d, J=8.1 Hz), 7.32(1H, t, J=1.5 Hz), 7.56(2H, d, J=8.1 Hz), 7.75–7.80(2H, m), 7.89–7.94(2H, m). IR(KBr) cm$^{-1}$: 1767, 1721, 1655, 1616. Mass m/z: 401(M$^+$).

2) Preparation of 4-aminomethyl-2-isobutyl-6-(4-methylphenyl)-2H-pyridazin-3-one Following the procedure of Example 24(2), 2-isobutyl-6-(4-methylphenyl)-4-phthalimidomethyl-2H-pyridazin-3-one was reacted to yield the title compound as colorless prisms (yield: 98.1%).

Melting point: 74.9–77.9° C. $^1$H NMR(400 MHz, CDCl$_3$) δ: 0.98(6H, d, J=6.9 Hz), 1.68(2H, br), 2.28–2.42(1H, m), 2.40(3H, s), 3.87(2H, d, J=1.2 Hz), 4.07 (2H, d, J=7.3 Hz), 7.26(2H, d, J=8.0 Hz), 7.69(1H, t, J=1.5 Hz), 7.71(2H, d, J=8.0 Hz). IR(KBr) cm$^{-1}$: 3363, 3289, 1648, 1604, 1519. Mass m/z: 271(M$^+$).

Example 51

Preparation of 4-aminomethyl-2-isobutyl-6-(4-methylphenyl)-2H-pyridazin-3-one hydrochloride Following the procedure of Example 4, 4-aminomethyl-2-isobutyl-6-(4-methylphenyl)-2H-pyridazin-3-one was reacted to yield the title compound as pale yellow prisms (yield: 93.1%).

Melting point: 207.4–209.4° C. (dec.) $^1$H NMR(400 MHz, DMSO-d$_5$)δ: 0.93(6H, d, J=6.6 Hz), 2.19–2.30(1H, m), 2.37(3H, s), 4.01(2H, d, J=7.1 Hz), 4.02 (2H, s), 7.34(2H, d, J=8.1 Hz), 7.80(2H, d, J=8.1 Hz), 8.26(1H, s). IR(KBr) cm$^{-1}$: 1655, 1616, 1520, 1467.

Example 52

Preparation of 4-(1,3-dihydroxypropan-2-yl)aminomethyl-2-isobutyl-6-(4-methylphenyl)-2H-pyridazin-3-one Following the procedure of Example 1(10), 2-isobutyl-4-methanesulfonyloxymethyl-6-(4-methylphenyl)-2H-pyridazin-3-one and 2-amino-1,3-propanediol were reacted to yield the title compound as colorless needles (yield: 83.7%).

Melting point: 134.1–135.2° C. $^1$H NMR(400 MHz, CDCl$_3$)δ: 0.97(6H, d, J=6.6 Hz), 2.29–2.39(1H, m), 2.40 (3H, s), 2.60(3H, br), 2.82–2.87(1H, m), 3.64(2H, dd, J=5.6, 11.2 Hz), 3.80 (2H, dd, J=4.5, 11.2 Hz), 3.86(2H, d, J=1.0 Hz), 4.07(2H, d, J=7.3 Hz), 7.26(2H, d, J=8.1 Hz), 7.71(2H, d, J=8.1 Hz), 7.74(1H, s). IR(KBr) cm$^{-1}$: 3408, 3293, 1641, 1592, 1520. Mass m/z: 345(M$^+$).

Example 53

Preparation of 4-(1,3-dihydroxypropan-2-yl)aminomethyl-2-isobutyl-6-(4-methylphenyl)-2H-pyridazin-3-one hydrochloride Following the procedure of Example 4, 4-(1,3-dihydroxypropan-2-yl)aminomethyl-2-isobutyl-6-(4-methylphenyl)-2H-pyridazin-3-one was reacted to yield the title compound as colorless needles (yield: 95.7%).

Melting point: 191.2–193.0° C. $^1$H NMR(400 MHz, DMSO-d$_6$)δ: 0.93(6H, d, J=6.6 Hz), 2.19–2.30(1H, m), 2.37(3H, s), 3.29(1H, br), 3.60–3.78(4H, m), 4.02(2H, d, J=7.1 Hz), 4.29(2H, s), 5.40(2H, brs), 7.34(2H, d, J=8.1 Hz), 7.81(2H, d, J=8.1 Hz), 8.38(1H, s). IR(KBr) cm$^{-1}$: 3392, 1652, 1610.

Example 54

Preparation of 2-isobutyl-4-methylaminomethyl-6-(4-methylphenyl)-2H-pyridazin-3-one Following the procedure of Example 9(4), 2-isobutyl-4-methanesulfonyloxymethyl-6-(4-methylphenyl)-2H-pyridazin-3-one and methylamine were reacted to yield the title compound as a slightly yellow oil (yield: 94.5%).

$^1$H NMR(400 MHz, CDCl$_3$)δ: 0.98(6H, d, J=6.6 Hz), 1.87(1H, br), 2.29–2.42(1H, m), 2.40(3H, s), 2.50(3H, s), 3.76(2H, d, J=1.2 Hz), 4.07(2H, d, J=7.3 Hz), 7.26(2H, d, J=8.1 Hz), 7.67(1H, t, J=1.2 Hz), 7.71(2H, d, J=8.1 Hz). IR(Neat) cm$^{-1}$: 3317, 1652, 1607. Mass m/z: 285(M$^+$).

Example 55

Preparation of 2-isobutyl-4-methylaminomethyl-6-(4-methylphenyl)-2H-pyridazin-3-one hydrochloride Following the procedure of Example 4, 2-isobutyl-4-methylaminomethyl-6-(4-methylphenyl)-2H-pyridazin-3-one was reacted to yield the title compound as colorless needles (yield: 97.5%).

Melting point: 198.3–201.0° C. $^1$H NMR(400 MHz, DMSO-$d_6$)δ: 0.94(6H, d, J=6.8 Hz), 2.20–2.31(1H, m), 2.37(3H, s), 2.65(3H, s), 4.02(2H, d, J=7.3 Hz), 4.12(2H, s), 7.34(2H, d, J=8.1 Hz), 7.80(2H, d, J=8.1 Hz), 8.35(1H, s). IR(KBr) cm$^{-1}$: 3085, 1652, 1612.

Example 56

Preparation of 4-(2-hydroxyethyl)aminomethyl-2-isobutyl-6-(4-methylphenyl)-2H-pyridazin-3-one Following the procedure of Example 9(4), 2-isobutyl-4-methanesulfonyloxymethyl-6-(4-methylphenyl)-2H-pyridazin-3-one and 2-aminoethanol were reacted to yield the title compound as a slightly yellow oil (yield: 80.3%). $^1$H NMR(400 MHz, CDCl$_3$)δ: 0.98(6H, d, J=6.8 Hz), 2.20–2.38 (3H, m), 2.39(3H, s), 2.84(2H, t, J=5.1 Hz), 3.72(2H, t, J=5.1 Hz), 3.82(2H, d, J=1.2 Hz), 4.07(2H, d, J=7.3 Hz), 7.26(2H, d, J=8.1 Hz), 7.68(1H, s), 7.70(2H, d, J=8.1 Hz). IR(Neat) cm$^{-1}$: 3429, 1652, 1601, 1519. Mass m/z: 315 (M$^+$).

Example 57

Preparation of 4-(2-hydroxyethyl)aminomethyl-2-isobutyl-6-(4-methylphenyl)-2H-pyridazin-3-one hydrochloride Following the procedure of Example 4, 4-(2-hydroxyethyl)aminomethyl-2-isobutyl-6-(4-methylphenyl)-2H-pyridazin-3-one was reacted to yield the title compound as colorless needles (yield: 93.4%).

Melting point: 190.8–191.9° C. $^1$H NMR(400 MHz, DMSO-$d_6$)δ: 0.94(6H, d, J=6.6 Hz), 2.20–2.31(1H, m), 2.37(3H, s), 3.12(2H, t, J=5.4 Hz), 3.70–3.76(2H, m), 4.02 (2H, d, J=7.3 Hz), 4.18(2H, s), 5.30(1H, br), 7.34(2H, d, J=8.3 Hz), 7.81(2H, d, J=8.3 Hz), 8.36(1H, s). IR(KBr) cm$^{-1}$: 3491, 1652, 1611.

Example 58

Preparation of 4-(4-tert-butoxycarbonyl-1-piperazinyl) methyl-2-isobutyl-6-(4-trifluoromethylphenyl)-2H-pyridazin-3-one 1) Preparation of ethyl 2-ethoxycarbonyl-2-hydroxy-4-(4-trifluoromethylphenyl)-4-oxobutanoate Following the procedure of Example 1(3), 4'-(trifluoromethyl)acetophenone was reacted to yield the title compound as pale yellow crystals (yield: 80.8%).

$^1$H NMR(400 MHz, CDCl$_3$)δ: 1.30(6H, t, J=7.1 Hz), 3.85(2H, s), 4.22(1H, s), 4.31(4H, q, J=7.1 Hz), 7.76 (2H, d, J=8.6 Hz), 8.07 (2H, d, J=8.6 Hz). IR(KBr) cm$^{-1}$: 3446, 1750, 1727, 1691. Mass m/z: 343(M$^+$—H$_2$O).

2) Preparation of 4-carboxy-6-(4-trifluoromethylphenyl)-2H-pyridazin-3-one

Following the procedure of Example 1(4), ethyl 2-ethoxycarbonyl-2-hydroxy-4-(4-trifluoromethylphenyl)-4-oxobutanoate was reacted to yield the title compound as a pale brown crystalline powder (yield: 91.4%).

3) Preparation of 4-methoxycarbonyl-6-(4-trifluoromethylphenyl)-2H-pyridazin-3-one Following the procedure of Example 1(5), 4-carboxy-6-(4-trifluoromethylphenyl)-2H-pyridazin-3-one was reacted to yield the title compound as a slightly yellow crystalline powder (yield: 88.5%).

$^1$H NMR(400 MHz, CDCl$_3$)δ: 4.02(3H, s), 7.75(2H, d, J=8.2 Hz), 7.95(2H, d, J=8.2 Hz), 8.39(1H, s), 11.69(1H, br). IR(KBr) cm$^{-1}$: 3218, 3140, 3097, 1720, 1678, 1326. Mass m/z: 298(M$^+$).

4) Preparation of 2-isobutyl-4-methoxycarbonyl-6-(4-trifluoromethylphenyl)-2H-pyridazin-3-one Following the procedure of Example 1(6), 4-methoxycarbonyl-6-(4-trifluoromethylphenyl)-2H-pyridazin-3-one was reacted to yield the title compound as yellow crystals (yield: 82.2%).

$^1$H NMR(400 MHz, CDCl$_3$)δ: 1.00(6H, d, J=6.6 Hz), 2.32–2.43(1H, m), 3.99(3H, s), 4.15(2H, d, J=7.2 Hz), 7.74(2H, d, J=8.4 Hz), 7.93(2H, d, J=8.4 Hz), 8.12(1H, s). IR(Neat) cm$^{-1}$: 2961, 1746, 1670, 1327, 1115, 1068. Mass m/z: 354(M$^+$).

5) Preparation of 4-carboxy-2-isobutyl-6-(4-trifluoromethylphenyl)-2H-pyridazin-3-one Following the procedure of Example 1(7), 2-isobutyl-4-methoxycarbonyl-6-(4-trifluoromethylphenyl)-2H-pyridazin-3-one was reacted to yield the title compound as colorless fine-needles (yield: 91.6%).

Melting point: 184.4–185.0° C. $^1$H NMR(400 MHz, CDCl$_3$)δ: 1.03(6H, d, J=6.6 Hz), 2.34–2.45(1H, m), 4.25 (2H, d, J=7.2 Hz), 7.78(2H, d, J=8.2 Hz), 7.99(2H, d, J=8.2 Hz), 8.70(1H, s), 14.02(1H, s). IR(KBr) cm$^{-1}$: 3447, 1739, 1631, 1570, 1330, 1174, 1114, 1070, 847. Mass m/z: 340 (M$^+$)

6) Preparation of 4-hydroxymethyl-2-isobutyl-6-(4-trifluoromethylphenyl)-2H-pyridazin-3-one Following the procedure of Example 1(8), 4-carboxy-2-isobutyl-6-(4-trifluoromethylphenyl)-2H-pyridazin-3-one was reacted to yield the title compound as colorless fine-needles (yield: 28.1%).

Melting point: 145.8–146.5° C. $^1$H NMR(400 MHz, CDCl$_3$)δ: 0.99(6H, d, J=6.8 Hz), 2.30–2.41(1H, m), 2.96 (1H, t, J=5.9 Hz), 4.11(2H, d, J=7.4 Hz), 4.74(2H, dd, J=1.4, 5.8 Hz), 7.70–7.74(3H, m), 7.94(2H, d, J=8.2 Hz). IR(KBr) cm$^{-1}$: 3339, 1646, 1596, 1328, 1131, 1070, 848.

7) Preparation of 2-isobutyl-4-methanesulfonyloxymethyl-6-(4-trifluoromethylphenyl)-2H-pyridazin-3-one Following the procedure of Example 1(9), 4-hydroxymethyl-2-isobutyl-6-(4-trifluoromethylphenyl)-2H-pyridazin-3-one was reacted to yield the title compound as colorless fine-needles (yield: 89.9%).

Melting Point: 122.9–123.8° C. ¹H NMR(400 MHz, CDCl₃)δ: 0.99(6H, d, J=6.6 Hz), 2.29–2.40(1H, m), 3.18 (3H, s), 4.11(2H, d, J=7.2 Hz), 5.29(2H, d, J=1.4 Hz), 7.73(2H, d, J=8.2 Hz), 7.83(1H, t, J=1.4 Hz), 7.93(2H, d, J=8.2 Hz). IR(KBr) cm⁻¹: 3447, 1659, 1613, 1359, 1329, 1169, 1123, 1071, 846. Mass m/z: 404(M⁺)

8) Preparation of 4-(4-tert-butoxycarbonyl-1-piperazinyl)methyl-2-isobutyl-6-(4-trifluoromethylphenyl)-2H-pyridazin-3-one Following the procedure of Example 1(10), 2-isobutyl-4-methanesulfonyloxymethyl-6-(4-trifluoromethyl phenyl)-2H-pyridazin-3-one and tert-butyl 1-piperazinecarboxylate were reacted to yield the title compound as a yellow oil (yield: 83.5%).
¹H NMR(400 MHz, CDCl₃)δ: 0.99(6H, d, J=6.6 Hz), 1.47(9H, s), 2.29–2.41(1H, m), 2.53(4H, t, J=4.9 Hz), 3.51 (4H, t, J=4.8 Hz), 3.60(2H, s), 4.10(2H, d, J=7.4 Hz), 7.72(2H, d, J=8.2 Hz), 7.84(1H, s), 7.94(2H, d, J=8.2 Hz).

Example 59

Preparation of 2-isobutyl-4-(1-piperazinyl)methyl-6-(4-trifluoromethylphenyl)-2H-pyridazin-3-one dihydrochloride Following the procedure of Example 2, 4-(4-tert-butoxycarbonyl-1-piperazinyl)methyl-2-isobutyl-6-(4-trifluoromethylphenyl)-2H-pyridazin-3-one was reacted to yield the title compound as a colorless crystalline powder (yield: 95.0%).
Melting point: 210.8–212.5° C. ¹H NMR(400 MHz, DMSO-d₆)δ: 0.96(6H, d, J=6.6 Hz), 2.22–2.35(1H,m), 3.12 (4H,br), 3.30(4H, t, J=5.2 Hz), 3.92(2H, s), 4.05(2H, d, J=7.1 Hz), 7.84(2H, d, J=8.3 Hz), 8.11(2H, d, J=8.1 Hz), 8.25(1H, s). IR(KBr) cm⁻¹: 1656, 1608, 1328, 1125, 1069. Mass m/z: 394(M⁺)

Example 60

Preparation of 2-isobutyl-4-(4-methyl-1-piperazinyl)methyl-6-(4-trifluoromethylphenyl)-2H-pyridazin-3-one Following the procedure of Example 1(10), 2-isobutyl-4-methanesulfonyloxymethyl-6-(4-trifluoromethylphenyl)-2H-pyridazin-3-one and 1-methylpiperazine were reacted to yield the title compound as a yellow oil (yield: 81.1%).
¹H NMR(400 MHz, CDCl₃)δ: 0.99(6H, d, J=6.6 Hz), 2.30–2.41(1H, m), 2.33(3H, s), 2.53(4H, br), 2.63(4H, br), 3.60(2H, s), 4.10(2H, d, J=7.2 Hz), 7.72(2H, d, J=8.2 Hz), 7.83(1H, s), 7.94(2H, d, J=8.2 Hz).

Example 61

Preparation of 2-isobutyl-4-(4-methyl-1-piperazinyl)-methyl-6-(4-trifluoromethylphenyl)-2H-pyridazin-3-one dihydrochloride Following the procedure of Example 4, 2-isobutyl-4-(4-methyl-1-piperazinyl)methyl-6-(4-trifluoromethylphenyl)-2H-pyridazin-3-one was reacted to yield the title compound as colorless flakes (yield: 88.6%).
Melting point: 249.9–252.8° C. ¹H NMR(400 MHz, DMSO-d₆)δ: 0.95(6H, d, J=6.8 Hz), 2.22–2.35(1H, m), 2.77(3H, s), 3.14(4H, br), 3.35(4H, br), 3.88(2H, s), 4.05 (2H, d, J=7.2 Hz), 7.84(2H, d, J=8.2 Hz), 8.10(2H, d, J=8.0 Hz), 8.19(1H, s). IR(KBr) cm⁻¹: 2966, 1653, 1610, 1328, 1125, 1069. Mass m/z: 408(M⁺)

Example 62

Preparation of 4-N,N-bis(2-hydroxyethyl)aminomethyl-2-isobutyl-6-(4-trifluoromethylphenyl)-2H-pyridazin-3-one Following the procedure of Example 1(10), 2-isobutyl-4-methanesulfonyloxymethyl-6-(4-trifluoromethylphenyl)-2H-pyridazin-3-one and diethanolamine were reacted to yield the title compound as a yellow oil (yield: 79.5%).
¹H NMR(400 MHz, CDCl₃)δ: 0.98(6H, d, J=6.6 Hz), 2.29–2.40(1H, m), 2.72(4H, br), 3.67(4H, t, J=4.2 Hz), 3.72(2H, s), 4.10(2H, d, J=7.4 Hz), 7.70(2H, d, J=7.6 Hz), 7.82(1H, s), 7.94(2H, d, J=8.2 Hz).

Example 63

Preparation of 4-N,N-bis(2-hydroxyethyl)aminomethyl-2-isobutyl-6-(4-trifluoromethylphenyl)-2H-pyridazin-3-one hydrochloride Following the procedure of Example 4, 4-N,N-bis(2-hydroxyethyl)aminomethyl-2-isobutyl-6-(4-trifluoromethylphenyl)-2H-pyridazin-3-one was reacted to yield the title compound as a colorless crystalline powder (yield: 58.2%).
Melting point: 134.9–135.4° C. ¹H NMR(400 MHz, DMSO-d₆)δ: 0.97(6H, d, J=6.6 Hz), 2.25–2.36(1H, m), 3.34(4H, br), 3.83(4H, t, J=5.1 Hz), 4.07(2H, d, J=7.0 Hz), 4.46(2H, s), 7.86(2H, d, J=8.2 Hz), 8.13(2H, d, J=8.2 Hz), 8.55(1H, s). IR(KBr) cm⁻¹: 1653, 1605, 1319, 1125, 1069. Mass m/z: 395(M⁺—H₂O)

Example 64

Preparation of 4-dimethylaminomethyl-2-isobutyl-6-(4-trifluoromethylphenyl)-2H-pyridazin-3-one Following the procedure of Example 7, 2-isobutyl-4-methanesulfonyloxymethyl-6-(4-trifluoromethylphenyl)-2H-pyridazin-3-one was reacted to yield the title compound as a yellow oil (yield: 80.7%).
¹H NMR(400 MHz, CDCl₃)δ: 0.99(6H, d, J=6.6 Hz), 2.31–2.40(1H, m), 2.36(6H, s), 3.51(2H, d, J=1.2 Hz), 4.10(2H, d, J=7.4 Hz), 7.71(2H, d, J=8.4 Hz), 7.83(1H, t, J=1.4 Hz), 7.97(2H, d, J=8.2 Hz).

Example 65

Preparation of 4-dimethylaminomethyl-2-isobutyl-6-(4-trifluoromethylphenyl)-2H-pyridazin-3-one hydrochloride Following the procedure of Example 4, 4-dimethylaminomethyl-2-isobutyl-6-(4-trifluoromethylphenyl)-2H-pyridazin-3-one was reacted to yield the title compound as pale yellow flakes (yield: 93.0%).
Melting point: 242.2–242.3° C. ¹H NMR(400 MHz, DMSO-d₆)δ: 0.97(6H, d, J=6.6 Hz), 2.25–2.36(1H, m), 2.83(6H, s), 4.07(2H, d, J=7.3 Hz), 4.30(2H, s), 7.86(2H, d, J=8.3 Hz), 8.14(2H, d, J=8.0 Hz), 8.61(1H, s). IR(KBr) cm⁻¹: 2963, 1646, 1606, 1321, 1115, 1069. Mass m/z: 353(M⁺)

Example 66

Preparation of 6-(4-biphenylyl)-4-(4-tert-butoxycarbonyl-1-piperazinyl)methyl-2-isobutyl-2H-pyridazin-3-one

1) Preparation of ethyl 4-(4-biphenylyl)-2-ethoxycarbonyl-2-hydroxy-4-oxobutanoate Following the procedure of Example 1(3), 4-acetylbiphenyl was reacted to yield the title compound as colorless flakes (yield: 83.3%).

Melting point: 88.0–88.3° C. $^1$H NMR(400 MHz, CDCl$_3$) δ: 1.31(6H, t, J=7.1 Hz), 3.87(2H, s), 4.32(4H, q, 7.1 Hz), 7.41(1H, tt, J=1.4, 7.2 Hz), 7.48(2H, dd, J=7.2, 7.2 Hz), 7.63(2H, d, J=7.0 Hz), 7.70(2H, d, J=8.6 Hz), 8.04(2H, d, J=8.6 Hz). IR(KBr) cm$^{-1}$: 3449, 1736, 1680, 1604, 1301, 1244, 1204, 763.

2) Preparation of 6-(4-biphenylyl)-4-carboxy-2H-pyridazin-3-one

Following the procedure of Example 1(4), ethyl 4-(4-biphenylyl)-2-ethoxycarbonyl-2-hydroxy-4-oxobutanoate was reacted to yield the title compound as a yellow crystalline powder (yield: 90.2%).

Melting point: 299.7–300.8° C. (dec.) $^1$H NMR(400 MHz, DMSO-d$_6$)δ: 7.40(1H, t, J=7.4 Hz), 7.49(2H, dd, J=7.4, 7.4 Hz), 7.74(2H, d, J=7.2 Hz), 7.82(2H, d, J=8.4 Hz), 8.03(2H, d, J=8.4 Hz), 8.54(1H, s). IR(KBr) cm$^{-1}$: 1753, 1652, 1590, 1446, 1201, 768.

3) Preparation of 6-(4-biphenylyl)-4-methoxycarbonyl-2H-pyridazin-3-one

Following the procedure of Example 1(5), 6-(4-biphenylyl)-4-carboxy-2H-pyridazin-3-one was reacted to yield the title compound as a pale yellow crystalline powder (yield: 90.4%).

Melting point: 277.0–277.9° C. (dec.) $^1$H NMR(400 MHz, CDCl$_3$)δ: 4.01(3H, s), 7.39–7.45(3H, m), 7.64(2H, d, J=7.2 Hz), 7.72(2H, d, J=8.2 Hz), 7.89(2H, d, J=8.0 Hz), 8.42(1H, s), 10.7(1H, s). IR(KBr) cm$^{-1}$: 2954, 1727, 1671, 1594, 1265, 1098, 768.

4) Preparation of 6-(4-biphenylyl)-2-isobutyl-4-methoxycarbonyl-2H-pyridazin-3-one Following the procedure of Example 1(6), 6-(4-biphenylyl)-4-methoxycarbonyl-2H-pyridazin-3-one was reacted to yield the title compound as yellow crystals (yield: 62.7%).

Melting point: 186.2–195.0° C. $^1$H NMR(400 MHz, CDCl$_3$)δ: 1.01(6H, d, J=6.8 Hz), 2.34–2.45(1H, m), 3.99(3H, s), 4.16(2H, d, J=7.4 Hz), 7.39(1H, tt, J=1.4, 7.4 Hz), 7.48(2H, dd, J=7.2, 7.2 Hz), 7.64(2H, d, J=7.0 Hz), 7.71(2H, d, J=8.6 Hz), 7.89(2H, d, J=8.6 Hz), 8.31(1H, s).

5) Preparation of 6-(4-biphenylyl)-4-carboxy-2-isobutyl-2H-pyridazin-3-one

Following the procedure of Example 1(7), 6-(4-biphenylyl)-2-isobutyl-4-methoxycarbonyl-2H-pyridazin-3-one was reacted to yield the title compound as a colorless crystalline powder (yield: 79.2%).

Melting point: 156.9–157.6° C. $^1$H NMR(400 MHz, CDCl$_3$)δ: 1.04(6H, d, J-6.6 Hz), 2.36–2.46(1H, m), 4.24(2H, d, J=7.4 Hz), 7.41 (1H, t, J=7.4 Hz), 7.49 (2H, dd, J=7.4, 7.4 Hz), 7.65 (2H, d, J=7.0 Hz), 7.74(2H, d, J=8.4 Hz), 7.95(2H, d, J=8.4 Hz), 8.73(1H, s), 14.22(1H, s). IR(KBr) cm$^{-1}$: 2963, 1749, 1631, 1565, 1470, 735.

6) Preparation of 6-(4-biphenylyl)-4-hydroxymethyl-2-isobutyl-2H-pyridazin-3-one Following the procedure of Example 1(8), 6-(4-biphenylyl)-4-carboxy-2-isobutyl-2H-pyridazin-3-one was reacted to yield the title compound as a while solid (yield: 15.6%).

Melting point: 146.4–147.5° C. $^1$H NMR(400 MHz, CDCl$_3$)δ: 1.01(6H, d, J=6.8 Hz), 2.32–2.43(1H, m), 3.13 (1H, t, J=6.2 Hz), 4.11(2H, d, J=7.4 Hz), 4.74(2H, dd, J=1.2, 6.2 Hz), 7.39(1H, t, J=7.3 Hz), 7.48(2H, dd, J=7.4, 7.4 Hz), 7.64(2H, d, J=7.0 Hz), 7.70(2H, d, J=8.6 Hz), 7.74(1H, t, J=1.2 Hz), 7.90(2H, d, J=8.6 Hz). IR(KBr) cm$^{-1}$: 3431, 2961, 1647, 1596, 1077, 769.

7) Preparation of 6-(4-biphenylyl)-2-isobutyl-4-methanesulfonyloxymethyl-2H-pyridazin-3-one Following the procedure of Example 1(9), 6-(4-biphenylyl)-4-hydroxymethyl-2-isobutyl-2H-pyridazin-3-one was reacted to yield the title compound as a colorless crystalline powder (yield: 79.3%).

Melting point: 121.3–122.0° C. $^1$H NMR(400 MHz, CDCl$_3$)δ: 1.01 (6H, d, J=6.8 Hz), 2.33–2.42 (1H, m), 3.18 (3H, s), 4.12 (2H, d, J=7.4 Hz), 5.30(2H, d, J=1.2 Hz), 7.39(1H, t, J=7.4 Hz), 7.48(2H, dd, J=7.6 Hz), 7.64(2H, d, J=7.4 Hz), 7.71(2H, d, J=8.4 Hz), 7.85–7.91(3H, m). IR(KBr) cm$^{-1}$: 2964, 1658, 1610, 1354, 1165, 874, 529.

8) Preparation of 6-(4-biphenylyl)-4-(4-tert-butoxycarbonyl-1-piperazinyl)methyl-2-isobutyl-2H-pyridazin-3-one Following the procedure of Example 1(10), 6-(4-biphenylyl)-2-isobutyl-4-methanesulfonyloxymethyl-2H-pyridazin-3-one and tert-butyl 1-pipeazinecarboxylate were reacted to yield the title compound as a yellow oil (yield: 87.7%).

$^1$H NMR(400 MHz, CDCl$_3$)δ: 1.00(6H, d, J=6.6 Hz), 1.47(9H, s), 2.30–2.43(1H, m), 2.54(4H, t, J=4.9 Hz), 3.51 (4H, t, J=4.9 Hz), 3.60(2H, d, J=1.4 Hz), 4.10(2H, d, J=7.4 Hz), 7.38(1H, tt, J=1.4, 7.2 Hz), 7.47(2H, dd, J=7.4, 7.4 Hz), 7.64(2H, d, J=7.0 Hz), 7.70(2H, d, J=8.6 Hz), 7.85–7.92(3H, m).

Example 67

Preparation of 6-(4-biphenylyl)-2-isobutyl-4-(1-piperazinyl)methyl-2H-pyridazin-3-one dihydrochloride Following the procedure of Example 2, 6-(4-biphenylyl)-4-(4-tert-butoxycarbonyl-1-piperazinyl)methyl-2-isobutyl-2H-pyridazin-3-one was reacted to yield the title compound as a colorless crystalline powder (yield: 51.5%).

Melting point: 226.8–228.0° C. $^1$H NMR(400 MHz, DMSO-d$_6$)δ: 0.97(6H, d, J=6.8 Hz), 2.25–2.36(1H, m), 3.19(4H, br), 3.34(4H, t, J=5.1 Hz), 3.98(2H, s), 4.05(2H, d, J=7.1 Hz), 7.39(1H, t, J=7.3 Hz), 7.49(2H, dd, J=7.7, 7.7 Hz), 7.71(2H, d, J=7.8 Hz), 7.79(2H, d, J=8.3 Hz), 7.99(2H, d, J=8.3 Hz), 8.29(1H, s). IR(KBr) cm$^{-1}$: 1653, 1604, 1446, 771. Mass m/z: 402(M$^+$)

Example 68

Preparation of 6-(4-biphenylyl)-2-isobutyl-4-(4-methyl-1-piperazinyl)methyl-2H-pyridazin-3-one Following the procedure of Example 1(10), 6-(4-biphenylyl)-2-isobutyl-4-methanesulfonyloxymethyl-2H-pyridazin-3-one and 1-methylpiperazine were reacted to yield the title compound as a yellow oil (yield: 68.2%).
$^1$H NMR(400 MHz, CDCl$_3$)δ: 1.00(6H, d, J=6.6 Hz), 2.30–2.43(1H, m), 2.34(3H, s), 2.55(4H, br), 2.65(4H, br), 3.61(2H, d, J=1.2 Hz), 4.10(2H, d, J=7.2 Hz), 7.38(1H, t, J=7.3 Hz), 7.47(2H, dd, J=7.5, 7.5 Hz), 7.64(2H, d, J=7.2 Hz), 7.70(2H, d, J=8.4 Hz), 7.84(1H, s), 7.90(2H, d, J=8.4 Hz).

Example 69

Preparation of 6-(4-biphenylyl)-2-isobutyl-4-(4-methyl-1-piperazinyl)methyl-2H-pyridazin-3-one dihydrochloride Following the procedure of Example 4, 6-(4-biphenylyl)-2-isobutyl-4-(4-methyl-1-piperazinyl)methyl-2H-pyridazin-3-one was reacted to yield the title compound as a colorless crystalline powder (yield: 69.9%).
Melting point: 262.2–263.6° C. $^1$H NMR(400 MHz, DMSO-d$_6$)δ: 0.97(6H, d, J=6.6 Hz), 2.26–2.35(1H, m), 2.77(3H, s), 3.10(4H, br), 3.34(4H, br), 3.85(2H, s), 4.04(2H, d, J=7.1 Hz), 7.39(1H, t, J=7.6 Hz), 7.49(2H, dd, J=8.0, 8.0 Hz), 7.71(2H, d, J=8.0 Hz), 7.78(2H, d, J=8.3 Hz), 7.89(2H, d, J=8.3 Hz), 8.13(1H, s). IR(KBr) cm$^{-1}$: 1652, 1607, 1465, 1050. Mass m/z: 416(M$^+$)

Example 70

Preparation of 6-(4-biphenylyl)-4-N,N-bis(2-hydroxyethyl)aminomethyl-2-isobutyl-2H-pyridazin-3-one Following the procedure of Example 1(10), 6-(4-biphenylyl)-2-isobutyl-4-methanesulfonyloxymethyl-2H-pyridazin-3-one and diethanolamine were reacted to yield the title compound as a yellow oil (yield: 62.4%).
$^1$H NMR(400 MHz, CDCl$_3$)δ: 0.99(6H, d, J=6.6 Hz), 2.30–2.43(1H, m), 2.73(4H, t, J=4.8 Hz), 3.67(4H, t, J=4.8 Hz), 3.73(2H, s), 4.12(2H, d, J=7.4 Hz), 7.38(1H, t, J=7.2 Hz), 7.47(2H, dd, J=7.2, 7.2 Hz), 7.63(2H, d, J=7.4 Hz), 7.68(2H, d, J=8.2 Hz), 7.79(1H, s), 7.89(2H, d, J=8.2 Hz).

Example 71

Preparation of 6-(4-biphenylyl)-4-N,N-bis(2-hydroxyethyl)aminomethyl-2-isobutyl-2H-pyridazin-3-one hydrochloride Following the procedure of Example 4, 6-(4-biphenylyl)-4-N,N-bis(2-hydroxyethyl)aminomethyl-2-isobutyl-2H-pyridazin-3-one was reacted to yield the title compound as a colorless crystalline powder (yield: 63.9%).
Melting point: 218.3–218.6° C. $^1$H NMR(400 MHz, DMSO-d$_6$)δ: 0.98(6H, d, J=6.8 Hz), 2.26–2.37(1H, m), 3.36(4H, t, J=5.1 Hz), 3.85(4H, t, J=5.1 Hz), 4.08 (2H, d, J=7.3 Hz), 4.48 (2H, s), 7.40(1H, t, J=1.2, 7.3 Hz), 7.49(2H, dd, J=7.3 Hz), 7.72(2H, dd, J=1.2, 7.3 Hz), 7.81(2H, d, J=8.3 Hz), 8.01(2H, d, J=8.3 Hz), 8.52(1H, s). IR(KBr) cm$^{-1}$: 1654, 1607, 1053, 847, 769. m/z(EI): 403(M$^+$–H$_2$O)

Example 72

Preparation of 6-(4-biphenylyl)-4-dimethylaminomethyl-2-isobutyl-2H-pyridazin-3-one Following the procedure of Example 7, 6-(4-biphenylyl)-2-isobutyl-4-methanesulfonyloxymethyl-2H-pyridazin-3-one was reacted to yield the title compound as a yellow oil (yield: 87.7%).
$^1$H NMR(400 MHz, CDCl$_3$)δ: 1.00(6H, d, J=6.6 Hz), 2.36(6H, s), 2.29–2.43(1H, m), 3.52(2H, d, J=1.0 Hz), 4.10(2H, d, J=7.2 Hz), 7.37(1H, t, J=7.4 Hz), 7.46(2H, dd, J=7.4, 7.4 Hz), 7.63(2H, d, J=7.2 Hz), 7.68(2H, d, J=8.4 Hz), 7.85(1H, s), 7.92(2H, d, J=8.4 Hz).

Example 73

Preparation of 6-(4-biphenylyl)-4-dimethylaminomethyl-2-isobutyl-2H-pyridazin-3-one hydrochloride Following the procedure of Example 4, 6-(4-biphenylyl)-4-dimethylaminomethyl-2-isobutyl-2H-pyridazin-3-one was reacted to yield the title compound as colorless flakes (yield: 58.2%).
Melting point: 243.9–244.1° C. $^1$H NMR(400 MHz, DMSO-d$_6$)δ: 0.98(6H, d, J=6.6 Hz), 2.26–2.37(1H, m), 2.83(6H, s), 4.03(2H, d, J=7.1 Hz), 4.30(2H, s), 7.39(1H, tt, J=1.2, 7.3 Hz), 7.49(2H, dd, J=7.3, 7.3 Hz), 7.72(2H, dd, J=1.2, 7.1 Hz), 7.81(2H, d, J=8.8 Hz), 8.02(2H, d, J=8.6 Hz), 8.57(1H, s). IR(KBr) cm$^{-1}$: 1647, 1604, 1460, 1409, 1052. Mass m/z: 361(M$^+$)

Example 74

Preparation of 4-(4-tert-butoxycarbonyl-1-piperazinyl)methyl-6-(3-chloro-4-methoxyphenyl)-2-isobutyl-2H-pyridazin-3-one Following the procedure of Example 1(10), 6-(3-chloro-4-methoxyphenyl)-2-isobutyl-4-methanesulfonyloxymethyl-2H-pyridazin-3-one and tert-butyl 1-piperazinecarboxylate were reacted to yield the title compound as a yellow oil (yield: 89.0%).
$^1$H NMR(400 MHz, CDCl$_3$)δ: 0.98(6H, d, J=6.8 Hz), 1.47(9H, s), 2.27–2.40(1H, m), 2.52(4H, t, J=4.9 Hz), 3.50 (4H, t, J=5.0 Hz), 3.57(2H, d, J=1.4 Hz), 3.96(3H, s), 4.07(2H, d, J=7.2 Hz), 7.00(1H, d, J=8.6 Hz), 7.66(1H, dd, J=2.4, 8.6 Hz), 7.74(1H, t, J=1.3 Hz), 7.86(1H, d, J=2.4 Hz).

Example 75

Preparation of 6-(3-chloro-4-methoxyphenyl)-2-isobutyl-4-(1-piperazinyl)methyl-2H-pyridazin-3-one dihydrochloride Following the procedure of Example 2, 4-(4-tert-butoxycarbonyl-1-piperazinyl)methyl-6-(3-chloro-4-methoxyphenyl)-2-isobutyl-2H-pyridazin-3-one was reacted to yield the title compound as a white solid (yield: 70.2%).
Melting point: 203.6–204.5° C. $^1$H NMR(400 MHz, DMSO-d$_6$)δ: 0.95(6H, d, J=6.6 Hz), 2.20–2.34(1H, m), 3.14(4H, br), 3.31(4H, t, J=5.2 Hz), 3.93(5H, s), 4.01(2H, d, J=7.0 Hz), 7.26(1H, d, J=8.8 Hz), 7.84(1H, dd, J=2.4, 8.6 Hz), 7.91(1H, d, J=2.4 Hz), 8.19(1H, s). IR(KBr) cm$^{-1}$: 1654, 1608, 1507, 1289, 1065. Mass m/z: 390(M$^+$), 392(M$^+$).

Example 76

Preparation of 6-(3-chloro-4-methoxyphenyl)-2-isobutyl-4-(4-methyl-1-piperazinyl)methyl-2H-pyridazin-3-one Following the procedure of Example 1(10), 6-(3-chloro-4-methoxyphenyl)-2-isobutyl-4-methanesulfonyloxymethyl-2H-pyridazin-3-one and 1-methylpiperazine were reacted to yield the title compound as a yellow oil (yield: 76.1%).
$^1$H NMR(400 MHz, CDCl$_3$)δ: 0.98(6H, d, J=6.6 Hz), 2.28–2.40 (1H, m), 2.33(3H, s), 2.53(4H, br), 2.63(4H, br), 3.58(2H, d, J=1.2 Hz), 3.96(3H, s), 4.06(2H, d, J=7.2 Hz), 7.01 (1H, d, J=8.6 Hz), 7.67(1H, dd, J=2.2, 8.6 Hz), 7.72 (1H, s), 7.86(1H, d, J=2.2 Hz).

Example 77

Preparation of 6-(3-chloro-4-methoxyphenyl)-2-isobutyl-4-(4-methyl-1-piperazinyl)methyl-2H-pyridazin-3-one dihydrochloride Following the procedure of Example 4, 6-(3-chloro-4-methoxyphenyl)-2-isobutyl-4-(4-methyl-1-piperazinyl)methyl-2H-pyridazin-3-one was reacted to yield the title compound as a colorless crystalline powder (yield: 67.5%).
Melting point: 235.8–236.7° C. $^1$H NMR(400 MHz, DMSO-d$_6$)δ: 0.94(6H, d, J=6.6 Hz), 2.25–2.32(1H, m), 2.77(3H, s), 3.15(4H, br), 3.36(4H, br), 3.88(2H, s), 3.93 (3H, s), 4.01(2H, d, J=7.0 Hz), 7.26(1H, d, J=8.6 Hz), 7.83(1H, dd, J=2.2, 8.6 Hz), 7.91(1H, d, J=2.2 Hz), 8.12(1H, s). IR(KBr) cm$^{-1}$: 1653, 1608, 1507, 1289, 1064. Mass m/z: 404(M$^+$), 406(M$^+$).

Example 78

Preparation of 4-N,N-bis(2-hydroxyethyl)aminomethyl-6-(3-chloro-4-methoxyphenyl)-2-isobutyl-2H-pyridazin-3-one Following the procedure of Example 1(10), 6-(3-chloro-4-methoxyphenyl)-2-isobutyl-4-methanesulfonyloxymethyl-2H-pyridazin-3-one and diethanolamine were reacted to yield the title compound as a yellow oil (yield: 79.6%).
$^1$H NMR(400 MHz, CDCl$_3$)δ: 0.96(6H, d, J=6.6 Hz), 2.28–2.39(1H, m), 2.71(4H, t, J=4.9 Hz), 3.66(4H, t, J=4.9 Hz), 3.70(2H, s), 3.94(3H, s), 4.07(2H, d, J=7.4 Hz), 6.98 (1H, d, J=8.8 Hz), 7.68(1H, dd, J=1.8, 8.7 Hz), 7.72(1H, s), 7.85(1H, d, J=2.1 Hz).

Example 79

Preparation of 4-N,N-bis(2-hydroxyethyl)aminomethyl-6-(3-chloro-4-methoxyphenyl)-2-isobutyl-2H-pyridazin-3-one hydrochloride Following the procedure of Example 4, 4-N,N-bis(2-hydroxyethyl)aminomethyl-6-(3-chloro-4-methoxyphenyl)-2-isobutyl-2H-pyridazin-3-one was reacted to yield the title compound as a colorless crystalline powder (yield: 60.1%).
Melting point: 153.0–153.5° C. $^1$H NMR(400 MHz, DMSO-d$_6$)δ: 0.95(6H, d, J=6.6 Hz), 2.23–2.34(1H, m), 3.34(4H, t, J=5.1 Hz), 3.83(4H, t, J=5.1 Hz), 3.94(3H, s), 4.04(2H, d, J=7.1 Hz), 4.44(2H, s), 7.28(1H, d, J=8.8 Hz), 7.85(1H, dd, J=2.4, 8.6 Hz), 7.94(1H, d, J=2.4 Hz), 8.45(1H, s). IR(KBr) cm$^{-1}$: 1652, 1607, 1508, 1421, 1293, 1062. Mass m/z: 391(M$^+$—H$_2$O)

Example 80

Preparation of 6-(3-chloro-4-methoxyphenyl)-4-dimethylaminomethyl-2-isobutyl-2H-pyridazin-3-one Following the procedure of Example 7, 6-(3-chloro-4-methoxyphenyl)-2-isobutyl-4-methanesulfonyloxymethyl-2H-pyridazin-3-one was reacted to yield the title compound as a yellow oil (yield: 84.8%).
$^1$H NMR(400 MHz, CDCl$_3$)δ: 0.98(6H, d, J=6.6 Hz), 2.31–2.39(1H, m), 2.35(6H, s), 3.50(2H, s), 3.95(3H, s), 4.07(2H, d, J=7.2 Hz), 6.99(1H, d, J=8.6 Hz), 7.70(1H, dd, J=1.4, 8.6 Hz), 7.88(1H, d, J=1.4 Hz).

Example 81

Preparation of 6-(3-chloro-4-methoxyphenyl)-4-dimethylaminomethyl-2-isobutyl-2H-pyridazin-3-one hydrochloride Following the procedure of Example 4, 6-(3-chloro-4-methoxyphenyl)-4-dimethylaminomethyl-2-isobutyl-2H-pyridazin-3-one was reacted to yield the title compound as a white solid (yield: 69.4%).
Melting point: 213.6–214.3° C. $^1$H NMR(400 MHz, DMSO-d$_6$)δ: 0.95(6H, d, J=6.8 Hz), 2.22–2.34(1H, m), 2.81(6H, s), 3.94(3H, s), 4.04(2H, d, J=7.1 Hz), 4.27(2H, s), 7.28(1H, d, J=8.8 Hz), 7.87(1H, dd, J=2.2, 8.8 Hz), 7.95(1H, d, J=2.2 Hz), 8.53(1H, s). IR(KBr) cm$^{-1}$: 1652, 1608, 1508, 1289, 1064. Mass m/z: 349(M$^+$), 351(M$^+$).

Example 82

Preparation of 6-(4-fluoro-3-methylphenyl)-2-isobutyl-4-(4-methyl-1-piperazinyl)methyl-2H-pyridazin-3-one

1) Preparation of ethyl 2-ethoxycarbonyl-4-(4-fluoro-3-methylphenyl)-2-hydroxy-4-oxobutanoate Following the procedure of Example 1(3), 5-acetyl-2-fluorotoluene was reacted to yield the title compound as pale yellow prisms (yield: 95.9%).
$^1$H NMR(400 MHz, CDCl$_3$)δ: 1.30(6H, t, J=7.1 Hz), 2.33(3H, d, J=1.7 Hz), 3.79(2H, s), 4.29(1H, s), 4.31(4H, q, J=7.1 Hz), 7.08(1H, dd, J=8.8, 8.8 Hz), 7.78–7.85(2H, m).

2) Preparation of 4-carboxy-6-(4-fluoro-3-methylphenyl)-2H-pyridazin-3-one

Following the procedure of Example 1(4), ethyl 2-ethoxycarbonyl-4-(4-fluoro-3-methylphenyl)-2-hydroxy-4-oxobutanoate was reacted to yield the title compound as a pale yellow crystalline powder (yield: 88.9%).
Melting point: 213.6–214.3° C. $^1$H NMR(400 MHz, DMSO-d$_6$)δ: 2.51(3H, d, J=1.7 Hz), 7.26(1H, dd, J=9.1, 9.1 Hz), 7.77–7.81(1H, m), 7.89(1H, d, J=7.3 Hz), 8.49(1H, s), 13.99(1H, br).

3) Preparation of 6-(4-fluoro-3-methylphenyl)-4-methoxycarbonyl-2H-pyridazin-3-one Following the procedure of Example 1(5), 4-carboxy-6-(4-fluoro-3-methylphenyl)-2H-pyridazin-3-one was reacted to yield the title compound as a pale yellow crystalline powder (yield: 76.8%).

¹H NMR(400 MHz, CDCl₃)δ: 2.35(3H, d, J=2.0 Hz), 3.99(3H, s), 7.10(1H, dd, J=8.9, 8.9 Hz), 7.58–7.62(1H, m), 7.60(1H, d, J=7.3 Hz), 8.31(1H, s).

4) Preparation of 6-(4-fluoro-3-methylphenyl)-2-isobutyl-4-methoxycarbonyl-2H-pyridazin-3-one Following the procedure of Example 1(6), 6-(4-fluoro-3-methylphenyl)-2-methoxycarbonyl-2H-pyridazin-3-one was reacted to yield the title compound as pale yellow prisms (yield: 86.3%).
Melting point: 71.4–73.8° C. ¹H NMR(400 MHz, CDCl₃) δ: 0.99(6H, d, J=6.8 Hz), 2.31–2.42(1H, m), 2.35(3H, d, J=2.0 Hz), 3.98(3H, s), 4.12(2H, d, J=7.3 Hz), 7.10(1H, dd, J=8.8, 8.8 Hz), 7.57–7.65(2H, m), 8.21(1H, s).

5) Preparation of 4-carboxy-6-(4-fluoro-3-methylphenyl)-2-isobutyl-2H-pyridazin-3-one Following the procedure of Example 1(7), 6-(4-fluoro-3-methylphenyl)-2-isobutyl-4-methoxycarbonyl-2H-pyridazin-3-one was reacted to yield the title compound as pale yellow needles (yield: 90.0%).
Melting point: 129.3–132.1° C. ¹H NMR(400 MHz, CDCl₃)δ: 1.02(6H, d, J=6.8 Hz), 2.33–2.44(1H, m), 2.37 (3H, d, J=2.0 Hz), 4.21(2H, d, J=7.3 Hz), 7.13(1H, dd, J=8.8, 8.8 Hz), 7.64–7.71(2H, m), 8.63(1H, s). IR(KBr) cm⁻¹: 1742, 1636, 1537, 1422. Mass m/z: 304(M⁺).

6) Preparation of 6-(4-fluoro-3-methylphenyl)-4-hydroxymethyl-2-isobutyl-2H-pyridazin-3-one Following the procedure of Example 1(8), 4-carboxy-6-(4-fluoro-3-methylphenyl)-2-isobutyl-2H-pyridazin-3-one was reacted to yield the title compound as colorless needles (yield: 24.7%).
Melting point: 107.4–110.4° C. ¹H NMR(400 MHz, CDCl₃)δ: 0.99(6H, d, J=6.6 Hz), 2.29–2.40(1H, m), 2.35 (3H, d, J=1.7 Hz), 3.14(1H, t, J=5.9 Hz), 4.08(2H, d, J=7.6 Hz), 4.71(2H, d, J=5.9 Hz), 7.08 (1H, dd, J=8.8, 8.8 Hz), 7.56–7.65(3H, m). IR(KBr) cm⁻¹: 3401, 1658, 1648, 1618, 1602, 1501. Mass m/z: 290(M⁺).

7) Preparation of 6-(4-fluoro-3-methylphenyl)-2-isobutyl-4-methanesulfonyloxymethyl-2H-pyridazin-3-one Following the procedure of Example 1(9), 6-(4-fluoro-3-methylphenyl)-4-hydroxymethyl-2-isobutyl-2H-pyridazin-3-one was reacted to yield the title compound as colorless needles (yield: 91.4%).
Melting point: 114.6–117.1° C. ¹H NMR(400 MHz, CDCl₃)δ: 0.99(6H, d, J=6.8 Hz), 2.29–2.40(1H, m), 2.36 (3H, s), 3.17(3H, s), 4.08(2H, d, J=7.6 Hz), 5.27(2H, d, J=1.5 Hz), 7.09 (1H, dd, J=8.9, 8.9 Hz), 7.56–7.69(2H, m), 7.75(1H, t, J=1.5 Hz). IR(KBr) cm⁻¹: 1656, 1611, 1505, 1354, 1166. Mass m/z: 368(M⁺).

8) Preparation of 6-(4-fluoro-3-methylphenyl)-2-isobutyl-4-(4-methyl-1-piperazinyl)methyl-2H-pyridazin-3-one Following the procedure of Example 1(10), 6-(4-fluoro-3-methylphenyl)-2-isobutyl-4-methanesulfonyloxymethyl-2H-pyridazin-3-one and 1-methylpiperazine were reacted to yield the title compound as a slightly yellow oil (yield: 79.1%).

¹H NMR(400 MHz, CDCl₃)δ: 0.98(6H, d, J=6.8 Hz), 2.27–2.40(1H, m), 2.32(3H, s), 2.36(3H, d, J=2.0 Hz), 2.51(4H, br), 2.62(4H, br), 3.58(2H, d, J=1.5 Hz), 4.07(2H, d, J=7.3 Hz), 7.09 (1H, dd, J=8.8, 8.8 Hz), 7.58(1H, ddd, J=2.0, 4.9, 8.8 Hz), 7.64(1H, dd, J=2.0, 7.3 Hz), 7.73(1H, t, J=1.5 Hz). IR(Neat) cm⁻¹: 1652, 1609, 1503. Mass m/z: 372(M⁺).

Example 83

Preparation of 6-(4-fluoro-3-methylphenyl)-2-isobutyl-4-(4-methyl-1-piperazinyl)methyl-2H-pyridazin-3-one dihydrochloride Following the procedure of Example 4, 6-(4-fluoro-3-methylphenyl)-2-isobutyl-4-(4-methyl-1-piperazinyl)methyl-2H-pyridazin-3-one was reacted to yield the title compound as colorless prisms (yield: 95.9%).
Melting point: 234.8–237.4° C. (dec.) ¹H NMR(400 MHz, DMSO-d₆)δ: 0.93(6H, d, J=6.8 Hz), 2.19–2.30(1H, m), 2.32(3H, d, J=2.0 Hz), 2.81(3H, s), 2.89–3.62(10H, brm), 4.00(2H, d, J=7.3 Hz), 7.29(1H, dd, J=9.0, 9.0 Hz), 7.72–7.78(1H, m), 7.83(1H, dd, J=2.4, 7.6 Hz), 8.31(1H, brs). IR(KBr) cm⁻¹: 1660, 1609, 1504.

Example 84

Preparation of 6-(4-fluoro-3-methylphenyl)-2-isobutyl-4-methylamino methyl-2H-pyridazin-3-one Following the procedure of Example 9(4), 6-(4-fluoro-3-methylphenyl)-2-isobutyl-4-methanesulfonyloxymethyl-2H-pyridazin-3-one was reacted to yield the title compound as a pale yellow oil (yield: 96.2%).
¹H NMR(400 MHz, CDCl₃)δ: 0.98(6H, d, J=6.8 Hz), 1.65(1H, br), 2.29–2.42(1H, m), 2.34(3H, d, J=1.7 Hz), 2.51(3H, s), 3.77(2H, d, J=1.2 Hz), 4.07(2H, d, J=7.3 Hz), 7.07(1H, dd, J=8.8, 8.8 Hz), 7.54–7.63(2H, m), 7.64(1H, t, J=1.2 Hz). IR(Neat) cm⁻¹: 3306, 1653, 1605, 1507. Mass m/z: 303(M⁺).

Example 85

Preparation of 6-(4-fluoro-3-methylphenyl)-2-isobutyl-4-methylaminomethyl-2H-pyridazin-3-one hydrochloride Following the procedure of Example 4, 6-(4-fluoro-3-methylphenyl)-2-isobutyl-4-methylaminomethyl-2H-pyridazin-3-one was reacted to yield the title compound as colorless prisms (yield: 86.6%).
Melting point: 196.8–199.7° C. ¹H NMR(400 MHz, DMSO-d₆)δ: 0.93(6H, d, J=6.8 Hz), 2.19–2.31(1H, m), 2.32(3H, s), 2.65(3H, s), 4.02(2H, d, J=7.3 Hz), 4.12(2H, s), 7.31(1H, dd, J=8.5, 8.5 Hz), 7.72–7.78(1H, m), 7.80–7.85 (1H, m), 8.32(1H, s). IR(KBr) cm⁻¹: 2722, 1652, 1615, 1505.

Example 86

Preparation of 4-(4-benzyl-1-piperazinyl)methyl-6-(4-fluoro-3-methylphenyl)-2-isobutyl-2H-pyridazin-3-one Following the procedure of Example 1(10), 6-(4-fluoro-3-methylphenyl)-2-isobutyl-4-methanesulfonyloxymethyl- 2H-pyridazin-3-one and 1-benzylpiperazine were reacted to yield the title compound as a pale yellow oil (yield: 98.6%).

$^1$H NMR(400 MHz, CDCl$_3$)δ: 0.97(6H, d, J=6.8 Hz), 2.29–2.39 (1H, m), 2.36(3H, d, J=1.7 Hz), 2.55(4H, br), 2.61(4H, br), 3.55(2H, s), 3.57(2H, d, J=1.2 Hz), 4.06(2H, d, J=7.6 Hz), 7.09(1H, dd, J=8.9, 8.9 Hz), 7.23–7.34 (5H, m), 7.51 (1H, ddd, J=2.4, 4.8, 8.9 Hz), 7.63(1H, dd, J=2.4, 7.2 Hz), 7.72(1H, s). IR(Neat) cm$^{-1}$: 1652, 1608, 1505. Mass m/z: 448(M$^+$).

Example 87

Preparation of 4-(4-benzyl-1-piperazinyl)methyl-6-(4-fluoro-3-methylphenyl)-2-isobutyl-2H-pyridazin-3-one dihydrochloride Following the procedure of Example 4, 4-(4-benzyl-1-piperazinyl)methyl-6-(4-fluoro-3-methylphenyl)-2-isobutyl-2H-pyridazin-3-one was reacted to yield the title compound as colorless needles (yield: 95.3%).

Melting point: 259.1–263.1° C. (dec.) $^1$H NMR(400 MHz, DMSO-d$_6$)δ: 0.93(6H, d, J=6.6 Hz), 2.17–2.29(1H, m), 2.32(3H, s), 2.55(4H, br), 3.23–3.56(8H, brm), 4.00(2H, d, J=7.3 Hz), 4.11(2H, brs), 4.38(2H, brs), 7.29(1H, dd, J=9.0, 9.0 Hz), 7.43–7.48(3H, m), 7.59–7.65(2H, m), 7.72–7.77(1H, m), 7.79–7.84(1H, m), 8.35(1H, brs). IR(KBr) cm$^{-1}$: 1660, 1618, 1612, 1453.

Example 88

Preparation of 4-dimethylaminomethyl-6-(4-fluoro-3-methylphenyl)-2-isobutyl-2H-pyridazin-3-one Following the procedure of Example 7, 6-(4-fluoro-3-methylphenyl)-2-isobutyl-4-methanesulfonyloxymethyl-2H-pyridazin-3-one was reacted to yield the title compound as a slightly yellow oil (yield: 96.4%).

$^1$H NMR(400 MHz, CDCl$_3$)δ: 0.98(6H, d, J=6.8 Hz), 2.28–2.39(1H, m), 2.35(3H, d, J=2.2 Hz), 2.56(6H, s), 3.50(2H, d, J=1.2 Hz), 4.07(2H, d, J=7.3 Hz), 7.07(1H, dd, J=8.9, 8.9 Hz), 7.59–7.67(2H, m), 7.74(1H, t, J=1.2 Hz). IR(Neat) cm$^{-1}$: 1652, 1608, 1506. Mass m/z: 317(M$^+$).

Example 89

Preparation of 4-dimethylaminomethyl-6-(4-fluoro-3-methylphenyl)-2-isobutyl-2H-pyridazin-3-one hydrochloride Following the procedure of Example 4, 4-dimethylaminomethyl-6-(4-fluoro-3-methylphenyl)-2-isobutyl-2H-pyridazin-3-one was reacted to yield the title compound as colorless needles (yield: 97.2%).

Melting point: 208.5–213.0° C. $^1$H NMR(400 MHz, DMSO-d$_5$)δ: 0.94(6H, d, J=6.6 Hz), 2.19–2.30(1H, m), 2.32(3H, s), 2.81(6H, s), 4.03(2H, d, J=7.0 Hz), 4.30(2H, s), 7.30(1H, dd, J=9.0, 9.0 Hz), 7.74–7.80(1H, m), 7.85(1H, m), 8.51(1H, s). IR(KBr) cm$^{-1}$: 1648, 1608, 1507.

Example 90

Preparation of 4-N,N-bis(2-hydroxyethyl)aminomethyl-6-(4-fluoro-3-methylphenyl)-2-isobutyl-2H-pyridazin-3-one Following the procedure of Example 1(10), 6-(4-fluoro-3-methylphenyl)-2-isobutyl-4-methanesulfonyloxymethyl-2H-pyridazin-3-one and diethanolamine were reacted to yield the title compound as a slightly yellow oil (yield: 91.5%).

$^1$H NMR(400 MHz, CDCl$_3$)δ: 0.97(6H, d, J=6.8 Hz), 2.27–2.40(1H, m), 2.34(3H, d, J=2.0 Hz), 2.70(4H, t, J=5.0 Hz), 3.66(4H, d, J=5.0 Hz), 3.69(2H, s), 3.91(2H, br), 4.07(2H, d, J=7.6 Hz), 7.07(1H, dd, J=8.9, 8.9 Hz), 7.60(1H, ddd, J=2.2, 5.1, 8.9 Hz), 7.64(1H, dd, J=2.2, 7.3 Hz), 7.71(1H, s). IR(Neat) cm$^{-1}$: 3391, 1654, 1371, 1505. Mass m/z: 359(M$^+$—H$_2$O).

Example 91

Preparation of 4-N,N-bis(2-hydroxyethyl)aminomethyl-6-(4-fluoro-3-methylphenyl)-2-isobutyl-2H-pyridazin-3-one hydrochloride Following the procedure of Example 4, 4-N,N-bis(2-hydroxyethyl)aminomethyl-6-(4-fluoro-3-methylphenyl)-2-isobutyl-2H-pyridazin-3-one was reacted to yield the title compound as slightly yellow needles (yield: 92.4%).

Melting point: 155.1–157.3° C. $^1$H NMR(400 MHz, DMSO-d$_6$)δ: 0.94(6H, d, J=6.6 Hz), 2.20–2.31(1H, m), 2.32(3H, d, J=1.2 Hz), 3.35(4H, br, overlapped with H$_2$O), 3.82(4H, br), 4.02(2H, d, J=7.3 Hz), 4.50(2H, s), 5.37(2H, br), 7.30(1H, dd, J=9.0, 9.0 Hz), 7.78(1H, ddd, J=2.0, 4.9, 9.0 Hz), 7.85(1H, dd, J=2.0, 7.3 Hz), 7.71(1H, s). IR(KBr) cm$^{-1}$: 3281, 1655, 1606.

Example 92

Preparation of 6-(4-fluoro-3-methylphenyl)-2-isobutyl-4-(piperidino)methyl-2H-pyridazin-3-one 6-(4-Fluoro-3-methylphenyl)-2-isobutyl-4-methanesulfonyloxymethyl-2H-pyridazin-3-one (80 mg, 0.22 mmol) and piperidine (55 mg, 0.65 mmol) were dissolved in ethanol (0.5 mL), and the mixture was heated at 80° C. for 1 hour under stirring. The solvent was distilled off under reduced pressure. The residue was purified by preparative thin-layer chromatography on silica gel [developing solvent: chloroform/methanol (10/1)] to yield the title compound as a slightly yellow oil (73 mg, 94.0%).

$^1$H NMR(400 MHz, CDCl$_3$)δ: 0.98(6H, d, J=6.9 Hz), 1.45–1.53(2H, m), 1.61–1.68(4H, m), 2.28–2.41(1H, m), 2.36(3H, d, J=2.0 Hz), 2.47–2.53(4H, m), 3.52(2H, d, J=1.5 Hz), 4.07(2H, d, J=7.3 Hz), 7.08(1H, dd, J=8.9, 8.9 Hz), 7.59(1H, ddd, J=1.7, 4.9, 8.9 Hz), 7.65(1H, dd, J=1.7, 7.3 Hz), 7.76(1H, t, J=1.5 Hz). IR(Neat) cm$^{-1}$: 1652, 1616, 1506. Mass m/z: 357(M$^+$).

Example 93

Preparation of 6-(4-fluoro-3-methylphenyl)-2-isobutyl-4-(piperidino)methyl-2H-pyridazin-3-one hydrochloride Following the procedure of Example 4, 6-(4-fluoro-3-methylphenyl)-2-isobutyl-4-(piperidino)methyl-2H-pyridazin-3-one was reacted to yield the title compound as slightly yellow prisms (yield: 90.7%).

$^1$H NMR(400 MHz, DMSO-d$_6$)δ: 0.94(6H, d, J=6.6 Hz), 1.34–1.47(1H, m), 1.64–1.73(1H, m), 1.74–1.83(4H, m), 2.20–2.30(1H, m), 2.32(3H, s), 2.95–3.02(2H, m), 3.36–3.45(1H, m), 4.02(2H, d, J=7.3 Hz), 4.25(2H, d, J=5.1 Hz), 7.30(1H, dd, J=9.0, 9.0 Hz), 7.75–7.80(1H, m), 7.83–7.87(1H, m), 8.59(1H, s). IR(KBr) cm$^{-1}$: 2532, 1652, 1616, 1505, 1433.

Example 94

Preparation of 6-(4-fluoro-3-methylphenyl)-2-isobutyl-4-(morpholino)methyl-2H-pyridazin-3-one Following the procedure of Example 92, 6-(4-fluoro-3-methylphenyl)-2-isobutyl-4-methanesulfonyloxymethyl-2H-pyridazin-3-one and morpholine were reacted to yield the title compound as a slightly yellow oil (yield: 97.4%).

$^1$H NMR(400 MHz, CDCl$_3$)δ: 0.98(6H, d, J=6.8 Hz), 2.28–2.41(1H, m), 2.36(3H, d, J=2.0 Hz), 2.58(4H, t, J=4.6 Hz), 3.57(2H, d, J=1.2 Hz), 3.78(4H, t, J=4.6 Hz), 4.07(2H, d, J=7.3 Hz), 7.09(1H, dd, J=8.8, 8.8 Hz), 7.58(1H, ddd, J=2.0, 4.9, 8.8 Hz), 7.64(1H, dd, J=2.0, 7.3 Hz), 7.75(1H, t, J=1.5 Hz). IR(Neat) cm$^{-1}$: 1659, 1606, 1503. Mass m/z: 359(M$^+$).

Example 95

Preparation of 6-(4-fluoro-3-methylphenyl)-2-isobutyl-4-(morpholino)methyl-2H-pyridazin-3-one hydrochloride Following the procedure of Example 4, 6-(4-fluoro-3-methylphenyl)-2-isobutyl-4-(morpholino)methyl-2H-pyridazin-3-one was reacted to yield the title compound as colorless prisms (yield: 92.4%).

Melting point: 215.4–216.6° C. $^1$H NMR(400 MHz, DMSO-d$_6$)δ: 0.94(6H, d, J=6.6 Hz), 2.19–2.30(1H, m), 2.32(3H, s), 3.21(2H, br), 3.79–3.98(6H, m), 4.02(2H, d, J=7.3 Hz), 4.33(2H, brs), 7.30(1H, dd, J=9.0, 9.0 Hz), 7.74–7.79(1H, m), 7.81–7.86(1H, m), 8.56(1H, brs). IR(KBr) cm$^{-1}$: 2392, 1647, 1607.

Example 96

Preparation of 4-aminomethyl-6-(4-fluoro-3-methylphenyl)-2-isobutyl-2H-pyridazin-3-one

1) Preparation of 6-(4-fluoro-3-methylphenyl)-2-isobutyl-4-phthalimidomethyl-2H-pyridazin-3-one Following the procedure of Example 24(1), 6-(4-fluoro-3-methylphenyl)-2-isobutyl-4-methanesulfonyloxymethyl-2H-pyridazin-3-one was reacted to yield the title compound as slightly yellow needles (yield: 93.7%).

Melting point: 181.2–187.2° C. $^1$H NMR(400 MHz, CDCl$_3$)δ: 0.98(6H, d, J=6.6 Hz), 2.29–2.40(1H, m), 2.30 (3H, s), 4.07(2H, d, J=7.3 Hz), 4.91 (2H, s), 7.01(1H, dd, J=9.0, 9.0 Hz), 7.31(1H, s), 7.41–7.46(1H, m), 7.50–7.53 (1H, m), 7.76–7.81(2H, m), 7.90–7.95(2H, m). IR(KBr) cm$^{-1}$: 1720, 1656, 1619, 1611. Mass m/z: 419(M$^+$).

2) Preparation of 4-aminomethyl-6-(4-fluoro-3-methylphenyl)-2-isobutyl-2H-pyridazin-3-one Following the procedure of Example 24(2), 6-(4-fluoro-3-methylphenyl)-2-isobutyl-4-phthalimidomethyl-2H-pyridazin-3-one was reacted to yield the title compound as a slightly yellow oil (yield: 99.6%).

$^1$H NMR(400 MHz, CDCl$_3$)δ: 0.98(6H, d, J=6.8 Hz), 1.64(2H, br), 2.30–2.40(1H, m), 2.35(3H, d, J=2.0 Hz), 3.89(2H, d, J=1.2 Hz), 4.07(2H, d, J=7.3 Hz), 7.07(1H, dd, J=8.8, 8.8 Hz), 7.60(1H, ddd, J=2.1, 4.9, 8.8 Hz), 7.64(1H, dd, J=2.1, 7.4 Hz), 7.67(1H, t, J=1.2 Hz). IR(Neat) cm$^{-1}$: 3372, 3301, 1655, 1605, 1504. Mass m/z: 289(M$^+$).

Example 97

Preparation of 4-aminomethyl-6-(4-fluoro-3-methylphenyl)-2-isobutyl-2H-pyridazin-3-one hydrochloride Following the procedure of Example 4, 4-aminomethyl-6-(4-fluoro-3-methylphenyl)-2-isobutyl-2H-pyridazin-3-one was reacted to yield the title compound as colorless needles (yield: 79.8%).

Melting point: 217.5–220.5° C. (dec.) $^1$H NMR(400 MHz, DMSO-d$_6$)δ: 0.93(6H, d, J=6.6 Hz), 2.20–2.30(1H, m), 2.32(3H, d, J=1.7 Hz), 4.01(2H, d, J=2.2 Hz), 4.02(2H, d, J=7.3 Hz), 7.31(1H, dd, J=9.0, 9.0 Hz), 7.75(1H, ddd, J=2.1, 4.9, 9.0 Hz), 7.83(1H, dd, J=2.1, 7.4 Hz), 8.28(1H, s). IR(KBr) cm$^{-1}$: 2960, 2927, 2872, 1656, 1614, 1507.

Example 98

Preparation of 4-diethylaminomethyl-6-(4-fluoro-3-methylphenyl)-2-isobutyl-2H-pyridazin-3-one Following the procedure of Example 9(4), 6-(4-fluoro-3-methylphenyl)-2-isobutyl-4-methanesulfonyloxymethyl-2H-pyridazin-3-one and diethylamine were reacted to yield the title compound as a slightly yellow oil (yield: 94.7%).

$^1$H NMR(400 MHz, CDCl$_3$)δ: 0.98(6H, d, J=6.8 Hz), 1.07(6H, t, J=7.1 Hz), 2.30–2.41(1H, m), 2.35(3H, d, J=1.5 Hz), 2.61(4H, q, J=7.1 Hz), 3.60(2H, d, J=1.7 Hz), 4.08(2H, d, J=7.5 Hz), 7.08(1H, dd, J=8.9, 8.9 Hz), 7.60(1H, ddd, J=2.2, 4.9, 8.9 Hz), 7.65(1H, dd, J=2.2, 7.3 Hz), 7.85(1H, t, J=1.5 Hz). IR(Neat) cm$^{-1}$: 1652, 1609, 1506. Mass m/z: 345(M$^+$).

Example 99

Preparation of 4-diethylaminomethyl-6-(4-fluoro-3-methylphenyl)-2-isobutyl-2H-pyridazin-3-one hydrochloride Following the procedure of Example 4, 4-diethylaminomethyl-6-(4-fluoro-3-methylphenyl)-2-isobutyl-2H-pyridazin-3-one was reacted to yield the title compound as slightly yellow needles (yield: 70.1%).

Melting point: 154.3–157.3° C. $^1$H NMR(400 MHz, CDCl$_3$)δ: 0.92(6H, d, J=6.8 Hz), 1.29(6H, t, J=7.2 Hz), 2.20–2.30(1H, m), 2.32(3H, d, J=1.2 Hz), 3.09–3.25(4H, m), 4.03(2H, d, J=7.3 Hz), 4.28(2H, d, J=5.6 Hz), 7.30(1H, dd, J=9.0, 9.0 Hz), 7.80(1H, ddd, J=2.0, 4.9, 9.0 Hz), 7.87(1H, dd, J=2.0, 7.3 Hz), 7.85(1H, t, J=1.5 Hz). IR(KBr) cm$^{-1}$: 2559, 2491, 1652, 1613, 1507.

Example 100

Preparation of 4-(4-tert-butoxycarbonyl-1-piperazinyl)methyl-6-(4-fluoro-3-methylphenyl)-2-isobutyl-2H-pyridazin-3-one Following the procedure of Example 1(10), 6-(4-fluoro-3-methylphenyl)-2-isobutyl-4-methanesulfonyloxymethyl-2H-pyridazin-3-one and tert-butyl 1-piperazinecarboxylate were reacted to yield the title compound as a slightly yellow oil (yield: 97.5%).

$^1$H NMR(400 MHz, CDCl$_3$)δ: 0.98(6H, d, J=6.6 Hz), 1.46(9H, s), 2.28–2.40(1H, m), 2.36(3H, d, J=1.7 Hz), 3.50 (4H, t, J=4.9 Hz), 3.58 (2H, d, J=1.0 Hz), 4.08(2H, d, J=7.3 Hz), 7.09(1H, dd, J=8.9, 8.9 Hz), 7.58(1H, ddd, J=2.0, 4.9, 8.9 Hz), 7.63(1H, dd, J=2.0, 7.3 Hz), 7.75(1H, s). IR(Neat) cm$^{-1}$: 1695, 1652, 1608, 1506.

Example 101

Preparation of 6-(4-fluoro-3-methylphenyl)-2-isobutyl-4-(1-piperazinyl)methyl-2H-pyridazin-3-one Following the procedure of Example 20, 4-(4-tert-butoxycarbonyl-1-piperazinyl)methyl-6-(4-fluoro-3-methylphenyl)-2-isobutyl-2H-pyridazin-3-one was reacted to yield the title compound as a pale yellow oil (yield: quantitative).
$^1$H NMR(400 MHz, CDCl$_3$)δ: 0.98(6H, d, J=6.8 Hz), 1.47(1H, br), 2.28–2.40(1H, m), 2.36(3H, d, J=1.7 Hz), 2.56(4H, t, J=4.9 Hz), 2.97(4H, t, J=4.9 Hz), 3.56(2H, d, J=1.4 Hz), 4.07(2H, d, J=7.3 Hz), 7.09(1H, dd, J=8.8, 8.8 Hz), 7.58(1H, ddd, J=2.0, 4.9, 8.8 Hz), 7.64(1H, dd, J=2.0, 7.3 Hz), 7.75(1H, t, J=1.4 Hz). IR(Neat) cm$^{-1}$: 3308, 1648, 1607, 1506. Mass m/z: 358(M$^+$).

Example 102

Preparation of 6-(4-fluoro-3-methylphenyl)-2-isobutyl-4-(1-piperazinyl)methyl-2H-pyridazin-3-one dihydrochloride Following the procedure of Example 4, 6-(4-fluoro-3-methylphenyl)-2-isobutyl-4-(1-piperazinyl)methyl-2H-pyridazin-3-one was reacted to yield the title compound as pale yellow prisms (yield: 87.2%).
Melting point: 154.9–158.0° C. $^1$H NMR(400 MHz, DMSO-d$_6$)δ: 0.94(6H, d, J=6.8 Hz), 2.19–2.30(1H, m), 2.32(3H, d, J=1.7 Hz), 3.04(4H, br), 3.71(4H, br), 4.01(2H, d, J=7.3 Hz), 7.28(1H, dd, J=8.8, 8.8 Hz), 7.76(1H, ddd, J=2.0, 4.9, 8.8 Hz), 7.83(1H, dd, J=2.0, 7.3 Hz), 8.40(1H, brs). IR(KBr) cm$^{-1}$: 1659, 1610, 1504, 1422.

Example 103

Preparation of 4-(4-tert-butoxycarbonyl-1-piperazinyl)methyl-6-(3,4-difluorophenyl)-2-isobutyl-2H-pyridazin-3-one 1) Preparation of ethyl 4-(3,4-difluorophenyl)-2-ethoxycarbonyl-2-hydroxy-4-oxobutanoate Following the procedure of Example 1(3), 3',4'-difluoroacetophenone was reacted to yield the title compound as a pale yellow oil (yield: 81.6%).
$^1$H NMR(400 MHz, CDCl$_3$)δ: 1.30(6H, t, J=7.1 Hz), 3.78(2H, s), 4.22(1H, s), 4.31(4H, q, J=7.1 Hz), 7.24–7.30 (1H, m), 7.73–7.82(2H, m). IR(Neat) cm$^{-1}$: 3483, 1740, 1695, 1612. Mass m/z: 312(M$^+$—H$_2$O).

2) Preparation of 4-carboxy-6-(3,4-difluorophenyl)-2H-pyridazin-3-one

Following the procedure of Example 1(4), ethyl 4-(3,4-difluorophenyl)-2-ethoxycarbonyl-2-hydroxy-4-oxobutanoate was reacted to yield the title compound as a pale yellow crystalline powder (yield: 88.9%).

3) Preparation of 4-methoxycarbonyl-6-(3,4-difluorophenyl)-2H-pyridazin-3-one

Following the procedure of Example 1(5), 4-carboxy-6-(3,4-difluorophenyl)-2H-pyridazin-3-one was reacted to yield the title compound as a pale yellow crystalline powder (yield: 85.8%).
$^1$H NMR(400 MHz, CDCl$_3$)δ: 4.01(3H, s), 7.25–7.32(1H, m), 7.53–7.57(1H, m), 7.67–7.73(1H, m), 8.31(1H, s), 11.70 (1H, br). IR(KBr) cm$^{-1}$: 3223, 3159, 1722, 1676, 1659. Mass m/z: 266(M$^+$).

4) Preparation of 6-(3,4-difluorophenyl)-2-isobutyl-4-methoxycarbonyl-2H-pyridazin-3-one Following the procedure of Example 1(6), 6-(3,4-difluorophenyl)-4-methoxycarbonyl-2H-pyridazin-3-one was reacted to yield the title compound as a yellow oil (yield: quantitative).
$^1$H NMR(400 MHz, CDCl$_3$)δ: 0.99(6H, d, J=6.8 Hz), 2.30–2.41(1H, m), 3.98(3H, s), 4.13(2H, d, J=7.2 Hz), 7.23–7.30(1H, m), 7.49–7.55(1H, m), 7.68(1H, ddd, J=2.2, 7.6, 11.1 Hz), 8.20(1H, s).

5) Preparation of 4-carboxy-6-(3,4-difluorophenyl)-2-isobutyl-2H-pyridazin-3-one Following the procedure of Example 1(7), 6-(3,4-difluorophenyl)-2-isobutyl-4-methoxycarbonyl-2H-pyridazin-3-one was reacted to yield the title compound as colorless fine-needles (yield: 91.4%).
Melting point: 163.4–163.7° C. $^1$H NMR(400 MHz, CDCl$_3$)δ: 1.02(6H, d, J=6.6 Hz), 2.33–2.43(1H, m), 4.22 (2H, d, J=7.4 Hz), 7.27–7.35(1H, m), 7.56–7.62(1H, m), 7.74(1H, ddd, J=2.4, 7.6, 11.2 Hz), 8.62(1H, s), 14.05(1H, s). IR(KBr) cm$^{-1}$: 3436, 1737, 1635, 1522, 1434, 1276, 1102, 806. Mass m/z: 308(M$^+$)

6) Preparation of 6-(3,4-difluorophenyl)-4-hydroxymethyl-2-isobutyl-2H-pyridazin-3-one Following the procedure of Example 1(8), 4-carboxy-6-(3,4-difluorophenyl)-2-isobutyl-2H-pyridazin-3-one was reacted to yield the title compound as colorless fine-needles (yield: 25.0%).
$^1$H NMR(400 MHz, CDCl$_3$)δ: 0.99(6H, d, J=6.8 Hz), 2.29–2.39(1H, m), 2.96(1H, t, J=5.9 Hz), 4.08(2H, d, J=7.4 Hz), 4.72(2H, dd, J=1.2, 5.8 Hz), 7.22–7.28(1H, m), 7.51–7.55(1H, m), 7.64–7.71(2H, m).

7) Preparation of 6-(3,4-difluorophenyl)-2-isobutyl-4-methanesulfonyloxymethyl-2H-pyridazin-3-one Following the procedure of Example 1(9), 6-(3,4-difluorophenyl)-4-hydroxymethyl-2-isobutyl-2H-pyridazin-3-one was reacted to yield the title compound as colorless fine-needles (yield: 81.4%).
Melting point: 113.3–113.4° C. $^1$H NMR(400 MHz, CDCl$_3$)δ: 0.99(6H, d, J=6.6 Hz), 2.27–2.40(1H, m), 3.18 (3H, s), 4.08(2H, d, J=7.4 Hz), 5.28(2H, d, J=1.6 Hz), 7.23–7.30(1H, m), 7.50–7.54(1H, m), 7.68(1H, ddd, J=2.2, 7.6, 11.1 Hz), 7.75(1H, t, J=1.4 Hz). IR(KBr) cm$^{-1}$: 3447, 1656, 1613, 1522, 1354, 1167, 1049, 877. Mass m/z: 372 (M$^+$)

8) Preparation of 4-(4-tert-butoxycarbonyl-1-piperazinyl)methyl-6-(3,4-di fluorophenyl)-2-isobutyl-2H-pyridazin-3-one Following the procedure of Example 1(10), 6-(3,4-difluorophenyl)-2-isobutyl-4-methanesulfonyloxymethyl-2H-pyridazin-3-one and tert-butyl 1-piperazinecarboxylate were reacted to yield the title compound as a yellow oil (yield: 85.5%).

¹H NMR(400 MHz, CDCl₃)δ: 0.98(6H, d, J=6.6 Hz), 1.47(9H, s), 2.28–2.38(1H, m), 2.52(4H, t, J=4.7 Hz), 3.51 (4H, t, J=4.7 Hz), 3.58(2H, s), 4.07(2H, d, J=7.2 Hz), 7.21–7.29(1H,m), 7.50–7.55(1H,m), 7.64–7.71(1H, m), 7.76(1H, d, J=1.0 Hz).

Example 104

Preparation of 6-(3,4-difluorophenyl)-2-isobutyl-4-(1-piperazinyl)methyl-2H-pyridazin-3-one dihydrochloride Following the procedure of Example 2, 4-(4-tert-butoxycarbonyl-1-piperazinyl)methyl-6-(3,4-difluorophenyl)-2-isobutyl-2H-pyridazin-3-one was reacted to yield the title compound as a white solid (yield: 72.5%).
Melting point: 182.5–186.0° C. ¹H NMR(400 MHz, DMSO-d₆)δ: 0.94(6H, d, J=6.6 Hz), 2.22–2.33(1H,m), 3.11 (4H,br), 3.30(4H, t, J=5.1 Hz), 3.90(2H, s), 4.02(2H, d, J=7.1 Hz), 7.52(1H, ddd, J=8.6, 8.6, 10.5 Hz), 7.73–7.78 (1H, m), 7.90(1H, ddd, J=2.2, 8.0, 11.7 Hz), 8.20(1H, s). IR(KBr) cm⁻¹: 1656, 1609, 1522, 1436, 1276, 1112. Mass m/z: 362(M⁺)

Example 105

Preparation of 6-(3,4-difluorophenyl)-2-isobutyl-4-(4-methyl-1-piperazinyl)methyl-2H-pyridazin-3-one Following the procedure of Example 1(10), 6-(3,4-difluorophenyl)-2-isobutyl-4-methanesulfonyloxymethyl-2H-pyridazin-3-one and 1-methylpiperazine were reacted to yield the title compound as a yellow oil (yield: 79.1%).
¹H NMR(400 MHz, CDCl₃)δ: 0.98(6H, d, J=6.8 Hz), 2.28–2.39(1H, m), 2.34(3H, s), 2.55(4H, br), 2.63(4H, br), 3.58(2H, s), 4.07(2H, d, J=7.2 Hz), 7.22–7.29(1H,m), 7.50–7.57(1H,m), 7.64–7.72(1H,m), 7.74(1H, s).

Example 106

Preparation of 6-(3,4-difluorophenyl)-2-isobutyl-4-(4-methyl-1-piperazinyl)methyl-2H-pyridazin-3-one dihydrochloride Following the procedure of Example 4, 6-(3,4-difluorophenyl)-2-isobutyl-4-(4-methyl-1-piperazinyl)methyl-2H-pyridazin-3-one was reacted to yield the title compound as a colorless crystalline powder (yield: 70.3%).
Melting point: 242.5–243.4° C. ¹H NMR(400 MHz, DMSO-d₆)δ: 0.94(6H, d, J=6.8 Hz), 2.22–2.33(1H, m), 2.77(3H, s), 3.11(4H, br), 3.34(4H, br), 3.84(2H, s), 4.02 (2H, d, J=7.1 Hz), 7.52(1H, ddd, J=8.6, 8.6, 10.5 Hz), 7.72–7.77(1H, m), 7.89(1H, ddd, J=2.2, 7.9, 11.7 Hz), 8.12(1H, s). IR(KBr) cm⁻¹: 1652, 1607, 1522, 1435, 1278. Mass m/z: 376(M⁺)

Example 107

Preparation of 4-N,N-bis(2-hydroxyethyl)aminomethyl-6-(3,4-difluorophenyl)-2-isobutyl-2H-pyridazin-3-one Following the procedure of Example 1(10), 6-(3,4-difluorophenyl)-2-isobutyl-4-methanesulfonyloxymethyl-2H-pyridazin-3-one and diethanolamine were reacted to yield the title compound as a yellow oil (yield: 75.8%).

¹H NMR(400 MHz, CDCl₃)δ: 0.97(6H, d, J=6.6 Hz), 2.25–2.38(1H, m), 2.70(4H, br), 3.64–3.70(6H, m), 4.06 (2H, d, J=7.4 Hz), 7.15–7.25(1H, m), 7.54–7.58(1H, m), 7.67–7.73(1H, m), 7.88(1H, s).

Example 108

Preparation of 4-N,N-bis(2-hydroxyethyl)aminomethyl-6-(3,4-difluorophenyl)-2-isobutyl-2H-pyridazin-3-one hydrochloride Following the procedure of Example 4, 4-N,N-bis(2-hydroxyethyl)aminomethyl-6-(3,4-difluorophenyl)-2-isobutyl-2H-pyridazin-3-one was reacted to yield the title compound as a white solid (yield: 70.3%).
Melting point: 127.5–128.3° C. ¹H NMR(400 MHz, DMSO₆)δ: 0.95(6H, d, J=6.8 Hz), 2.23–2.34(1H, m), 3.35 (4H, t, J=5.1 Hz), 3.84(4H, t, J=5.1 Hz), 4.05(2H, d, J=7.1 Hz), 4.45(2H, s), 7.54(1H, ddd, J=8.6, 8.6, 10.5 Hz), 7.76–7.81(1H, m), 7.93(1H, ddd, J=2.2, 7.8, 12.0 Hz), 8.53(1H, s). IR(KBr) cm⁻¹: 1653, 1604, 1521, 1437, 1275. Mass m/z: 363(M⁺—H₂O)

Example 109

Preparation of 6-(3,4-difluorophenyl)-4-dimethylaminomethyl-2-isobutyl-2H-pyridazin-3-one Following the procedure of Example 7, 6-(3,4-difluorophenyl)-2-isobutyl-4-methanesulfonyloxymethyl-2H-pyridazin-3-one was reacted to yield the title compound as a yellow oil (yield: 85.5%).
¹H NMR(400 MHz, CDCl₃)δ: 0.98(6H, d, J=6.6 Hz), 2.29–2.40(1H, m), 2.35(6H, s), 3.50(2H, s), 4.07(2H, d, J=7.4 Hz), 7.20–7.30(1H, m), 7.53–7.60(1H, m), 7.67–7.73 (1H, m), 7.74(1H, s).

Example 110

Preparation of 6-(3,4-difluorophenyl)-4-dimethylaminomethyl-2-isobutyl-2H-pyridazin-3-one hydrochloride Following the procedure of Example 4, 6-(3,4-difluorophenyl)-4-dimethylaminomethyl-2-isobutyl-2H-pyridazin-3-one was reacted to yield the title compound as slightly yellow flakes (yield: 85.9%).
Melting point: 226.5–227.7° C. ¹H NMR(400 MHz, DMSO-d₆)δ: 0.96(6H, d, J=6.8 Hz), 2.23–2.34(1H, m), 2.81(6H, s), 4.05(2H, d, J=7.1 Hz), 4.28(2H, s), 7.54(ddd, J=8.7, 8.7, 10.5 Hz), 7.76–7.81(1H, m), 7.93(1H, ddd, J=2.2, 7.9, 12.0 Hz), 8.57(1H, s). IR(KBr) cm⁻¹: 1648, 1607, 1525, 1437, 1288, 1112. Mass m/z: 321(M⁺)

Example 111

Preparation of 4-aminomethyl-6-(2,4-difluorophenyl)-2-isobutyl-2H-pyridazin-3-one 1) Preparation of ethyl 4-(2,4-difluorophenyl)-2-ethoxycarbonyl-2-hydroxy-4-oxobutanoate Following the procedure of Example 1(3), 2',4'-difluoroacetophenone was reacted to yield the title compound as a pale yellow oil (yield: 76.8%).
¹H NMR(400 MHz, CDCl₃)δ: 1.30(6H, t, J=7.1 Hz), 3.81(2H, d, J=3.4 Hz), 4.18(1H, s), 4.30(4H, q, J=7.1 Hz), 6.90(1H, ddd, J=2.4, 8.5, 10.0 Hz), 6.94–7.00(1H, m), 7.94(1H, ddd, J=6.6, 8.5, 8.5 Hz). IR(Neat) cm$^{-1}$: 3491, 1743, 1692, 1612. Mass m/z: 312(M$^+$—H$_2$O)

2) Preparation of 4-carboxy-6-(2,4-difluorophenyl)-2H-pyridazin-3-one

Following the procedure of Example 1(4), ethyl 4-(2,4-difluorophenyl)-2-ethoxycarbonyl-2-hydroxy-4-oxobutanoate was reacted to yield the title compound as a pale yellow crystalline powder (yield: 95.2%).

3) Preparation of 6-(2,4-difluorophenyl)-4-methoxycarbonyl-2H-pyridazin-3-one Following the procedure of Example 1(5), 4-carboxy-6-(2,4-difluorophenyl)-2H-pyridazin-3-one was reacted to yield the title compound as a pale yellow crystalline powder (yield: 81.2%).

$^1$H NMR(400 MHz, CDCl$_3$)δ: 3.99(3H, s), 6.96(1H, ddd, J=2.4, 8.8, 10.1 Hz), 6.99–7.04(1H, m), 7.77(1H, ddd, J=6.3, 8.8, 8.8 Hz), 8.30(1H, d, J=2.0 Hz), 12.05(1H, br). IR(KBr) cm$^{-1}$: 3217, 3148, 1721, 1673, 1611. Mass m/z: 266(M$^+$).

4) Preparation of 6-(2,4-difluorophenyl)-2-isobutyl-4-methoxycarbonyl-2H-pyridazin-3-one Following the procedure of Example 1(6), 6-(2,4-difluorophenyl)-4-methoxycarbonyl-2H-pyridazin-3-on e was reacted to yield the title compound as a pale yellow oil (yield: 84.8%).

$^1$H NMR(400 MHz, CDCl$_3$)δ: 0.99(6H, d, J=6.6 Hz), 2.29–2.42(1H, m), 3.97(3H, s), 4.12(2H, d, J=7.3 Hz), 6.94(1H, ddd, J=2.4, 8.8, 11.2 Hz), 6.98–7.04(1H, m), 7.73(1H, ddd, J=6.3, 6.3, 8.8 Hz), 8.18(1H, d, J=2.0 Hz). IR(Neat) cm$^{-1}$: 1755, 1748, 1668, 1620, 1506. Mass m/z: 322(M$^+$).

5) Preparation of 4-carboxy-6-(2,4-difluorophenyl)-2-isobutyl-2H-pyridazin-3-one Following the procedure of Example 1(7), 6-(2,4-difluorophenyl)-2-isobutyl-4-methoxycarbonyl-2H-pyridazin-3-one was reacted to yield the title compound as slightly yellow needles (yield: 92.7%).

Melting point: 126.5–128.2° C. $^1$H NMR(400 MHz, CDCl$_3$)δ: 1.02(6H, d, J=6.6 Hz), 2.31–2.43(1H, m), 4.22 (2H, d, J=7.6 Hz), 6.96–7.07(2H, m), 7.74(1H, ddd, J=6.3, 6.3, 8.8 Hz), 8.61(1H, d, J=2.2 Hz), 14.02(1H, s). IR(KBr) cm$^{-1}$: 1739, 1636, 1618, 1573, 1465. Mass m/z: 308(M$^+$).

6) Preparation of 6-(2,4-difluorophenyl)-4-hydroxymethyl-2-isobutyl-2H-pyridazin-3-one Following the procedure of Example 1(8), 4-carboxy-6-(2,4-difluorophenyl)-2-isobutyl-2H-pyridazin-3-one was reacted to yield the title compound as a pale yellow oil (yield: 45.0%).

$^1$H NMR(400 MHz, CDCl$_3$)δ: 0.98(6H, d, J=6.8 Hz), 2.27–2.40(1H, m), 3.15(1H, t, J=6.1 Hz), 4.08(2H, d, J=7.3 Hz), 4.69(2H, dd, J=1.2, 6.1 Hz), 6.93(1H, ddd, J=2.4, 8.8, 11.2 Hz), 6.96–7.02(1H, m), 7.61–7.63(1H, m), 7.72(1H, ddd, J=6.3, 6.3, 8.8 Hz). IR(Neat) cm$^{-1}$: 3412, 1652, 1620, 1507. Mass m/z: 294(M$^+$).

7) Preparation of 6-(2,4-difluorophenyl)-2-isobutyl-4-methanesulfonyloxymethyl-2H-pyridazin-3-one Following the procedure of Example 1(9), 6-(2,3-difluorophenyl)-4-hydroxymethyl-2-isobutyl-2H-pyridazin-3-one was reacted to yield the title compound as colorless needles (yield: 96.3%).

Melting point: 86.7–88.6° C. $^1$H NMR(400 MHz, CDCl$_3$) δ: 0.99(6H, d, J=6.8 Hz), 2.26–2.39(1H, m), 3.16(3H, s), 4.08(2H, d, J=7.3 Hz), 5.26(2H, d, J=1.2 Hz), 6.94(1H, ddd, J=2.4, 8.8, 11.2 Hz), 6.97–7.03(1H, m), 7.71(1H, ddd, J=6.3, 6.3, 8.8 Hz), 7.73–7.75(1H, m). IR(KBr) cm$^{-1}$: 1659, 1612, 1508, 1359, 1166. Mass m/z: 372(M$^+$).

8) Preparation of 6-(2,4-difluorophenyl)-2-isobutyl-4-phthalimidomethyl-2H-pyridazin-3-one Following the procedure of Example 24(1), 6-(2,4-difluorophenyl)-2-isobutyl-4-methanesulfonyloxymethyl-2H-pyridazin-3-one was reacted to yield the title compound as colorless needles (yield: 91.1%).

Melting point: 152.3–155.6° C. $^1$H NMR(400 MHz, CDCl$_3$)δ: 0.98(6H, d, J=6.6 Hz), 2.28–2.39(1H, m), 4.07 (2H, d, J=7.3 Hz), 4.89(2H, d, J=1.0 Hz), 6.83(1H, ddd, J=2.4, 8.8, 11.0 Hz), 6.91–6.97(1H, m), 7.27–7.31(1H, m), 7.66(1H, ddd, J=6.3, 6.3, 8.8 Hz), 7.74–7.80(2H, m), 7.86–7.94(2H, m). IR(KBr) cm$^{-1}$: 1773, 1720, 1650, 1617, 1509, 1418, 1389. Mass m/z: 423(M$^+$).

9) Preparation of 4-aminomethyl-6-(2,4-difluorophenyl)-2-isobutyl-2H-pyridazin-3-one Following the procedure of Example 24(2), 2-isobutyl-6-(2,4-difluorophenyl)-4-phthalimidomethyl-2H-pyridazin-3-one was reacted to yield the title compound as a slightly yellow oil (yield: 98.4%).

$^1$H NMR(400 MHz, CDCl$_3$)δ: 0.98(6H, d, J=6.8 Hz), 1.66(2H, br), 2.24–2.41(1H, m), 3.87(2H, s), 4.08(2H, d, J=7.3 Hz), 6.92(1H, ddd, J=2.4, 8.8, 11.2 Hz), 6.97–7.02 (1H, m), 7.63(1H, t, J=1.1 Hz), 7.71(1H, ddd, J=6.3, 6.3, 8.8 Hz). IR(Neat) cm$^{-1}$: 3381, 3307, 1652, 1611, 1508. Mass m/z: 293(M$^+$).

Example 112

Preparation of 4-aminomethyl-6-(2,4-difluorophenyl)-2-isobutyl-2H-pyridazin-3-one hydrochloride Following the procedure of Example 4, 4-aminomethyl-6-(2,4-difluorophenyl)-2-isobutyl-2H-pyridazin-3-one was reacted to yield the title compound as slightly yellow needles (yield: 94.9%).

Melting point: 161.4–163.9° C. $^1$H NMR(400 MHz, DMSO-d$_6$)δ: 0.93(6H, d, J=6.8 Hz), 2.18–2.34(1H, m), 4.01(2H, s), 4.02(2H, d, J=7.3 Hz), 7.24–7.31(1H, m), 7.46(1H, ddd, J=2.4, 8.8, 11.5 Hz), 7.76(1H, ddd, J=6.3, 6.3, 8.8 Hz), 7.95(1H, s). IR(KBr) cm$^{-1}$: 1652, 1616, 1597, 1509.

Example 113

Preparation of 6-(2,4-difluorophenyl)-4-dimethylaminomethyl-2-isobutyl-2H-pyridazin-3-one Following the procedure of Example 7, 6-(2,4-difluorophenyl)-2-isobutyl-4-methanesulfonyloxymethyl-2H-pyridazin-3-one was reacted to yield the title compound as a slightly yellow oil (yield: 94.1%).

$^1$H NMR(400 MHz, CDCl$_3$)δ: 0.98(6H, d, J=6.8 Hz), 2.27–2.38(1H, m), 2.34(6H, s), 3.49(2H, d, J=1.5 Hz), 4.07(2H, d, J=7.6 Hz), 6.92(1H, ddd, J=2.4, 8.8, 11.2 Hz), 6.95–7.01(1H, m), 7.70(1H, t, J=1.5 Hz), 7.71(1H, ddd, J=6.3, 6.3, 8.8 Hz). IR(Neat) cm$^{-1}$: 1652, 1612, 1508. Mass m/z: 321(M$^+$).

Example 114

Preparation of 6-(2,4-difluorophenyl)-4-dimethylaminomethyl-2-isobutyl-2H-pyridazin-3-one hydrochloride Following the procedure of Example 4, 6-(2,4-difluorophenyl)-4-dimethylaminomethyl-2-isobutyl-2H-pyridazin-3-one was reacted to yield the title compound as pale yellow prisms (yield: 89.8%).

Melting point: 170.1–173.5° C. $^1$H NMR(400 MHz, DMSO-d$_6$)δ: 0.94(6H, d, J=6.8 Hz), 2.18–2.29(1H, m), 2.80(6H, s), 4.03(2H, d, J=7.3 Hz), 4.30(2H, s), 7.25–7.31(1H, m), 7.45(1H, ddd, J=2.4, 8.8, 11.2 Hz), 7.81(1H, ddd, J=6.3, 6.3, 8.8 Hz). 8.15(1H, d, J=1.7 Hz), IR(KBr) cm$^{-1}$: 1648, 1612, 1523, 1510.

Example 115

Preparation of 4-diethylaminomethyl-6-(2,4-difluorophenyl)-2-isobutyl-2H-pyridazin-3-one Following the procedure of Example 9(4), 6-(2,4-difluorophenyl)-2-isobutyl-4-methanesulfonyloxymethyl-2H-pyridazin-3-one and diethylamine were reacted to yield the title compound as a pale yellow oil (yield: quantitative)

$^1$H NMR(400 MHz, CDCl$_3$)δ: 0.98(6H, d, J=6.8 Hz), 1.06(6H, t, J=7.1 Hz), 2.27–2.39(1H, m), 2.59(4H, q, J=7.1 Hz), 3.59(2H, d, J=1.7 Hz), 4.07(2H, d, J=7.3 Hz), 6.92 (1H, ddd, J=2.4, 8.8, 11.2 Hz), 6.95–7.01 (1H, m), 7.72(1H, ddd, J=6.3, 6.3, 8.8 Hz), 7.83(1H, td, J=1.5, 2.9 Hz). IR(Neat) cm$^{-1}$: 1656, 1613, 1508. Mass m/z: 349(M$^+$).

Example 116

Preparation of 4-diethylaminomethyl-6-(2,4-difluorophenyl)-2-isobutyl-2H-pyridazin-3-one hydrochloride Following the procedure of Example 4, 4-diethylaminomethyl-6-(2,4-difluorophenyl)-2-isobutyl-2H-pyridazin-3-one was reacted to yield the title compound as colorless needles (yield: 80.9%).

Melting point: 128.9–131.7° C. $^1$H NMR(400 MHz, DMSO-d$_6$)δ: 0.94(6H, d, J=6.8 Hz), 1.28(6H, t, J=7.2 Hz), 2.18–2.29(1H, m), 3.10–3.23(4H, m), 4.03(2H, d, J=7.3 Hz), 4.29(2H, d, J=5.4 Hz), 7.28(1H, ddd, J=2.2, 8.8, 8.8 Hz), 7.45(1H, ddd, J=2.2, 8.8, 8.8 Hz), 7.81(1H, ddd, J=6.3, 8.8, 8.8 Hz), 8.24(1H, d, J=1.5 Hz).

Example 117

Preparation of 4-N,N-bis(2-hydroxyethyl)aminomethyl-6-(2,4-difluorophenyl)-2-isobutyl-2H-pyridazin-3-one Following the procedure of Example 1(10), 6-(2,4-difluorophenyl)-2-isobutyl-4-methanesulfonyloxymethyl-2H-pyridazin-3-one and diethanolamine were reacted to yield the title compound as a slightly yellow oil (yield: 97.6%).

$^1$H NMR(400 MHz, CDCl$_3$)δ: 0.97(6H, d, J=6.6 Hz), 2.26–2.40(1H, m), 2.70(4H, t, J=5.0 Hz), 3.65(4H, t, J=5.0 Hz), 3.70(2H, s), 4.09(2H, d, J=7.3 Hz), 6.92(1H, ddd, J=2.7, 8.8, 11.2 Hz), 6.97–7.03(1H, m), 7.63(1H, d, J=2.4 Hz), 7.75(1H, ddd, J=6.3, 6.3, 8.8 Hz). IR(Neat) cm$^{-1}$: 3401, 1648, 1597, 1508. Mass m/z: 363(M$^+$—H$_2$O).

Example 118

Preparation of 4-N,N-bis(2-hydroxyethyl)aminomethyl-6-(2,4-difluorophenyl)-2-isobutyl-2H-pyridazin-3-one hydrochloride Following the procedure of Example 4, 4-N,N-bis(2-hydroxyethyl)aminomethyl-6-(2,4-difluorophenyl)-2-isobutyl-2H-pyridazin-3-one was reacted to yield the title compound as slightly yellow prisms (yield: 89.0%).

Melting point: 161.8–163.9° C. $^1$H NMR(400 MHz, DMSO-d$_6$)δ: 0.93(6H, d, J=6.6 Hz), 2.18–2.29(1H, m), 3.27–3.40(4H, br, overlapped with H$_2$O), 3.76–3.84(4H, m), 4.03(2H, d, J=7.3 Hz), 4.51(2H, brs), 5.34(2H, br), 7.24–7.31(1H, m), 7.41–7.48(1H, m), 7.76–7.84(1H, m), 8.15(1H, m). IR(KBr) cm$^{-1}$: 3233, 3172, 1645, 1613, 1593, 1421.

Example 119

Preparation of 6-(2,4-difluorophenyl)-2-isobutyl-4-(4-methyl-1-piperazinyl)methyl-2H-pyridazin-3-one Following the procedure of Example 1(10), 6-(2,4-difluorophenyl)-2-isobutyl-4-methanesulfonyloxymethyl-2H-pyridazin-3-one and 1-methylpiperazine were reacted to yield the title compound as a pale yellow oil (yield: 94.0%).

$^1$H NMR(400 MHz, CDCl$_3$)δ: 0.97(6H, d, J=6.6 Hz), 2.28–2.38(1H, m), 2.31(3H, s), 2.50(4H, br), 2.61(4H, br), 3.57(2H, d, J=1.5 Hz), 4.07(2H, d, J=7.3 Hz), 6.93(1H, ddd, J=2.4, 8.8, 11.2 Hz), 6.96–7.02(1H, m), 7.69–7.75(2H, m). IR(Neat) cm$^{-1}$: 1655, 1616, 1596, 1508. Mass m/z: 376 (M$^+$).

Example 120

Preparation of 6-(2,4-difluorophenyl)-2-isobutyl-4-(4-methyl-1-piperazinyl)methyl-2H-pyridazin-3-one dihydrochloride Following the procedure of Example 4, 6-(2,4-difluorophenyl)-2-isobutyl-4-(4-methyl-1-piperazinyl)methyl-2H-pyridazin-3-one was reacted to yield the title compound as colorless needles (yield: 90.4%).

Melting point: 248.1–251.7° C. (dec.). $^1$H NMR(400 MHz, DMSO-d$_6$, 100° C.)δ: 0.93(6H, d, J=6.8 Hz), 2.20–2.29(1H, m), 2.76(3H, s), 3.09(4H, br, overlapped with H$_2$O), 3.27(4H, br), 3.74(2H, s), 4.00(2H, d, J=7.1 Hz), 7.14–7.29(2H, m), 7.71–7.79(2H, m). IR(KBr) cm$^{-1}$: 1652, 1612, 1514.

Example 121

Preparation of 4-(4-tert-butoxycarbonyl-1-piperazinyl)methyl-6-(2,4-difluorophenyl)-2-isobutyl-2H-pyridazin-3-one Following the procedure of Example 1(10), 6-(2,4-difluorophenyl)-2-isobutyl-4-methanesulfonyloxymethyl-2H-pyridazin-3-one and tert-butyl 1-piperazinecarboxylate were reacted to yield the title compound as a slightly yellow oil (yield: 97.5%).

$^1$H NMR(400 MHz, CDCl$_3$)δ: 0.98(6H, d, J=6.8 Hz), 1.47(9H, s), 2.28–2.39(1H, m), 2.52(4H, t, J=4.9 Hz), 3.49 (4H, t, J=4.9 Hz), 3.57(2H, d, J=1.2 Hz), 4.07(2H, d, J=7.3 Hz), 6.93(1H, ddd, J=2.4, 8.8, 11.2 Hz), 6.96–7.02(1H, m), 7.69–7.75(2H, m). IR(Neat) cm$^{-1}$: 1695, 1655, 1613, 1508, 1425. Mass m/z: 462(M$^+$).

Example 122

Preparation of 6-(2,4-difluorophenyl)-2-isobutyl-4-(1-piperazinyl)methyl-2H-pyridazin-3-one Following the procedure of Example 20, 4-(4-tert-butoxycarbonyl-1-piperazinyl)methyl-6-(2,4-difluorophenyl)-2-isobutyl-2H-pyridazin-3-one was reacted to yield the title compound as a pale yellow oil (yield: quantitative)

$^1$H NMR(400 MHz, CDCl$_3$)δ: 0.98(6H, d, J=6.8 Hz), 1.81(1H, br), 2.27–2.39(1H, m), 2.50–2.56(4H, brm), 2.94 (4H, t, J=4.8 Hz), 3.54(2H, d, J=1.2 Hz), 4.07(2H, d, J=7.3 Hz), 6.93(1H, ddd, J=2.4, 8.8, 11.2 Hz), 6.94–7.02(1H, m), 7.69–7.76(2H, m). IR(Neat) cm$^{-1}$: 3314, 1655, 1613, 1508. Mass m/z: 362(M$^+$).

Example 123

Preparation of 6-(2,4-difluorophenyl)-2-isobutyl-4-(1-piperazinyl)methyl-2H-pyridazin-3-one dihydrochloride Following the procedure of Example 4, 6-(2,4-difluorophenyl)-2-isobutyl-4-(1-piperazinyl)methyl-2H-pyridazin-3-one was reacted to yield the title compound as a slightly yellow crystalline powder (yield: 90.8%).

Melting point: 136.3–140.9° C. $^1$H NMR(400 MHz, DMSO-d$_6$)δ: 0.93(6H, d, J=6.6 Hz), 2.20–2.30(1H, m), 2.95(4H, t, J=5.0 Hz), 3.02(4H, t, J=5.0 Hz), 3.76(2H, s), 4.00(2H, d, J=7.3 Hz), 7.14–7.20(1H, m), 7.26(1H, ddd, J=2.7, 8.8, 11.2 Hz), 7.86(1H, ddd, J=6.6, 6.6, 8.8 Hz), 7.81(1H, s). IR(KBr) cm$^{-1}$: 1656, 1616, 1597, 1509, 1426.

Example 124

Preparation of 2-benzyl-4-(4-tert-butoxycarbonyl-1-piperazinyl)methyl-6-(4-fluoro-3-methylphenyl)-2H-pyridazin-3-one 1) Preparation of 2-benzyl-6-(4-fluoro-3-methylphenyl)-4-methoxycarbonyl-2H-pyridazin-3-one Following the procedure of Example 1(6), 6-(4-fluoro-3-methylphenyl)-4-methoxycarbonyl-2H-pyridazin-3-one and benzyl chloride were reacted to yield the title compound as yellow needles (yield: 71.0%).

Melting point: 109.0–110.5° C. $^1$H NMR(400 MHz, CDCl$_3$)δ: 2.35(3H, d, J=1.7 Hz), 3.96(3H, s), 5.44(2H, s), 7.10(1H, dd, J=8.8, 8.8 Hz), 7.28–7.37(3H, m), 7.52(2H, d, J=6.3 Hz), 7.57–7.64(2H, m), 8.21(1H, s). IR(KBr) cm$^{-1}$: 1750, 1744, 1657, 1278, 1233, 1123. Mass m/z: 352(M$^+$).

2) Preparation of 2-benzyl-4-carboxy-6-(4-fluoro-3-methylphenyl)-2H-pyridazin-3-one Following the procedure of Example 1(7), 2-benzyl-6-(4-fluoro-3-methylphenyl)-4-methoxycarbonyl-2H-pyridazin-3-one was reacted to yield the title compound as a pale yellow crystalline powder (yield: 65.2%).

Melting point: 191.2–192.3° C. $^1$H NMR(400 MHz, CDCl$_3$)δ: 2.37(3H, d, J=2.0 Hz), 5.52(2H, s), 7.13(1H, dd, J=8.8, 8.8 Hz), 7.33–7.41(3H, m), 7.48–7.52(2H, m), 7.64–7.70(2H, m), 8.62(1H, s), 14.01(1H, br). IR(KBr) cm$^{-1}$: 1739, 1633, 1569, 1457, 1423, 1240. Mass m/z: 338(M$^+$).

3) Preparation of 2-benzyl-6-(4-fluoro-3-methylphenyl)-4-hydroxymethyl-2H-pyridazin-3-one Following the procedure of Example 1(8), 2-benzyl-4-carboxy-6-(4-fluoro-3-methylphenyl)-2H-pyridazin-3-one was reacted to yield the title compound as slightly yellow needles (yield: 28.4%).

Melting point: 119.5–120.6° C. $^1$H NMR(400 MHz, CDCl$_3$)δ: 2.34(3H, d, J=1.7 Hz), 3.01(1H, t, J=5.9 Hz), 4.70(2H, dd, J=1.2, 5.9 Hz), 5.41(2H, s), 7.08 (1H, dd, J=8.8, 8.8 Hz), 7.27–7.37(3H, m), 7.48(1H, d, J=6.6 Hz), 7.57–7.65(2H, m) 7.66(1H, t, J=1.2 Hz). IR(KBr) cm$^{-1}$: 3330, 1657, 1643, 1611, 1597, 1506, 1239. Mass m/z: 324(M$^+$).

4) Preparation of 2-benzyl-6-(4-fluoro-3-methylphenyl)-4-methanesulfonyloxymethyl-2H-pyridazin-3-one Following the procedure of Example 1(9), 2-benzyl-6-(4-fluoro-3-methylphenyl)-4-hydroxymethyl-2H-pyridazin-3-one was reacted to yield the title compound as slightly yellow needles (yield: 98.9%).

Melting point: 147.6–148.3° C. $^1$H NMR(400 MHz, CDCl$_3$)δ: 2.35(3H, d, J=2.0 Hz), 3.15(3H, s), 5.26(2H, d, J=1.2 Hz), 5.41(2H, s), 7.09 (1H, dd, J=8.8, 8.8 Hz), 7.27–7.37(3H, m), 7.47(2H, d, J=6.6 Hz), 7.62(1H, d, J=7.3 Hz), 7.57–7.60(1H, m), 7.75(1H, s). IR(KBr) cm$^{-1}$: 1656, 1617, 1507, 1355, 1168, 1033, 879. Mass m/z: 402(M$^+$).

5) Preparation of 2-benzyl-4-(4-tert-butoxycarbonyl-1-piperazinyl)methyl-6-(4-fluoro-3-methylphenyl)-2H-pyridazin-3-one Following the procedure of Example 1(10), 2-benzyl-6-(4-fluoro-3-methylphenyl)-4-methanesulfonyloxymethyl-2H-pyridazin-3-one and tert-butyl 1-piperazinecarboxylate were reacted to yield the title compound as a yellow oil (yield: 91.8%).

$^1$H NMR(400 MHz, CDCl$_3$)δ: 1.46(9H, s), 2.35(3H, d, J=1.8 Hz), 2.50(4H, t, J=4.9 Hz), 3.49(4H, t, J=4.9 Hz), 3.56(2H, d, J=1.4 Hz), 5.40(2H, s), 7.26–7.36(4H, m), 7.49(2H, d, J=6.6 Hz), 7.55–7.60(1H, m), 7.63(1H, dd, J=1.8, 7.2 Hz), 7.74(1H, s).

Example 125

Preparation of 2-benzyl-6-(4-fluoro-3-methylphenyl)-4-(1-piperazinyl)methyl-2H-pyridazin-3-one dihydrochloride Following the procedure of Example 2, 2-benzyl-4-(4-tert-butoxycarbonyl-1-piperazinyl)methyl-6-(4-fluoro-3-methylphenyl)-2H-pyridazin-3-one was reacted to yield the title compound as a colorless crystalline powder (yield: 60.9%).

Melting point: 162.7–180.7° C. (dec.) $^1$H NMR(400 MHz, DMSO-$d_6$)δ: 2.31(3H, d, J=2.0 Hz), 3.09(4H, br), 3.28(4H, t, J=5.2 Hz), 3.89(2H, s), 5.36(2H, s), 7.21–7.40 (6H, m), 7.70–7.76(1H, m), 7.79(1H, dd, J=1.7, 7.3 Hz), 8.16(1H, s). IR(KBr) cm$^{-1}$: 1656, 1607, 1505, 1239, 1126, 700. Mass m/z: 392(M$^+$)

Example 126

Preparation of 2-benzyl-6-(4-fluoro-3-methylphenyl)-4-(4-methyl-1-piperazinyl)methyl-2H-pyridazin-3-one Following the procedure of Example 1(10), 2-benzyl-6-(4-fluoro-3-methylphenyl)-4-methanesulfonyloxymethyl-2H-pyridazin-3-one and 1-methylpiperazine were reacted to yield the title compound as a yellow oil (yield: 81.3%).

$^1$H NMR(400 MHz, CDCl$_3$)δ: 2.33(3H, s), 2.36(3H, d, J=1.8 Hz), 2.53(4H, br), 2.61(4H, br), 3.57(2H, d, J=1.4 Hz), 5.40(2H, s), 7.08(1H, t, J=8.9 Hz), 7.26–7.36(3H, m), 7.49 (2H, d, J=6.8 Hz), 7.56–7.60(1H, m), 7.64(1H, dd, J=1.8, 7.2 Hz), 7.73(1H, s).

Example 127

Preparation of 2-benzyl-6-(4-fluoro-3-methylphenyl)-4-(4-methyl-1-piperazinyl)methyl-2H-pyridazin-3-one dihydrochloride Following the procedure of Example 4, 2-benzyl-6-(4-fluoro-3-methylphenyl)-4-(4-methyl-1-piperazinyl)methyl-2H-pyridazin-3-one was reacted to yield the title compound as a colorless crystalline powder (yield: 78.6%).

Melting point: 240.0–242.5° C. (dec.) $^1$H NMR(400 MHz, DMSO-$d_6$)δ: 2.31(3H, d, J=1.7 Hz), 2.76(3H, s), 3.10(4H, br), 3.33(4H, br), 3.84 (2H, s), 5.36 (2H, s), 7.21–7.39 (6H, m), 7.69–7.74 (1H, m), 7.78(1H, dd, J=2.1, 7.8 Hz), 8.09(1H, s). IR(KBr) cm$^{-1}$: 1653, 1607, 1504, 1454, 1240, 1127. Mass m/z: 406(M$^+$)

Example 128

Preparation of 2-benzyl-4-N,N-bis(2-hydroxyethyl) aminomethyl-6-(4-fluoro-3-methylphenyl)-2H-pyridazin-3-one Following the procedure of Example 1(10), 2-benzyl-6-(4-fluoro-3-methylphenyl)-4-methanesulfonyloxymethyl-2H-pyridazin-3-one and diethanolamine were reacted to yield the title compound as a yellow oil (yield: 87.6%).

$^1$H NMR(400 MHz, CDCl$_3$)δ: 2.33(3H, s), 2.69(4H, t, J=4.9 Hz), 3.64(4H, t, J=5.0 Hz), 3.68(2H, s), 5.40(2H, s), 7.06(1H, t, J=8.9 Hz), 7.26–7.38(3H, m), 7.45(2H, d, J=7.0 Hz), 7.58–7.68(2H, m), 7.75(1H, s).

Example 129

Preparation of 2-benzyl-4-N,N-bis(2-hydroxyethyl) aminomethyl-6-(4-fluoro-3-methylphenyl)-2H-pyridazin-3-one hydrochloride Following the procedure of Example 4, 2-benzyl-4-N,N-bis(2-hydroxyethyl)aminomethyl-6-(4-fluoro-3-methylphenyl)-2H-pyridazin-3-one was reacted to yield the title compound as a pale yellow crystalline powder (yield: 75.9%).

Melting point: 161.7–163.0° C. $^1$H NMR(400 MHz, DMSO-$d_6$)δ: 2.31(2H, d, J=2.0 Hz), 3.34(4H, t, J=5.2 Hz), 3.83(4H, t, J=5.4 Hz), 4.47(2H, s), 5.39(2H, s), 7.23–7.40 (6H, m), 7.73–7.77(1H, m), 7.82(1H, dd, J=1.7, 7.3 Hz), 8.47(1H, s). IR(KBr) cm$^{-1}$: 1602, 1503, 1239, 1088. Mass m/z: 393(M$^+$—H$_2$O)

Example 130

Preparation of 2-benzyl-4-dimethylaminomethyl-6-(4-fluoro-3-methylphenyl)-2H-pyridazin-3-one Following the procedure of Example 7, 2-benzyl-6-(4-fluoro-3-methylphenyl)-4-methanesulfonyloxymethyl-2H-pyridazin-3-one and dimethylamine were reacted to yield the title compound as a yellow oil (yield: 92.7%).

$^1$H NMR(400 MHz, CDCl$_3$)δ: 2.34(9H, s), 3.49(2H, s), 5.40(2H, s), 7.06(1H, t, J=8.9 Hz), 7.25–7.35(3H, m), 7.49 (2H, d, J=7.4 Hz), 7.58–7.67(2H, m), 7.75(1H, s).

Example 131

Preparation of 2-benzyl-4-dimethylaminomethyl-6-(4-fluoro-3-methylphenyl)-2H-pyridazin-3-one hydrochloride Following the procedure of Example 4, 2-benzyl-4-dimethylaminomethyl-6-(4-fluoro-3-methylphenyl)-2H-pyridazin-3-one was reacted to yield the title compound as colorless flakes (yield: 72.6%).

Melting point: 225.3–226.0° C. $^1$H NMR(400 MHz, DMSO-$d_6$)δ: 2.31(3H, d, J=2.0 Hz), 2.81(6H, s), 4.28(2H, s), 5.39(2H, s), 7.21–7.41(6H, m), 7.73–7.78(1H, m), 7.83 (1H, dd, J=2.2, 7.6 Hz), 8.52(1H, s). IR(KBr) cm$^{-1}$: 1652, 1610, 1506, 1240, 1126, 702. Mass m/z: 351(M$^+$)

Example 132

Preparation of 4-(4-tert-butoxycarbonyl-1-piperazinyl)methyl-2-cinnamyl-6-(4-fluoro-3-methylphenyl)-2H-pyridazin-3-one 1) Preparation of 2-cinnamyl-6-(4-fluoro-3-methylphenyl)-4-methoxycarbonyl-2H-pyridazin-3-one Following the procedure of Example 1(6), 6-(3-fluoro-4-methylphenyl)-4-methoxycarbonyl-2H-pyridazin-3-one and cinnamyl bromide were reacted to yield the title compound as pale yellow needles (yield: 58.7%).

Melting point: 95.9–96.7° C. $^1$H NMR(400 MHz, CDCl$_3$) δ: 2.35(3H, d, J=1.7 Hz), 3.99(3H, s), 5.04(2H, dd, J=1.2, 6.8 Hz), 6.45(1H, dt, J=15.9, 6.8 Hz), 6.75(1H, d, J=15.9 Hz), 7.10(1H, dd, J=8.9, 8.9 Hz), 7.20–7.33(3H, m), 7.39 (2H, d, J=7.1 Hz), 7.58–7.66(2H, m), 8.23(1H, s). IR(KBr) cm$^{-1}$: 1724, 1661, 1603, 1501, 1292, 1234, 1123. Mass m/z: 378(M$^+$).

2) Preparation of 4-carboxy-2-cinnamyl-6-(4-fluoro-3-methylphenyl)-2H-pyridazin-3-one Following the procedure of Example 1(7), 2-cinnamyl-6-(4-fluoro-3-methylphenyl)-4-methoxycarbonyl-2H-pyridazin-3-one was reacted to yield the title compound as pale yellow needles (yield: 85.1%).

Melting point: 142.8–143.6° C. $^1$H NMR(400 MHz, CDCl$_3$)δ: 2.36(3H, d, J=2.0 Hz), 5.12(2H, dd, J=1.2, 6.8 Hz), 6.42(1H, dt, J=15.9, 6.8 Hz), 6.80(1H, d, J=15.9 Hz), 7.13(1H, dd, J=8.8, 8.8 Hz), 7.22–7.36(3H, m), 7.40–7.43 (2H, m), 7.65–7.72(2H, m), 8.64(1H, s), 14.04(1H, br). IR(KBr) cm$^{-1}$: 3438, 3061, 2688, 1747, 1637, 1567, 1463, 1244. Mass m/z: 364(M$^+$).

3) Preparation of 2-cinnamyl-6-(4-fluoro-3-methylphenyl)-4-hydroxymethyl-2H-pyridazin-3-one Following the procedure of Example 1(8), 4-carboxy-2-cinnamyl-6-(4-fluoro-3-methylphenyl)-2H-pyridazin-3-one was reacted to yield the title compound as slightly yellow needles (yield: 20.1%).

Melting point: 139.9–140.9° C. $^1$H NMR(400 MHz, CDCl$_3$)δ: 2.34(3H, d, J=1.5 Hz), 3.00(1H, br), 4.73(2H, s), 5.01(2H, d, J=6.6 Hz), 6.44(1H, dt, J=15.9, 6.6 Hz), 6.72 (2H, d, J=15.9 Hz), 7.08(1H, dd, J=8.9, 8.9 Hz), 7.24(1H, t, J=7.3 Hz), 7.30(2H, dd, J=7.3, 7.3 Hz), 7.39(2H, d, J=7.3 Hz), 7.58–7.62(1H, m), 7.64(1H, d, J=7.3 Hz), 7.67(1H, s). IR(KBr) cm$^{-1}$: 3393, 1655, 1648, 1602, 1505, 1451, 1238, 1077. Mass m/z: 350(M$^+$).

4) Preparation of 2-cinnamyl-6-(4-fluoro-3-methylphenyl)-4-methanesulfonyloxymethyl-2H-pyridazin-3-one Following the procedure of Example 1(9), 2-cinnamyl-6-(4-fluoro-3-methylphenyl)-4-hydroxymethyl-2H-pyridazin-3-one was reacted to yield the title compound as colorless needles (yield: 91.9%).

Melting point: 78.4–80.5° C. $^1$H NMR(400 MHz, CDCl$_3$) δ: 2.35(3H, d, J=2.0 Hz), 3.17(3H, s), 5.10(2H, dd, J=1.2, 6.8 Hz), 5.28(2H, d, J=1.2 Hz), 6.42(1H, dt, J=15.9, 6.8 Hz), 6.73(1H, d, J=15.9 Hz), 7.09(1H, dd, J=8.9, 8.9 Hz), 7.21–7.33(3H, m), 7.40(2H, d, J=8.8 Hz), 7.57–7.62(1H, m), 7.64(1H, d, J=8.8 Hz), 7.77(1H, t, J=1.3 Hz). IR(KBr) cm$^{-1}$: 1663, 1612, 1508, 1355, 1241, 1167, 988, 958, 873. Mass m/z: 428(M$^+$).

5) Preparation of 4-(4-tert-butoxycarbonyl-1-piperazinyl)-methyl-2-cinnamyl-6-(4-fluoro-3-methylphenyl)-2H-pyridazin-3-one Following the procedure of Example 1(10), 2-cinnamyl-6-(4-fluoro-3-methylphenyl)-4-methanesulfonyloxymethyl-2H-pyridazin-3-one and tert-butyl 1-piperazinecarboxylate were reacted to yield the title compound as a yellow oil (yield: 86.7%).

$^1$H NMR(400 MHz, CDCl$_3$)δ: 1.47(9H, s), 2.35(3H, d, J=1.6 Hz), 2.52(4H, t, J=5.0 Hz), 3.51(4H, t, J=4.9 Hz), 3.59(2H, d, J=1.4 Hz), 5.00(2H, dd, J=1.0, 6.6 Hz), 6.45(1H, dt, J=15.8, 6.6 Hz), 6.72(1H, d, J=15.8 Hz), 7.08(1H, dd, J=8.9, 8.9 Hz), 7.22(1H, t, J=7.2 Hz), 7.29(2H, dd, J=7.0, 7.0 Hz), 7.38(2H, d, J=7.7 Hz), 7.56–7.61(1H, m), 7.65(1H, dd, J=1.8, 7.2 Hz), 7.77(1H, s).

Example 133

Preparation of 2-cinnamyl-6-(4-fluoro-3-methylphenyl)-4-(1-piperazinyl)methyl-2H-pyridazin-3-one dihydrochloride Following the procedure of Example 2, 4-(4-tert-butoxycarbonyl-1-piperazinyl)methyl-2-cinnamyl-6-(4-fluoro-3-methylphenyl)-2H-pyridazin-3-one was reacted to yield the title compound as a colorless crystalline powder (yield: 96.0%).

Melting point: 171.1–187.1° C. (dec.) $^1$H NMR(400 MHz, DMSO-d$_6$)δ: 2.31(3H, d, J=2.0 Hz), 3.21(4H, t, J=4.9 Hz), 3.34(4H, t, J=5.1 Hz), 3.99(2H, s), 4.95(2H, dd, J=1.3, 6.4 Hz), 6.45(1H, dt, J=16.1, 6.3 Hz), 6.68(1H, d, J=16.1 Hz), 7.20–7.26(2H, m), 7.29–7.34(2H, m), 7.41–7.45(2H, m), 7.73–7.79(1H, m), 7.83(1H, dd, J=1.7, 7.3 Hz), 8.26(1H, s). IR(KBr) cm$^{-1}$: 1656, 1605, 1505, 1239, 962. Mass m/z: 418(M$^+$)

Example 134

Preparation of 2-cinnamyl-6-(4-fluoro-3-methylphenyl)-4-(4-methyl-1-piperazinyl)methyl-2H-pyridazin-3-one Following the procedure of Example 1(10), 2-cinnamyl-6-(4-fluoro-3-methylphenyl)-4-methanesulfonyloxymethyl-2H-pyridazin-3-one and 1-methylpiperazine were reacted to yield the title compound as a yellow oil (yield: 80.1%).

$^1$H NMR(400 MHz, CDCl$_3$)δ: 2.32(3H, s), 2.35(3H, d, J=1.8 Hz), 2.51(4H, br), 2.62(4H, br), 3.59(2H, d, J=1.4 Hz), 4.99(2H, dd, J=1.1, 6.6 Hz), 6.45(1H, dt, J=15.8, 6.0 Hz), 6.72(1H, d, J=15.8 Hz), 7.08(1H, dd, J=8.9, 8.9 Hz), 7.22 (1H, tt, J=1.6, 7.2 Hz), 7.29(2H, dd, J=7.2, 7.2 Hz), 7.39(2H, dd, J=1.4, 7.2 Hz), 7.56–7.61(1H, m), 7.65(1H, dd, J=1.8, 7.2 Hz), 7.75(1H, t, J=1.4 Hz).

Example 135

Preparation of 2-cinnamyl-6-(4-fluoro-3-methylphenyl)-4-(4-methyl-1-piperazinyl)methyl-2H-pyridazin-3-one dihydrochloride Following the procedure of Example 4, 2-cinnamyl-6-(4-fluoro-3-methylphenyl)-4-(4-methyl-1-piperazinyl)methyl-2H-pyridazin-3-one was reacted to yield the title compound as a colorless crystalline powder (yield: 66.3%).

Melting point: 236.1–237.1° C. $^1$H NMR(400 MHz, DMSO-d$_6$)δ: 2.32(3H, d, J=2.2 Hz), 2.76(3H, s), 3.08(4H, br), 3.32(4H, br), 3.83(2H, s), 4.94(2H, dd, J=1.2, 6.4 Hz), 6.45(1H, dt, J=16.1, 6.3 Hz), 6.67(1H, d, J=15.8 Hz), 7.19–7.26(2H, m), 7.29–7.34(2H,m), 7.41–7.44(2H,m), 7.71–7.76(1H,m), 7.81(1H, dd, J=2.2, 7.6 Hz), 8.07(1H, s). IR(KBr) cm$^{-1}$: 1652, 1607, 1505, 1239, 1129. Mass m/z: 432(M$^+$)

Example 136

Preparation of 4-N,N-bis(2-hydroxyethyl)aminomethyl-2-cinnamyl-6-(4-fluoro-3-methylphenyl)-2H-pyridazin-3-one Following the procedure of Example 1(10), 2-cinnamyl-6-(4-fluoro-3-methylphenyl)-4-methanesulfonyloxymethyl-2H-pyridazin-3-one and diethanolamine were reacted to yield the title compound as a yellow oil (yield: 83.7%).

¹H NMR(400 MHz, CDCl₃)δ: 2.32(3H, s), 2.69(4H, t, J=4.9 Hz), 3.65(4H, d, J=4.9 Hz), 3.69(2H, s), 4.98(2H, d, J=6.6 Hz), 6.41(1H, dt, J=15.8, 6.5 Hz), 6.68(1H, d, J=15.8 Hz), 7.05(1H, dd, J=8.9, 8.9 Hz), 7.21(1H, t, J=7.2 Hz), 7.28(2H, dd, J=7.2, 7.2 Hz), 7.37(2H, d, J=7.6 Hz), 7.58–7.63(1H, m), 7.66(1H, dd, J=1.8, 7.2 Hz), 7.81(1H, s).

Example 137

Preparation of 4-N,N-bis(2-hydroxyethyl)aminomethyl-2-cinnamyl-6-(4-fluoro-3-methylphenyl)-2H-pyridazin-3-one hydrochloride Following the procedure of Example 4, 4-N,N-bis(2-hydroxyethyl)aminomethyl-2-cinnamyl-6-(4-fluoro-3-methylphenyl)-2H-pyridazin-3-one was reacted to yield the title compound as a colorless crystalline powder (yield: 63.2%).

Melting point: 112.5–113.2° C. ¹H NMR(400 MHz, DMSO-d₆)δ: 2.32(3H, d, J=1.9 Hz), 3.35(4H, t, J=5.1 Hz), 3.84(4H, t, J=5.1 Hz), 4.46(2H, s), 4.98(2H, dd, J=1.5, 6.1 Hz), 6.45(1H, dt, J=15.8, 6.1 Hz), 6.69(1H, d, J=16.0 Hz), 7.21–7.27(2H, m), 7.29–7.34(2H, m), 7.41–7.44(2H, m), 7.75–7.80(1H, m), 7.85(1H, dd, J=2.0, 7.3 Hz), 8.47(1H, s). IR(KBr) cm⁻¹: 1652, 1604, 1505, 1241, 971. Mass m/z: 419(M⁺—H₂O)

Example 138

Preparation of 2-cinnamyl-4-dimethylaminomethyl-6-(4-fluoro-3-methylphenyl)-2H-pyridazin-3-one Following the procedure of Example 7, 2-cinnamyl-6-(4-fluoro-3-methylphenyl)-4-methanesulfonyloxymethyl-2H-pyridazin-3-one and dimethylamine were reacted to yield the title compound as a yellow oil (yield: 90.9%).

¹H NMR(400 MHz, CDCl₃)δ: 2.34(3H, d, J=2.0 Hz), 2.36(6H, s), 3.51(2H, d, J=1.4 Hz), 5.00(2H, dd, J=1.3, 6.8 Hz), 6.46(1H, dt, J=15.8, 6.6 Hz), 6.72(1H, d, J=15.8 Hz), 7.07(1H, dd, J=8.9, 8.9 Hz), 7.22(1H, tt, J=1.4, 7.2 Hz), 7.29(2H, dd, J=7.2, 7.2 Hz), 7.39(2H, dd, J=1.6, 7.0 Hz), 7.60–7.65(1H, m), 7.67(1H, dd, J=2.2, 7.2 Hz), 7.76(1H, s).

Example 139

Preparation of 2-cinnamyl-4-dimethylaminomethyl-6-(4-fluoro-3-methylphenyl)-2H-pyridazin-3-one hydrochloride Following the procedure of Example 4, 2-cinnamyl-4-dimethylaminomethyl-6-(4-fluoro-3-methylphenyl)-2H-pyridazin-3-one was reacted to yield the title compound as a colorless crystalline powder (yield: 81.1%).

Melting point: 183.6–184.5° C. ¹H NMR(400 MHz, DMSO-d₆)δ: 2.32(3H, d, J=2.0 Hz), 2.83(6H, s), 4.29(2H, s), 4.98(2H, dd, J=1.3, 6.4 Hz), 6.46(1H, dt, J=16.1, 6.3 Hz), 6.69(1H, d,J=16.1 Hz), 7.22–7.27(2H,m), 7.29–7.35(2H,m), 7.41–7.44(2H, m), 7.76–7.81(1H, m), 7.86(1H, dd, J=2.2, 7.3 Hz), 8.50(1H, s). IR(KBr) cm⁻¹: 1652, 1607, 1505, 1240, 965. Mass m/z: 377(M⁺)

Example 140

Preparation of 4-(4-tert-butoxycarbonyl-1-piperazinyl)methyl-2-(4-chlorocinnamyl)-6-(4-fluoro-3-methylphenyl)-2H-pyridazin-3-one 1) Preparation of 2-(4-chlorocinnamyl)-6-(4-fluoro-3-methylphenyl)-4-methoxycarbonyl-2H-pyridazin-3-one Following the procedure of Example 1(6), 6-(3-fluoro-4-methylphenyl)-4-methoxycarbonyl-2H-pyridazin-3-one and 4-chlorocinnamyl chloride were reacted to yield the title compound as yellow needles (yield: 71.7%).

Melting point: 137.8–138.8° C. ¹H NMR(400 MHz, CDCl₃)δ: 2.35(3H, d, J=1.7 Hz), 3.99(3H, s), 5.03(2H, d, J=6.6 Hz), 6.43(1H, dt, J=15.6, 6.6 Hz), 6.70(1H, d, J=15.6 Hz), 7.10(1H, d, J=8.8 Hz), 7.27(2H, d, J=8.8 Hz), 7.31(2H, d, J=8.8 Hz), 7.58–7.63(1H, m), 7.64(1H, dd, J=2.1, 7.0 Hz), 8.24(1H, s). IR(KBr) cm⁻¹: 1724, 1709, 1667, 1506, 1291, 1236, 1126, 831. Mass m/z: 412(M⁺), 414(M⁺).

2) Preparation of 4-carboxy-2-(4-chlorocinnamyl)-6-(4-fluoro-3-methylphenyl)-2H-pyridazin-3-one Following the procedure of Example 1(7), 2-(4-chlorocinnamyl)-6-(4-fluoro-3-methylphenyl)-4-methoxy carbonyl-2H-pyridazin-3-one was reacted to yield the title compound as a yellow crystalline powder (yield: 86.2%).

Melting point: 186.0–186.6° C. ¹H NMR(400 MHz, CDCl₃)δ: 2.36(3H, d, J=2.0 Hz), 5.11(2H, dd, J=1.2, 6.8 Hz), 6.39(1H, dt, J=15.9, 6.8 Hz), 6.75(1H, d, J=15.6 Hz), 7.13(1H, dd, J=8.8, 8.8 Hz), 7.29(2H, d, J=8.5 Hz), 7.33(2H, d, J=8.5 Hz), 7.65–7.71(2H, m), 8.64(1H, s), 13.98(1H, br). IR(KBr) cm⁻¹: 3471, 1738, 1631, 1566, 1490, 1467, 1403, 1242, 812, 802. Mass m/z: 398(M⁺), 400(M⁺).

3) Preparation of 2-(4-chlorocinnamyl)-6-(4-fluoro-3-methylphenyl)-4-hydroxymethyl-2H-pyridazin-3-one Following the procedure of Example 1(8), 4-carboxy-2-(4-chlorocinnamyl)-6-(4-fluoro-3-methylphenyl)-2H-pyridazin-3-one was reacted to yield the title compound as slightly yellow needles (yield: 17.2%).

Melting point: 131.8–133.1° C. ¹H NMR(400 MHz, CDCl₃)δ: 2.34(3H, d, J=2.0 Hz), 4.73 (2H, d, J=1.2 Hz), 4.99(2H, dd, J=1.0, 6.6 Hz), 6.40(1H, dt, J=15.9, 6.6 Hz), 6.75(1H, d, J=15.9 Hz), 7.08(1H, dd, J=8.9, 8.9 Hz), 7.26 (2H, d, J=8.8 Hz), 7.31(2H, d, J=8.8. Hz), 7.57–7.62(1H, m), 7.64(1H, dd, J=2.2, 7.3 Hz), 7.69(1H, t, J=1.2 Hz). IR(KBr) cm⁻¹: 3359, 1653, 1598, 1506, 1492, 1240, 1091, 1076. Mass m/z: 384(M⁺), 386 (M⁺).

4) Preparation of 2-(4-chlorocinnamyl)-6-(4-fluoro-3-methylphenyl)-4-methanesulfonyloxymethyl-2H-pyridazin-3-one Following the procedure of Example 1(9), 2-(4-chlorocinnamyl)-6-(4-fluoro-3-methylphenyl)-4-hydroxymethyl-2H-pyridazin-3-one was reacted to yield the title compound as colorless needles (yield: 94.9%).

Melting point: 117.8–119.5° C. ¹H NMR(400 MHz, CDCl₃)δ: 2.35(3H, d, J=2.0 Hz), 3.17(3H, s), 4.99(2H, dd, J=1.2, 6.6 Hz), 5.28(2H, d, J=1.2 Hz), 6.38(1H, dt, J=15.9, 6.6 Hz), 6.75(1H, d, J=15.9 Hz), 7.10(1H, dd, J=8.8, 8.8 Hz), 7.27(2H, d, J=8.5 Hz), 7.32(2H, d, J=8.5. Hz), 7.57–7.65(2H, m), 7.78(1H, t, J=1.3 Hz). IR(KBr) cm$^{-1}$: 1663, 1619, 1506, 1492, 1346, 1240, 1172, 960, 830. Mass m/z: 462(M$^+$), 464(M$^+$).

5) Preparation of 4-(4-tert-butoxycarbonyl-1-piperazinyl)-methyl-2-(4-chlorocinnamyl)-6-(4-fluoro-3-methylphenyl)-2H-pyridazin-3-one Following the procedure of Example 1(10), 2-(4-chlorocinnamyl)-6-(4-fluoro-3-methylphenyl)-4-methanesulfonyloxymethyl-2H-pyridazin-3-one and tert-butyl 1-piperazinecarboxylate were reacted to yield the title compound as a yellow oil (yield: 87.9%).

$^1$H NMR(400 MHz, CDCl$_3$)δ: 1.47(9H, s), 2.35(3H, d, J=1.6 Hz), 2.52(4H, t, J=4.9 Hz), 3.50(4H, t, J=5.0 Hz), 3.59(2H, d, J=1.2 Hz), 4.99(2H, dd, J=1.0, 6.6 Hz), 6.42(1H, dt, J=15.8, 6.6 Hz), 6.67(1H, d, J=16.0 Hz), 7.09(1H, dd, J=8.9, 8.9 Hz), 7.25(2H, d, J=8.8 Hz), 7.31(2H, d, J=8.6 Hz), 7.55–7.61(1H, m), 7.64(1H, dd, J=2.0, 7.2 Hz), 7.77(1H, s).

Example 141

Preparation of 2-(4-chlorocinnamyl)-6-(4-fluoro-3-methylphenyl)-4-(1-piperazinyl)methyl-2H-pyridazin-3-one dihydrochloride Following the procedure of Example 2, 4-(4-tert-butoxycarbonyl-1-piperazinyl)methyl-2-(4-chlorocinnamyl)-6-(4-fluoro-3-methylphenyl)-2H-pyridazin-3-one was reacted to yield the title compound as a pale brown crystalline powder (yield: 84.7%).

Melting point: 186.7–197.0° C. (dec.) $^1$H NMR(400 MHz, DMSO-d$_6$)δ: 2.31(3H, d, J=2.0 Hz), 3.15(4H, br), 3.31(4H, t, J=5.2 Hz), 3.94(2H, s), 4.95(2H, dd, J=1.3, 6.3 Hz), 6.47(1H, dt, J=15.9, 6.1 Hz), 6.66(1H, d, J=15.9 Hz), 7.22(1H, dd, J=9.0, 9.0 Hz), 7.34(2H, d, J=8.6 Hz), 7.45(2H, d, J=8.6 Hz), 7.73–7.78(1H, m), 7.82(1H, dd, J=1.9, 7.6 Hz), 8.21(1H, s). IR(KBr) cm$^{-1}$: 1656, 1606, 1240, 1090, 964. Mass m/z: 452(M$^+$), 454(M$^+$).

Example 142

Preparation of 2-(4-chlorocinnamyl)-6-(4-fluoro-3-methylphenyl)-4-(4-methyl-1-piperazinyl)methyl-2H-pyridazin-3-one Following the procedure of Example 1(10), 2-(4-chlorocinnamyl)-6-(4-fluoro-3-methylphenyl)-4-methanesulfonyloxymethyl-2H-pyridazin-3-one and 1-methylpiperazine were reacted to yield the title compound as a yellow oil (yield: 71.8%).

$^1$H NMR(400 MHz, CDCl$_3$)δ: 2.32(3H, s), 2.35(3H, s), 2.51(4H, br), 2.62(4H, br), 3.59(2H, s), 4.99(2H, d, J=6.6 Hz), 6.42(1H, dt, J=15.8, 6.4 Hz), 6.66(1H, d, J=15.9 Hz), 7.09(1H, dd, J=8.9, 8.9 Hz), 7.24(2H, d, J=8.6 Hz), 7.30(2H, d, J=8.6 Hz), 7.56–7.62(1H, m), 7.65(1H, dd, J=1.8, 7.2 Hz), 7.76(1H, s).

Example 143

Preparation of 2-(4-chlorocinnamyl)-6-(4-fluoro-3-methylphenyl)-4-(4-methyl-1-piperazinyl)methyl-2H-pyridazin-3-one dihydrochloride Following the procedure of Example 4, 2-(4-chlorocinnamyl)-6-(4-fluoro-3-methylphenyl)-4-(4-methyl-1-piperazinyl)methyl-2H-pyridazin-3-one was reacted to yield the title compound as a colorless crystalline powder (yield: 80.4%).

Melting point: 229.7–243.3° C. (dec.) $^1$H NMR(400 MHz, DMSO-d$_6$)δ: 2.31(3H, d, J=1.8 Hz), 2.76(3H, s), 3.09(4H, br), 3.33(4H, br), 3.83(2H, s), 4.94(2H, dd, J=1.2, 6.0 Hz), 6.42(1H, dt, J=16.0, 6.2 Hz), 6.65(1H, d, J=16.0 Hz), 7.22(1H, dd, J=9.1, 9.1 Hz), 7.34(2H, d, J=8.6 Hz), 7.45(2H, d, J=8.6 Hz), 7.71–7.76(1H, m), 7.80(1H, dd, J=2.2, 7.0 Hz), 8.08(1H, s). IR(KBr) cm$^{-1}$: 1652, 1608, 1492, 1239, 1130. Mass m/z: 466(M$^+$), 468(M$^+$).

Example 144

Preparation of 4-N,N-bis(2-hydroxyethyl)aminomethyl-2-(4-chlorocinnamyl)-6-(4-fluoro-3-methylphenyl)-2H-pyridazin-3-one Following the procedure of Example 1(10), 2-(4-chlorocinnamyl)-6-(4-fluoro-3-methylphenyl)-4-methanesulfonyloxymethyl-2H-pyridazin-3-one and diethanolamine were reacted to yield the title compound as a yellow oil (yield: 76.6%).

$^1$H NMR(400 MHz, CDCl$_3$)δ: 2.33(3H, s), 2.70(4H, t, J=4.5 Hz), 3.66(4H, t, J=4.9 Hz), 3.70(2H, s), 4.98(2H, d, J=6.6 Hz), 6.36(1H, dt, J=15.8, 6.5 Hz), 6.63(1H, d, J=15.8 Hz), 7.06(1H, dd, J=8.6, 8.6 Hz), 7.24(2H, d, J=8.6 Hz), 7.30(2H, d, J=8.2 Hz), 7.58–7.63(1H, m), 7.65(1H, dd, J=1.8, 7.2 Hz), 7.78(1H, s).

Example 145

Preparation of 4-N,N-bis(2-hydroxyethyl)aminomethyl-2-(4-chlorocinnamyl)-6-(4-fluoro-3-methylphenyl)-2H-pyridazin-3-one hydrochloride Following the procedure of Example 4, 4-N,N-bis(2-hydroxyethyl)aminomethyl-2-(4-chlorocinnamyl)-6-(4-fluoro-3-methylphenyl)-2H-pyridazin-3-one was reacted to yield the title compound as a colorless crystalline powder (yield: 76.1%).

Melting point: 151.9–153.4° C. $^1$H NMR(400 MHz, DMSO-d$_6$)δ: 2.32(3H, d, J=1.7 Hz), 3.35(4H, t, J=5.1 Hz), 3.83(4H, t, J=5.4 Hz), 4.46(2H, s), 4.97(2H, dd, J=1.2, 6.1 Hz), 6.48(1H, dt, J=15.9, 6.2 Hz), 6.67(1H, d, J=15.9 Hz), 7.24(1H, dd, J=9.1, 9.1 Hz), 7.35(2H, d, J=8.8 Hz), 7.45(2H, d, J=8.6 Hz), 7.75–7.80(1H, m), 7.85(1H, dd, J=1.7, 7.9 Hz), 8.48(1H, s). IR(KBr) cm$^{-1}$: 1652, 1604, 1492, 1240, 1090, 968. Mass m/z: 440(M$^+$), 442(M$^+$).

Example 146

Preparation of 2-(4-chlorocinnamyl)-4-dimethylaminomethyl-6-(4-fluoro-3-methylphenyl)-2H-pyridazin-3-one Following the procedure of Example 7, 2-(4-chlorocinnamyl)-6-(4-fluoro-3-methylphenyl)-4-methanesulfonyloxymethyl-2H-pyridazin-3-one was reacted to yield the title compound as a yellow oil (yield: 84.6%).

$^1$H NMR(400 MHz, CDCl$_3$)δ: 2.33(3H, d, J=1.6 Hz), 2.36(6H, s), 3.52(2H, d, J=1.2 Hz), 4.99(2H, dd, J=1.0, 6.6 Hz), 6.43(1H, dt, J=15.8, 6.6 Hz), 6.66(1H, d, J=15.8 Hz), 7.07(1H, dd, J=8.9, 8.9 Hz), 7.24(2H, d, J=8.6 Hz), 7.30(2H, d, J=8.6 Hz), 7.60–7.68(2H, m), 7.77(1H, s).

Example 147

Preparation of 2-(4-chlorocinnamyl)-4-dimethylaminomethyl-6-(4-fluoro-3-methylphenyl)-2H-pyridazin-3-one hydrochloride Following the procedure of Example 4, 2-(4-chlorocinnamyl)-4-dimethylaminomethyl-6-(4-fluoro-3-methylphenyl)-2H-pyridazin-3-one was reacted to yield the title compound as a colorless crystalline powder (yield: 34.4%).

Melting point: 201.3–201.9° C. $^1$H NMR(400 MHz, DMSO-$d_6$)δ: 2.32(3H, d, J=1.7 Hz), 2.83(6H, s), 4.28(2H, s), 4.98(2H, dd, J=1.3, 6.1 Hz), 6.48(1H, dt, J=16.1, 6.1 Hz), 6.67(1H, d, J=16.1 Hz), 7.24(1H, dd, J=9.3, 9.3 Hz), 7.35 (2H, d, J=8.6 Hz), 7.45(2H, d, J=8.6 Hz), 7.75–7.80(1H, m), 7.85(1H, dd, J=2.3, 7.6 Hz), 8.47(1H, s). IR(KBr) cm$^{-1}$: 1652, 1608, 1491, 1239, 968. Mass m/z: 411(M$^+$), 413(M$^+$).

Example 148

Preparation of 2-cyclopropylmethyl-4-(4-methyl-1-piperazinyl)methyl-6-[4-(methylthio)phenyl]-2H-pyridazin-3-one

1) Preparation of 4-carboxy-2-cyclopropylmethyl-6-[4-(methylthio)phenyl]-2H-pyridazin-3-one Following the procedure of Example 1(7), 2-cyclopropylmethyl-4-methoxycarbonyl-6-[4-(methylthio)phenyl]-2H-pyridazin-3-one was reacted to yield the title compound as a yellow crystalline powder (yield: 98.2%).

$^1$H NMR(400 MHz, CDCl$_3$)δ: 0.50–0.66(4H, m), 1.40–1.53(1H, m), 2.54(3H, s), 4.24(2H, d, J=7.4 Hz), 7.34 (2H, d, J=8.6 Hz), 7.78 (2H, d, J=8.6 Hz), 8.66(1H, s), 14.22(1H, s). IR(KBr) cm$^{-1}$: 3430, 1752, 1631, 1472, 1452, 1403, 1093, 825. Mass m/z: 316(M$^+$)

2) Preparation of 2-cyclopropylmethyl-4-hydroxymethyl-6-[4-(methylthio)phenyl]-2H-pyridazin-3-one Following the procedure of Example 1(8), 4-carboxy-2-cyclopropylmethyl-6-[4-(methylthio)phenyl]-2H-pyridazin-3-one was reacted to yield the title compound as a pale yellow crystalline powder (yield: 22.6%).

$^1$H NMR(400 MHz, CDCl$_3$)δ: 0.45–0.60(4H, m), 1.37–1.46(1H, m), 2.53(3H, s), 3.09(1H, t, J=6.1 Hz), 4.11 (2H, d, J=7.2 Hz), 4.72(2H, d, J=6.0 Hz), 7.32(2H, d, J=8.6 Hz), 7.67(1H, s), 7.74(2H, d, J=8.6 Hz). IR(KBr) cm$^{-1}$: 3393, 1657, 1602, 1514, 1095, 822. Mass m/z: 302(M$^+$).

3) Preparation of 2-cyclopropylmethyl-4-methanesulfonyloxymethyl-6-[4-(methylthio)phenyl]-2H-pyridazin-3-one Following the procedure of Example 1(9), 2-cyclopropylmethyl-4-hydroxymethyl-6-[4-(methylthio)phenyl]-2H-pyridazin-3-one was reacted to yield the title compound as pale yellow fine-needles (yield: 78.6%).

$^1$H NMR(400 MHz, CDCl$_3$)δ: 0.45–1.61(4H, m), 1.37–1.47(1H, m), 2.53(3H, s), 3.17(3H, s), 4.11(2H, d, J=7.2 Hz), 5.28(2H, s), 7.33(2H, d, J=8.4 Hz), 7.74(2H, d, J=8.4 Hz), 7.79(1H, s). IR(KBr) cm$^{-1}$: 3446, 1652, 1607, 1359, 1178, 1024, 829. Mass m/z: 380(M$^+$).

4) Preparation of 2-cyclopropylmethyl-4-(4-methyl-1-piperazinyl)methyl-6-[4-(methylthio)phenyl]-2H-pyridazin-3-one Following the procedure of Example 1(10), 2-cyclopropylmethyl-4-methanesulfonyloxymethyl-6-[4-(methylthio)phenyl]-2H-pyridazin-3-one and 1-methylpiperazine were reacted to yield the title compound as a yellow oil (yield: 85.7%).

$^1$H NMR(400 MHz, CDCl$_3$)δ: 0.44–0.58(4H, m), 1.36–1.48(1H, m), 2.33(3H, s), 2.53(3H, s), 2.47–2.66(8H, m), 3.59(2H, s), 4.10(2H, d, J=7.3 Hz), 7.33(2H, d, J=8.3 Hz), 7.75(2H, d, J=8.3 Hz), 7.78(1H, s).

Example 149

Preparation of 2-cyclopropylmethyl-4-(4-methyl-1-piperazinyl)methyl-6-[4-(methylthio)phenyl]-2H-pyridazin-3-one dihydrochloride Following the procedure of Example 4, 2-cyclopropylmethyl-4-(4-methyl-1-piperazinyl)methyl-6-[4-(methylthio)phenyl]-2H-pyridazin-3-one was reacted to yield the title compound as a colorless crystalline powder (yield: 69.1%).

Melting point: 234.6–239.2° C. $^1$H NMR(400 MHz, DMSO-$d_6$)δ: 0.40–0.45(2H, m), 0.50–0.56(2H, m), 1.30–1.40(1H, m), 2.53(3H, s), 2.77(3H, s), 2.97(4H, br), 3.28(4H, br), 3.72(2H, s), 4.05(2H, d, J=7.1 Hz), 7.39(2H, d, J=8.6 Hz), 7.82(2H, d, J=8.3 Hz), 7.96(1H, s). IR(KBr) cm$^{-1}$: 3438, 1651, 1606, 1402, 1095. Mass m/z: 384(M$^+$).

Example 150

Preparation of 4-N,N-bis(2-hydroxyethyl)aminomethyl-2-cyclopropylmethyl-6-[4-(methylthio)phenyl]-2H-pyridazin-3-one Following the procedure of Example 1(10), 2-cyclopropylmethyl-4-methanesulfonyloxymethyl-6-[4-(methylthio)phenyl]-2H-pyridazin-3-one and diethanolamine were reacted to yield the title compound as a yellow oil (yield: 78.9%).

$^1$H NMR(400 MHz, CDCl$_3$)δ: 0.44–0.59(4H, m), 1.36–1.45(1H, m), 2.53(3H, s), 2.73(4H, br), 3.67(4H, t, J=4.9 Hz), 3.73(2H, s), 4.13(2H, d, J=7.3 Hz), 7.32(2H, d, J=8.3 Hz), 7.70(1H, s), 7.74(2H, d, J=8.3 Hz).

Example 151

Preparation of 4-N,N-bis(2-hydroxyethyl)aminomethyl-2-cyclopropylmethyl-6-[4-(methylthio)phenyl]-2H-pyridazin-3-one hydrochloride Following the procedure of Example 4, 4-N,N-bis(2-hydroxyethyl)aminomethyl-2-cyclopropylmethyl-6-[4-(methylthio)phenyl]-2H-pyridazin-3-one was reacted to yield the title compound as a slightly yellow solid (yield: 75.1%).

Melting point: 169.2–171.7° C. $^1$H NMR(400 MHz, DMSO-$d_6$)δ: 0.42–0.46(2H, m), 0.52–0.57(2H, m), 1.30–1.40(1H, m), 2.53(3H, s), 3.31(4H, br), 3.81(4H, t, J=5.3 Hz), 4.42(2H, d, J=8.8 Hz), 7.85(2H, d, J=9.0 Hz), 8.37(1H, s). IR(KBr) cm$^{-1}$: 3242, 1652, 1604, 1420, 1094, 1059, 823. Mass m/z: 358 (M$^+$—CH$_2$OH).

Example 152

Preparation of 2-cyclopropylmethyl-4-dimethylaminomethyl-6-[4-(methylthio)phenyl]-2H-pyridazin-3-one Following the procedure of Example 7, 2-cyclopropylmethyl-4-methanesulfonyloxymethyl-6-[4-(methylthio)phenyl]-2H-pyridazin-3-one was reacted to yield the title compound as a yellow oil (yield: 98.6%).

$^1$H NMR(400 MHz, CDCl$_3$)δ: 0.44–0.58(4H, m), 1.36–1.48(1H, m), 2.35(6H, s), 3.51(2H, s), 4.51(2H, d, J=7.3 Hz), 7.31(2H, d, J=8.3 Hz), 7.77(2H, d, J=7.8 Hz), 7.78(1H, s).

Example 153

Preparation of 2-cyclopropylmethyl-4-dimethylaminomethyl-6-[4-(methylthio)phenyl]-2H-pyridazin-3-one hydrochloride Following the procedure of Example 4, 2-cyclopropylmethyl-4-dimethylaminomethyl-6-[4-(methylthio)phenyl]-2H-pyridazin-3-one was reacted to yield the title compound as a pale yellow crystalline powder (yield: 75.5%).

Melting point: 230.2–232.3° C. $^1$H NMR(400 MHz, DMSO-d$_6$)δ: 0.42–0.46(2H, m), 0.52–0.58(2H, m), 1.31–1.40(1H, m), 2.53(3H, s), 2.82(6H, s), 4.09(2H, d, J=7.1 Hz), 4.25(2H, s), 7.41(2H, d, J=8.6 Hz), 7.84(2H, d, J=8.5 Hz), 8.34(1H, s). IR(KBr) cm$^{-1}$: 3435, 1646, 1604, 1402, 1093, 829. Mass m/z: 329(M$^+$).

Example 154

Preparation of 4-(4-tert-butoxycarbonyl-1-piperazinyl)methyl-2-isobutyl-6-[4-(methylthio)phenyl]-2H-pyridazin-3-one 1) Preparation of 4-carboxy-2-isobutyl-6-[4-(methylthio)phenyl]-2H-pyridazin-3-one To a solution of 4-methoxycarbonyl-6-[4-(methylthio)phenyl]-2H-pyridazin-3-one (8.00 g, 29.0 mmol) in N,N-dimethylformamide (80 mL) were added potassium carbonate (8.02 g, 58.0 mmol) and isobutyl bromide (4.76 g, 34.8 mmol), and the mixture was stirred at 80° C. for 2 hours. The temperature of the reaction mixture was allowed to drop back to room temperature, and a saturated aqueous solution of sodium hydrogencarbonate was added. The mixture was then extracted with ethyl acetate. The extract was washed with brine, and dried over anhydrous sodium sulfate. The solvent was distilled off under reduced pressure. Following the procedure of Example 1(7), the residue was reacted to yield the title compound as a yellow solid [yield: 65.1% (2 steps)].

$^1$H NMR(400 MHz, CDCl$_3$)δ: 1.01(6H, d, J=6.6 Hz), 2.33–2.46(1H, m), 2.54(3H, s), 4.21(2H, d, J=7.4 Hz), 7.34(2H, d, J=8.4 Hz), 7.80(2H, d, J=8.4 Hz), 8.68(1H, s), 12.72(1H, s). Mass m/z: 318(M$^+$).

2) Preparation of 4-hydroxymethyl-2-isobutyl-6-[4-(methylthio)phenyl]-2H-pyridazin-3-one Following the procedure of Example 1(8), 4-carboxy-2-isobutyl-6-[4-(methylthio)phenyl]-2H-pyridazin-3-one was reacted to yield the title compound as a yellow oil (yield: 35.3%).

$^1$H NMR(400 MHz, CDCl$_3$)δ: 0.98(6H, d, J=6.6 Hz), 2.27–2.39(1H, m), 2.53(3H, s), 4.08(2H, d, J=7.4 Hz), 4.71(2H, d, J=5.9 Hz), 7.26(2H, d, J=8.4 Hz), 7.66(1H, s), 7.73(2H, d, J=8.6 Hz).

3) Preparation of 2-isobutyl-4-methanesulfonyloxymethyl-6-[4-(methylthio)phenyl]-2H-pyridazin-3-one Following the procedure of Example 1(9), 4-hydroxymethyl-2-isobutyl-6-[4-(methylthio)phenyl]-2H-pyridazin-3-one was reacted to yield the title compound as a pale yellow crystalline powder (yield: 73.2%).

$^1$H NMR(400 MHz, CDCl$_3$)δ: 0.99(6H, d, J=6.6 Hz), 2.28–2.40(1H, m), 2.53(3H, s), 3.17(3H, s), 4.08(2H, d, J=7.4 Hz), 5.27(2H, d, J=1.2 Hz), 7.32(2H, d, J=8.4 Hz), 7.73(2H, d, J=8.4 Hz), 7.75(1H, d, J=1.4 Hz). Mass m/z: 382(M$^+$).

4) Preparation of 4-(4-tert-butoxycarbonyl-1-piperazinyl)methyl-2-isobutyl-6-[4-(methylthio)phenyl]-2H-pyridazin-3-one Following the procedure of Example 1(10), 2-isobutyl-4-methanesulfonyloxymethyl-6-[47 (methylthio)phenyl]-2H-pyridazin-3-one and tert-butyl 1-piperazinecarboxylate were reacted to yield the title compound as a yellow oil (yield: 88.0%).

$^1$H NMR(400 MHz, CDCl$_3$)δ: 0.98(6H, d, J=6.6 Hz), 1.47(9H, s), 2.28–2.40(1H, m), 2.50–2.55(4H, m), 2.53(3H, s), 3.50(4H, t, J=4.8 Hz), 3.58(2H, s), 4.07(2H, d, J=7.4 Hz), 7.32(2H, d, J=8.4 Hz), 7.73(2H, d, J=8.6 Hz), 7.78(1H, s).

Example 155

Preparation of 2-isobutyl-6-[4-(methylthio)phenyl]-4-(1-piperazinyl)methyl-2H-pyridazin-3-one dihydrochloride Following the procedure of Example 2, 4-(4-tert-butoxycarbonyl-1-piperazinyl)methyl-2-isobutyl-6-[4-(methylthio)phenyl]-2H-pyridazin-3-one was reacted to yield the title compound as a yellow crystalline powder (yield: 70.5%).

Melting point: 248.5–253.7° C. (dec.). $^1$H NMR(400 MHz, DMSO-d$_6$)δ: 0.95(6H, d, J=6.6 Hz), 2.21–2.33(1H, m), 2.52(3H, s), 3.10(4H, t, J=4.8 Hz), 3.30(4H, t, J=5.2 Hz), 3.90(2H, s), 4.01(2H, d, J=7.3 Hz), 7.39(2H, d, J=8.3 Hz), 7.83(2H, d, J=8.3 Hz), 8.15(1H, s). IR(KBr) cm$^{-1}$: 2961, 2442, 1640, 1596, 1511, 1433, 1406, 1089, 912. Mass m/z: 372(M$^+$).

Example 156

Preparation of 2-isobutyl-4-(4-methyl-1-piperazinyl)methyl-6-[4-(methylthio)phenyl]-2H-pyridazin-3-one Following the procedure of Example 1(10), 2-isobutyl-4-methanesulfonyloxymethyl-6-[4-(methylthio)phenyl]-2H-pyridazin-3-one and 1-methylpiperazine were reacted to yield the title compound as a yellow oil (yield: 68.3%).

$^1$H NMR(400 MHz, CDCl$_3$)δ: 0.98(6H, d, J=6.6 Hz), 2.29–2.39(1H, m), 2.32(3H, s), 2.51(4H, br), 2.53(3H, s), 2.62(4H, br), 3.58(2H, d, J=1.4 Hz), 4.07(2H, d, J=7.4 Hz), 7.33(2H, d, J=8.6 Hz), 7.74(2H, d, J=6.8 Hz), 7.76(1H, s).

Example 157

Preparation of 2-isobutyl-4-(4-methyl-1-piperazinyl)methyl-6-[4-(methylthio)phenyl]-2H-pyridazin-3-one dihydrochloride Following the procedure of Example 4, 2-isobutyl-4-(4-methyl-1-piperazinyl)methyl-6-[4-(methylthio)phenyl]-2H-pyridazin-3-one was reacted to yield the title compound as a colorless crystalline powder (yield: 86.4%).
Melting point: 242.6–243.7° C. $^1$H NMR(400 MHz, DMSO-d$_6$)δ: 0.94(6H, d, J=6.6 Hz), 2.21–2.33(1H, m), 2.52(3H, s), 2.76(3H, s), 3.09(4H, br), 3.33(4H, br), 3.83 (2H, s), 4.01(2H, d, J=7.1 Hz), 7.39(2H, d, J=8.6 Hz), 7.82(2H, d, J=8.5 Hz), 8.07(1H, s). IR(KBr) cm$^{-1}$: 3432, 2957, 2437, 1652, 1607, 1090, 953. Mass m/z: 386(M$^+$).

Example 158

Preparation of 4-N,N-bis(2-hydroxyethyl)aminomethyl-2-isobutyl-6-[4-(methylthio)phenyl]-2H-pyridazin-3-one Following the procedure of Example 1(10), 2-isobutyl-4-methanesulfonyloxymethyl-6-[4-(methylthio)phenyl]-2H-pyridazin-3-one and diethanolamine were reacted to yield the title compound as a yellow oil (yield: 71.2%).
$^1$H NMR(400 MHz, CDCl$_3$)δ: 0.96(6H, d, J=6.6 Hz), 2.27–2.39(1H, m), 2.51(3H, s), 2.71(4H, t, J=5.1 Hz), 3.66 (4H, t, J=5.1 Hz), 3.70(2H, s), 4.08(2H, d, J=7.2 Hz), 7.30(2H, d, J=8.6 Hz), 7.71–7.76(3H, m).

Example 159

Preparation of 4-N,N-bis(2-hydroxyethyl)aminomethyl-2-isobutyl-6-[4-(methylthio)phenyl]-2H-pyridazin-3-one oxalate To a solution of 4-N,N-bis(2-hydroxyethyl)aminomethyl-2-isobutyl-6-[4-(methylthio)phenyl]-2H-pyridazin-3-one (69.7 mg, 0.18 mmol) in methanol (1 mL) was added at room temperature oxalic acid dihydrate (22.4 mg, 0.18 mmol). The solvent was distilled off under reduced pressure. The residue was recrystallized from chloroform-diethyl ether to obtain the title compound as a white solid (59.5 mg, 69.4%).
Melting point: 116.4–118.1° C. $^1$H NMR(400 MHz, DMSO-d$_6$)δ: 0.94(6H, d, J=6.6 Hz), 2.20–2.33(1H, m), 2.52(3H, s), 2.91(4H, t, J=5.8 Hz), 3.61(4H, t, J=5.6 Hz), 3.94(2H, s), 4.01(2H, d, J=7.3 Hz), 7.39 (2H, d, J=8.6 Hz), 7.81 (2H, d, J=8.6 Hz), 8.14(1H, s). IR(KBr) cm$^{-1}$: 3344, 2927, 1659, 1611, 1402, 1049, 721. Mass m/z: 360(M$^+$—CH$_2$OH).

Example 160

Preparation of 4-dimethylaminomethyl-2-isobutyl-6-[4-(methylthio)phenyl]-2H-pyridazin-3-one Following the procedure of Example 7, 2-isobutyl-4-methanesulfonyloxymethyl-6-[4-(methylthio)phenyl]-2H-pyridazin-3-one was reacted to yield the title compound as a yellow oil (yield: 73.9%).
$^1$H NMR(400 MHz, CDCl$_3$)δ: 0.98(6H, d, J=6.6 Hz), 2.29–2.41(1H, m), 2.36(6H, s), 2.52(3H, s), 3.52(2H, d, J=1.2 Hz), 4.07(2H, d, J=7.4 Hz), 7.31(2H, d, J=8.6 Hz), 7.77(2H, d, J=8.4 Hz), 7.79(1H, s).

Example 161

Preparation of 4-dimethylaminomethyl-2-isobutyl-6-[4-(methylthio)phenyl]-2H-pyridazin-3-one hydrochloride Following the procedure of Example 4, 4-dimethylaminomethyl-2-isobutyl-6-[4-(methylthio)phenyl]-2H-pyridazin-3-one was reacted to yield the title compound as a colorless crystalline powder (yield: 82.3%).
Melting point: 216.8–218.4° C. $^1$H NMR(400 MHz, DMSO-d$_6$)δ: 0.96(6H, d, J=6.8 Hz), 2.23–2.36(1H, m), 2.53(3H, s), 2.82(6H, s), 4.05(2H, d, J=7.1 Hz), 4.27(2H, s), 7.41(2H, d, J=8.3 Hz), 7.84(2H, d, J=8.3 Hz), 8.42(1H, s). IR(KBr) cm$^{-1}$: 3485, 1740, 1684, 1253, 856, 577. Mass m/z: 331(M$^+$).

Example 162

Preparation of 2-isobutyl-6-[4-(methylthio)phenyl]-4-propargylaminomethyl-2H-pyridazin-3-one Following the procedure of Example 1(10), 2-isobutyl-4-methanesulfonyloxymethyl-6-[4-(methylthio)phenyl]-2H-pyridazin-3-one and propargylamine were reacted to yield the title compound as a yellow oil (yield: 52.2%).
$^1$H NMR(400 MHz, CDCl$_3$)δ: 0.98(6H, d, J=6.6 Hz), 2.26(1H, t, J=2.3 Hz), 2.29–2.40(1H, m), 2.52(3H, s), 3.51 (2H, d, J=2.4 Hz), 3.90(2H, s), 4.07(2H, d, J=7.4 Hz), 7.31(2H, d, J=8.4 Hz), 7.70(1H, s), 7.73(2H, d, J=8.4 Hz).

Example 163

Preparation of 2-isobutyl-6-[4-(methylthio)phenyl]-4-propargylaminomethyl-2H-pyridazin-3-one hydrochloride Following the procedure of Example 4, 2-isobutyl-6-[4-(methylthio)phenyl]-4-propargylaminomethyl-2H-pyridazin-3-one was reacted to yield the title compound as a white solid (yield: 73.6%).
Melting point: 197.5–198.4° C. $^1$H NMR(400 MHz, DMSO-d$_6$)δ: 0.96(6H, d, J=6.6 Hz), 2.23–2.36(1H, m), 2.53(3H, s), 3.48(1H, t, J=2.4 Hz), 3.95(2H, d, J=2.4 Hz), 4.03(2H, d, J=7.1 Hz), 4.17(2H, s), 7.41(2H, d, J=8.3 Hz), 7.82(2H, d, J=8.6 Hz), 8.28(1H, s). IR(KBr) cm$^{-1}$: 3447, 3207, 2958, 2122, 1651, 1607, 1441, 1093. Mass m/z: 341(M$^+$).

Example 164

Preparation of 2-cyclopropylmethyl-4-(4-methyl-1-piperazinyl)methyl-6-[4-(methylsulfinyl)phenyl]-2H-pyridazin-3-one 1) Preparation of 2-cyclopropylmethyl-4-methanesulfonyloxymethyl-6-[4-(methylsulfinyl)phenyl]-2H-pyridazin-3-one To a solution of 2-cyclopropylmethyl-4-methanesulfonyloxymethyl-6-[4-(methylthio)phenyl]-2H-pyridazin-3-one (300 mg, 0.79 mmol) in methylene chloride (10 mL) was added dropwise at −20° C. a solution of 3-chloroperbenzoic acid (204 mg, 1.12 mmol) in methylene chloride (2 mL), and at the same temperature, the mixture was stirred for 30 minutes. A 10% aqueous sodium hydrogensulfite was added to the reaction mixture, and then, the mixture was extracted with chloroform. The extract was successively washed with a saturated aqueous sodium hydrogencarbonate and brine, and was then dried over anhydrous sodium sulfate. The solvent was distilled off under reduced pressure. The residue was recrystallized from chloroform-hexane to yield the title compound as a colorless crystalline powder (139 mg, 44.5%).

$^1$H NMR(400 MHz, CDCl$_3$)δ: 0.48–0.63(4H, m), 1.37–1.46(1H, m), 2.77(3H, s), 3.18(3H, s), 4.14(2H, d, J=7.3 Hz), 5.30(2H, d, J=1.4 Hz), 7.76(2H, d, J=8.6 Hz), 7.84(1H, t, J=1.4 Hz), 7.98(2H, d, J=8.8 Hz). Mass m/z: 396(M$^+$).

2) Preparation of 2-cyclopropylmethyl-4-(4-methyl-1-piperazinyl)methyl-6-[4-(methylsulfinyl)phenyl]-2H-pyridazin-3-one Following the procedure of Example 1(10), 2-cyclopropylmethyl-4-methanesulfonyloxymethyl-6-[4-(methylsulfinyl)phenyl]-2H-pyridazin-3-one and 1-methylpiperazine were reacted to yield the title compound as a yellow oil (yield: 60.6%).

$^1$H NMR(400 MHz, CDCl$_3$)δ: 0.46–0.60(4H, m), 1.37–1.49(1H, m), 2.34(3H, s), 2.54(4H, br), 2.64(4H, br), 2.78(3H, s), 3.61(2H, s), 4.13(2H, d, J=7.2 Hz), 7.75(2H, d, J=8.2 Hz), 7.84(1H, s), 7.99(2H, d, J=8.2 Hz).

Example 165

Preparation of 2-cyclopropylmethyl-4-(4-methyl-1-piperazinyl)methyl-6-[4-(methylsulfinyl)phenyl]-2H-pyridazin-3-one dihydrochloride Following the procedure of Example 4, 2-cyclopropylmethyl-4-(4-methyl-1-piperazinyl)methyl-6-[4-(methylsulfinyl)phenyl]-2H-pyridazin-3-one was reacted to yield the title compound as a colorless crystalline powder (yield: 64.3%).

Melting point: 80° C. (dec.) $^1$H NMR(400 MHz, DMSO-d$_6$)δ: 0.41–0.57(4H, m), 1.30–1.41(1H, m), 2.76(3H, s), 2.77(3H, s), 3.01(4H, br), 3.31(4H, br), 3.77(2H, s), 4.08(2H, d, J=6.8 Hz), 7.80(2H, d, J=8.3 Hz), 8.05–8.09(3H, m). IR(KBr) cm$^{-1}$: 3430, 3005, 1652, 1607, 1458, 1401, 1010, 838. Mass m/z: 400(M$^+$).

Example 166

Preparation of 2-isobutyl-4-(4-methyl-1-piperazinyl)methyl-6-[4-(methylsulfinyl)phenyl]-2H-pyridazin-3-one 1) Preparation of 2-isobutyl-4-methanesulfonyloxymethyl-6-[4-(methylsulfinyl)phenyl]-2H-pyridazin-3-one Following the procedure of Example 166(1), 2-isobutyl-4-methanesulfonyloxymethyl-6-[4-(methylthio)-phenyl]-2H-pyridazin-3-one was reacted to yield the title compound as a colorless crystalline powder (yield: 54.3%).

$^1$H NMR(400 MHz, CDCl$_3$)δ: 1.00(6H, d, J=6.8 Hz), 2.29–2.41(1H, m), 2.77(3H, s), 3.18(3H, s), 4.11(2H, d, J=7.3 Hz), 5.29(2H, d, J=1.5 Hz), 7.76(2H, d, J=8.8 Hz), 7.83(1H, t, J=1.2 Hz), 7.98(2H, d, J=8.6 Hz). Mass m/z: 398(M$^+$).

2) Preparation of 2-isobutyl-4-(4-methyl-1-piperazinyl)methyl-6-[4-(methylsulfinyl)phenyl]-2H-pyridazin-3-one Following the procedure of Example 1(10), 2-isobutyl-4-methanesulfonyloxymethyl-6-[4-(methylsulfinyl)phenyl]-2H-pyridazin-3-one and 1-methylpiperazine were reacted to yield the title compound as a yellow oil (yield: 61.8%).

$^1$H NMR(400 MHz, CDCl$_3$)δ: 0.99(6H, d, J=6.6 Hz), 2.30–2.41(1H, m), 2.34(3H, s), 2.54(4H, br), 2.64(4H, br), 2.77(3H, s), 3.60(2H, s), 4.10(2H, d, J=7.4 Hz), 7.75(2H, d, J=8.2 Hz), 7.82(1H, s), 7.99(2H, d, J=8.2 Hz).

Example 167

Preparation of 2-isobutyl-4-(4-methyl-1-piperazinyl)methyl-6-[4-(methylsulfinyl)phenyl]-2H-pyridazin-3-one dihydrochloride Following the procedure of Example 4, 2-isobutyl-4-(4-methyl-1-piperazinyl)methyl-6-[4-(methylsulfinyl)phenyl]-2H-pyridazin-3-one was reacted to yield the title compound as a colorless crystalline powder (yield: 76.1%).

Melting point: 224.5–229.1° C. (dec.) $^1$H NMR(400 MHz, DMSO-d$_6$)δ: 0.96(6H, d, J=6.6 Hz), 2.22–2.35(1H, m), 2.76(3H, s), 2.77(3H, s), 3.14(4H, br), 3.35(4H, br), 3.87(2H, s), 4.04(2H, d, J=7.1 Hz), 7.80(2H, d, J=8.3 Hz), 8.07(2H, d, J=8.3 Hz), 8.18(1H, s). IR(KBr) cm$^{-1}$: 3426, 2960, 1656, 1608, 1459, 1400, 1044, 1011. Mass m/z: 402(M$^+$).

Example 168

Preparation of 4-dimethylaminomethyl-2-isobutyl-6-[4-(methylsulfinyl)phenyl]-2H-pyridazin-3-one Following the procedure of Example 7, 2-isobutyl-4-methanesulfonyloxymethyl-6-[4-(methylsulfinyl)phenyl]-2H-pyridazin-3-one was reacted to yield the title compound as a yellow oil (yield: 46.2%).

$^1$H NMR(400 MHz, CDCl$_3$)δ: 0.99(6H, d, J=6.8 Hz), 2.30–2.43(1H, m), 2.38(6H, s), 2.76(3H, s), 3.54(2H, s), 4.10(2H, d, J=7.4 Hz), 7.74(2H, d, J=8.2 Hz), 7.87(1H, s), 8.02(2H, d, J=8.2 Hz).

Example 169

Preparation of 4-dimethylaminomethyl-2-isobutyl-6-[4-(methylsulfinyl)phenyl]-2H-pyridazin-3-one hydrochloride Following the procedure of Example 4, 4-dimethylaminomethyl-2-isobutyl-6-[4-(methylsulfinyl)phenyl]-2H-pyridazin-3-one was reacted to yield the title compound as a colorless crystalline powder (yield: 77.4%).

Melting point: 204.2–206.0° C. $^1$H NMR(400 MHz, DMSO-d$_6$)δ: 0.97(6H, d, J=6.6 Hz), 2.24–2.36(1H, m), 2.78(3H, s), 2.83(6H, s), 4.07(2H, d, J=7.1 Hz), 4.28(2H, s), 7.82(2H, d, J=8.3 Hz), 8.09(2H, d, J=8.3 Hz), 8.49(1H, s). IR(KBr) cm$^{-1}$: 3438, 2961, 1652, 1607, 1467, 1400, 1047. Mass m/z: 347(M$^+$).

Example 170

Preparation of 2-cyclopropylmethyl-4-(4-methyl-1-piperazinyl)methyl-6-[4-(methylsulfonyl)phenyl]-2H-pyridazin-3-one 1) Preparation of 2-cyclopropylmethyl-4-methanesulfonyloxymethyl-6-[4-(methylsulfonyl)phenyl]-2H-pyridazin-3-one To a solution of 2-cyclopropylmethyl-4-methanesulfonyloxymethyl-6-[4-(methylthio)phenyl]-2H-pyridazin-3-one (226 mg, 0.59 mmol) in methylene chloride (10 mL) was added dropwise at −20° C. a solution of 3-chloroperbenzoic acid (410 mg, 2.38 mmol) in methylene chloride (2 mL), and at the same temperature, the mixture was stirred for 30 minutes. A 10% aqueous sodium hydrogensulfite was added to the reaction mixture, and then, the mixture was extracted with chloroform. The extract was successively washed with a saturated aqueous sodium hydrogencarbonate and brine, and was then dried over anhydrous sodium sulfate. The solvent was distilled off under reduced pressure. The residue was recrystallized from chloroform-hexane to yield the title compound as a colorless crystalline powder (209 mg, 85.3%).

$^1$H NMR(400 MHz, CDCl$_3$)δ: 0.46–0.63(4H, m), 1.37–1.46(1H, m), 3.10(3H, s), 3.18(3H, s), 4.20(2H, d, J=7.3 Hz), 5.31(2H, d, J=1.2 Hz), 7.86(1H, t, J=1.2 Hz), 8.02(2H, d, J=8.8 Hz), 8.06(2H, d, J=9.0 Hz). Mass m/z: 412(M$^+$).

2) Preparation of 2-cyclopropylmethyl-4-(4-methyl-1-piperazinyl)methyl-6-[4-(methylsulfonyl)phenyl]-2H-pyridazin-3-one Following the procedure of Example 1(10), 2-cyclopropylmethyl-4-methanesulfonyloxymethyl-6-[4-(methylsulfonyl)phenyl]-2H-pyridazin-3-one and 1-methylpiperazine were reacted to yield the title compound as a yellow oil (yield: 80.9%).

$^1$H NMR(400 MHz, CDCl$_3$)δ: 0.46–0.61(4H, m), 1.38–1.48(1H, m), 2.34(3H, s), 2.54(4H, br), 2.64 (4H, br), 3.10 (3H, s), 3.61 (2H, d, J=1.2 Hz), 4.13 (2H, d, J=7.1 Hz), 7.85(1H, t, J=11.2 Hz), 8.03(2H, d, J=9.0 Hz), 8.05(2H, d, J=9.0 Hz).

Example 171

Preparation of 2-cyclopropylmethyl-4-(4-methyl-1-piperazinyl)methyl-6-[4-(methylsulfonyl)phenyl]-2H-pyridazin-3-one dihydrochloride Following the procedure of Example 4, 2-cyclopropylmethyl-4-(4-methyl-1-piperazinyl)methyl-6-[4-(methylsulfonyl)phenyl]-2H-pyridazin-3-one was reacted to yield the title compound as a colorless crystalline powder (yield: 76.8%).

Melting point: 209.0–211.4° C. $^1$H NMR(400 MHz, DMSO-d$_6$)δ: 0.41–0.46(2H, m), 0.52–0.57(2H, m), 1.31–1.41(1H, m), 2.77(3H, s), 3.04(4H, br), 3.21(3H, s), 3.31(4H, br), 3.80(2H, s), 4.09(2H, d, J=7.1 Hz), 8.04(2H, d, J=8.3 Hz), 8.12(1H, s), 8.14(2H, d, J=8.3 Hz). IR(KBr) cm$^{-1}$: 3434, 3012, 1652, 1596, 1458, 1402, 1302, 1150. Mass m/z: 416(M$^+$).

Example 172

Preparation of 2-cyclopropylmethyl-4-dimethylaminomethyl-6-[4-(methylsulfonyl)phenyl]-2H-pyridazin-3-one Following the procedure of Example 1(10), 2-cyclopropylmethyl-4-methanesulfonyloxymethyl-6-[4-(methylsulfonyl)phenyl]-2H-pyridazin-3-one and dimethylamine were reacted to yield the title compound as a yellow oil (yield: 65.6%).

$^1$H NMR(400 MHz, CDCl$_3$)δ: 0.45–0.62(4H, m), 1.39–1.49(1H, m), 2.38(6H, s), 3.09(3H, s), 3.55(2H, s), 4.14(2H, d, J=7.2 Hz), 7.89(1H, s), 8.02(2H, d, J=8.4 Hz), 8.06(2H, d, J=8.6 Hz).

Example 173

Preparation of 2-cyclopropylmethyl-4-dimethylaminomethyl-6-[4-(methylsulfonyl)phenyl]-2H-pyridazin-3-one hydrochloride Following the procedure of Example 4, 2-cyclopropylmethyl-4-dimethylaminomethyl-6-[4-(methylsulfonyl)phenyl]-2H-pyridazin-3-one was reacted to yield the title compound as a colorless crystalline powder (yield: 63.4%).

Melting point: 239.5–240.7° C. $^1$H NMR(400 MHz, DMSO-d$_6$)δ: 0.43–0.59(4H, m), 1.33–1.43(1H, m), 2.83 (6H, s), 3.23(3H, s), 4.13(2H, d, J=7.1 Hz), 4.29(2H, s), 8.06(2H, d, J=7.8 Hz), 8.17(2H, d, J=8.3 Hz), 8.57(1H, s). IR(KBr) cm$^{-1}$: 3447, 2674, 1646, 1608, 1596, 1306, 1150, 777. Mass m/z: 361(M$^+$).

Example 174

Preparation of 4-(4-tert-butoxycarbonyl-1-piperazinyl)methyl-2-isobutyl-6-[4-(methylsulfonyl)phenyl]-2H-pyridazin-3-one 1) Preparation of 2-isobutyl-4-methanesulfonyloxymethyl-6-[4-(methylsulfonyl)phenyl]-2H-pyridazin-3-one Following the procedure of Example 170(1), 2-isobutyl-4-methanesulfonyloxymethyl-6-[4-(methylthio)phenyl]-2H-pyridazin-3-one was reacted to yield the title compound as a colorless crystalline powder (yield: 97.8%).

$^1$H NMR(400 MHz, CDCl$_3$)δ: 0.99(6H, d, J=6.6 Hz), 2.29–2.41(1H, m), 3.10(3H, s), 3.18(3H, s), 4.12(2H, d, J=7.3 Hz), 5.29(2H, d, J=1.2 Hz), 7.85(1H, t, J=1.4 Hz), 8.02(2H, d, J=8.8 Hz), 8.05(2H, d, J=8.8 Hz). Mass m/z: 414(M$^+$).

2) Preparation of 4-(4-tert-butoxycarbonyl-1-piperazinyl)methyl-2-isobutyl-6-[4-(methylsulfonyl)phenyl]-2H-pyridazin-3-one Following the procedure of Example 1(10), 2-isobutyl-4-methanesulfonyloxymethyl-6-[4-(methylsulfonyl)phenyl]-2H-pyridazin-3-one and tert-butyl 1-piperazinecarboxylate were reacted to yield the title compound as a yellow oil (yield: 75.9%).

$^1$H NMR(400 MHz, CDCl$_3$)δ: 0.99(6H, d, J=6.6 Hz), 1.47(9H, s), 2.29–2.41(1H, m), 2.54(4H, br), 3.09(3H, s), 3.51(4H, br), 3.60(2H, s), 4.11(2H, d, J=7.2 Hz), 7.86(1H, s), 8.02(2H, d, J=8.8 Hz), 8.05(2H, d, J=8.8 Hz).

Example 175

Preparation of 2-isobutyl-6-[4-(methylsulfonyl)phenyl]-4-(1-piperazinyl)methyl-2H-pyridazin-3-one dihydrochloride Following the procedure of Example 2, 4-(4-tert-butoxycarbonyl-1-piperazinyl)methyl-2-isobutyl-6-[4-(methylsulfonyl)phenyl]-2H-pyridazin-3-one was reacted to yield the title compound as a colorless crystalline powder (yield: 88.2%).

Melting point: 222.4–224.2° C. $^1$H NMR(400 MHz, DMSO-$d_6$)δ: 0.96(6H, d, J=6.8 Hz), 2.22–2.35(1H, m), 3.06(4H, br), 3.21(3H, s), 3.28(4H, t, J=5.2 Hz), 3.87(2H, s), 4.05(2H, d, J=7.1 Hz), 8.04(2H, d, J=8.6 Hz), 8.14(2H, d, J=8.3 Hz), 8.22(1H, s). IR(KBr) cm$^{-1}$: 3421, 2957, 1656, 1611, 1597, 1305, 1149, 961. Mass m/z: 404(M$^+$).

Example 176

Preparation of 2-isobutyl-4-(4-methyl-1-piperazinyl)methyl-6-[4-(methylsulfonyl)phenyl]-2H-pyridazin-3-one Following the procedure of Example 1(10), 2-isobutyl-4-methanesulfonyloxymethyl-6-[4-(methylsulfonyl)phenyl]-2H-pyridazin-3-one and 1-methylpiperazine were reacted to yield the title compound as a yellow oil (yield: 88.5%).

$^1$H NMR(400 MHz, CDCl$_3$)δ: 0.99(6H, d, J=6.8 Hz), 2.28–2.40(1H, m), 2.37(3H, s), 2.53(4H, br), 2.63(4H, br), 3.10(3H, s), 3.60(2H, s), 4.10(2H, d, J=7.3 Hz), 7.84(1H, s), 8.02(2H, d, J=9.0 Hz), 8.05(2H, d, J=8.8 Hz).

Example 177

Preparation of 2-isobutyl-4-(4-methyl-1-piperazinyl)methyl-6-[4-(methylsulfonyl)phenyl]-2H-pyridazin-3-one dihydrochloride Following the procedure of Example 4, 2-isobutyl-4-(4-methyl-1-piperazinyl)methyl-6-[4-(methylsulfonyl)phenyl]-2H-pyridazin-3-one was reacted to yield the title compound as a colorless crystalline powder (yield: 62.0%).

Melting point: 224.5–228.0° C. $^1$H NMR(400 MHz, DMSO-$d_6$)δ: 0.95(6H, d, J=6.8 Hz), 2.23–2.35(1H, m), 2.76(3H, s), 3.08(4H, br), 3.21(3H, s), 3.32(4H, br), 3.83(2H, s), 4.05(2H, d, J=7.1 Hz), 8.04(2H, d, J=8.3 Hz), 8.13(2H, d, J=8.5 Hz), 8.15(1H, s). IR(KBr) cm$^{-1}$: 3447, 2958, 1652, 1610, 1596, 1319, 1152, 955. Mass m/z: 418 (M$^+$).

Example 178

Preparation of 4-N,N-bis(2-hydroxyethyl)aminomethyl-2-isobutyl-6-[4-(methylsulfonyl)phenyl]-2H-pyridazin-3-one Following the procedure of Example 1(10), 2-isobutyl-4-methanesulfonyloxymethyl-6-[4-(methylsulfonyl)phenyl]-2H-pyridazin-3-one and diethanolamine were reacted to yield the title compound as a yellow oil (yield: 51.1%).

$^1$H NMR(400 MHz, CDCl$_3$)δ: 0.98(6H, d, J=6.6 Hz), 2.28–2.40(1H, m), 2.73(4H, t, J=4.8 Hz), 3.08(3H, s), 3.68 (4H, t, J=4.9 Hz), 3.73(2H, s), 4.11(2H, d, J=7.4 Hz), 7.93(1H, s), 8.00(2H, d, J=8.6 Hz), 8.05(2H, d, J=8.8 Hz). Mass m/z: 392(M$^+$—CH$_2$OH).

Example 179

Preparation of 4-dimethylaminomethyl-2-isobutyl-6-[4-(methylsulfonyl)phenyl]-2H-pyridazin-3-one Following the procedure of Example 7, 2-isobutyl-4-methanesulfonyloxymethyl-6-[4-(methylsulfonyl)phenyl]-2H-pyridazin-3-one was reacted to yield the title compound as a yellow oil (yield: 82.1%).

$^1$H NMR(400 MHz, CDCl$_3$)δ: 0.99(6H, d, J=6.6 Hz), 2.30–2.41(1H, m), 2.37(6H, s), 3.09(3H, s), 3.52(2H, s), 4.11(2H, d, J=7.2 Hz), 7.86(1H, s), 8.02(2H, d, J=8.8 Hz), 8.05(2H, d, J=8.8 Hz).

Example 180

Preparation of 4-dimethylaminomethyl-2-isobutyl-6-[4-(methylsulfonyl)phenyl]-2H-pyridazin-3-one hydrochloride Following the procedure of Example 4, 4-dimethylaminomethyl-2-isobutyl-6-[4-(methylsulfonyl)-phenyl]-2H-pyridazin-3-one was reacted to yield the title compound as a colorless crystalline powder (yield: 58.6%).

Melting point: 221.4–223.3° C. $^1$H NMR(400 MHz, DMSO-$d_6$)δ: 0.97(6H, d, J=6.6 Hz), 2.25–2.36(1H, m), 2.82(6H, s), 3.22(3H, s), 4.08(2H, d, J=7.3 Hz), 4.28(2H, s), 8.06(2H, d, J=8.3 Hz), 8.15(2H, d, J=8.5 Hz), 8.55(1H, s). IR(KBr) cm$^{-1}$: 3447, 2963, 1653, 1609, 1597, 1307, 1152, 777. Mass m/z: 363(M$^+$).

Example 181

Preparation of 2-cyclopropylmethyl-6-(3-fluoro-4-methoxyphenyl)-4-pyrrolidinomethyl-2H-pyridazin-3-one Following the procedure of Example 1(10), 2-cyclopropylmethyl-6-(3-fluoro-4-methoxyphenyl)-4-methanesulfonyloxymethyl-2H-pyridazin-3-one and pyrrolidine were reacted to yield the title compound as a yellow oil (yield: 75.9%).

$^1$H NMR(400 MHz, CDCl$_3$)δ: 0.44–0.61(4H, m), 1.42 (1H, m), 1.85–2.00(4H, m), 2.70–3.00(4H, m), 3.83(2H, brs), 3.94 (3H, s), 4.10 (2H, d, J=7.3 Hz), 7.03(1H, dd, J=8.5, 8.5 Hz), 7.60(1H, d, J=8.5 Hz), 7.65(1H, dd, J=8.5, 2.0 Hz), 8.00(1H, brs). IR(Neat) cm$^{-1}$: 1652, 1608, 1523, 1438, 1286, 758. Mass m/z: 357(M$^+$).

Example 182

Preparation of 2-cyclopentylmethyl-6-(3-fluoro-4-methoxyphenyl)-4-(4-methyl-1-piperazinyl)methyl-2H-pyridazin-3-one 1) Preparation of 2-cyclopentylmethyl-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and cyclopentylmethyl bromide {*J. Org. Chem.*, 36, 3103 (1971)} were reacted to yield the title compound as yellow needles (yield: 72.0%).

Melting point: 56–66° C. $^1$H NMR(400 MHz, CDCl$_3$)δ: 1.30–1.45(2H, m), 1.53–1.65(2H, m), 1.65–1.80(4H, m), 2.57(1H, m), 3.95(3H, s), 3.98(3H, s), 4.24(2H, d, J=7.8

Hz), 7.03(1H, dd, J=8.5, 8.5 Hz), 7.50(1H, d, J=8.8 Hz), 7.61(1H, d, J=10.2 Hz), 8.19(1H, s).

2) Preparation of 4-carboxy-2-cyclopentylmethyl-6-(3-fluoro-4-methoxyphenyl)-2H-pyridazin-3-one Following the procedure of Example 1(7), 2-cyclopentylmethyl-6-(3-fluoro-4-methoxyphenyl)-4-methoxycarbonyl-2H-pyridazin-3-one was reacted to yield the title compound as a yellow powder (yield: 71.1%).

Melting point: 159–161° C. $^1$H NMR(400 MHz, CDCl$_3$) δ: 1.33–1.45(2H, m), 1.58–1.65(2H, m), 1.68–1.82(4H, m), 2.57(1H, m), 3.97(3H, s), 4.32(2H, d, J=7.6 Hz), 7.06(1H, dd, J=8.5, 8.5 Hz), 7.56(1H, d, J=8.5 Hz), 7.68(1H, dd, J=12.2, 2.0 Hz), 8.61(1H, s).

3) Preparation of 2-cyclopentylmethyl-6-(3-fluoro-4-methoxyphenyl)-4-hydroxymethyl-2H-pyridazin-3-one Following the procedure of Example 1(8), 4-carboxy-2-cyclopentylmethyl-6-(3-fluoro-4-methoxyphenyl)-2H-pyridazin-3-one was reacted to yield the title compound as a yellow powder (yield: 47.3%).

Melting point: 130–133° C. $^1$H NMR(400 MHz, CDCl$_3$) δ: 1.30–1.42(2H, m), 1.50–1.62(2H, m), 1.62–1.80(4H, m), 2.54(1H, m), 3.95(3H, s), 4.19(2H, d, J=7.6 Hz), 4.71(2H, s), 7.02(1H, dd, J=8.5, 8.5 Hz), 7.51(1H, d, J=8.5 Hz), 7.62(1H, dd, J=12.8, 1.5 Hz), 7.63(1H, s).

4) Preparation of 2-cyclopentylmethyl-6-(3-fluoro-4-methoxyphenyl)-4-methanesulfonyloxymethyl-2H-pyridazin-3-one Following the procedure of Example 1(9), 2-cyclopentylmethyl-6-(3-fluoro-4-methoxyphenyl)-4-hydroxymethyl-2H-pyridazin-3-one was reacted to yield the title compound as a yellow powder (yield: 75.3%).

Melting point: 108–116° C. $^1$H NMR(400 MHz, CDCl$_3$) δ: 1.25–1.32(2H, m), 1.32–1.45(2H, m), 1.65–1.77(4H, m), 2.54(1H, m), 3.17(3H, s), 3.95(3H, s), 4.19(2H, d, J=7.6 Hz), 5.27(2H, s), 7.03(1H, dd, J=8.5, 8.5 Hz), 7.50(1H, d, J=8.5 Hz), 7.62(1H, dd, J=12.2, 2.2 Hz), 7.74(1H, s).

5) Preparation of 2-cyclopentylmethyl-6-(3-fluoro-4-methoxyphenyl)-4-(4-methyl-1-piperazinyl)methyl-2H-pyridazin-3-one Following the procedure of Example 1(10), 2-cyclopentylmethyl-6-(3-fluoro-4-methoxyphenyl)-4-methanesulfonyloxymethyl-2H-pyridazin-3-one and 1-methylpiperazine were reacted to yield the title compound as a yellow oil (yield: 61.4%).

$^1$H NMR(400 MHz, CDCl$_3$)δ: 1.32–1.42(2H, m), 1.50–1.60(2H, m), 1.65–1.80(4H, m), 2.38, 2.40(each s, 3H in total), 2.54(1H, m), 2.60–2.75(8H, m), 3.59(2H, s), 3.95 (3H, s), 4.18(2H, d, J=7.6 Hz), 7.04(1H, dd, J=8.5, 8.5 Hz), 7.54(1H, d, J=8.5 Hz), 7.61(1H, dd, J=8.5, 2.2 Hz), 7.72(1H, s). IR(Neat) cm$^{-1}$: 1652, 1608, 1523, 1439, 1286, 760. Mass m/z: 414(M$^+$).

Example 183

Preparation of 2-cyclopentylmethyl-6-(3-fluoro-4-methoxyphenyl)-4-(4-methyl-1-piperazinyl)methyl-2H-pyridazin-3-one dihydrochloride Following the procedure of Example 4, 2-cyclopentylmethyl-6-(3-fluoro-4-methoxyphenyl)-4-(4-methyl-1-piperazinyl)methyl-2H-pyridazin-3-one was reacted to yield the title compound as a pale brown crystalline powder (yield: 59.6%).

Melting point: 234–236° C. (dec.) $^1$H NMR(400 MHz, DMSO-d$_6$)δ: 1.28–1.40(2H, m), 1.48–1.56(2H, m), 1.60–1.73(4H, m), 2.46(1H, m), 2.82(3H, s), 3.50–3.75 (10H, m), 3.91(3H, s), 4.10(2H, d, J=7.6 Hz), 7.31(1H, dd, J=8.8, 8.8 Hz), 7.68–7.76(2H, m), 8.25(1H, s). IR(KBr) cm$^{-1}$: 1652, 1606, 1523, 1439, 1292, 764.

Example 184

Preparation of 4-N,N-bis(2-hydroxyethyl)aminomethyl-2-cyclopentylmethyl-6-(3-fluoro-4-methoxyphenyl)-2H-pyridazin-3-one Following the procedure of Example 1(10), 2-cyclopentylmethyl-6-(3-fluoro-4-methoxyphenyl)-4-methanesulfonyloxymethyl-2H-pyridazin-3-one and diethanolamine were reacted to yield the title compound as a yellow oil (yield: 54.9%).

$^1$H NMR(400 MHz, CDCl$_3$)δ: 1.30–1.45(2H, m), 1.50–1.62(2H, m), 1.62–1.80(4H, m), 2.53(1H, m), 2.75–2.90(4H, m), 3.70–3.75(4H, m), 3.80–3.85(2H, m), 3.94(3H, s), 4.20(2H, d, J=7.6 Hz), 7.02(1H, dd, J=8.5, 8.5 Hz), 7.56(1H, d, J=8.5 Hz), 7.63(1H, dd, J=8.5, 2.0 Hz), 7.65 (1H, m). IR(Neat) cm$^{-1}$: 1648, 1598, 1523, 1439, 1267, 728. Mass m/z: 383(M$^{+-2}$H$_2$O).

Example 185

Preparation of 2-cyclopentylmethyl-4-dimethylaminomethyl-6-(3-fluoro-4-methoxyphenyl)-2H-pyridazin-3-one Following the procedure of Example 7, 2-cyclopentylmethyl-6-(3-fluoro-4-methoxyphenyl)-4-methanesulfonyloxymethyl-2H-pyridazin-3-one and dimethylamine were reacted to yield the title compound as a yellow oil (yield: 63.7%).

$^1$H NMR(400 MHz, CDCl$_3$)δ: 1.30–1.45(2H, m), 1.50–1.63(2H, m), 1.63–1.80(4H, m), 2.43(6H, s), 2.55(1H, m), 3.61(2H, s), 3.94(3H, s), 4.19(2H, d, J=7.6 Hz), 7.20 (1H, d, J=8.5, 8.5 Hz), 7.58(1H, d, J=8.5 Hz), 7.65(1H, dd, J=8.5, 2.2 Hz), 7.91(1H, brs). IR(Neat) cm$^{-1}$: 1652, 1608, 1523, 1438, 1288, 762. Mass m/z: 359(M$^+$).

Example 186

Preparation of 2-cyclopentylmethyl-6-(3-fluoro-4-methoxyphenyl)-4-(1-piperazinyl)methyl-2H-pyridazin-3-one 1) Preparation of 4-(4-tert-butoxycarbonyl-1-piperazinyl)methyl-2-cyclopentylmethyl-6-(3-fluoro-4-methoxyphenyl)-2H-pyridazin-3-one Following the procedure of Example 1(10), 2-cyclopentylmethyl-6-(3-fluoro-4-methoxyphenyl)-4-methanesulfonyloxymethyl-2H-pyridazin-3-one and tert-butyl 1-piperazinecarboxylate were reacted to yield the title compound as a yellow oil (yield: 78.8%).

$^1$H NMR(400 MHz, CDCl$_3$)δ: 1.35–1.43(2H, m), 1.47 (9H, s), 1.55–1.60(2H, m), 1.65–1.75(4H, m), 2.45–2.60 (5H, m), 3.45–3.55(4H, m), 3.95(3H, s), 4.18(2H, d, J=7.6 Hz), 7.03(1H, dd, J=8.5, 8.5 Hz), 7.52(1H, m), 7.62(1H, d, J=12.4 Hz), 7.74(1H, m).

2) Preparation of 2-cyclopentylmethyl-6-(3-fluoro-4-methoxyphenyl)-4-(1-piperazinyl)methyl-2H-pyridazin-3-one Following the procedure of Example 20, 4-(4-tert-butoxycarbonyl-1-piperazinyl)methyl-2-cyclopentylmethyl-6-(3-fluoro-4-methoxyphenyl)-2H-pyridazin-3-one was reacted to yield the title compound as a yellow oil (yield: 88.0%).

$^1$H NMR(400 MHz, CDCl$_3$)δ: 1.33–1.43(2H, m), 1.50–1.62(2H, m), 1.62–1.80(4H, m), 2.55(1H, m), 2.57–2.63(4H, m), 3.00–3.02(4H, m), 3.56(2H, brs), 3.95 (3H,s), 4.18(2H, d, J=7.6 Hz), 7.04(1H, dd, J=8.5, 8.5 Hz), 7.52(1H, d, J=8.5 Hz), 7.62(1H, dd, J=8.5, 2.2 Hz), 7.73(1H, s). IR(Neat) cm$^{-1}$: 1652, 1608, 1523, 1439, 1287, 761. Mass m/z: 400(M$^+$).

Example 187

Preparation of 4-aminomethyl-2-cyclopentylmethyl-6-(3-fluoro-4-methoxyphenyl)-2H-pyridazin-3-one Following the procedure of Example 24(1), 2-cyclopentylmethyl-6-(3-fluoro-4-methoxyphenyl)-4-methanesulfonyloxymethyl-2H-pyridazin-3-one was reacted to yield a crude product. Without purification, the crude product was reacted further in accordance with the procedure of Example 24(2) to yield the title compound as a yellow oil (yield: 53.7%).

$^1$H NMR(400 MHz, CDCl$_3$)δ: 1.30–1.45(2H, m), 1.50–1.63(2H, m), 1.63–1.80(4H, m), 2.54(1H, m), 3.91(2H, s), 3.93(3H, s), 4.17(2H, d, J=7.6 Hz), 7.01(1H, dd, J=8.5, 8.5 Hz), 7.52(1H, d, J=8.5 Hz), 7.62(1H, dd, J=8.5, 2.2 Hz), 7.71(1H, brs). IR(Neat) cm$^{-1}$: 3376, 1649, 1606, 1523, 1439, 1285, 761. Mass m/z: 331(M$^+$).

Example 188

Preparation of 4-aminomethyl-2-cyclopentylmethyl-6-(3-fluoro-4-methoxyphenyl)-2H-pyridazin-3-one hydrochloride Following the procedure of Example 4, 4-aminomethyl-2-cyclopentylmethyl-6-(3-fluoro-4-methoxyphenyl)-2H-pyridazin-3-one was reacted to yield the title compound as a slightly-yellow crystalline powder (yield: 59.0%).

Melting point: 193–196° C. $^1$H NMR(400 MHz, DMSO-d$_6$)δ: 1.29–1.40(2H, m), 1.45–1.57(2H, m), 1.60–1.70(4H, m), 2.45(1H, m), 3.91(3H, s), 4.00(2H, s), 4.12(2H, d, J=7.6 Hz), 7.34(1H, dd, J=8.5, 8.5 Hz), 7.69–7.72(2H, m), 8.47 (1H, brs). IR(KBr) cm$^{-1}$: 3436, 1656, 1617, 1521, 1438, 1295, 763.

Example 189

Preparation of 2-(4-fluorobenzyl)-6-(3-fluoro-4-methoxyphenyl)-4-(4-methyl-1-piperazinyl)methyl-2H-pyridazin-3-one 1) Preparation of 2-(4-fluorobenzyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 4-fluorobenzyl chloride were reacted to yield the title compound as a slightly-yellow crystalline powder (yield: 86.6%).

$^1$H NMR(400 MHz, CDCl$_3$)δ: 3.95(3H, s), 3.97(3H, s), 5.39(2H, s), 7.00–7.06(3H, m), 7.48–7.63(4H, m), 8.19(1H, s).

2) Preparation of 4-carboxy-2-(4-fluorobenzyl)-6-(3-fluoro-4-methoxyphenyl)-2H-pyridazin-3-one Following the procedure of Example 1(7), 2-(4-fluorobenzyl)-6-(3-fluoro-4-methoxyphenyl)-4-methoxycarbonyl-2H-pyridazin-3-one was reacted to yield the title compound as a yellow powder (yield: 97.7%).

Melting point: 222–224° C. $^1$H NMR(400 MHz, CDCl$_3$) δ: 3.97(3H, s), 5.47(2H, s), 7.03–7.10(3H, m), 7.49–7.56 (3H, m), 7.67(1H, dd, J=12.1, 2.2 Hz), 8.60(1H, s).

3) Preparation of 2-(4-fluorobenzyl)-6-(3-fluoro-4-methoxyphenyl)-4-hydroxymethyl-2H-pyridazin-3-one Following the procedure of Example 1(8), 4-carboxy-2-(4-fluorobenzyl)-6-(3-fluoro-4-methoxyphenyl)-2H-pyridazin-3-one was reacted to yield the title compound as a yellow powder (yield: 27.0%).

Melting point: 127–130° C. $^1$H NMR(400 MHz, CDCl$_3$) δ: 3.95(3H, s), 4.79(2H, d, J=1.5 Hz), 5.36(2H, s), 6.98–7.05 (3H, m), 7.46–7.52(3H, m), 7.61(1H, dd, J=12.2, 2.2 Hz), 7.65(1H, s).

4) Preparation of 2-(4-fluorobenzyl)-6-(3-fluoro-4-methoxyphenyl)-4-methanesulfonyloxymethyl-2H-pyridazin-3-one Following the procedure of Example 1(9), 2-(4-fluorobenzyl)-6-(3-fluoro-4-methoxyphenyl)-4-hydroxymethyl-2H-pyridazin-3-one was reacted to yield the title compound as a pale yellow powder (yield: 49.4%).

Melting point: 125–133° C. $^1$H NMR(400 MHz, CDCl$_3$) δ: 3.15(3H, s), 3.95(3H, s), 5.25(2H, d, J=1.2 Hz), 5.35(2H, s), 7.00–7.06(3H, m), 7.45–7.55(3H, m), 7.61(1H, dd, J=12.4, 2.2 Hz), 7.74(1H, s).

5) Preparation of 2-(4-fluorobenzyl)-6-(3-fluoro-4-methoxyphenyl)-4-(4-methyl-1-piperazinyl)methyl-2H-pyridazin-3-one Following the procedure of Example 1(10), 2-(4-fluorobenzyl)-6-(3-fluoro-4-methoxyphenyl)-4-methanesulfo nyloxymethyl-2H-pyridazin-3-one and 1-methylpiprazine were reacted to yield the title compound as a slightly-brown crystalline powder (yield: 45.8%).

Melting point: 112–113° C. $^1$H NMR(400 MHz, CDCl$_3$)δ: 2.39(3H, s), 2.60–2.90(8H, m), 3.60(2H, s), 3.95(3H, s), 5.34(2H, s), 6.99–7.06(3H, m), 7.47–7.51(3H, m), 7.59(1H, dd, J=12.4, 2.0 Hz), 7.71(1H, s). IR(KBr) cm$^{-1}$: 1651, 1608, 1518, 1439, 1289, 764. Mass m/z: 440(M$^+$).

Example 190

Preparation of 4-dimethylaminomethyl-2-(4-fluorobenzyl)-6-(3-fluoro-4-methoxyphenyl)-2H-pyridazin-3-one Following the procedure of Example 7, 2-(4-fluorobenzyl)-6-(3-fluoro-4-methoxyphenyl)-4-methanesulfonyloxymethyl-2H-pyridazin-3-one and dimethylamine were reacted to yield the title compound as a slightly-yellow crystalline powder (yield: 60.8%).

Melting point: 127–129° C. $^1$H NMR(400 MHz, CDCl$_3$) δ: 2.41(6H, s), 3.58(2H, s), 3.94(3H, s), 5.35(2H, s), 6.98–7.05(3H, m), 7.46–7.52(2H, m), 7.56(1H, d, J=8.8 Hz), 7.64(1H, dd, J=12.4, 2.2 Hz), 7.90(1H, brs). IR(KBr) cm$^{-1}$: 1652, 1612, 1519, 1439, 1291, 763. Mass m/z: 385(M$^+$).

Example 191

Preparation of 4-N,N-bis(2-hydroxyethyl)aminomethyl-2-(4-fluorobenzyl)-6-(3-fluoro-4-methoxyphenyl)-2H-pyridazin-3-one Following the procedure of Example 1(10), 2-(4-fluorobenzyl)-6-(3-fluoro-4-methoxyphenyl)-4-methanesulfonyloxymethyl-2H-pyridazin-3-one and diethanolamine were reacted to yield the title compound as a yellow oil (yield: 66.1%).

$^1$H NMR(400 MHz, CDCl$_3$)δ: 2.70–2.92(4H, m), 3.70–3.85(6H, m), 3.93(3H, s), 5.35(2H, s), 6.99–7.04(3H, m), 7.45–7.50(2H, m), 7.55(1H, d, J=8.3 Hz), 7.63(1H, dd, J=12.4, 2.0 Hz), 7.90(1H, m). IR(Neat) cm$^{-1}$: 1652, 1606, 1520, 1435, 1281, 762. Mass m/z: 385(M$^+$—CH$_2$OH).

Example 192

Preparation of 2-(4-fluorobenzyl)-6-(3-fluoro-4-methoxyphenyl)-4-(1-piperazinyl)methyl-2H-pyridazin-3-one 1) Preparation of 4-(4-tert-butoxycarbonyl-1-piperazinyl)methyl-2-(4-fluorobenzyl)-6-(3-fluoro-4-methoxyphenyl)-2H-pyridazin-3-one Following the procedure of Example 1(10), 2-(4-fluorobenzyl)-6-(3-fluoro-4-methoxyphenyl)-4-methanesulfonyloxymethyl-2H-pyridazin-3-one and tert-butyl 1-piperazinecarboxylate were reacted to yield the title compound as a yellow oil (yield: 78.8%).

$^1$H NMR(400 MHz, CDCl$_3$)δ: 1.46(9H, s), 1.55–1.65(4H, m), 3.40–3.60(4H, m), 3.95(3H, s), 5.34(2H, s), 6.96–7.05 (3H, m), 7.47–7.50(3H, m), 7.41(1H, d, J=12.4 Hz), 7.74 (1H, brs).

2) Preparation of 2-(4-fluorobenzyl)-6-(3-fluoro-4-methoxyphenyl)-4-(1-piperazinyl)methyl-2H-pyridazin-3-one Following the procedure of Example 20, 4-(4-tert-butoxycarbonyl-1-piperazinyl)methyl-2-(4-fluorobenzyl)-6-(3-fluoro-4-methoxyphenyl)-2H-pyridazin-3-one was reacted to yield the title compound as a pale yellow crystalline powder (yield: 63.4%).

Melting point: 142–143° C. $^1$H NMR(400 MHz, CDCl$_3$) δ: 2.50–2.60 (4H, m), 2.96–3.02 (4H, m), 3.54 (2H, d, J=1.2 Hz), 3.95(3H, s), 5.34(2H, s), 6.98–7.06(3H, m), 7.46–7.53 (3H, m), 7.61(1H, dd, J=12.5, 2.2 Hz), 7.74(1H, br.s). IR(KBr) cm$^{-1}$: 1652, 1609, 1523, 1437, 1290, 762. Mass m/z: 426(M$^+$).

Example 193

Preparation of 2-(4-fluorobenzyl)-6-(3-fluoro-4-methoxyphenyl)-4-(1-piperazinyl)methyl-2H-pyridazin-3-one dihydrochloride Following the procedure of Example 4, 2-(4-fluorobenzyl)-6-(3-fluoro-4-methoxyphenyl)-4-(1-piperazinyl)methyl-2H-pyridazin-3-one was reacted to yield the title compound as a colorless crystalline powder (yield: 76.9%).

Melting point: 153–156° C. $^1$H NMR(400 MHz, DMSO-d$_6$)δ: 3.30–3.75(10H, m), 3.90(3H, s), 5.33(2H, s), 7.15–7.21(2H, m), 7.30(1H, m), 7.43–7.49(2H, m), 7.69–7.78(3H, m). IR(KBr) cm$^{-1}$: 1660, 1609, 1524, 1439, 1292, 766.

Example 194

Preparation of 4-aminomethyl-2-(4-fluorobenzyl)-6-(3-fluoro-4-methoxyphenyl)-2H-pyridazin-3-one Following the procedure of Example 24(1), 2-(4-fluorobenzyl)-6-(3-fluoro-4-methoxyphenyl)-4-methanesulfonyloxymethyl-2H-pyridazin-3-one was reacted to yield a crude product. Without purification, the crude product was reacted further in accordance with the procedure of Example 24 (2) to yield the title compound as a pale brown crystalline powder (yield: 50.4%).

Melting point: 145–149° C. $^1$H NMR(400 MHz, CDCl$_3$) δ: 3.92(3H, s), 3.94(2H, s), 5.31(2H, s), 6.95–7.03(3H, m), 7.40–7.52(3H, m), 7.60(1H, dd, J=12.5, 2.2 Hz), 7.75(1H, brs). IR(KBr) cm$^{-1}$: 3391, 1648, 1606, 1519, 1437, 1292, 761. Mass m/z: 357(M$^+$).

Example 195

Preparation of 4-aminomethyl-2-(4-fluorobenzyl)-6-(3-fluoro-4-methoxyphenyl)-2H-pyridazin-3-one hydrochloride Following the procedure of Example 4, 4-aminomethyl-2-(4-fluorobenzyl)-6-(3-fluoro-4-methoxyphenyl)-2H-pyridazin-3-one was reacted to yield the title compound as a slightly-yellow crystalline powder (yield: 72.5%).

Melting point: 210–214° C. $^1$H NMR(400 MHz, DMSO-d$_6$)δ: 3.91(3H, s), 4.01(2H, s), 5.35(2H, s), 7.16–7.21(2H, m), 7.34(1H, dd, J=8.8, 8.8 Hz), 7.45–7.49(2H, m), 7.68–7.78(2H, m), 8.29(1H, s). IR(KBr) cm$^{-1}$: 3429, 1653, 1612, 1522, 1439, 1292, 764.

Example 196

Preparation of 6-(3-fluoro-4-methoxyphenyl)-2-[3-(4-fluorophenyl)propyl]-4-(4-methyl-1-piperazinyl)methyl-2H-pyridazin-3-one

1) Preparation of 6-(3-fluoro-4-methoxyphenyl)-2-[3-(4-fluorophenyl)propyl]-4-methoxycarbonyl-2H-pyridazin-3-one Following the procedure of Example 1(6), 6-(3-fluoro-4-methoxyphenyl)-4-methoxycarbonyl-2H-pyridazin-3-one- and the mesylate derivative of 3-(4-fluorophenyl)-1-propanol {*J. Med. Chem.*, 19, 461 (1976)} were reacted to yield the title compound as a yellow oil (yield: 90.1%). The mesylate derivative was prepared in accordance with the procedure of Example 1(9).

$^1$H NMR(400 MHz, CDCl$_3$)δ: 2.16–2.26(2H, m), 2.71 (2H, t, J=7.3 Hz), 3.95(3H, s), 3.98(3H, s), 4.32(2H, t, J=7.3 Hz), 6.93–7.06(3H, m), 7.14–7.18(2H, m), 7.49(1H, m), 7.60(1H, dd, J=13.2, 2.2 Hz), 8.17(1H, s).

2) Preparation of 4-carboxy-6-(3-fluoro-4-methoxyphenyl)-2-[3-(4-fluorophenyl)propyl]-2H-pyridazin-3-one Following the procedure of Example 1(7), 6-(3-fluoro-4-methoxyphenyl)-2-[3-(4-fluorophenyl)propyl]-4-methoxycarbonyl-2H-pyridazin-3-one was reacted to yield the title compound as a yellow powder (yield: 89.2%).

Melting point: 185–187° C. $^1$H NMR(400 MHz, CDCl$_3$) δ: 2.20–2.30(2H, m), 2.74(2H, t, J=7.3 Hz), 3.97(3H, s), 4.40(2H, t, J=7.3 Hz), 6.94–7.17(5H, m), 7.55(1H, d, J=8.5 Hz), 7.66(1H, dd, J=12.2, 2.2 Hz), 8.58(1H, s).

3) Preparation of 6-(3-fluoro-4-methoxyphenyl)-2-[3-(4-fluorophenyl)propyl]-4-hydroxymethyl-2H-pyridazin-3-one Following the procedure of Example 1(8), 4-carboxy-6-(3-fluoro-4-methoxyphenyl)-2-[3-(4-fluorophenyl)propyl]-2H-pyridazin-3-one was reacted to yield the title compound as a yellow powder (yield: 37.0%).

Melting point: 130–133° C. $^1$H NMR(400 MHz, CDCl$_3$) δ: 2.15–2.22(2H, m), 2.71(2H, t, J=7.3 Hz), 3.95(3H, s), 4.27(2H, t, J=7.3 Hz), 4.70(2H, d, J=1.2 Hz), 6.93–7.06(3H, m), 7.14–7.18(2H, m), 7.50(1H, d, J=8.8 Hz), 7.61(1H, dd, J=12.7, 2.2 Hz), 7.63(1H, s).

4) Preparation of 6-(3-fluoro-4-methoxyphenyl)-2-[3-(4-fluorophenyl)propyl]-4-methanesulfonyloxymethyl-2H-pyridazin-3-one Following the procedure of Example 1(9), 6-(3-fluoro-4-methoxyphenyl)-2-[3-(4-fluorophenyl)propyl]-4-hydroxymethyl-2H-pyridazin-3-one was reacted to yield the title compound as a yellow powder (yield: 92.3%).

Melting point: 112–116° C. $^1$H NMR(400 MHz, CDCl$_3$)δ: 2.15–2.25(2H, m), 2.71(2H, t, J=7.3 Hz), 3.17(3H, s), 3.95 (3H, s), 4.27(2H, t, J=7.3 Hz), 5.25(2H, d, J=1.2 Hz), 6.93–7.05(3H, m), 7.14–7.18(2H, m), 7.49(1H, d, J=8.5 Hz), 7.61(1H, dd, J=13.4, 2.0 Hz), 7.72(1H, s).

5) Preparation of 6-(3-fluoro-4-methoxyphenyl)-2-[3-(4-fluorophenyl)propyl]-4-(4-methyl-1-piperazinyl)methyl-2H-pyridazin-3-one Following the procedure of Example 1(10), 6-(3-fluoro-4-methoxyphenyl)-2-[3-(4-fluorophenyl)propyl]-4-methanesulfonyloxymethyl-2H-pyridazin-3-one and 1-methylpiperazine were reacted to yield the title compound as a yellow oil (yield: 79.3%).

$^1$H NMR(400 MHz, CDCl$_3$)δ: 2.15–2.25(2H, m), 2.41 (3H, s), 2.60–2.75(10H, m), 3.58(2H, s), 3.75(3H, s), 4.27 (2H, t, J=7.3 Hz), 6.92–7.06(3H, m), 7.14–7.18(2H, m), 7.51(1H, d, J=8.5 Hz), 7.60(1H, dd, J=12.4, 2.0 Hz), 7.69 (1H, s). IR(Neat) cm$^{-1}$: 1652, 1608, 1511, 1439, 1284, 758. Mass m/z: 468(M$^+$)

Example 197

Preparation of 4-dimethylaminomethyl-6-(3-fluoro-4-methoxyphenyl)-2-[3-(4-fluorophenyl)propyl]-2H-pyridazin-3-one Following the procedure of Example 7, 6-(3-fluoro-4-methoxyphenyl)-2-[3-(4-fluorophenyl)propyl]-4-methanesulfonyloxymethyl-2H-pyridazin-3-one and dimethylamine were reacted to yield the title compound as a pale yellow crystalline powder (yield: 61.8%).

Melting point: 97–100° C. $^1$H NMR(400 MHz, CDCl$_3$)δ: 2.15–2.25(2H, m), 2.43(6H, s), 2.71(2H, t, J=7.3 Hz), 3.60 (2H, s), 3.94(3H, s), 4.27(2H, t, J=7.3 Hz), 6.93–7.05(3H, m), 7.15–7.18(2H, m), 7.57(1H, d, J=8.5 Hz), 7.64(1H, dd, J=12.6, 2.2 Hz), 7.90(1H, brs). IR(KBr) cm$^{-1}$: 1653, 1611, 1510, 1436, 1296, 763. Mass m/z: 413(M$^+$).

Example 198

Preparation of 4-N,N-bis(2-hydroxyethyl)aminomethyl-6-(3-fluoro-4-methoxyphenyl)-2-[3-(4-fluorophenyl)propyl]-2H-pyridazin-3-one Following the procedure of Example 1(10), 6-(3-fluoro-4-methoxyphenyl)-2-[3-(4-fluorophenyl)propyl]-4-methanesulfonyloxymethyl-2H-pyridazin-3-one and diethanolamine were reacted to yield the title compound as a yellow oil (yield: 67.3%).

$^1$H NMR(400 MHz, CDCl$_3$)δ: 2.14–2.22(2H, m), 2.70 (2H, t, J=7.6 Hz), 2.75–2.95(4H, m), 3.70–3.80(6H, m), 3.94(3H, s), 4.28(2H, t, J=7.6 Hz), 6.93–7.05(3H, m), 7.15–7.18(2H, m), 7.56(1H, m), 7.63(1H, m), 7.85(1H, m). IR(Neat) cm$^{-1}$: 1645, 1601, 1510, 1439, 1277, 763. Mass m/z: 473(M$^+$).

Example 199

Preparation of 6-(3-fluoro-4-methoxyphenyl)-2-[3-(4-fluorophenyl)propyl]-4-(1-piperazinyl)methyl-2H-pyridazin-3-one

1) Preparation of 4-(4-tert-butoxycarbonyl-1-piperazinyl)methyl-6-(3-fluoro-4-methoxyphenyl)-2-[3-(4-fluorophenyl)propyl]-2H-pyridazin-3-one Following the procedure of Example 1(10), 6-(3-fluoro-4-methoxyphenyl)-2-[3-(4-fluorophenyl)propyl]-4-methanesulfonyloxymethyl-2H-pyridazin-3-one and tert-butyl 1-piperazinecarboxylate were reacted to yield the title compound as a yellow oil (yield: 72.6%).

¹H NMR(400 MHz, CDCl₃)δ: 1.40(9H, s), 2.07–2.16(2H, m), 2.40–2.50(4H, m), 2.63(2H, t, J=7.6 Hz), 3.36–3.46(4H, m), 3.48(2H, brs), 3.88(3H, s), 4.20(2H, t, J=7.6 Hz), 6.84–6.98(3H, m), 7.07–7.11(2H, m), 7.43(1H, d, J=8.1 Hz), 7.53(1H, d, J=12.4 Hz), 7.65(1H, brs).

2) Preparation of 6-(3-fluoro-4-methoxyphenyl)-2-[3-(4-fluorophenyl)propyl]-4-(1-piperazinyl)methyl-2H-pyridazin-3-one Following the procedure of Example 20, 4-(4-tert-butoxycarbonyl-1-piperazinyl)methyl-6-(3-fluoro-4-methoxyphenyl)-2-[3-(4-fluorophenyl)propyl]-2H-pyridazin-3-one was reacted to yield the title compound as a yellow oil (yield: 97.2%).

¹H NMR(400 MHz, CDCl₃)δ: 2.12–2.22(2H, m), 2.50–2.60(4H, m), 2.71(2H, t, J=7.3 Hz), 2.92–3.02(4H, m), 3.53(2H, s), 3.95(3H, s), 4.27(2H, t, J=7.3 Hz), 6.91–7.06 (3H, m), 7.15–7.18(2H, m), 7.51(1H, d, J=8.8 Hz), 7.61(1H, dd, J=12.5, 2.2 Hz), 7.73(1H, s). IR(Neat) cm⁻¹: 1650, 1607, 1510, 1439, 1275, 758. Mass m/z: 454(M⁺).

Example 200

Preparation of 4-aminomethyl-6-(3-fluoro-4-methoxyphenyl)-2-[3-(4-fluorophenyl)propyl]-2H-pyridazin-3-one Following the procedure of Example 24(1), 6-(3-fluoro-4-methoxyphenyl)-2-[3-(4-fluorophenyl)propyl]-4-methanesulfonyloxymethyl-2H-pyridazin-3-one was reacted to yield a crude product. Without purification, the crude product was reacted in accordance with the procedure of Example 24(2) to yield the title compound as a pale yellow crystalline powder (yield: 41.7%).

Melting point: 82–84° C. ¹H NMR(400 MHz, CDCl₃)δ: 2.12–2.22(2H, m), 2.70(2H, t, J=7.6 Hz), 3.89(2H, s), 3.94 (3H, s), 4.27(2H, t, J=7.6 Hz), 6.93–7.04(3H, m), 7.15–7.18 (2H, m), 7.51(1H, d, J=7.3 Hz), 7.61(1H, dd, J=12.4, 2.0 Hz), 7.67(1H, s). IR(KBr) cm⁻¹: 3366, 1651, 1605, 1509, 1436, 1273, 764. Mass m/z: 385(M⁺).

Example 201

Preparation of 4-aminomethyl-6-(3-fluoro-4-methoxyphenyl)-2-[3-(4-fluorophenyl)propyl]-2H-pyridazin-3-one hydrochloride Following the procedure of Example 4, 4-aminomethyl-6-(3-fluoro-4-methoxyphenyl)-2-[3-(4-fluorophenyl)propyl]-2H-pyridazin-3-one was reacted to yield the title compound as a slightly-yellow crystalline powder (yield: 73.1%).

Melting point: 160–165° C. ¹H NMR(400 MHz, DMSO-d₆)δ: 2.05–2.15(2H,m), 2.66(2H, t, J=7.3 Hz), 3.92(3H, s), 3.99(2H, s), 4.19(2H, t, J=7.3 Hz), 7.05–7.12(2H, m), 7.23–7.30(2H, m), 7.34(1H,dd, J=8.8, 8.8 Hz), 7.66–7.76 (2H, m), 8.25(1H,s). IR(KBr) cm⁻¹: 3430, 1652, 1515, 1436, 1269, 763.

Example 202

Preparation of 2-(4-chlorobenzyl)-6-(3-fluoro-4-methoxyphenyl)-4-(4-methyl-1-piperazinyl)methyl-2H-pyridazin-3-one 1) Preparation of 2-(4-chlorobenzyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 4-chlorobenzyl chloride were reacted to yield the title compound as yellow needles (yield: 97.6%).

Melting point: 170.5–171.1° C. ¹H NMR(400 MHz, CDCl₃)δ: 3.95(3H, s), 3.99(3H, s), 5.38((2H, s), 7.03(1H, dd, J=8.5, 8.5 Hz), 7.31(2H, d, J=8.5 Hz), 7.47(2H, d, J=8.5 Hz), 7.49(1H, m), 7.60(1H, dd, J=12.2, 2.2 Hz), 8.20(1H, s) IR(KBr) cm⁻¹: 1723, 1670, 1526, 1271, 1128. Mass m/z: 402(M⁺), 404(M⁺).

2) Preparation of 4-carboxy-2-(4-chlorobenzyl)-6-(3-fluoro-4-methoxyphenyl)-2H-pyridazin-3-one Following the procedure of Example 1(7), 2-(4-chlorobenzyl)-6-(3-fluoro-4-methoxyphenyl)-4-methoxycarbonyl-2H-pyridazin-3-one was reacted to yield the title compound as a pale yellow crystalline powder (yield: 96.0%).

Melting point: 228.3–229.1° C. ¹H NMR(400 MHz, CDCl₃)δ: 3.97(3H, s), 5.46(2H, s), 7.07(1H, dd, J=8.5, 8.5 Hz), 7.35(2H, d, J=8.3 Hz), 7.46(2H, d, J=8.3 Hz), 7.55(1H, d, J=8.4 Hz), 7.67(1H, dd, J=12.2, 2.2 Hz), 8.61(1H, s). IR(KBr) cm⁻¹: 1745, 1635, 1456, 1447, 1431, 1298, 1273. Mass m/z: 388(M⁺), 390(M⁺).

3) Preparation of 2-(4-chlorobenzyl)-6-(3-fluoro-4-methoxyphenyl)-4-hydroxymethyl-2H-pyridazin-3-one Following the procedure of Example 1(8), 4-carboxy-2-(4-chlorobenzyl)-6-(3-fluoro-4-methoxyphenyl)-2H-pyridazin-3-one was reacted to yield the title compound as pale yellow needles (yield: 20.4%).

Melting point: 164.6–165.3° C. ¹H NMR(400 MHz, CDCl₃)δ: 3.94(3H, s), 4.69(2H, s), 5.34 (2H, s), 7.01(1H, dd, J=8.5, 8.5 Hz), 7.30(2H, d, J=8.5 Hz), 7.42(2H, d, J=8.5 Hz), 7.50(1H, m), 7.63(1H, dd, J=12.4, 2.2 Hz), 7.67(1H, s). IR(KBr) cm⁻¹: 3373, 1653, 1610, 1527, 1291, 1135. Mass m/z: 374(M⁺), 376(M⁺).

4) Preparation of 2-(4-chlorobenzyl)-6-(3-fluoro-4-methoxyphenyl)-4-methanesulfonyloxymethyl-2H-pyridazin-3-one Following the procedure of Example 1(9), 2-(4-chlorobenzyl)-6-(3-fluoro-4-methoxyphenyl)-4-hydroxymethyl-2H-pyridazin-3-one was reacted to yield the title compound as pale yellow needles (yield: 81.6%).

Melting point: 156.5–157.4° C. ¹H NMR(400 MHz, CDCl₃)δ: 3.15(3H, s), 3.95(3H, s), 5.22(2H, d, J=1.5 Hz), 5.35(2H, s), 7.03(1H, dd, J=8.5, 8.5 Hz), 7.31(2H, d, J=8.5 Hz), 7.42(2H, d, J=8.5 Hz), 7.49(1H, m), 7.61(1H, dd, J=12.2, 2.2 Hz), 7.75(1H, s). IR(KBr) cm⁻¹: 1658, 1616, 1358, 1183, 1017.

5) Preparation of 2-(4-chlorobenzyl)-6-(3-fluoro-4-methoxyphenyl)-4-(4-methyl-1-piperazinyl)methyl-2H-pyridazin-3-one Following the procedure of Example 1(10), 2-(4-chlorobenzyl)-6-(3-fluoro-4-methoxyphenyl)-4-methanesulfonyloxymethyl-2H-pyridazin-3-one and 1-methylpiperazine were reacted to yield the title compound as pale brown prisms (yield: 39.5%).

Melting point: 128.7–130.2° C. $^1$H NMR(400 MHz, CDCl$_3$)δ: 2.33(3H, s), 2.52(4H, brs), 2.60(4H, brs), 3.55 (2H, s), 3.95(3H, s), 5.34(2H, s), 7.04(1H, dd, J=8.5, 8.5 Hz), 7.30(2H, d, J=8.5 Hz), 7.43(2H, d, J=8.5 Hz), 7.51(1H, m), 7.60(1H, dd, J=12.4, 2.0 Hz), 7.73(1H, s). IR(KBr) cm$^{-1}$: 1652, 1607, 1524, 1516, 1438, 1288, 1135.

Example 203

Preparation of 2-(4-chlorobenzyl)-4-dimethylaminomethyl-6-(3-fluoro-4-methoxyphenyl)-2H-pyridazin-3-one Following the procedure of Example 7, 2-(4-chlorobenzyl)-6-(3-fluoro-4-methoxyphenyl)-4-methanesulfonyloxymethyl-2H-pyridazin-3-one and dimethylamine were reacted to yield the title compound as a slightly-yellow crystalline powder (yield: 74.7%).

Melting point: 95.3–96.7° C. $^1$H NMR(400 MHz, CDCl$_3$) δ: 2.33(6H,s), 3.47(2H, d, J=1.2 Hz), 3.94(3H, s), 5.34(2H, s), 7.01(1H, dd, J=8.5, 8.5 Hz), 7.30(2H, d, J=8.5 Hz), 7.44(2H, d, J=8.5 Hz), 7.53(1H, ddd, J=8.5, 2.0, 1.2 Hz), 7.62(1H, dd, J=12.4, 2.2 Hz), 7.74(1H, s). IR(KBr) cm$^{-1}$: 1652, 1609, 1524, 1515, 1436, 1289, 1264, 1017. Mass m/z: 401(M$^+$), 403(M$^+$).

Example 204

Preparation of 2-(4-chlorobenzyl)-4-dimethylaminomethyl-6-(3-fluoro-4-methoxyphenyl)-2H-pyridazin-3-one hydrochloride Following the procedure of Example 4, 2-(4-chlorobenzyl)-4-dimethylaminomethyl-6-(3-fluoro-4-methoxyphenyl)-2H-pyridazin-3-one was reacted to yield the title compound as a slightly-yellow crystalline powder (yield: 59.7%).

Melting point: 193.4–194.7° C. $^1$H NMR(400 MHz, CD$_3$OD)δ: 2.96(6H, s), 3.94(3H, s), 4.33(2H, s), 5.43(2H, s), 7.22(1H, dd, J=8.5, 8.5 Hz), 7.36(2H, d, J=8.5 Hz), 7.46(2H, d, J=8.5 Hz), 7.67–7.72(2H, m), 8.20(1H, s). IR(KBr) cm$^{-1}$: 1655, 1616, 1529, 1327, 1279.

Example 205

Preparation of 4-aminomethyl-2-(4-chlorobenzyl)-6-(3-fluoro-4-methoxyphenyl)-2H-pyridazin-3-one

1) Preparation of 2-(4-chlorobenzyl)-6-(3-fluoro-4-methoxyphenyl)-4-phthalimidomethyl-2H-pyridazin-3-one Following the procedure of Example 24(1), 2-(4-chlorobenzyl)-6-(3-fluoro-4-methoxyphenyl)-4-methanesulfonyloxymethyl-2H-pyridazin-3-one was reacted to yield the title compound as slightly-yellow needles (yield: 75.4%).

Melting point: 212.5–213.9° C. $^1$H NMR(400 MHz, CDCl$_3$)δ: 3.90(3H, s), 4.88(2H, d, J=0.73 Hz), 5.35(2H, s), 6.95(1H, dd, J=8.5, 8.5 Hz), 7.29(1H, s), 7.31(2H, d, J=8.5 Hz), 7.36(1H, m), 7.44(2H, d, J=8.5 Hz), 7.47(1H, dd, J=12.2, 2.0 Hz), 7.76–7.81(2H, m), 7.89–7.94(2H, m). IR(KBr) cm$^{-1}$: 1773, 1713, 1651, 1610, 1522, 1439, 1419, 1393, 1300. Mass m/z: 503(M$^+$), 505 (M$^+$).

2) Preparation of 4-aminomethyl-2-(4-chlorobenzyl)-6-(3-fluoro-4-methoxyphenyl)-2H-pyridazin-3-one Following the procedure of Example 24(2), 2-(4-chlorobenzyl)-6-(3-fluoro-4-methoxyphenyl)-4-phthalimidomethyl-2H-pyridazin-3-one was reacted to yield the title compound as pale yellow needles (yield: 48.8%).

Melting point: 128.5–131.4° C. $^1$H NMR(400 MHz, CDCl$_3$)δ: 3.88(2H, s), 3.94(3H, s), 5.34(2H, s), 7.02(1H, dd, J=8.5, 8.5 Hz), 7.30(2H, d, J=8.5 Hz), 7.43(2H, d, J=8.5 Hz), 7.51(1H, ddd, J=8.5, 2.2, 1.2 Hz), 7.61(1H, dd, J=12.4, 2.2 Hz), 7.69(1H, t, J=1.2 Hz). IR(KBr) cm$^{-1}$: 3392, 1615, 1604, 1520, 1434, 1292, 1133, 1018. Mass m/z: 373(M$^+$), 375((M$^+$).

Example 206

Preparation of 4-aminomethyl-2-(4-chlorobenzyl)-6-(3-fluoro-4-methoxyphenyl)-2H-pyridazin-3-one hydrochloride Following the procedure of Example 4, 4-aminomethyl-2-(4-chlorobenzyl)-6-(3-fluoro-4-methoxyphenyl)-2H-pyridazin-3-one was reacted to yield the title compound as a slightly-yellow crystalline powder (yield: 66.0%).

Melting point: 202.0–205.5° C. $^1$H NMR(400 MHz, CD$_3$OD)δ: 3.94(3H, s), 4.13(2H, s), 5.41(2H, s), 7.21(1H, dd, J=8.8, 8.8 Hz), 7.35(2H, d, J=8.5 Hz), 7.46(2H, d, J=8.5 Hz), 7.65–7.71(2H, m), 8.08(1H, s). IR(KBr) cm$^{-1}$: 2940, 1655, 1616, 1526, 1439, 1292.

Example 207

Preparation of 2-(3,4-difluorobenzyl)-6-(3-fluoro-4-methoxyphenyl)-4-(4-methyl-1-piperazinyl)methyl-2H-pyridazin-3-one

1) Preparation of 2-(3,4-difluorobenzyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 3,4-difluorobenzyl bromide were reacted to yield the title compound as a yellow crystalline powder (yield: 92.1%).

Melting point: 144–148° C. $^1$H NMR(400 MHz, CDCl$_3$) δ: 3.96(3H, s), 3.97(3H, s), 5.35(2H, s), 7.04(1H, dd, J=8.5, 8.5 Hz), 7.12(1H, m), 7.28(1H, m), 7.36(1H, m), 7.50(1H, m), 7.60(1H, dd, J=12.2, 1.5 Hz), 8.21(1H, s). IR(KBr) cm$^{-1}$: 1756, 1656, 1609, 1518, 1439, 1239, 1293, 1278, 1204. Mass m/z: 404(M$^+$).

2) Preparation of 4-carboxy-2-(3,4-difluorobenzyl)-6-(3-fluoro-4-methoxyphenyl)-2H-pyridazin-3-one Following the procedure of Example 1(7), 2-(3,4-difluorobenzyl)-6-(3-fluoro-4-methoxyphenyl)-4-methoxycarbonyl-2H-pyridazin-3-one was reacted to yield the title compound as a yellow crystalline powder (yield: 97.6%).

Melting point: 196.4–197.0° C. $^1$H NMR(400 MHz, CDCl$_3$)δ: 3.97(3H, s), 5.44(2H, s), 7.07(1H, dd, J=8.5, 8.5 Hz), 7.17(1H, m), 7.27(1H, m), 7.36(1H, ddd, J=8.1, 8.1, 2.2 Hz), 7.56(1H, m), 7.66(1H, dd, J=12.2, 2.2 Hz), 8.61(1H, s), 13.83(1H, s). IR(KBr) cm$^{-1}$: 1757, 1636, 1567, 1518, 1463, 1440, 1284. Mass m/z: 390(M$^+$).

3) Preparation of 2-(3,4-difluorobenzyl)-6-(3-fluoro-4-methoxyphenyl)-4-hydroxymethyl-2H-pyridazin-3-one Following the procedure of Example 1(8), 4-carboxy-2-(3,4-difluorobenzyl)-6-(3-fluoro-4-methoxyphenyl)-2H-pyridazin-3-one was reacted to yield the title compound as slightly-yellow needles (yield: 7.7%).

Melting point: 154.1–155.5° C. $^1$H NMR(400 MHz, CDCl$_3$)δ: 2.85(1H, t, J=5.6 Hz), 3.95(3H, s), 4.71(2H, d, J=5.6 Hz), 5.33(2H, s), 7.03(1H, dd, J=8.5, 8.5 Hz), 7.12(1H, m), 7.23(1H, m), 7.31(1H, ddd, J=11.0, 7.6, 2.2 Hz), 7.51(1H, ddd, J=8.5, 2.2, 1.2 Hz), 7.61(1H, dd, J=12.4, 2.2 Hz), 7.68(1H, t, J=1.2 Hz). IR(KBr) cm$^{-1}$: 3390, 1648, 1602, 1518, 1440, 1285, 1141. Mass m/z: 376(M$^+$).

4) Preparation of 2-(3,4-difluorobenzyl)-6-(3-fluoro-4-methoxyphenyl)-4-methanesulfonyloxymethyl-2H-pyridazin-3-one Following the procedure of Example 1(9), 2-(3,4-difluorobenzyl)-6-(3-fluoro-4-methoxyphenyl)-4-hydroxymethyl-2H-pyridazin-3-one was reacted to yield the title compound as slightly-yellow needles (yield: 91.5%).

Melting point: 145.6–146.6° C. $^1$H NMR(400 MHz, CDCl$_3$)δ: 3.16(3H, s), 3.96(3H, s), 5.26(2H, d, J=1.2 Hz), 5.32(2H, s), 7.04(1H, dd, J=8.5, 8.5 Hz), 7.13(1H, m), 7.23(1H, m), 7.32(1H, m), 7.50(1H, m), 7.61(1H, dd, J=12.4, 2.2 Hz), 7.76(1H, t, J=1.2 Hz). IR (KBr) cm$^{-1}$: 1656, 1612, 1522, 1440, 1352, 1277, 1163. Mass m/z: 454(M$^+$).

5) Preparation of 2-(3,4-difluorobenzyl)-6-(3-fluoro-4-methoxyphenyl)-4-(4-methyl-1-piperazinyl)methyl-2H-pyridazin-3-one Following the procedure of Example 1(10), 2-(3,4-difluorobenzyl)-6-(3-fluoro-4-methoxyphenyl)-4-methanesulfonyloxymethyl-2H-pyridazin-3-one and 1-methylpiperazine were reacted to yield the title compound as slightly-yellow needles (yield: 55.0%).

Melting point: 135.4–136.0° C. $^1$H NMR(400 MHz, CDCl$_3$)δ: 2.33(3H, s), 2.51(4H, brs), 2.62(4H, brs), 3.56(2H, d, J=1.5 Hz), 3.95(3H, s), 5.31(2H, s), 7.04(1H, dd, J=8.5, 8.5 Hz), 7.11(1H, m), 7.23(1H, m), 7.32(1H, ddd, J=11.0, 7.6, 2.0 Hz), 7.52(1H, ddd, J=8.5, 2.2, 1.2 Hz), 7.59(1H, dd, J=12.2, 2.2 Hz), 7.74(1H, t, J=1.2 Hz). IR(KBr) cm$^{-1}$: 1652, 1608, 1522, 1437, 1291, 1273, 1139. Mass m/z: 458(M$^+$).

Example 208

Preparation of 2-(3,4-difluorobenzyl)-4-dimethylaminomethyl-6-(3-fluoro-4-methoxyphenyl)-2H-pyridazin-3-one Following the procedure of Example 7, 2-(3,4-difluorobenzyl)-6-(3-fluoro-4-methoxyphenyl)-4-methanesulfonyloxymethyl-2H-pyridazin-3-one and dimethylamine were reacted to yield the title compound as slightly-yellow needles (yield: 77.1%).

Melting point: 129.9–130.4° C. $^1$H NMR(400 MHz, CDCl$_3$)δ: 2.35(6H, s), 3.49(2H, s), 3.95(3H, s), 5.32(2H, s), 7.02(1H, dd, J=8.5, 8.5 Hz), 7.11(1H, m), 7.24(1H, m), 7.32(1H, ddd, J=11.0, 7.6, 2.2 Hz), 7.54(1H, ddd, J=8.5, 2.2, 1.2 Hz), 7.62(1H, dd, J=12.4, 2.2 Hz), 7.77(1H, s). IR(KBr) cm$^{-1}$: 1653, 1610, 1519, 1437, 1291, 1283, 1267, 1138, 1114. Mass m/z: 403(M$^+$).

Example 209

Preparation of 2-(4-chlorocinnamyl)-6-(3-fluoro-4-methoxyphenyl)-4-(4-methyl-1-piperazinyl)methyl-2H-pyridazin-3-one

1) Preparation of 2-(4-chlorocinnamyl)-6-(3-fluoro-4-methoxyphenyl)-4-methoxycarbonyl-2H-pyridazin-3-one Following the procedure of Example 1(6), 6-(3-fluoro-4-methoxyphenyl)-4-methoxycarbonyl-2H-pyridazin-3-one and 4-chlorocinnamyl chloride were reacted to yield the title compound as a pale yellow crystalline powder (yield: 51.1%).

Melting point: 117–119° C. $^1$H NMR(400 MHz, CDCl$_3$)δ: 3.95(3H, s), 3.98(3H, s), 5.02(2H, dd, J=6.8, 1.2 Hz), 6.43(1H, dt, J=15.9, 6.8 Hz), 6.70(1H, d, J=15.9 Hz), 7.03(1H, dd, J=8.5, 8.5 Hz), 7.25(2H, d, J=8.8 Hz), 7.31(2H, d, J=8.8 Hz), 7.50(1H, dt, J=8.5, 2.2 Hz), 7.62(1H, dd, J=12.2, 2.2 Hz), 8.22(1H,s). IR(KBr) cm$^{-1}$: 1724, 1709, 1667, 1506, 1291, 1236, 1126, 831. Mass m/z: 412(M$^+$), 414(M$^+$).

2) Preparation of 4-carboxy-2-(4-chlorocinnamyl)-6-(3-fluoro-4-methoxyphenyl)-2H-pyridazin-3-one Following the procedure of Example 1(7), 2-(4-chlorocinnamyl)-6-(3-fluoro-4-methoxyphenyl)-4-methoxycarbonyl-2H-pyridazin-3-one was reacted to yield the title compound as a pale yellow crystalline powder (yield: 98.2%).

Melting point: 217.2–218.5° C. $^1$H NMR(400 MHz, CDCl$_3$)δ: 3.97(3H, s), 5.10(2H, d, J=6.8 Hz), 6.39(1H, dt, J=15.9, 6.8 Hz), 6.75(1H, d, J=15.9 Hz), 7.06(1H, dd, J=8.5, 8.5 Hz), 7.30(2H, d, J=8.5 Hz), 7.34(2H, d, J=8.5 Hz), 7.57(1H, m), 7.69(1H, dd, J=12.2, 2.2 Hz), 8.63(1H, s), 13.99(1H, s). IR(KBr) cm$^{-1}$: 3059, 1744, 1629, 1523, 1480, 1438, 1426, 1296, 1272. Mass m/z: 414(M$^+$), 416(M$^+$).

3) Preparation of 2-(4-chlorocinnamyl)-6-(3-fluoro-4-methoxyphenyl)-4-hydroxymethyl-2H-pyridazin-3-one Following the procedure of Example 1(8), 4-carboxy-2-(4-chlorocinnamyl)-6-(3-fluoro-4-methoxyphenyl)-2H-pyridazin-3-one was reacted to yield the title compound as pale yellow crystals (yield: 17.0%).

Melting point: 158.2–160.5° C. $^1$H NMR(400 MHz, CDCl$_3$)δ: 2.95(1H, t, J=5.9 Hz), 3.94(3H, s), 4.73(2H, dd, J=5.9, 1.2 Hz), 4.98(2H, dd, J=6.6, 1.2 Hz), 6.40(1H, dt, J=15.9, 6.6 Hz), 6.67(1H, d, J=15.9 Hz), 7.02(1H, dd, J=8.5, 8.5 Hz), 7.27 (2H, d, J=8.5 Hz), 7.32 (2H, d, J=8.5 Hz), 7.51 (1H, ddd, J=8.8, 2.2, 1.2 Hz), 7.63(1H, dd, J=12.4, 2.2 Hz), 7.67(1H, t, J=1.2 Hz). IR(KBr) cm$^{-1}$: 3392, 1648, 1603, 1523, 1440, 1284, 1273, 1140. Mass m/z: 400(M$^+$), 402 (M$^+$).

4) Preparation of 2-(4-chlorocinnamyl)-6-(3-fluoro-4-methoxyphenyl)-4-methanesulfonyloxymethyl-2H-pyridazin-3-one Following the procedure of Example 1(9), 2-(4-chlorocinnamyl)-6-(3-fluoro-4-methoxyphenyl)-4-hydroxymethyl-2H-pyridazin-3-one was reacted to yield the title compound as pale yellow needles (yield: 90.7%).

Melting point: 135.8–136.4° C. $^1$H NMR(400 MHz, CDCl$_3$)δ: 3.17(3H, s), 3.95(3H, s), 4.98(2H, dd, J=6.6, 0.98 Hz), 5.28(2H, d, J=1.5 Hz), 6.39(1H, dt, J=15.9, 6.6 Hz), 6.67(1H, d, J=15.9 Hz), 7.03(1H, dd, J=8.5, 8.5 Hz), 7.27 (2H, d, J=8.5 Hz), 7.32(2H, d, J=8.5 Hz), 7.50(1H, m), 7.62(1H, dd, J=12.2, 2.2 Hz), 7.77(1H, t, J=1.2 Hz). IR(KBr) cm$^{-1}$: 1660, 1615, 1523, 1436, 1360, 1335, 1287, 1273, 1179. Mass m/z: 478(M$^+$), 480(M$^+$).

5) Preparation of 2-(4-chlorocinnamyl)-6-(3-fluoro-4-methoxyphenyl)-4-(4-methyl-1-piperazinyl)methyl-2H-pyridazin-3-one Following the procedure of Example 1(10), 2-(4-chlorocinnamyl)-6-(3-fluoro-4-methoxyphenyl)-4-methanesulfonyloxymethyl-2H-pyridazin-3-one and 1-methylpiperazine were reacted to yield the title compound as pale brown needles (yield: 66.3%).

Melting point: 123.9–125.5° C. $^1$H NMR(400 MHz, CDCl$_3$)δ: 2.33(3H, s), 2.52(4H, brs), 2.62(4H, brs), 3.58 (2H, d, J=1.2 Hz), 3.95(3H, s), 4.98(2H, dd, J=6.8, 1.2 Hz), 6.41(1H, dt, J=15.9, 6.8 Hz), 6.66(1H, d, J=15.9 Hz), 7.04(1H, dd, J=8.5, 8.5 Hz), 7.26(2H, d, J=8.5 Hz), 7.32(2H, d, J=8.5 Hz), 7.53 (1H, ddd, J=8.5, 2.0, 1.2 Hz), 7.62(1H, dd, J=12.4, 2.2 Hz), 7.75(1H, t, J=1.2 Hz). IR(KBr) cm$^{-1}$: 1647, 1606, 1522, 1439, 1282, 1270. Mass m/z: 482(M$^+$), 484 (M$^+$).

Example 210

Preparation of 2-(4-chlorocinnamyl)-6-(3-fluoro-4-methoxyphenyl)-4-[4-(2-hydroxyethyl)-1-piperazinyl]methyl-2H-pyridazin-3-one Following the procedure of Example 1(10), 2-(4-chlorocinnamyl)-6-(3-fluoro-4-methoxyphenyl)-4-methanesulfonyloxymethyl-2H-pyridazin-3-one and 1-piperazineethanol were reacted to yield the title compound as slightly-yellow needles (yield: 65.1%).

Melting point: 133.1–134.9° C. $^1$H NMR(400 MHz, CDCl$_3$)δ: 2.57–2.62(11H, m), 3.58(2H, d,J=1.2 Hz), 3.63 (2H, t, J=5.4 Hz), 3.94(3H, s), 4.97(2H, d, J=6.6 Hz), 6.41(1H, dt, J=15.9, 6.6 Hz), 6.67(1H, d, J=15.9 Hz), 7.03(1H, dd, J=8.5, 8.5 Hz), 7.26(2H, d, J=8.5 Hz), 7.32(2H, d, J=8.5 Hz), 7.53(1H, m), 7.61(1H, dd, J=12.4, 2.2 Hz), 7.75(1H, s). IR(KBr) cm$^{-1}$: 3451, 1647, 1605, 1523, 1438, 1285, 1274, 1137. Mass m/z: 478(M$^+$), 480(M$^+$).

Example 211

Preparation of 2-cyclopropylmethyl-6-(3-fluoro-4-methoxyphenyl)-4-[3-(4-methyl-1-piperazinyl)propyl]-2H-pyridazin-3-one 1) Preparation of 4-bromomethyl-2-cyclopropylmethyl-6-(3-fluoro-4-methoxyphenyl)-2H-pyridazin-3-one 2-Cyclopropylmethyl-6-(3-fluoro-4-methoxyphenyl)-4-hydroxymethyl-2H-pyridazin-3-one (185 mg, 0.61 mmol), carbon tetrabromide (404 mg, 1.2 mmol) and pyridine (48 mg, 0.61 mmol) were dissolved in tetrahydrofuran (3 mL), and under ice-cold stirring, a solution of triphenylphosphine (319 mg, 1.2 mmol) in tetrahydrofuran (3 mL) was added. Under ice cooling, the mixture was stirred for 1 hour, and further stirred at room temperature. Insoluble materials were filtered off, the solvent was distilled off under reduced pressure, and the residue was isolated and purified by column chromatography on silica gel (hexane/ethyl acetate=2/1) to yield the title compound as a yellow powder (yield: 155 mg, 69.5%).

$^1$H NMR(400 MHz, CDCl$_3$)δ: 0.45–0.60(4H, m), 1.58 (1H, m), 3.95(3H, s), 4.12(2H, d, J=7.3 Hz), 4.49(2H, s), 7.03(1H, dd, J=8.5, 8.5 Hz), 7.50(1H, m), 7.60(1H, dd, J=13.4, 2.2 Hz), 7.77(1H, s).

2) Preparation of 2-cyclopropylmethyl-4-[2,2-di (tert-butoxycarbonyl)ethyl]-6-(3-fluoro-4-methoxyphenyl)-2H-pyridazin-3-one After 55% sodium hydride (322 mg, 7.38 mmol) was added to a solution of di-tert-butyl malonate (970 mg, 4.48 mmol) in N,N-dimethylformamide (10 mL), 4-bromomethyl-2-cyclopropylmethyl-6-(3-fluoro-4-methoxyphenyl)-2H-pyridazin-3-one (1.8 g, 4.90 mmol) was added under ice-cold stirring. The reaction mixture was stirred at room temperature for 1 hour, poured into water, and extracted with ethyl acetate. The extract was washed with brine and dried over anhydrous sodium sulfate. The solvent was distilled off under reduced pressure. The residue was isolated and purified by column chromatography on silica gel (hexane/ethyl acetate=3/1) to yield the title compound as a yellow powder (yield: 1.39 mg, 61.8%).

$^1$H NMR(400 MHz, CDCl$_3$)δ: 0.44–0.50(2H, m), 0.50–0.58(2H, m), 1.41(18H, s), 1.56(1H, m), 3.12(2H, d, J=7.8 Hz), 3.87(1H, t, J=7.8 Hz), 3.94(3H, s), 4.09(2H, d, J=7.8 Hz), 7.01 (1H, dd, J=8.5, 8.5 Hz), 7.43(1H, d, J=8.5 Hz), 7.50(1H, s), 7.57(1H, dd, J=12.4, 2.2 Hz).

3) Preparation of 4-(2-carboxyethyl)-2-cyclopropylmethyl-6-(3-fluoro-4-methoxyphenyl)-2H-pyridazin-3-one Trifluoroacetic acid (21 mL) was added to 2-cyclopropylmethyl-4-[2,2-di(tert-butoxycarbonyl)ethyl]-6-(3-fluoro-4-methoxyphenyl)-2H-pyridazin-3-one (1.39 g, 2.77 mmol), and the mixture was stirred at room temperature for 30 minutes. The solvent was distilled off under reduced pressure, and toluene was added further, followed by azeotropic boiling. The residue was heated at 190 to 200° C. for 30 minutes under a nitrogen atmosphere to yield the title compound as a pale brown powder (yield: 907 mg, 94.7%).

$^1$H NMR(400 MHz, CDCl$_3$)δ: 0.45–0.50(2H, m), 0.50–0.60(2H, m), 1.41(1H, m), 2.80(2H, t, J=7.1 Hz), 2.97(2H, t, J=7.1 Hz), 3.94(3H, s), 4.10(2H, d, J=7.3 Hz),

4) Preparation of 2-cyclopropylmethyl-6-(3-fluoro-4-methoxyphenyl)-4-(3-hydroxypropyl)-2H-pyridazin-3-one Following the procedure of Example 1(8), 4-(2-carboxyethyl)-2-cyclopropylmethyl-6-(3-fluoro-4-methoxyphenyl)-2H-pyridazin-3-one was reacted to yield the title compound as a brown oil (yield: 82.9%).

$^1$H NMR(400 MHz, CDCl$_3$)δ: 0.44–0.52(2H, m), 0.52–0.60(2H, m), 1.42(1H, m), 1.88–1.94(2H, m), 2.81(2H, t, J=6.1 Hz), 3.63(2H, t, J=5.9 Hz), 3.95(3H, s), 4.12(2H, d, J=7.3 Hz), 7.02(1H, dd, J=8.5, 8.5 Hz), 7.50(1H, m), 7.52 (1H, s), 7.60(1H, dd, J=12.4, 2.2 Hz).

5) Preparation of 2-cyclopropylmethyl-6-(3-fluoro-4-methoxyphenyl)-4-(3-methanesulfonyloxypropyl)-2H-pyridazin-3-one Following the procedure of Example 1(9), 2-cyclopropylmethyl-6-(3-fluoro-4-methoxyphenyl)-4-(3-hydroxypropyl)-2H-pyridazin-3-one was reacted to yield the title compound as a pale brown powder (yield: 82.0%).

$^1$H NMR(400 MHz, CDCl$_3$)δ: 0.44–0.51(2H, m), 0.51–0.60(2H, m), 1.41(1H, m), 2.13–2.21(2H, m), 2.80(2H, t, J=7.1 Hz), 3.04(3H, s), 3.94(3H, s), 4.09(2H, d, J=7.3 Hz), 4.31(2H, t, J=6.1 Hz), 7.02(1H, dd, J=8.5, 8.5 Hz), 7.49(1H, d, J=8.5 Hz), 7.53(1H, s), 7.61(1H, dd, J=12.4, 2.2 Hz).

6) Preparation of 2-cyclopropylmethyl-6-(3-fluoro-4-methoxyphenyl)-4-[3-(4-methyl-1-piperazinyl)propyl]-2H-pyridazin-3-one Following the procedure of Example 1(10), 2-cyclopropylmethyl-6-(3-fluoro-4-methoxyphenyl)-4-(3-methanesulfonyloxypropyl)-2H-pyridazin-3-one and 1-methylpiperazine were reacted to yield the title compound as a yellow oil (yield: 62.0%).

$^1$H NMR(400 MHz, CDCl$_3$)δ: 0.44–0.50(2H, m), 0.50–0.60(2H, m), 1.41(1H, m), 1.90–2.00(2H, m), 2.45(3H, s), 2.50–3.00(12H, m), 3.94(3H, s), 4.08(2H, d, J=7.3 Hz), 7.02(1H, dd, J=8.5, 8.5 Hz), 7.48(1H, s), 7.50(1H, d, J=8.5 Hz), 7.70(1H, dd, J=12.3, 2.0 Hz). IR(Neat) cm$^{-1}$: 1648, 1607, 1524, 1286, 1122, 1022, 755. Mass m/z: 414(M$^+$).

Example 212

Preparation of 2-cyclopropylmethyl-4-(3-dimethylaminopropyl)-6-(3-fluoro-4-methoxyphenyl)-2H-pyridazin-3-one Following the procedure of Example 7, 2-cyclopropylmethyl-6-(3-fluoro-4-methoxyphenyl)-4-(3-methanesulfonyloxypropyl)-2H-pyridazin-3-one and dimethylamine were reacted to yield the title compound as a yellow oil (yield: 64.7%).

$^1$H NMR(400 MHz, CDCl$_3$)δ: 0.44–0.50(2H, m), 0.53–0.60(2H, m), 1.40(1H, m), 2.24–2.35(2H, m), 2.75–2.80(2H, m), 2.79(6H, s), 3.03(2H, t, J=7.3 Hz), 3.94 (3H, s), 4.08(2H, d, J=7.1 Hz), 7.04(1H, dd, J=8.5, 8.5 Hz), 7.57(1H, d, J=8.5 Hz), 7.65(1H, dd, J=12.4, 2.2 Hz), 7.72 (1H, s). IR(Neat) cm$^{-1}$: 1649, 1608, 1524, 1288, 1122, 1022, 761. Mass m/z: 359(M$^+$).

Example 213

Preparation of 2-cyclopropylmethyl-6-(3-fluoro-4-methoxyphenyl)-4-[3-(1-piperazinyl)propyl]-2H-pyridazin-3-one

1) Preparation of 2-cyclopropylmethyl-4-[3-(4-tert-butoxycarbonyl-1-piperazinyl)propyl]-6-(3-fluoro-4-methoxyphenyl)-2H-pyridazin-3-one Following the procedure of Example 1(10), 2-cyclopropylmethyl-6-(3-fluoro-4-methoxyphenyl)-4-(3-methanesulfonyloxypropyl)-2H-pyridazin-3-one and tert-butyl 1-piperazinecarboxylate were reacted to yield the title compound as a yellow oil (yield: 76.9%).

$^1$H NMR(400 MHz, CDCl$_3$)δ: 0.44–0.50(2H, m), 0.52–0.60(2H, m), 1.44(1H, m), 1.46(9H, s), 2.00–2.40(2H, m), 2.50–2.80(6H, m), 3.50–3.75(6H, m), 3.94(3H, s), 4.08 (2H, d, J=7.1 Hz), 7.02(1H, dd, J=8.5, 8.5 Hz), 7.47–7.65 (3H, m).

2) Preparation of 2-cyclopropylmethyl-6-(3-fluoro-4-methoxyphenyl)-4-[3-(1-piperazinyl)propyl]-2H-pyridazin-3-one Following the procedure of Example 20, 2-cyclopropylmethyl-4-[3-(4-tert-butoxycarbonyl-1-piperazinyl)propyl]-6-(3-fluoro-4-methoxyphenyl)-2H-pyridazin-3-one was reacted to yield the title compound as a yellow oil (yield: 78.9%).

$^1$H NMR(400 MHz, CDCl$_3$)δ: 0.43–0.50(2H, m), 0.50–0.59(2H, m), 1.42(1H, m), 1.82–1.92(2H, m), 2.40–2.50(6H, m), 2.68(2H, t, J=7.6 Hz), 2.93–2.95(4H, m), 3.94(3H, s), 4.08(2H, d, J=7.3 Hz), 7.01(1H, dd, J=8.5, 8.5 Hz), 7.45(1H, s), 7.48(1H, d, J=8.5 Hz), 7.59(1H, dd, J=11.4, 2.0 Hz). IR(Neat) cm$^{-1}$: 1648, 1607, 1523, 1288, 1122, 1023, 760. Mass m/z: 400(M$^+$).

Example 214

Preparation of 2-cyclopropylmethyl-6-(3-fluoro-4-methoxyphenyl)-4-[3-(1-piperazinyl)propyl]-2H-pyridazin-3-one dihydrochloride Following the procedure of Example 4, 2-cyclopropylmethyl-6-(3-fluoro-4-methoxyphenyl)-4-[3-(1-piperazinyl)propyl]-2H-pyridazin-3-one was reacted to yield the title compound as a slightly-yellow crystalline powder (yield: 83.1%).

Melting point: 174–178° C. $^1$H NMR(400 MHz, DMSO-d$_6$)δ: 0.39–0.45(2H, m), 0.45–0.55(2H, m), 1.32(1H, m), 2.00–2.25(2H, m), 2.62–2.66 (2H, m), 3.20–3.85(10H, m), 3.90(3H, s), 4.01(2H, d, J=7.1 Hz), 7.28(1H, dd, J=8.8, 8.8 Hz), 7.72–7.80(2H, m), 7.96(1H, s). IR(KBr) cm$^{-1}$: 1647, 1604, 1523, 1297, 1123, 1020, 762.

Example 215

Preparation of 4-[3-[N,N-bis(2-hydroxyethyl)amino]propyl]-2-cyclopropylmethyl-6-(3-fluoro-4-methoxyphenyl)-2H-pyridazin-3-one Following the procedure of Example 1(10), 2-cyclopropylmethyl-6-(3-fluoro-4-methoxyphenyl)-4-(3-methanesulfonyloxypropyl)-2H-pyridazin-3-one and diethanolamine were reacted to yield the title compound as a yellow oil (yield: 13.1%).

$^1$H NMR(400 MHz, CDCl$_3$)δ: 0.44–0.50(2H, m), 0.50–0.60(2H, m), 1.41(1H, m), 2.10–2.20(2H, m), 2.76(2H, t, J=7.3 Hz), 3.00–3.15(6H, m), 3.87–3.92(4H, m), 3.94(3H, s), 4.08(2H, d, J=7.3 Hz), 7.02(1H, dd, J=8.5, 8.5 Hz), 7.53(1H, d, J=8.5 Hz), 7.60(1H, s), 7.62(1H, dd, J=12.4, 2.2 Hz). IR(Neat) cm$^{-1}$: 1645, 1602, 1524, 1288, 1123, 1024, 756. Mass m/z: 400(M$^+$—CH$_2$OH).

Example 216

Preparation of 4-(3-aminopropyl)-2-cyclopropylmethyl-6-(3-fluoro-4-methoxyphenyl)-2H-pyridazin-3-one Following the procedure of Example 24(1), 2-cyclopropylmethyl-6-(3-fluoro-4-methoxyphenyl)-4-(3-methanesulfonyloxypropyl)-2H-pyridazin-3-one was reacted to yield a crude product. Without purification, the crude product was reacted further in accordance with the procedure of Example 24(2) to yield the title compound as a yellow oil (yield: 67.8%).

$^1$H NMR(400 MHz, CDCl$_3$)δ: 0.44–0.50(2H, m), 0.50–0.60(2H, m), 1.41(1H, m), 1.84–1.96(2H, m), 2.67–2.80(4H, m), 2.87(2H, t, J=6.1 Hz), 3.94(3H, s), 4.08 (2H, d, J=7.3 Hz), 7.01(1H, dd, J=8.5, 8.5 Hz), 7.49(1H, d, J=8.5 Hz), 7.50(1H, s), 7.59(1H, dd, J=12.4, 2.2 Hz). IR(Neat) cm$^{-1}$: 3370, 1648, 1606, 1523, 1289, 1122, 1023, 760. Mass m/z: 331(M$^+$).

Example 217

Preparation of 4-(3-aminopropyl)-2-cyclopropylmethyl-6-(3-fluoro-4-methoxyphenyl)-2H-pyridazin-3-one hydrochloride Following the procedure of Example 4, 4-(3-aminopropyl)-2-cyclopropylmethyl-6-(3-fluoro-4-methoxyphenyl)-2H-pyridazin-3-one was reacted to yield the title compound as a slightly-yellow crystalline powder (yield: 70.6%).

Melting point: 183–185° C. $^1$H NMR(400 MHz, DMSO-d$_6$)δ: 0.40–0.45(2H, m), 0.45–0.55(2H, m), 1.32(1H, m), 1.88–1.93(2H, m), 2.64(2H, t, J=7.3 Hz), 2.78–2.88(2H, m), 3.90(3H, s), 4.00(2H, d, J=7.3 Hz), 7.28(1H, dd, J=8.5, 8.5 Hz), 7.70–7.78(2H, m), 7.96(1H, s). IR(KBr) cm$^{-1}$: 3437, 1648, 1608, 1526, 1273, 1122, 1021, 762.

Referential Example

Preparation of 3-(2,6-dichlorophenyl)-1-propanol methanesulfonate

1) Preparation of ethyl 2,6-dichlorocinnamate

To a solution of 2,6-dichlorobenzaldehyde (350 mg, 2.0 mmol) and triethyl phosphonoacetate (448 mg, 2.6 mmol) in THF (5 mL), potassium tert-butoxide (291 mg, 2.6 mmol) was added under ice cooling, and at the same temperature, the mixture was stirred for 2 hours. A saturated aqueous solution of ammonium chloride was added to the reaction mixture, followed by extraction with ethyl acetate. The organic layer was dried over anhydrous sodium sulfate and then concentrated under reduced pressure. Further, the residue was purified by column chromatography on silica gel (hexane/ethyl acetate=50/1) to yield the title compound as a colorless syrupy substance (yield: 65.1%).

$^1$H NMR(400 MHz, CDCl$_3$)δ: 1.35(3H, t, J=7.2 Hz), 4.30(2H, q, J=7.2 Hz), 6.59(1H, d, J=16.4 Hz), 7.19(1H, t, J=8.0 Hz), 7.36(2H, t, J=8.0 Hz), 7.79(1H, d, J=16.4 Hz).

2) Preparation of 3-(2,6-dichlorophenyl)-1-propanol

Lithium aluminum hydride (98.8 mg, 2.60 mmol) was added to THF (5 mL), and under ice-cold stirring, a solution of ethyl 2,6-dichlorocinnamate (319 mg, 1.30 mmol) in THF (5 mL) was added dropwise. The mixture was then stirred at room temperature for 30 minutes. A small amount of a saturated aqueous solution of ammonium chloride was added to the reaction mixture, followed by drying over anhydrous magnesium sulfate. Subsequent to filtration through Celite, the mixture was concentrated under reduced pressure and further, purified by column chromatography on silica gel (hexane/ethyl acetate=10/1) to yield the title compound as a pale yellow syrupy substance (yield: 46.9%).

$^1$H NMR(400 MHz, CDCl$_3$)δ: 1.83–1.93(2H, m), 3.02 (2H, t, J=7.8 Hz), 3.73(2H, t, J=6.3 Hz), 7.09(1H, t, J=8.3 Hz), 7.27(2H, d, J=8.3 Hz).

3) Preparation of 3-(2,6-dichlorophenyl)-1-propanol methanesulfonate

To a solution of 3-(2,6-dichlorophenyl)-1-propanol (125 mg, 0.61 mmol) and triethylamine (123 mg, 1.22 mmol) in methylene chloride (3 mL), methanesulfonyl chloride (105 mg, 0.915 mmol) was added under ice cooling, followed by stirring at room temperature for 2 hours. Brine was added to the reaction mixture. The organic layer was allowed to separate, was collected, and was then dried over anhydrous sodium sulfate. Subsequent to concentration under reduced pressure, the residue was purified by column chromatography on silica gel (hexane/ethyl acetate=10/1) to yield the title compound as a pale yellow syrupy substance (yield: quantitative).

$^1$H NMR(400 MHz, CDCl$_3$)δ: 2.02–2.12(2H, m), 3.00–3.10(5H, m), 4.32(2H, t, J=6.3 Hz), 7.10(1H, t, J=8.3 Hz), 7.28(2H, d, J=8.3 Hz).

Example 218

Preparation of 2-[3-(4-chlorophenyl)propyl]-6-(4-fluoro-3-methylphenyl)-4-(4-methyl-1-piperazinyl) methyl-2H-pyridazin-3-one 1) Preparation of 4-carboxy-2-[3-(4-chlorophenyl) propyl]-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 3-(4-chlorophenyl)-1-propanol methanesulfonate were reacted to yield a crude product. Without purification, the crude product was reacted further in accordance with the procedure of Example 1(7) to yield the title compound as a yellow crystalline powder (yield: 80.8%).

Melting point: 120–123° C. $^1$H NMR(400 MHz, CDCl$_3$) δ: 2.22–2.32(2H, m), 2.37(3H, d, J=1.7 Hz), 2.74(2H, t, J=7.3 Hz), 4.06 (2H, t, J=7.3 Hz), 7.13 (2H, d, J=8.5 Hz), 7.14 (1H, m), 7.24(2H, d, J=8.5 Hz), 7.60–7.70(2H, m), 8.59(1H, s).

2) Preparation of 2-[3-(4-chlorophenyl)propyl]-6-(4-fluoro-3-methylphenyl)-4-hydroxymethyl-2H-pyridazin-3-one Following the procedure of Example 1(8), 4-carboxy-2-[3-(4-chlorophenyl)propyl]-6-(4-fluoro-3-methylphenyl)-

2H-pyridazin-3-one was reacted to yield the title compound as a yellow oil (yield: 25.2%).

$^1$H NMR(400 MHz, CDCl$_3$)δ: 2.16–2.24(2H, m), 2.35 (3H, d, J=1.7 Hz), 2.70(2H, t, J=7.3 Hz), 4.28(2H, t, J=7.3 Hz), 4.69(2H, d, J=1.2 Hz), 7.09(1H, m), 7.14(2H, d, J=8.3 Hz), 7.23(2H, d, J=8.3 Hz), 7.55–7.64(2H, m), 7.64(1H, s).

3) Preparation of 2-[3-(4-chlorophenyl)propyl]-6-(4-fluoro-3-methylphenyl)-4-methanesulfonyloxymethyl-2H-pyridazin-3-one Following the procedure of Example 1(9), 2-[3-(4-chlorophenyl)propyl]-6-(4-fluoro-3-methylphenyl)-4-hydroxymethyl-2H-pyridazin-3-one was reacted to yield the title compound as a yellow oil (yield: 89.8%).

$^1$H NMR(400 MHz, CDCl$_3$)δ: 2.16–2.24(2H, m), 2.36 (3H, d, J=2.0 Hz), 2.71(2H, t, J=7.3 Hz), 3.17(3H, s), 4.28(2H, t, J=7.3 Hz), 5.25(2H, d, J=1.5 Hz), 7.10(1H, m), 7.13(2H, d, J=8.5 Hz), 7.23(2H, d, J=8.5 Hz), 7.55–7.66(2H, m), 7.73(1H, t, J=1.2 Hz).

4) Preparation of 2-[3-(4-chlorophenyl)propyl]-6-(4-fluoro-3-methylphenyl)-4-(4-methyl-1-piperazinyl)methyl-2H-pyridazin-3-one Following the procedure of Example 1(10), 2-[3-(4-chlorophenyl)propyl]-6-(4-fluoro-3-methylphenyl)-4-methanesulfonyloxymethyl-2H-pyridazin-3-one was reacted to yield the title compound as a yellow oil (yield: 59.2%).

$^1$H NMR(400 MHz, CDCl$_3$)δ: 2.16–2.23(2H, m), 2.36 (3H, s), 2.37(3H, d, J=1.7 Hz), 2.55–2.73(10H, m), 3.56(2H, d, J=1.5 Hz), 4.27(2H, t, J=7.3 Hz), 7.10(1H, m), 7.14(2H, d, J=8.5 Hz), 7.21(2H, d, J=8.5 Hz), 7.55–7.65(2H, m), 7.69(1H, s). IR(Neat) cm$^{-1}$: 1652, 1608, 1493, 1239, 1015, 755. Mass m/z: 468(M$^+$), 470(M$^+$).

Example 219

Preparation of 2-[3-(2-chlorophenyl)propyl]-6-(4-fluoro-3-methylphenyl)-4-(4-methyl-1-piperazinyl)methyl-2H-pyridazin-3-one

1) Preparation of 4-carboxy-2-[3-(2-chlorophenyl)propyl]-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 3-(2-chlorophenyl)-1-propanol methanesulfonate were reacted to yield a crude product. Without purification, the crude product was reacted further in accordance with the procedure of Example 1(7) to yield the title compound as a yellow crystalline powder (76.8%).

Melting point: 156–159° C. $^1$H NMR(400 MHz, CDCl$_3$) δ: 2.27–2.35(2H, m), 2.37(3H, d, J=2.0 Hz), 2.88(2H, t, J=7.3 Hz), 4.45(2H, t, J=7.3 Hz), 7.11–7.34(5H, m), 7.63–7.72(2H, m), 8.60(1H, s).

2) Preparation of 2-[3-(2-chlorophenyl)propyl]-6-(4-fluoro-3-methylphenyl)-4-hydroxymethyl-2H-pyridazin-3-one Following the procedure of Example 1(8), 4-carboxy-2-[3-(2-chlorophenyl)propyl]-6-(4-fluoro-3-methylphenyl)-2H-pyridazin-3-one was reacted to yield the title compound as a yellow oil (yield: 38.9%).

$^1$H NMR(400 MHz, CDCl$_3$)δ: 2.20–2.27(2H, m), 2.35 (3H, d, J=2.0 Hz), 2.85(2H, t, J=7.3 Hz), 4.33(2H, t, J=7.3 Hz), 4.71(2H, d, J=1.2 Hz), 7.06–7.34(5H, m), 7.56–7.64 (2H,m), 7.65(1H, s).

3) Preparation of 2-[3-(2-chlorophenyl)propyl]-6-(4-fluoro-3-methylphenyl)-4-methanesulfonyloxymethyl-2H-pyridazin-3-one Following the procedure of Example 1(9), 2-[3-(2-chlorophenyl)propyl]-6-(4-fluoro-3-methylphenyl)-4-hydroxymethyl-2H-pyridazin-3-one was reacted to yield the title compound as a brown oil (yield: 92.5%).

$^1$H NMR(400 MHz, CDCl$_3$)δ: 2.20–2.27(2H, m), 2.36 (3H, d, J=1.7 Hz), 2.85(2H, t, J=7.1 Hz), 3.17(3H, s), 4.33(2H, t, J=7.1 Hz), 5.27(2H, d, J=1.2 Hz), 7.07–7.34(5H, m), 7.56–7.65(2H, m), 7.75(1H, s).

4) Preparation of 2-[3-(2-chlorophenyl)propyl]-6-(4-fluoro-3-methylphenyl)-4-(4-methyl-1-piperazinyl)methyl-2H-pyridazin-3-one Following the procedure of Example 1(10), 2-[3-(2-chlorophenyl)propyl]-6-(4-fluoro-3-methylphenyl)-4-methanesulfonyloxymethyl-2H-pyridazin-3-one was reacted to yield the title compound as a yellow oil (yield: 66.7%).

$^1$H NMR(400 MHz, CDCl$_3$)δ: 2.17–2.26(2H, m), 2.34 (3H, s), 2.36(3H, d, J=2.0 Hz), 2.50–2.68(8H, m), 2.85(2H, t, J=7.6 Hz), 3.58(2H, d, J=1.5 Hz), 4.32(2H, t, J=7.3 Hz), 7.07–7.35(5H, m), 7.58(1H, m), 7.65(1H, m), 7.72(1H, s). IR(Neat) cm$^{-1}$: 1652, 1608, 1456, 1238, 1015, 753. Mass m/z: 468(M$^+$), 470(M$^+$).

Example 220

Preparation of 2-[3-(2-chlorophenyl)propyl]-6-(4-fluoro-3-methylphenyl)-4-(4-methyl-1-piperazinyl)methyl-2H-pyridazin-3-one dihydrochloride Following the procedure of Example 4, 2-[3-(2-chlorophenyl)propyl]-6-(4-fluoro-3-methylphenyl)-4-(4-methyl-1-piperazinyl)methyl-2H-pyridazin-3-one was reacted to yield the title compound as colorless flakes (yield: 62.0%).

Melting point: 230–236° C. $^1$H NMR(400 MHz, DMSO-d$_6$)δ: 2.08–2.16(2H, m), 2.32(3H, s), 2.79(2H, t, J=7.6 Hz), 2.81(3H, s), 3.20–3.63(10H, m), 4.23(2H, t, J=7.6 Hz), 7.20–7.32(3H, m), 7.38–7.39(2H, m), 7.41(1H, s), 7.71(1H, m), 8.27(1H, brs). IR(KBr) cm$^{-1}$: 3301, 2984, 1651, 1608.

Example 221

Preparation of 2-[3-(3-chlorophenyl)propyl]-6-(4-fluoro-3-methylphenyl)-4-(4-methyl-1-piperazinyl)methyl-2H-pyridazin-3-one

1) Preparation of 4-carboxy-2-[3-(3-chlorophenyl)propyl]-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 3-(3-chlorophenyl)-1-propanol methanesulfonate were reacted to yield a crude product. Without purification, the crude product was reacted further in accordance with the procedure of Example 1(7) to yield the title compound as a yellow crystalline powder (79.1%).

Melting point: 117–120° C. ¹H NMR(400 MHz, CDCl₃) δ: 2.26–2.33(2H, m), 2.37(3H, d, J=2.0 Hz), 2.75(2H, t, J=7.3 Hz), 4.42(2H, t, J=7.3 Hz), 7.06–7.22(5H, m), 7.63–7.70(2H, m), 8.58(1H, s).

2) Preparation of 2-[3-(3-chlorophenyl)propyl]-6-(4-fluoro-3-methylphenyl)-4-hydroxymethyl-2H-pyridazin-3-one Following the procedure of Example 1(8), 4-carboxy-2-[3-(3-chlorophenyl)propyl]-6-(4-fluoro-3-methylphenyl)-2H-pyridazin-3-one was reacted to yield the title compound as a yellow oil (yield: 51.8%).

¹H NMR(400 MHz, CDCl₃)δ: 2.18–2.26(2H, m), 2.36 (3H, d, J=2.0 Hz), 2.72(2H, t, J=7.6 Hz), 4.30(2H, t, J=7.3 Hz), 4.70(2H, s), 7.07–7.22(5H, m), 7.55–7.63(2H,m), 7.64 (1H, s).

3) Preparation of 2-[3-(3-chlorophenyl)propyl]-6-(4-fluoro-3-methylphenyl)-4-methanesulfonyloxymethyl-2H-pyridazin-3-one Following the procedure of Example 1(9), 2-[3-(3-chlorophenyl)propyl]-6-(4-fluoro-3-methylphenyl)-4-hydroxymethyl-2H-pyridazin-3-one was reacted to yield the title compound as a brown oil (yield: 86.7%).

¹H NMR(400 MHz, CDCl₃)δ: 2.20–2.26(2H, m), 2.36 (3H, d, J=1.7 Hz), 2.71(2H, t, J=7.6 Hz), 3.17(3H, s), 4.30(2H, t, J=7.1 Hz), 5.25(2H, d, J=1.2 Hz), 7.07–7.22(5H, m), 7.55–7.64(2H, m), 7.73(1H, s).

4) Preparation of 2-[3-(3-chlorophenyl)propyl]-6-(4-fluoro-3-methylphenyl)-4-(4-methyl-1-piperazinyl)methyl-2H-pyridazin-3-one Following the procedure of Example 1(10), 2-[3-(3-chlorophenyl)propyl]-6-(4-fluoro-3-methylphenyl)-4-methanesulfonyloxymethyl-2H-pyridazin-3-one was reacted to yield the title compound as a yellow oil (yield: 56.2%).

¹H NMR(400 MHz, CDCl₃)δ: 2.17–2.25(2H, m), 2.36 (3H, s), 2.37(3H, s), 2.55–2.68(8H, m), 2.71(2H, t, J=7.6 Hz), 3.57(2H, d, J=1.2 Hz), 4.28(2H, t, J=7.3 Hz), 7.07–7.22 (5H, m), 7.57(1H, m), 7.64(1H, m), 7.70(1H, s). IR(Neat) cm⁻¹: 1652, 1607, 1456, 1239, 1015, 755. Mass m/z: 468 (M⁺), 470(M⁺).

Example 222

Preparation of 2-(4-chlorobenzyl)-6-(4-fluoro-3-methylphenyl)-4-(4-methyl-1-piperazinyl)methyl-2H-pyridazin-3-one

1) Preparation of 4-carboxy-2-(4-chlorobenzyl)-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 4-chlorobenzyl chloride were reacted to yield a crude product. Without purification, the crude product was reacted further in accordance with the procedure of Example 1(7) to yield the title compound as a pale yellow crystalline powder (46.5%).

Melting point: 219.5–220.5° C. ¹H NMR(400 MHz, CDCl₃)δ: 2.37(3H, d, J=1.7 Hz), 5.48(2H, s), 7.14(1H, dd, J=8.8, 8.8 Hz), 7.35(2H, d, J=8.3 Hz), 7.46(2H, d, J=8.3 Hz), 7.63–7.70(2H, m), 8.62(1H, s), 13.90(1H, brs). IR(KBr) cm⁻¹: 1745, 1634, 1561, 1493, 1475, 1245, 806.

2) Preparation of 2-(4-chlorobenzyl)-6-(4-fluoro-3-methylphenyl)-4-hydroxymethyl-2H-pyridazin-3-one Following the procedure of Example 1(8), 4-carboxy-2-(4-chlorobenzyl)-6-(4-fluoro-3-methylphenyl)-2H-pyridazin-3-one was reacted to yield the title compound as a slightly-yellow needles (yield: 23.3%).

Melting point: 157.1–158.3° C. ¹H NMR(400 MHz, CDCl₃)δ: 2.35(3H, d, J=2.0 Hz), 4.70(2H, s), 5.36(2H, s), 7.09(1H, dd, J=8.8, 8.8 Hz), 7.31(2H, d, J=8.3 Hz), 7.42(2H, d, J=8.3 Hz), 7.56–7.65(2H, m), 7.67(1H, s). IR(KBr) cm⁻¹: 3422, 1645, 1604, 1508, 1459, 1239, 1091, 819. Mass m/z: 358(M⁺), 360(M⁺).

3) Preparation of 2-(4-chlorobenzyl)-6-(4-fluoro-3-methylphenyl)-4-methanesulfonyloxymethyl-2H-pyridazin-3-one Following the procedure of Example 1(9), 2-(4-chlorobenzyl)-6-(4-fluoro-3-methylphenyl)-4-hydroxymethyl-2H-pyridazin-3-one was reacted to yield the title compound as pale yellow needles (yield: 89.1%).

Melting point: 131.8–132.7° C. ¹H NMR(400 MHz, CDCl₃)δ: 2.36(3H, d, J=2.0 Hz), 3.15(3H, s), 5.25(2H, d, J=1.5 Hz), 5.36(2H, s), 7.10(1H, dd, J=9.0, 9.0 Hz), 7.31 (2H, d, J=8.3 Hz), 7.42(2H, d, J=8.3 Hz), 7.55–7.63(2H, m), 7.76(1H, s). IR(KBr) cm⁻¹: 1661, 1618, 1352, 1165, 877. Mass m/z: 436(M⁺), 438(M⁺).

4) Preparation of 2-(4-chlorobenzyl)-6-(4-fluoro-3-methylphenyl)-4-(4-methyl-1-piperazinyl)methyl-2H-pyridazin-3-one Following the procedure of Example 1(10), 2-(4-chlorobenzyl)-6-(4-fluoro-3-methylphenyl)-4-methanesulfonyloxymethyl-2H-pyridazin-3-one was reacted to yield the title compound as pale yellow needles (yield: 58.7%).

Melting point: 133.3–133.8° C. ¹H NMR(400 MHz, CDCl₃)δ: 2.35(3H, d, J=2.0 Hz), 2.43(3H, s), 2.70(8H, brs), 3.58(2H, d, J=1.2 Hz), 5.35(2H, s), 7.10(1H, dd, J=8.8, 8.8 Hz), 7.30(2H, d, J=8.3 Hz), 7.43(2H, d, J=8.3 Hz), 7.59(1H, m), 7.62(1H, dd, J=7.3, 2.0 Hz), 7.71(1H, s). IR(KBr) cm⁻¹: 2798, 1655, 1606, 1492, 1235, 1166, 1104. Mass m/z: 440(M⁺), 442(M⁺).

Example 223

Preparation of 2-(4-chlorobenzyl)-6-(4-fluoro-3-methylphenyl)-4-(4-methyl-1-piperazinyl)methyl-2H-pyridazin-3-one dihydrochloride Following the procedure of Example 4, 2-(4-chlorobenzyl)-6-(4-fluoro-3-methylphenyl)-4-(4-methyl-1-piperazinyl)methyl-2H-pyridazin-3-one was reacted to yield the title compound as a colorless crystalline powder (yield: 88.5%).

Melting point: 246.4–249.7° C. (dec.) ¹H NMR(400 MHz, DMSO-d₆)δ: 2.31(3H, s), 2.82(3H, s), 3.17(8H, brs), 4.09(2H, brs), 5.36(2H, s), 7.30(1H, dd, J=9.0, 9.0 Hz), 7.42(4H, s), 7.76(1H, m), 7.84(1H, dd, J=7.3, 2.2 Hz), 8.34(1H, s). IR(KBr) cm⁻¹: 1654, 1612, 1505. Mass m/z: 440(M⁺), 442(M⁺).

Example 224

Preparation of 2-(2-chlorobenzyl)-6-(4-fluoro-3-methylphenyl)-4-(4-methyl-1-piperazinyl)methyl-2H-pyridazin-3-one

1) Preparation of 4-carboxy-2-(2-chlorobenzyl)-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 2-chlorobenzyl chloride were reacted to yield a crude product. Without purification, the crude product was reacted further in accordance with the procedure of Example 1(7) to yield the title compound as pale yellow needles (76.4%).

Melting point: 185.1–185.9° C. $^1$H NMR(400 MHz, CDCl$_3$)δ: 2.34(3H, s), 5.67(2H, s), 7.10(1H, dd, J=8.8, 8.8 Hz), 7.25–7.35(3H, m), 7.46(1H, m), 7.62(1H, m), 7.65(1H, d, J=7.3 Hz), 8.66(1H, s), 13.92(1H, s). IR(KBr) cm$^{-1}$: 1751, 1638, 1565, 1472, 1239. Mass m/z: 372(M$^+$), 374(M$^+$).

2) Preparation of 2-(2-chlorobenzyl)-6-(4-fluoro-3-methylphenyl)-4-hydroxymethyl-2H-pyridazin-3-one Following the procedure of Example 1(8), 4-carboxy-2-(2-chlorobenzyl)-6-(4-fluoro-3-methylphenyl)-2H-pyridazin-3-one was reacted to yield the title compound as pale yellow needles (yield: 21.3%).

Melting point: 149.0–149.7° C. $^1$H NMR(400 MHz, CDCl$_3$)δ: 2.32(3H, d, J=1.7 Hz), 4.73(2H, d, J=1.2 Hz), 5.55(2H, s), 7.06(1H, dd, J=8.8, 8.8 Hz), 7.15–7.26(3H, m), 7.40(1H, m), 7.57(1H, m), 7.62(1H, dd, J=7.3, 2.2 Hz), 7.73(1H, t, J=1.2 Hz). IR(KBr) cm$^{-1}$: 3409, 1668, 1652, 1506, 1446, 1241. Mass m/z: 358(M$^+$), 360(M$^+$).

3) Preparation of 2-(2-chlorobenzyl)-6-(4-fluoro-3-methylphenyl)-4-methanesulfonyloxymethyl-2H-pyridazin-3-one Following the procedure of Example 1(9), 2-(2-chlorobenzyl)-6-(4-fluoro-3-methylphenyl)-4-hydroxymethyl-2H-pyridazin-3-one was reacted to yield the title compound as slightly-yellow needles (yield: 82.1%).

Melting point: 142.3–143.0° C. $^1$H NMR(400 MHz, CDCl$_3$)δ: 2.33(3H, d, J=1.7 Hz), 3.16(3H, s), 5.29(2H, d, J=1.2 Hz), 5.56(2H, s), 7.07(1H, dd, J=8.8, 8.8 Hz), 7.19–7.28(3H, m), 7.42(1H, m), 7.56(1H, m), 7.60(1H, dd, J=7.3, 2.2 Hz), 7.81(1H, s). IR(KBr) cm$^{-1}$: 1659, 1618, 1613, 1355, 1166, 1034. Mass m/z: 436(M$^+$), 438(M$^+$).

4) Preparation of 2-(2-chlorobenzyl)-6-(4-fluoro-3-methylphenyl)-4-(4-methyl-1-piperazinyl)methyl-2H-pyridazin-3-one Following the procedure of Example 1(10), 2-(2-chlorobenzyl)-6-(4-fluoro-3-methylphenyl)-4-methanesulfonyloxymethyl-2H-pyridazin-3-one was reacted to yield the title compound as pale yellow needles (yield: 53.4%).

Melting point: 149.7–150.9° C. $^1$H NMR(400 MHz, CDCl$_3$)δ: 2.33(3H, d, J=1.7 Hz), 2.38(3H, s), 2.61(4H, brs), 2.68(4H, brs), 3.61(2H, d, J=1.5 Hz), 5.55(2H, s), 7.06(1H, dd, J=8.8, 8.8 Hz), 7.17–7.26(3H, m), 7.41 (1H, m), 7.56 (1H, m), 7.62 (1H, dd, J=7.1, 2.0 Hz), 7.77(1H, s). IR(KBr) cm$^{-1}$: 2792, 1659, 1618, 1611, 1504, 1285, 1237, 1170. Mass m/z: 440(M$^+$), 442(M$^+$).

Example 225

Preparation of 2-(2-chlorobenzyl)-6-(4-fluoro-3-methylphenyl)-4-(4-methyl-1-piperazinyl)methyl-2H-pyridazin-3-one dihydrochloride

Following the procedure of Example 4, 2-(2-chlorobenzyl)-6-(4-fluoro-3-methylphenyl)-4-(4-methyl-1-piperazinyl)methyl-2H-pyridazin-3-one was reacted to yield the title compound as a slightly-yellow crystalline powder (yield: 78.1%).

Melting point: 191–202° C. (dec.) $^1$H NMR(400 MHz, CD$_3$OD)δ: 2.31(3H, d, J=1.7 Hz), 3.01(3H, s), 3.68(8H, brs), 4.40(2H, s), 5.57(2H, s), 7.12(1H, dd, J=8.8, 8.8 Hz), 7.27–7.35(3H, m), 7.46(1H, m), 7.72(1H, m), 7.77(1H, d, J=7.1 Hz), 8.40(1H, s). IR(KBr) cm$^{-1}$: 1656, 1612, 1504, 1446, 1128. Mass m/z: 440(M$^+$), 442(M$^+$).

Example 226

Preparation of 2-(2-chlorobenzyl)-6-(4-fluoro-3-methylphenyl)-4-[3-(4-methyl-1-piperazinyl)propyl]-2H-pyridazin-3-one

1) Preparation of 4-bromomethyl-2-(2-chlorobenzyl)-6-(4-fluoro-3-methylphenyl)-2H-pyridazin-3-one Following the procedure of Example 211(1), 2-(2-chlorobenzyl)-6-(4-fluoro-3-methylphenyl)-4-hydroxymethyl-2H-pyridazin-3-one was reacted to yield the title compound as slightly-yellow needles (yield: 46.2%).

Melting point: 113–115° C. $^1$H NMR(400 MHz, CDCl$_3$)δ: 2.33(3H, d, J=2.0 Hz), 4.50(2H, d, J=0.98 Hz), 5.75(2H, s), 7.07(1H, dd, J=8.8, 8.8 Hz), 7.21–7.25(3H, m), 7.42(1H, m), 7.51–7.61(2H,m), 7.83(1H, t, J=0.98 Hz).

2) Preparation of 2-(2-chlorobenzyl)-4-[2,2-di(tert-butoxycarbonyl)ethyl]-6-(4-fluoro-3-methylphenyl)-2H-pyridazin-3-one Following the procedure of Example 211(2), 4-bromomethyl-2-(2-chlorobenzyl)-6-(4-fluoro-3-methylphenyl)-2H-pyridazin-3-one was reacted to yield the title compound as a yellow oil (yield: 88.4%).

$^1$H NMR(400 MHz, CDCl$_3$)δ: 1.41(18H, s), 2.31(3H, d, J=1.7 Hz), 3.14(2H, d, J=7.8 Hz), 3.87(1H, t, J=7.8 Hz), 5.54(2H, s), 7.04(1H, dd, J=8.8, 8.8 Hz), 7.14–7.24(3H, m), 7.40(1H, m), 7.48–7.56(2H, m), 7.57(1H, s).

3) Preparation of 4-(2-carboxyethyl)-2-(2-chlorobenzyl)-6-(4-fluoro-3-methylphenyl)-2H-pyridazin-3-one Following the procedure of Example 211(3), 2-(2-chlorobenzyl)-4-[2,2-di(tert-butoxycarbonyl)ethyl]-6-(4-fluoro-3-methylphenyl)-2H-pyridazin-3-one was reacted to yield the title compound as a yellow powder (yield: 99.1%).

$^1$H NMR(400 MHz, CDCl$_3$)δ: 2.31(3H, d, J=1.7 Hz), 2.81(2H, t, J=6.8 Hz), 2.98(2H, t, J=6.8 Hz), 5.55(2H, s), 7.05(1H, dd, J=9.0, 9.0 Hz), 7.16–7.25(3H, m), 7.41(1H, m), 7.50–7.57(2H, m), 7.59(1H, s).

4) Preparation of 2-(2-chlorobenzyl)-6-(4-fluoro-3-methylphenyl)-4-(3-hydroxypropyl)-2H-pyridazin-3-one Following the procedure of Example 1(8), 4-(2-carboxyethyl)-2-(2-chlorobenzyl)-6-(4-fluoro-3-methylphenyl)-2H-pyridazin-3-one was reacted to yield the title compound as a pale yellow oil (yield: 77.2%).

$^1$H NMR(400 MHz, CDCl$_3$)δ: 1.88–1.95(2H, m), 2.32 (3H, d, J=1.5 Hz), 2.82(2H, t, J=7.1 Hz), 3.63(2H, t, J=6.8 Hz), 5.56(2H, s), 7.05(1H, dd, J=8.8, 8.8 Hz), 7.25–7.28(3H, m), 7.41(1H, m), 7.55–7.60(2H, m), 7.56(1H, s).

5) Preparation of 2-(2-chlorobenzyl)-6-(4-fluoro-3-methylphenyl)-4-(3-methanesulfonyloxypropyl)-2H-pyridazin-3-one Following the procedure of Example 1(9), 2-(2-chlorobenzyl)-6-(4-fluoro-3-methylphenyl)-4-(3-hydroxypropyl)-2H-pyridazin-3-one was reacted to yield the title compound as a yellow oil (yield: 97.0%).

$^1$H NMR(400 MHz, CDCl$_3$)δ: 2.14–2.21(2H, m), 2.32 (3H, d, J=1.7 Hz), 2.81(2H, t, J=7.1 Hz), 3.02(3H, s), 4.30(2H, t, J=6.1 Hz), 5.54(2H, s), 7.05(1H, dd, J=8.8, 8.8 Hz), 7.17–7.25(3H, m), 7.41(1H, m), 7.53–7.62(2H, m), 7.58(1H, s).

6) Preparation of 2-(2-chlorobenzyl)-6-(4-fluoro-3-methylphenyl)-4-[3-(4-methyl-1-piperazinyl)propyl]-2H-pyridazin-3-one Following the procedure of Example 1(9), 2-(2-chlorobenzyl)-6-(4-fluoro-3-methylphenyl)-4-(3-methanesulfonyloxypropyl)-2H-pyridazin-3-one was reacted to yield the title compound as a yellow oil (yield: 75.9%).

$^1$H NMR(400 MHz, CDCl$_3$)δ: 1.84–1.95(2H, m), 2.32 (3H, brs), 2.33(3H, s), 2.45–2.58(8H,m), 2.70(2H, t, J=7.8 Hz), 3.26(2H, t, J=4.9 Hz), 5.54(2H, s), 7.05(1H, dd, J=8.8, 8.8 Hz), 7.15–7.23(3H, m), 7.40(1H, m), 7.51(1H, s), 7.53–7.59(2H, m). IR(Neat) cm$^{-1}$: 1655, 1608, 1447, 1239, 1014, 754. Mass m/z: 468 (M$^+$), 470 (M$^+$).

Example 227

Preparation of 4-(3-aminopropyl)-2-(2-chlorobenzyl)-6-(4-fluoro-3-methylphenyl)-2H-pyridazin-3-one Following the procedure of Example 24(1), 2-(2-chlorobenzyl)-6-(4-fluoro-3-methylphenyl)-4-(3-methanesulfonyloxypropyl)-2H-pyridazin-3-one was reacted to yield a crude product. Without purification, the crude product was reacted further in accordance with the procedure of Example 24(2) to yield the title compound as a slightly-yellow crystalline powder (yield: 43.9%).

Melting point: 80–85° C. $^1$H NMR(400 MHz, CDCl$_3$)δ: 1.85–1.95 (2H, m), 2.31 (3H, d, J=1.7 Hz), 2.74 (2H, t, J=7.8 Hz), 2.85(2H, t, J=6.8 Hz), 5.54(2H, s), 7.04(1H, dd, J=8.8, 8.8 Hz), 7.15–7.24(3H, m), 7.40(1H, m), 7.56(1H, s), 7.58–7.59(2H, m). IR(KBr) cm$^{-1}$: 3425, 1652, 1607, 1445, 1238, 1039, 749. Mass m/z: 385(M$^+$), 387(M$^+$).

Example 228

Preparation of 4-(3-aminopropyl)-2-(2-chlorobenzyl)-6-(4-fluoro-3-methylphenyl)-2H-pyridazin-3-one hydrochloride Following the procedure of Example 4, 4-(3-aminopropyl)-2-(2-chlorobenzyl)-6-(4-fluoro-3-methylphenyl)-2H-pyridazin-3-one was reacted to yield the title compound as a pale brown crystalline powder (yield: 55.9%).

Melting point: 161–165° C. $^1$H NMR(400 MHz, CD$_3$OD) δ: 1.98–2.06(2H, m), 2.30(3H, brs), 2.77(2H, t, J=7.8 Hz), 3.00(2H, t, J=7.6 Hz), 5.56(2H, s), 7.10(1H, dd, J=9.0, 9.0 Hz), 7.19(1H, m), 7.24–7.33(2H, m), 7.45(1H, m), 7.67(1H, m), 7.72(1H, m), 7.94(1H, s). IR(KBr) cm$^{-1}$: 3435, 1644, 1602, 1445, 1240, 1040, 748.

Example 229

Preparation of 2-[2-(2-chlorophenyl)ethyl]-6-(4-fluoro-3-methylphenyl)-4-(4-methyl-1-piperazinyl)methyl-2H-pyridazin-3-one

1) Preparation of 2-[2-(2-chlorophenyl)ethyl]-6-(4-fluoro-3-methylphenyl)-4-methoxycarbonyl-2H-pyridazin-3-one Following the procedure of Example 1(6), 6-(4-fluoro-3-methylphenyl)-4-methoxycarbonyl-2H-pyridazin-3-one and 2-(2-chlorophenyl)ethanol methanesulfonate were reacted to yield the title compound as a pale yellow solid (yield: 59.8%).

$^1$H NMR(400 MHz, CDCl$_3$)δ: 2.32(3H, s), 3.33(2H, t, J=7.3 Hz), 3.99(3H, s), 4.58(2H, t, J=7.3 Hz), 7.05(1H, dd, J=8.8, 8.8 Hz), 7.14–7.27(3H, m), 7.34–7.44(3H, m), 8.19 (1H, s).

2) Preparation of 2-[2-(2-chlorophenyl)ethyl]-6-(4-fluoro-3-methylphenyl)-4-hydroxymethyl-2H-pyridazin-3-one To a solution of 2-[2-(2-chlorophenyl)ethyl]-6-(4-fluoro-3-methylphenyl)-4-methoxycarbonyl-2H-pyridazin-3-one (480 mg, 1.20 mmol) in THF/methanol (2 mL/1 mL), cerium(III) chloride hexahydrate (425 mg, 1.20 mmol) was added at −15° C., followed by the addition of sodium borohydride (45 mg, 1.20 mmol). After stirred for 10 minutes, a saturated aqueous solution of ammonium chloride was added to the reaction mixture, and the mixture was extracted with ethyl acetate. The extract was dried over anhydrous sodium sulfate, and was concentrated under reduced pressure. Further, the concentrate was purified by column chromatography on silica gel [hexane/ethyl acetate (2/1)] to yield the title compound as a pale yellow syrupy substance (yield: 11.0%).

$^1$H NMR(400 MHz, CDCl$_3$)δ: 2.32(3H, d, J=2.0 Hz), 3.32(2H, t, J=7.2 Hz), 4.54(2H, t, J=7.2 Hz), 4.69(2H, s), 7.05(1H, dd, J=9.2, 9.2 Hz), 7.13–7.23(3H, m), 7.36(1H, m), 7.42–7.48(2H, m), 7.62(1H, d, J=1.0 Hz).

3) Preparation of 2-[2-(2-chlorophenyl)ethyl]-6-(4-fluoro-3-methylphenyl)-4-methanesulfonyloxymethyl-2H-pyridazin-3-one Following the procedure of Example 1(9), 2-[2-(2-chlorophenyl)ethyl]-6-(4-fluoro-3-methylphenyl)-4-hydroxymethyl-2H-pyridazin-3-one was reacted to yield the title compound as a pale yellow syrup (yield: 86.1%).

¹H NMR(400 MHz, CDCl₃)δ: 2.33(3H, d, J=1.8 Hz), 3.16(3H, s), 3.31(2H, t, J=7.2 Hz), 4.55(2H, t, J=7.2 Hz), 5.26(2H, d, J=1.4 Hz), 7.06(1H, dd, J=9.2, 9.2 Hz), 7.14–7.21(3H, m), 7.37(1H, m), 7.40–7.47(2H, m), 7.72(1H, t, J=1.8 Hz).

4) Preparation of 2-[2-(2-chlorophenyl)ethyl]-6-(4-fluoro-3-methylphenyl)-4-(4-methyl-1-piperazinyl)methyl-2H-pyridazin-3-one Following the procedure of Example 1(10), 2-[2-(2-chlorophenyl)ethyl]-6-(4-fluoro-3-methylphenyl)-4-methanesulfonyloxymethyl-2H-pyridazin-3-one was reacted to yield the title compound as a pale yellow syrup (yield: 61.2%).

¹H NMR(400 MHz, CDCl₃)δ: 2.33(6H, s), 2.46–2.67(8H, m), 3.31(2H, t, J=7.3 Hz), 3.57(2H, d, J=1.2 Hz), 4.53(2H, t, J=7.3 Hz), 7.05(1H, dd, J=9.3, 9.3 Hz), 7.13–7.24(3H, m), 7.36(1H, m), 7.42–7.47(2H, m), 7.70(1H, s). IR(Neat) cm⁻¹: 1653, 1606, 1504, 1284, 1238, 1116.

Example 230

Preparation of 2-[2-(4-chlorophenyl)ethyl]-6-(4-fluoro-3-methylphenyl)-4-(4-methyl-1-piperazinyl)methyl-2H-pyridazin-3-one 1) Preparation of 4-carboxy-2-[2-(4-chlorophenyl)ethyl]-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 2-(4-chlorophenyl)ethanol methanesulfonate were reacted to yield a crude product. Without purification, the crude product was reacted further in accordance with the procedure of Example 1 (7) to yield the title compound as a pale yellow solid (yield: 56.3%).

¹H NMR(400 MHz, CDCl₃)δ: 2.36(3H, d, J=1.8 Hz), 3.20(2H, t, J=7.4 Hz), 4.60(2H, t, J=7.4 Hz), 7.11(1H, dd, J=8.2, 8.2 Hz), 7.17(2H, d, J=8.4 Hz), 7.22–7.31(2H, m), 7.49–7.55(2H, m), 8.59(1H, s).

2) Preparation of 2-[2-(4-chlorophenyl)ethyl]-6-(4-fluoro-3-methylphenyl)-4-hydroxymethyl-2H-pyridazin-3-one Following the procedure of Example 1(8), 4-carboxy-2-[2-(4-chlorophenyl)ethyl]-6-(4-fluoro-3-methylphenyl)-2H-pyridazin-3-one was reacted to yield the title compound as a pale yellow oil (yield: 37.2%).

¹H NMR(400 MHz, CDCl₃)δ: 2.34(3H, d, J=2.0 Hz), 3.14(2H, t, J=7.4 Hz), 4.47(2H, t, J=7.4 Hz), 4.70(2H, s), 7.07(1H, dd, J=9.2, 9.2 Hz), 7.18(2H, d, J=8.4 Hz), 7.26(2H, d, J=8.4 Hz), 7.45–7.51(2H, m), 7.63(1H, t, J=1.2 Hz).

3) Preparation of 2-[2-(4-chlorophenyl)ethyl]-6-(4-fluoro-3-methylphenyl)-4-methanesulfonyloxymethyl-2H-pyridazin-3-one Following the procedure of Example 1(9), 2-[2-(4-chlorophenyl)ethyl]-6-(4-fluoro-3-methylphenyl)-4-hydroxymethyl-2H-pyridazin-3-one was reacted to yield the title compound as a pale yellow solid (yield: 34.0%).

¹H NMR(400 MHz, CDCl₃)δ: 2.35(3H, d, J=1.9 Hz), 3.11–3.17(5H, m), 4.48(2H, t, J=7.3 Hz), 5.26(2H, d, J=1.5 Hz), 7.08(1H, dd, J=9.3, 9.3 Hz), 7.17(2H, d, J=8.3 Hz), 7.24–7.29(2H, m), 7.44–7.53(2H, m), 7.73(1H, t, J=1.2 Hz).

4) Preparation of 2-[2-(4-chlorophenyl)ethyl]-6-(4-fluoro-3-methylphenyl)-4-(4-methyl-1-piperazinyl)methyl-2H-pyridazin-3-one Following the procedure of Example 1(10), 2-[2-(4-chlorophenyl)ethyl]-6-(4-fluoro-3-methylphenyl)-4-methanesulfonyloxymethyl-2H-pyridazin-3-one was reacted to yield the title compound as a colorless crystalline powder (yield: 45.2%).

Melting point: 113–114° C. ¹H NMR(400 MHz, CDCl₃)δ: 2.32(3H, s), 2.35(3H, d, J=2.0 Hz), 2.45–2.66(8H, m), 3.13(2H, t, J=7.6 Hz), 3.57(2H, d, J=1.4 Hz), 4.46(2H, t, J=7.6 Hz), 7.08(1H, dd, J=8.5, 8.5 Hz), 7.18(2H, d, J=8.3 Hz), 7.24–7.28(2H, m), 7.45–7.50(2H, m), 7.70(1H, t, J=1.4 Hz). IR(KBr) cm⁻¹: 1654, 1613, 1505, 1285, 1242, 1167, 1123.

Example 231

Preparation of 2-(2,6-dichlorobenzyl)-6-(4-fluoro-3-methylphenyl)-4-(4-methyl-1-piperazinyl)methyl-2H-pyridazin-3-one 1) Preparation of 4-carboxy-2-(2,6-dichlorobenzyl)-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 2,6-dichlorobenzyl bromide were reacted to yield a crude product. Without purification, the crude product was reacted further in accordance with the procedure of Example 1(7) to yield the title compound as a pale yellow solid (90.3%).

¹H NMR(400 MHz, CDCl₃)δ: 2.28(3H, d, J=1.8 Hz), 5.81(2H, s), 7.03(1H, dd, J=8.8, 8.8 Hz), 7.31(1H, dd, J=8.8, 7.4 Hz), 7.39–7.49(4H, m), 8.62(1H, s).

2) Preparation of 2-(2,6-dichlorobenzyl)-6-(4-fluoro-3-methylphenyl)-4-hydroxymethyl-2H-pyridazin-3-one Following the procedure of Example 1(8), 4-carboxy-2-(2,6-dichlorobenzyl)-6-(4-fluoro-3-methylphenyl)-2H-pyridazin-3-one was reacted to yield the title compound as a pale yellow solid (yield: 46.1%).

¹H NMR(400 MHz, CDCl₃)δ: 2.26(3H, d, J=1.7 Hz), 4.74(2H, s), 5.70(2H, s), 6.98(1H, dd, J=9.0, 9.0 Hz), 7.25(1H, dd, J=8.6, 7.3 Hz), 7.32–7.45(4H, m), 7.66(1H, s).

3) Preparation of 2-(2,6-dichlorobenzyl)-6-(4-fluoro-3-methylphenyl)-4-methanesulfonyloxymethyl-2H-pyridazin-3-one Following the procedure of Example 1(9), 2-(2,6-dichlorobenzyl)-6-(4-fluoro-3-methylphenyl)-4-hydroxymethyl-2H-pyridazin-3-one was reacted to yield the title compound as a pale yellow solid (yield: 78.9%).

¹H NMR(400 MHz, CDCl₃)δ: 2.27(3H, d, J=1.7 Hz), 3.17(3H, s), 5.31(2H, d, J=1.2 Hz), 5.69(2H, s), 6.99(1H, dd, J=8.8, 8.8 Hz), 726(1H, m), 7.34–7.44(4H, m), 7.75(1H, t, J=1.4 Hz).

4) Preparation of 2-(2,6-dichlorobenzyl)-6-(4-fluoro-3-methylphenyl)-4-(4-methyl-1-piperazinyl)methyl-2H-pyridazin-3-one Following the procedure of Example 1(10), 2-(2,6-dichlorobenzyl)-6-(4-fluoro-3-methylphenyl)-4-methanesulfonyloxymethyl-2H-pyridazin-3-one was reacted to yield the title compound as a colorless crystalline powder (yield: 69.4%).
Melting point: 150–152° C. $^1$H NMR(400 MHz, CDCl$_3$) δ: 2.27(3H, d, J=1.8 Hz), 2.33(3H, s), 2.45–2.67(8H, m), 3.62(2H, d, J=1.4 Hz), 5.69(2H, s), 6.99(1H, dd, J=9.0, 9.0 Hz), 7.23(1H, dd, J=8.6, 7.4 Hz), 7.34–7.44(4H, m), 7.73 (1H, s). IR(KBr) cm$^{-1}$: 1658, 1619, 1505, 1437, 1238, 1168.

Example 232

Preparation of 2-(2,6-dichlorobenzyl)-6-(4-fluoro-3-methylphenyl)-4-(1-piperazinyl)methyl-2H-pyridazin-3-one 1) Preparation of 4-(4-tert-butoxycarbonyl-1-piperazinyl)methyl-2-(2,6-dichlorobenzyl)-6-(4-fluoro-3-methylphenyl)-2H-pyridazin-3-one Following the procedure of Example 1(10), 2-(2,6-dichlorobenzyl)-6-(4-fluoro-3-methylphenyl)-4-methanesulfonyloxymethyl-2H-pyridazin-3-one and tert-butyl 1-piperazinecarboxylate were reacted to yield the title compound as a yellow oil (yield: 90.8%).
$^1$H NMR(400 MHz, CDCl$_3$)δ: 1.47(9H, s), 2.26(3H,s), 2.53(4H, t, J=4.9 Hz), 3.50((4H, t, J=4.9 Hz), 3.61(2H, s), 5.69(2H, s), 6.98(1H, dd, J=8.8, 8.8 Hz), 7.23(1H, dd, J=8.5, 7.3 Hz), 7.35–7.43(4H, m), 7.75(1H, s).

2) Preparation of 2-(2,6-dichlorobenzyl)-6-(4-fluoro-3-methylphenyl)-4-(1-piperazinyl)methyl-2H-pyridazin-3-one Following the procedure of Example 20, 4-(4-tert-butoxycarbonyl-1-piperazinyl)methyl-2-(2,6-dichlorobenzyl)-6-(4-fluoro-3-methylphenyl)-2H-pyridazin-3-one was reacted to yield the title compound as a colorless amorphous powder (yield: 84.6%).
$^1$H NMR(400 MHz, CDCl$_3$)δ: 2.27(3H, d, J=1.7 Hz), 2.51–2.60(4H, m), 2.95(4H, t, J=4.6 Hz), 3.59(2H, d, J=1.2 Hz), 5.69(2H, s), 6.99(1H, dd, J=8.8, 8.8 Hz), 7.24(1H, m), 7.35–7.44(4H, m), 7.76(1H, s). IR(KBr) cm$^{-1}$: 1652, 1606, 1504, 1438, 1239, 1119.

Example 233

Preparation of 4-aminomethyl-2-(2,6-dichlorobenzyl)-6-(4-fluoro-3-methylphenyl)-2H-pyridazin-3-one Following the procedure of Example 24(1), 2-(2,6-dichlorobenzyl)-6-(4-fluoro-3-methylphenyl)-4-methanesulfonyloxymethyl-2H-pyridazin-3-one was reacted to yield a crude product. Without purification, the crude product was reacted further in accordance with the procedure of Example 24(2) to yield the title compound as a yellow-brown crystalline powder (yield: 12.7%).
$^1$H NMR(400 MHz, CDCl$_3$)δ: 2.17(2H, brs), 2.25(3H, d, J=2.0 Hz), 3.94(2H, d, J=1.0 Hz), 5.69(2H, s), 6.97(1H, dd, J=9.0, 9.0 Hz), 7.24(1H, dd, J=8.5, 7.3 Hz), 7.34–7.45(4H, m), 7.70(1H, s). IR(KBr) cm$^{-1}$: 3362, 1643, 1598, 1504, 1438, 1238, 1121.

Example 234

Preparation of 2-[3-(2,6-dichlorophenyl)propyl]-6-(4-fluoro-3-methylphenyl)-4-(4-methyl-1-piperazinyl)methyl-2H-pyridazin-3-one 1) Preparation of 4-carboxy-2-[3-(2,6-dichlorophenyl)propyl]-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 3-(2,6-dichlorophenyl)-1-propanol methanesulfonate were reacted to yield a crude product. Without purification, the crude product was reacted further in accordance with the procedure of Example 1 (7) to yield the title compound as a pale yellow solid (yield: 89.8%).
$^1$H NMR(400 MHz, CDCl$_3$)δ: 2.22–2.32(2H, m), 2.37 (3H, d, J=2.0 Hz), 3.03–3.08(2H, m), 4.50(2H, t, J=7.0 Hz), 7.06–7.17(2H, m), 7.25–7.29(2H, m), 7.64–7.72(2H, m), 8.63(1H, s), 14.12(1H, s).

2) Preparation of 2-[3-(2,6-dichlorophenyl)propyl]-6-(4-fluoro-3-methylphenyl)-4-hydroxymethyl-2H-pyridazin-3-one Following the procedure of Example 1(8), 4-carboxy-2-[3-(2,6-dichlorophenyl)propyl]-6-(4-fluoro-3-methylphenyl)-2H-pyridazin-3-one was reacted to yield the title compound as a pale yellow syrup (yield: 31.9%).
$^1$H NMR(400 MHz, CDCl$_3$)δ: 2.14–2.24(2H, m), 2.35 (3H, d, J=1.8 Hz), 3.00–3.06(2H, m), 4.38(2H,t, J=7.0 Hz), 4.72(2H, d, J=1.5 Hz), 7.01–7.12(2H, m), 7.23–7.28(2H, m), 7.57–7.70(3H, m).

3) Preparation of 2-[3-(2,6-dichlorophenyl)propyl]-6-(4-fluoro-3-methylphenyl)-4-methanesulfonyloxymethyl-2H-pyridazin-3-one Following the procedure of Example 1(9), 2-[3-(2,6-dichlorophenyl)propyl]-6-(4-fluoro-3-methylphenyl)-4-hydroxymethyl-2H-pyridazin-3-one was reacted to yield the title compound as a pale yellow syrup (yield: 25.8%).
$^1$H NMR(400 MHz, CDCl$_3$)δ: 2.14–2.23(2H, m), 2.36 (3H, d, J=1.8 Hz), 2.94–3.05(2H, m), 3.17(3H, s), 4.38(2H, t, J=7.0 Hz), 5.28(2H, d, J=11.4 Hz), 7.02–7.12(2H, m), 7.23–7.27(2H, m), 7.57–7.69(2H, m), 7.76(1H, t, J=1.4 Hz).

4) Preparation of 2-[3-(2,6-dichlorophenyl)propyl]-6-(4-fluoro-3-methylphenyl)-4-(4-methyl-1-piperazinyl)methyl-2H-pyridazin-3-one Following the procedure of Example 1(10), 2-[3-(2,6-dichlorophenyl)propyl]-6-(4-fluoro-3-methylphenyl)-4-methanesulfonyloxymethyl-2H-pyridazin-3-one was reacted to yield the title compound as a pale yellow syrup (yield: 49.7%).
$^1$H NMR(400 MHz, CDCl$_3$)δ: 2.13–2.22(2H, m), 2.33 (3H, s), 2.36(3H, d, J=1.8 Hz), 2.45–2.67(8H, m), 2.99–3.05 (2H, m), 3.58(2H, d, J=1.4 Hz), 4.37(2H, t, J=7.0 Hz), 7.02–7.12(2H, m), 7.23–7.40(2H, m), 7.59(1H, m), 7.65(1H, m), 7.73(1H, s). IR(Neat) cm$^{-1}$: 1653, 1607, 1504, 1436, 1238.

Example 235

Preparation of 2-(3,4-difluorobenzyl)-6-(4-fluoro-3-methylphenyl)-4-(4-methyl-1-piperazinyl)methyl-2H-pyridazin-3-one

1) Preparation of 4-carboxy-2-(3,4-difluorobenzyl)-6-(4-fluoro-3-methylphenyl)-2H-pyridazin-3-one Following the procedure of Example 1(6), 6-(4-fluoro-3-methylphenyl)-4-methoxycarbonyl-2H-pyridazin-3-one and 3,4-difluorobenzyl chloride were reacted to yield a crude product. Without purification, the crude product was reacted further in accordance with the procedure of Example 1(7) to yield the title compound as a pale yellow solid (66.7%).

$^1$H NMR(400 MHz, CDCl$_3$)δ: 2.36(3H, d, J=2.0 Hz), 5.43(2H, s), 7.09–7.20(2H, m), 7.25(1H, m), 7.34(1H, m), 7.60–7.68(2H, m), 8.61(1H, s).

2) Preparation of 2-(3,4-difluorobenzyl)-6-(4-fluoro-3-methylphenyl)-4-hydroxymethyl-2H-pyridazin-3-one Following the procedure of Example 1(8), 4-carboxy-2-(3,4-difluorobenzyl)-6-(4-fluoro-3-methylphenyl)-2H-pyridazin-3-one was reacted to yield the title compound as a pale yellow solid (yield: 40.8%).

$^1$H NMR(400 MHz, CDCl$_3$)δ: 2.33(3H, d, J=2.0 Hz), 4.69(2H, d, J=1.2 Hz), 5.31(2H, s), 6.98–7.17(2H, m), 7.21(1H, m), 7.30(1H, m), 7.53–7.62(2H, m), 7.67(1H, s).

3) Preparation of 2-(3,4-difluorobenzyl)-6-(4-fluoro-3-methylphenyl)-4-methanesulfonyloxymethyl-2H-pyridazin-3-one Following the procedure of Example 1(9), 2-(3,4-difluorobenzyl)-6-(4-fluoro-3-methylphenyl)-4-hydroxymethyl-2H-pyridazin-3-one was reacted to yield the title compound as a pale yellow solid (yield: 58.1%).

$^1$H NMR(400 MHz, CDCl$_3$)δ: 2.34(3H, d, J=1.7 Hz), 3.13(3H, s), 5.24(2H, d, J=1.2 Hz), 5.31(2H, s), 7.05–7.15(2H, m), 7.22(1H, m), 7.30(1H, m), 7.54–7.62(2H, m), 7.75(1H, s).

4) Preparation of 2-(3,4-difluorobenzyl)-6-(4-fluoro-3-methylphenyl)-4-(4-methyl-1-piperazinyl)methyl-2H-pyridazin-3-one Following the procedure of Example 1(10), 2-(3,4-difluorobenzyl)-6-(4-fluoro-3-methylphenyl)-4-methanesulfonyloxymethyl-2H-pyridazin-3-one was reacted to yield the title compound as a pale yellow amorphous powder (yield: 70.6%).

$^1$H NMR(400 MHz, CDCl$_3$)δ: 2.32(3H, s), 2.36(3H, d, J=1.5 Hz), 2.45–2.70(8H, m), 3.56(2H, d, J=1.3 Hz), 5.32(2H, s), 7.07–7.15(2H, m), 7.23(1H, m), 7.31(1H, m), 7.57(1H, m), 7.63(1H, m), 7.75(1H, s).

Example 236

Preparation of 2-(3,4-difluorobenzyl)-6-(4-fluoro-3-methylphenyl)-4-(4-methyl-1-piperazinyl)methyl-2H-pyridazin-3-one dihydrochloride Following the procedure of Example 4, 2-(3,4-difluorobenzyl)-6-(4-fluoro-3-methylphenyl)-4-(4-methyl-1-piperazinyl)methyl-2H-pyridazin-3-one was reacted to yield the title compound as a colorless crystalline powder (yield: 47.9%).

Melting point: 220–225° C. $^1$H NMR(400 MHz, DMSO-d$_6$)δ: 2.31(3H, s), 2.81(3H, s), 3.52(2H, brs), 3.60–4.25(8H, m), 5.35(2H, s), 7.25(1H, m), 7.30(1H, dd, J=9.3, 9.3 Hz), 7.38–7.50(2H, m), 7.76(1H, m), 7.84(1H, d, J=7.3 Hz), 8.27(1H, m). IR(KBr) cm$^{-1}$: 3438, 3011, 2446, 1652, 1605, 1519.

Example 237

Preparation of 4-aminomethyl-2-(2-chlorobenzyl)-6-(4-fluoro-3-methylphenyl)-2H-pyridazin-3-one Following the procedure of Example 24(1), 2-(2-chlorobenzyl)-6-(4-fluoro-3-methylphenyl)-4-methanesulfonyloxymethyl-2H-pyridazin-3-one was reacted to yield a crude product. Without purification, the crude product was reacted further in accordance with the procedure of Example 24(2) to yield the title compound as a pale yellow crystalline powder (26.7%).

Melting point: 97.6–102.2° C. $^1$H NMR(400 MHz, CDCl$_3$)δ: 2.31(3H, d, J=1.7 Hz), 3.48(2H, s), 5.55(2H, s), 7.05(1H, dd, J=8.8, 8.8 Hz), 7.15–7.25(3H, m), 7.41(1H, m), 7.58(1H, m), 7.62(1H, dd, J=7.3, 1.7 Hz), 7.76(1H, s). IR(KBr) cm$^{-1}$: 3404, 1648, 1600, 1505, 1239. Mass m/z: 357(M$^+$), 359(M$^+$).

Example 238

Preparation of 4-aminomethyl-2-(2-chlorobenzyl)-6-(4-fluoro-3-methylphenyl)-2H-pyridazin-3-one hydrochloride Following the procedure of Example 4, 4-aminomethyl-2-(2-chlorobenzyl)-6-(4-fluoro-3-methylphenyl)-2H-pyridazin-3-one was reacted to yield the title compound as pale yellow needles (yield: 68.9%).

Melting point: 201.9–206.4° C. $^1$H NMR(400 MHz, CD$_3$OD)δ: 2.31(3H, d, J=1.7 Hz), 4.17(2H, s), 5.57(2H, s), 7.12(1H, dd, J=8.8, 8.8 Hz), 7.25–7.35(3H, m), 7.46(1H, m), 7.67(1H, m), 7.73(1H, d, J=6.9 Hz), 8.15(1H, s). IR(KBr) cm$^{-1}$: 3430, 2929, 1652, 1604, 1507, 1476, 1445, 1241. Mass m/z: 357(M$^+$), 359(M$^+$).

Example 239

Preparation of 2-(4-fluorobenzyl)-6-(3-fluoro-4-methoxyphenyl)-4-[3-(4-methyl-1-piperazinyl)propyl]-2H-pyridazin-3-one

1) Preparation of 4-bromomethyl-2-(4-fluorobenzyl)-6-(3-fluoro-4-methoxyphenyl)-2H-pyridazin-3-one Following the procedure of Example 211(1), 2-(4-fluorobenzyl)-6-(3-fluoro-4-methoxyphenyl)-4-hydroxymethyl-2H-pyridazin-3-one was reacted to yield the title compound as pale yellow needles (yield: 28.8%).

Melting point: 120–125° C. $^1$H NMR(400 MHz, CDCl$_3$) δ: 3.95(3H, s), 4.46(2H, s), 5.37(2H, s), 6.95–7.06(4H, m), 7.46–7.52(2H, m), 7.60(1H, m), 7.77(1H, s).

2) Preparation of 4-[2,2-di(tert-butoxycarbonyl) ethyl]-2-(4-fluorobenzyl)-6-(3-fluoro-4-methoxyphenyl)-2H-pyridazin-3-one Following the procedure of Example 211(2), 4-bromomethyl-2-(4-fluorobenzyl)-6-(3-fluoro-4-methoxyphenyl)-2H-pyridazin-3-one was reacted to yield the title compound as a yellow oil (yield: 75.1%).

$^1$H NMR(400 MHz, CDCl$_3$)δ: 1.38(18H, s), 3.10(2H, d, J=7.6 Hz), 3.84(1H, t, J=7.6 Hz), 3.94(3H, s), 5.34(2H, s), 6.98–7.04(3H,m), 7.41–7.50(4H, m), 7.56(1H, m).

3) Preparation of 4-(2-carboxyethyl)-2-(4-fluorobenzyl)-6-(3-fluoro-4-methoxyphenyl)-2H-pyridazin-3-one Following the procedure of Example 211(3), 4-[2,2-di-(tert-butoxycarbonyl)ethyl]-2-(4-fluorobenzyl)-6-(3-fluoro-4-methoxyphenyl)-2H-pyridazin-3-one was reacted to yield the title compound as a slightly-yellow powder (yield: 78.8%).

$^1$H NMR(400 MHz, CDCl$_3$)δ: 2.78(2H, t, J=7.1 Hz), 2.95(2H, t, J=7.1 Hz), 3.94(3H, s), 534(2H, s), 6.99–7.05 (3H,m), 7.44–7.51(3H, m), 7.52(1H, s), 7.58(1H, dd, J=12.4, 2.2 Hz).

4) Preparation of 2-(4-fluorobenzyl)-6-(3-fluoro-4-methoxyphenyl)-4-(3-hydroxypropyl)-2H-pyridazin-3-one Following the procedure of Example 1(8), 4-(2-carboxyethyl)-2-(4-fluorobenzyl)-6-(3-fluoro-4-methoxyphenyl)-2H-pyridazin-3-one was reacted to yield the title compound as a pale yellow powder (yield: 98.0%).

$^1$H NMR(400 MHz, CDCl$_3$)δ: 1.85–1.97(2H, m), 2.78 (2H, t, J=7.1 Hz), 3.61(2H, t, J=5.9 Hz), 3.95(3H, s), 5.36(2H, s), 6.99–7.05(3H, m), 7.45–7.50(4H, m), 7.58(1H, dd, J=12.4, 2.2 Hz).

5) Preparation of 2-(4-fluorobenzyl)-6-(3-fluoro-4-methoxyphenyl)-4-(3-methanesulfonyloxypropyl)-2H-pyridazin-3-one Following the procedure of Example 1(9), 2-(4-fluorobenzyl)-6-(3-fluoro-4-methoxyphenyl)-4-(3-hydroxypropyl)-2H-pyridazin-3-one was reacted to yield the title compound as a pale brown crystalline powder (yield: 97.0%).

Melting point: 101–103° C. $^1$H NMR(400 MHz, CDCl$_3$) δ: 2.11–2.18(2H, m), 2.78(2H, t, J=7.3 Hz), 3.02(3H, s), 3.94(3H, s), 4.28(2H, t, J=6.1 Hz), 5.34(2H, s), 7.00–7.04 (3H, m), 7.47–7.50(3H, m), 7.52(1H, s), 7.61(1H, dd, J=12.4, 2.2 Hz).

6) Preparation of 2-(4-fluorobenzyl)-6-(3-fluoro-4-methoxyphenyl)-4-[3-(4-methyl-1-piperazinyl)propyl]-2H-pyridazin-3-one Following the procedure of Example 1(9), 2-(4-fluorobenzyl)-6-(3-fluoro-4-methoxyphenyl)-4-(3-methanesulfonyloxypropyl)-2H-pyridazin-3-one was reacted to yield the title compound as a pale brown powder (yield: 29.8%).

Melting point: 108–109° C. $^1$H NMR(400 MHz, CDCl$_3$) δ: 1.84–1.90(2H, m), 2.32(3H, s), 2.45(2H, t, J=7.1 Hz), 2.48–2.60(8H, m), 2.66(2H, t, J=7.3 Hz), 3.94(3H, s), 5.33 (2H, s), 6.98–7.05(3H, m), 7.44(1H, s), 7.45–7.51(3H, m), 7.58(1H, dd, J=12.4, 2.2 Hz). IR(KBr) cm$^{-1}$: 1645, 1601, 1438, 1220, 1016, 807. Mass m/z: 468(M$^+$).

Example 240

Preparation of 2-(4-fluorobenzyl)-6-(3-fluoro-4-methoxyphenyl)-4-[3-(1-piperazinyl)propyl]-2H-pyridazin-3-one

1) Preparation of 4-[3-(4-tert-butoxycarbonyl-1-piperazinyl)propyl]-2-(4-fluorobenzyl)-6-(3-fluoro-4-methoxyphenyl)-2H-pyridazin-3-one Following the procedure of Example 1(10), 2-(4-fluorobenzyl)-6-(3-fluoro-4-methoxyphenyl)-4-(3-methanesulfonyloxypropyl)-2H-pyridazin-3-one and tert-butyl 1-piperazinecarboxylate were reacted to yield the title compound as a brown oil (yield: 37.4%).

$^1$H NMR(400 MHz, CDCl$_3$)δ: 1.46(9H, s), 1.80–2.00(2H, m), 2.30–2.60(8H, m), 2.67(2H, t, J=7.1 Hz), 3.40–3.52(2H, m), 3.94(3H, s), 5.33(2H, s), 6.99–7.05(3H, m), 7.45–7.51 (4H, m), 7.59(1H, dd, J=12.4, 2.0 Hz).

2) Preparation of 2-(4-fluorobenzyl)-6-(3-fluoro-4-methoxyphenyl)-4-[3-(1-piperazinyl)propyl]-2H-pyridazin-3-one Following the procedure of Example 20, 4-[3-(4-tert-butoxycarbonyl-1-piperazinyl)propyl]-2-(4-fluorobenzyl)-6-(3-fluoro-4-methoxyphenyl)-2H-pyridazin-3-one was reacted to yield the title compound as a brown oil (yield: 100%).

$^1$H NMR(400 MHz, CDCl$_3$)δ: 1.80–1.91(2H, m), 2.37–2.51(6H, m), 2.66(2H, t, J=7.6 Hz), 2.89–2.95(4H, m), 3.94(3H, s), 5.34(2H, s), 6.98–7.05(3H, m), 7.44(1H, s), 7.45–7.51(3H, m), 7.58(1H, dd, J=11.5, 2.2 Hz). IR(Neat) cm$^{-1}$: 1651, 1608, 1438, 1222, 1025, 757. Mass m/z: 454 (M$^+$).

Example 241

Preparation of 2-[3-(2-chlorophenyl)propyl]-6-(3-fluoro-4-methoxyphenyl)-4-(4-methyl-1-piperazinyl) methyl-2H-pyridazin-3-one

1) Preparation of 4-carboxy-2-[3-(2-chlorophenyl) propyl]-6-(3-fluoro-4-methoxyphenyl)-2H-pyridazin-3-one Following the procedure of Example 1(6), 6-(3-fluoro-4-methoxyphenyl)-4-methoxycarbonyl-2H-pyridazin-3-one and 3-(2-chlorophenyl)-1-propanol methanesulfonate were reacted to yield a crude product. Without purification, the crude product was reacted further in accordance with the procedure of Example 1 (7) to yield the title compound as a pale yellow solid (yield: 56.0%).

$^1$H NMR(400 MHz, CDCl$_3$)δ: 2.25–2.38(2H, m), 2.86 (2H, t, J=7.8 Hz), 3.95(3H, s), 4.42(2H, t, J=7.8 Hz), 7.04(1H, dd, J=8.5, 8.5 Hz), 7.09–7.19(2H, m), 7.23(1H, m), 7.30(1H, m), 7.54(1H, m), 7.65(1H, dd, J=12.2, 2.4 Hz), 8.56(1H, s).

2) Preparation of 2-[3-(2-chlorophenyl)propyl]-6-(3-fluoro-4-methoxyphenyl)-4-hydroxymethyl-2H-pyridazin-3-one Following the procedure of Example 1(8), 4-carboxy-2-[3-(2-chlorophenyl)propyl]-6-(3-fluoro-4-methoxyphenyl)-2H-pyridazin-3-one was reacted to yield the title compound as a pale yellow solid (yield: 32.5%).

$^1$H NMR(400 MHz, CDCl$_3$)δ: 2.17–2.28(2H, m), 2.84 (2H, t, J=7.6 Hz), 3.94(3H, s), 4.31(2H, t, J=7.0 Hz), 4.71(2H, d, J=0.8 Hz), 7.01(1H, dd, J=8.6, 8.6 Hz), 7.13(1H, ddd, J=7.6, 7.6, 2.0 Hz), 7.18(1H, ddd, J=7.4, 7.4, 1.4 Hz), 7.26(1H, dd, J=7.4, 1.7 Hz), 7.32(1H, dd, J=7.6, 1.4 Hz), 7.51(1H, ddd, J=8.6, 2.1, 1.2 Hz), 7.61(1H, dd, J=12.3, 2.2 Hz), 7.66(1H, s).

3) Preparation of 2-[3-(2-chlorophenyl)propyl]-6-(3-fluoro-4-methoxyphenyl)-4-methanesulfonyloxymethyl-2H-pyridazin-3-one Following the procedure of Example 1(9), 2-[3-(2-chlorophenyl)propyl]-6-(3-fluoro-4-methoxyphenyl)-4-hydroxymethyl-2H-pyridazin-3-one was reacted to yield the title compound as a yellow solid (yield: 79.3%).

$^1$H NMR(400 MHz, CDCl$_3$)δ: 2.18–2.28(2H, m), 2.85 (2H, t, J=7.6 Hz), 3.17(3H, s), 3.95(3H, s), 4.32(2H, t, J=7.3 Hz), 5.27(2H, d, J=1.2 Hz), 7.03(1H, dd, J=8.5, 8.5 Hz), 7.13(1H, ddd, J=7.6, 7.6, 2.0 Hz), 7.18(1H, ddd, J=7.3, 7.3, 1.4 Hz), 7.26(1H, m), 7.32(1H, dd, J=7.6, 1.4 Hz), 7.50(1H, ddd, J=8.6, 2.2, 1.2 Hz), 7.62(1H, dd, J=12.2, 2.2 Hz), 7.74(1H, t, J=1.2 Hz).

4) Preparation of 2-[3-(2-chlorophenyl)propyl]-6-(3-fluoro-4-methoxyphenyl)-4-(4-methyl-1-piperazinyl)methyl-2H-pyridazin-3-one Following the procedure of Example 1(10), 2-[3-(2-chlorophenyl)propyl]-6-(3-fluoro-4-methoxyphenyl)-4-methanesulfonyloxymethyl-2H-pyridazin-3-one was reacted to yield the title compound as a pale yellow syrup (yield: 76.7%).

$^1$H NMR(400 MHz, CDCl$_3$)δ: 2.17–2.26(2H, m), 2.33 (3H, s), 2.46–2.68(8H, m), 2.84(2H, t, J=7.6 Hz), 3.57(2H, d, J=1.5 Hz), 3.95(3H, s), 4.31(2H, t, J=7.1 Hz), 7.04(1H, dd, J=8.6, 8.6 Hz), 7.12(1H, ddd, J=7.6, 7.6, 1.7 Hz), 7.18(1H, ddd, J=7.3, 7.3, 1.4 Hz), 7.27(1H, m), 7.32(1H, dd, J=7.8, 1.5 Hz), 7.53(1H, ddd, J=8.6, 2.2, 1.0 Hz), 7.61(1H, dd, J=12.4, 2.2 Hz), 7.73(1H, s). IR(Neat) cm$^{-1}$: 1652, 1608, 1521, 1437, 1290.

Example 242

Preparation of 2-[3-(4-chlorophenyl)propyl]-6-(3-fluoro-4-methoxyphenyl)-4-(4-methyl-1-piperazinyl)methyl-2H-pyridazin-3-one

1) Preparation of 4-carboxy-2-[3-(4-chlorophenyl)propyl]-6-(3-fluoro-4-methoxyphenyl)-2H-pyridazin-3-one Following the procedure of Example 1(6), 6-(3-fluoro-4-methoxyphenyl)-4-methoxycarbonyl-2H-pyridazin-3-one and 3-(4-chlorophenyl)-1-propanol methanesulfonate were reacted to yield a crude product. Without purification, the crude product was reacted further in accordance with the procedure of Example 1 (7) to yield the title compound as a pale yellow solid (yield: 56.1%).

$^1$H NMR(400 MHz, CDCl$_3$)δ: 2.20–2.29(2H, m), 2.72 (2H, t, J=7.3 Hz), 3.95(3H, s), 4.37(2H, t, J=7.3 Hz), 7.05(1H, dd, J=8.5, 8.5 Hz), 7.10(2H, d, J=8.5 Hz), 7.22(2H, d, J=8.5 Hz), 7.53(1H, m), 7.63(1H, dd, J=12.2, 2.2 Hz), 8.56(1H, s).

2) Preparation of 2-[3-(4-chlorophenyl)propyl]-6-(3-fluoro-4-methoxyphenyl)-4-hydroxymethyl-2H-pyridazin-3-one Following the procedure of Example 1(8), 4-carboxy-2-[3-(4-chlorophenyl)propyl]-6-(3-fluoro-4-methoxyphenyl)-2H-pyridazin-3-one was reacted to yield the title compound as a pale yellow solid (yield: 32.5%).

$^1$H NMR(400 MHz, CDCl$_3$)δ: 2.14–2.24(2H, m), 2.69 (2H, t, J=7.6 Hz), 3.33(1H, m), 3.94(3H, s), 4.26(2H, t, J=7.2 Hz), 4.69(2H, d, J=1.4 Hz), 7.01(1H, dd, J=8.4, 8.4 Hz), 7.13(2H, d, J=8.2 Hz), 7.22(2H, d, J=8.2 Hz), 7.49(1H, ddd, J=8.4, 2.0, 1.2 Hz), 7.60(1H, dd, J=12.5, 2.1 Hz), 7.65(1H, s).

3) Preparation of 2-[3-(4-chlorophenyl)propyl]-6-(3-fluoro-4-methoxyphenyl)-4-methanesulfonyloxymethyl-2H-pyridazin-3-one Following the procedure of Example 1(9), 2-[3-(4-chlorophenyl)propyl]-6-(3-fluoro-4-methoxyphenyl)-4-hydroxymethyl-2H-pyridazin-3-one was reacted to yield the title compound as a pale yellow solid (yield: 79.3%).

$^1$H NMR(400 MHz, CDCl$_3$)δ: 2.15–2.24(2H, m), 2.70 (2H, t, J=7.3 Hz), 3.17(3H, s), 3.95(3H, s), 4.27(2H, t, J=6.8 Hz), 5.25(2H, d, J=1.2 Hz), 7.03(1H, dd, J=8.6, 8.6 Hz), 7.13(2H, d, J=8.5 Hz), 7.23(2H, d, J=8.5 Hz), 7.49(1H, ddd, J=8.6, 2.2, 1.2 Hz), 7.61(1H, dd, J=12.2, 2.2 Hz), 7.72(1H, t, J=1.2 Hz).

4) Preparation of 2-[3-(4-chlorophenyl)propyl]-6-(3-fluoro-4-methoxyphenyl)-4-(4-methyl-1-piperazinyl)methyl-2H-pyridazin-3-one Following the procedure of Example 1(10), 2-(3-(4-chlorophenyl)propyl]-6-(3-fluoro-4-methoxyphenyl)-4-methanesulfonyloxymethyl-2H-pyridazin-3-one was reacted to yield the title compound as a pale yellow syrup (yield: 76.9%).

$^1$H NMR(400 MHz, CDCl$_3$)δ: 2.15–2.24(2H, m), 2.33 (3H, s), 2.47–2.66(8H, m), 2.70(2H, t, J=7.6 Hz), 3.55(2H, d, J=1.4 Hz), 3.95(3H, s), 4.27(2H, t, J=7.1 Hz), 7.04(1H, dd, J=8.8, 8.8 Hz), 7.13(2H, d, J=8.5 Hz), 7.21(2H, d, J=8.5 Hz), 7.49(1H, m), 7.60(1H, dd, J=12.4, 2.2 Hz), 7.70(1H, s). IR(Neat) cm$^{-1}$: 1652, 1608, 1521, 1437, 1282.

Example 243

Preparation of 4-aminomethyl-2-[3-(2-chlorophenyl)propyl]-6-(3-fluoro-4-methoxyphenyl)-2H-pyridazin-3-one Following the procedure of Example 24(1), 2-[3-(2-chlorophenyl)propyl]-6-(3-fluoro-4-methoxyphenyl)-4-methanesulfonyloxymethyl-2H-pyridazin-3-one was reacted to yield a crude product. Without purification, the crude product was reacted further in accordance with the procedure of Example 24(2) to yield the title compound as a pale yellow syrup (yield: 48.2%).

¹H NMR(400 MHz, CDCl₃)δ: 2.17–2.27(2H, m), 2.85 (2H, t, J=7.4 Hz), 3.89(2H, d, J=1.2 Hz), 3.94(3H, s), 4.32(2H, t, J=7.0 Hz), 7.02(1H, dd, J=8.6, 8.6 Hz), 7.13(1H, ddd, J=7.6, 7.6, 2.0 Hz), 7.18(1H, ddd, J=7.4, 7.4, 1.6 Hz), 7.27(1H, m), 7.32(1H, dd, J=7.6, 1.4 Hz), 7.52(1H, m), 7.62(1H, dd, J=12.5, 2.2 Hz), 7.67(1H, s). IR(Neat) cm⁻¹: 1652, 1604, 1522, 1438, 1275.

Example 244

Preparation of 4-aminomethyl-2-[3-(4-chlorophenyl) propyl]-6-(3-fluoro-4-methoxyphenyl)-2H-pyridazin-3-one Following the procedure of Example 24(1), 2-[3-(4-chlorophenyl)propyl]-6-(3-fluoro-4-methoxyphenyl)-4-methanesulfonyloxymethyl-2H-pyridazin-3-one was reacted to yield a crude product. Without purification, the crude product was reacted further in accordance with the procedure of Example 24(2) to yield the title compound as a pale yellow solid (yield: 48.2%).

¹H NMR(400 MHz, CDCl₃)δ: 2.14–2.26(2H, m), 2.70 (2H, t, J=7.4 Hz), 3.87(2H, s), 3.95(3H, s), 4.27(2H, t, J=7.2 Hz), 7.02(1H, dd, J=8.6, 8.6 Hz), 7.14(2H, d, J=8.4 Hz), 7.22(2H, d, J=8.4 Hz), 7.51(1H, d, J=8.0 Hz), 7.61(1H, dd, J=12.5, 2.2 Hz), 7.65(1H, s). IR(KBr) cm⁻¹: 1652, 1604, 1522, 1438, 1275.

Example 245

Preparation of 2-(3,4-difluorobenzyl)-6-(3-fluoro-4-methoxyphenyl)-4-(4-methyl-1-piperazinyl)methyl-2H-pyridazin-3-one dihydrochloride Following the procedure of Example 4, 2-(3,4-difluorobenzyl)-6-(3-fluoro-4-methoxyphenyl)-4-(4-methyl-1-piperazinyl)methyl-2H-pyridazin-3-one was reacted to yield the title compound as a colorless crystalline powder (yield: 91.6%).

Melting point: 235–239° C. (dec.) ¹H NMR(400 MHz, DMSO-d₆)δ: 2.75(3H, s), 3.16–3.42(8H, m), 3.63(2H, s), 3.90(3H, s), 5.31(2H, s), 7.19–7.40(4H, m), 7.60–7.67(2H, m), 7.87(1H, s). IR(KBr) cm⁻¹: 3439, 1652, 1605, 1519, 1441, 1290, 1139.

Example 246

Preparation of 2-(3,4-difluorobenzyl)-4-dimethylaminomethyl-6-(3-fluoro-4-methoxyphenyl)-2H-pyridazin-3-one hydrochloride Following the procedure of Example 4, 2-(3,4-difluorobenzyl)-4-dimethylaminomethyl-6-(3-fluoro-4-methoxyphenyl)-2H-pyridazin-3-one was reacted to yield the title compound as a colorless crystalline powder (yield: 91.1%).

Melting point: 216–218° C. ¹H NMR(400 MHz, DMSO-d₆)δ: 2.77(6H, s), 3.91(3H, s), 4.24(2H, s), 5.35(2H, s), 7.21–7.44(4H, m), 7.66–7.74(2H, m), 8.45(1H, s). IR(KBr) cm⁻¹: 3435, 1647, 1606, 1519, 1438, 1284.

Example 247

Preparation of 2-[3-(4-chlorophenyl)propyl]-6-(4-fluoro-3-methylphenyl)-4-(4-methyl-1-piperazinyl) methyl-2H-pyridazin-3-one dihydrochloride Following the procedure of Example 4, 2-[3-(4-chlorophenyl)propyl]-6-(4-fluoro-3-methylphenyl)-4-(4-methyl-1-piperazinyl)methyl-2H-pyridazin-3-one was reacted to yield the title compound as a colorless crystalline powder (yield: 50.0%).

Melting point: 244–245° C. ¹H NMR(400 MHz, DMSO-d₆)δ: 2.05–2.15(2H, m), 2.32(3H, s), 2.68(2H, t, J=7.8 Hz), 2.81(3H, s), 3.20–3.60(10H, m), 4.18(2H, t, J=7.8 Hz), 7.27(2H, d, J=8.6 Hz), 7.29–7.39(3H, m), 7.75(1H, m), 7.80(1H, m), 8.37(1H, brs). IR(KBr) cm⁻¹: 1650, 1607, 1493, 1241, 1158, 1016, 942, 827.

Example 248

Preparation of 2-(4-chlorocinnamyl)-6-(3-fluoro-4-methoxyphenyl)-4-(4-methyl-1-piperazinyl)methyl-2H-pyridazin-3-one dihydrochloride Following the procedure of Example 4, 2-(4-chlorocinnamyl)-6-(3-fluoro-4-methoxyphenyl)-4-(4-methyl-1-piperazinyl)methyl-2H-pyridazin-3-one was reacted to yield the title compound as a colorless crystalline powder (yield: 85.2%).

Melting point: 248–250° C. (dec.) ¹H NMR(400 MHz, DMSO-d₆)δ: 2.76(3H, s), 2.98–3.18(4H, m), 3.25–3.39(4H, m), 3.82(2H, s), 3.90(3H, s), 4.92(2H, d, J=6.4 Hz), 6.46 (1H, dt, J=15.6, 6.4 Hz), 6.65(1H, d, J=15.6 Hz), 7.25(1H, dd, J=8.5, 8.5 Hz), 7.33(2H, d, J=8.5 Hz), 7.44(2H, d, J=8.5 Hz), 7.65–7.73(2H, m), 8.07(1H, s). IR(KBr) cm⁻¹: 2936, 1652, 1607, 1523, 1439, 1286.

Example 249

Preparation of 2-(4-chlorocinnamyl)-6-(3-fluoro-4-methoxyphenyl)-4-[4-(2-hydroxyethyl)-1-piperazinyl]methyl-2H-pyridazin-3-one dihydrochloride Following the procedure of Example 4, 2-(4-chlorocinnamyl)-6-(3-fluoro-4-methoxyphenyl)-4-[4-(2-hydroxyethyl)-1-piperazinyl]methyl-2H-pyridazin-3-one was reacted to yield the title compound as a colorless crystalline powder (yield: 82.6%).

Melting point: 220–228° C. (dec.) ¹H NMR(400 MHz, DMSO-d₆)δ: 2.96–3.08(4H, m), 3.17(2H, t, J=5.4 Hz), 3.28–3.44(4H, m), 3.75(2H, s), 3.79(2H, t, J=5.1 Hz), 3.90 (3H, s), 4.92(2H, dd, J=6.4, 1.2 Hz), 6.46(1H, dt, J=16.1, 6.4 Hz), 6.65(1H, d, J=16.1 Hz), 7.25(1H, dd, J=8.5, 8.5 Hz), 7.33(2H, d, J=8.5 Hz), 7.44(2H, d, J=8.5 Hz), 7.65–7.72(2H, m), 8.00(1H, s). IR(KBr) cm⁻¹: 2937, 1656, 1611, 1525, 1438, 1285.

Experiment 1

Inhibitory Activity Against Interleukin-1β Production

HL-60 cells were cultured for 4 days until confluence on RPMI 1640 medium with 10% fetal bovine serum (FBS) added thereto. The medium was centrifuged. The supernatant was discarded, and the cells were then suspended at 1×10⁶ cells/mL on RPMI 1640 medium with 3% FBS, and lipopolysaccharide was added to give a final concentration of 10 μg/mL. The culture was inoculated at 1 mL/well to a 24-well plate. A sample compound was added at 1 μL/well, followed by culturing for 3 days. Three days later, the amount of interleukin-1β in each culture was determined by ELISA. Each $IC_{50}$ value was determined by a comparison in yield with a control to which no test sample was added. Results on some representative compounds are shown in Tables 1 and 2.

TABLE 1

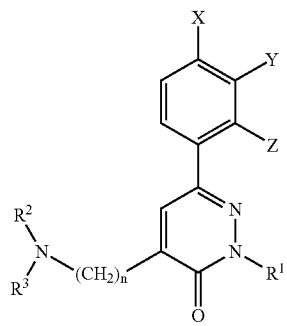

(1)

CyprCH₂ Cyclopropylmethyl

| Example No. | X | Y | Z | n | R¹ | R²(R³)N— | Salt | IL-1β production inhibiting activity IC50 (μM) |
|---|---|---|---|---|---|---|---|---|
| 8 | Me | F | H | 1 | iso-Bu | Me₂N— | HCl | 3.45 |
| 14 | MeO | F | H | 1 | CyprCH₂ | Me₂N— | HCl | 3.61 |
| 18 | MeO | F | H | 1 | CyprCH₂ | Bn—N(piperazine)N— | 2HCl | 5.40 |
| 21 | MeO | F | H | 1 | CyprCH₂ | H—N(piperazine)N— | 2HCl | 1.01 |
| 23 | MeO | F | H | 1 | CyprCH₂ | (HOCH₂CH₂)₂N— | HCl | 0.33 |
| 25 | MeO | F | H | 1 | CyprCH₂ | H₂N— | HCl | 2.74 |
| 45 | Me | H | H | 1 | iso-Bu | Me₂N— | HCl | 6.21 |
| 47 | Me | H | H | 1 | iso-Bu | Et₂N— | HCl | 5.20 |
| 49 | Me | F | H | 1 | iso-Bu | (HOCH₂CH₂)₂N— | HCl | 3.53 |
| 83 | F | Me | H | 1 | iso-Bu | Me—N(piperazine)N— | 2HCl | 0.27 |
| 89 | F | Me | H | 1 | iso-Bu | Me₂N— | HCl | 5.50 |
| 108 | F | F | H | 1 | iso-Bu | (HOCH₂CH₂)₂N— | HCl | 3.44 |
| 143 | F | Me | H | 1 | Cl-C₆H₄-CH=CH-CH₂- (4-chlorocinnamyl) | Me—N(piperazine)N— | 2HCl | 8.55 |
| 149 | MeS | H | H | 1 | CyprCH₂ | Me—N(piperazine)N— | 2HCl | 1.63 |
| 153 | MeS | H | H | 1 | CyprCH₂ | Me₂N— | HCl | 0.58 |
| 161 | MeS | H | H | 1 | iso-Bu | Me₂N— | HCl | 2.78 |
| 163 | MeS | H | H | 1 | iso-Bu | HC≡C-CH₂-N(H)(Me)— | HCl | 2.78 |
| 189 | MeO | F | H | 1 | 4-F-C₆H₄-CH₂ | Me—N(piperazine)N— | free | 0.87 |

TABLE 1-continued
(1)
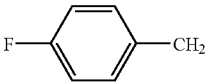
CyprCH₂ Cyclopropylmethyl
| Example No. | X | Y | Z | n | R¹ | R²(R³)N— | Salt | IL-1β production inhibiting activity IC50 (μM) |
|---|---|---|---|---|---|---|---|---|
| 192 | MeO | F | H | 1 |  | 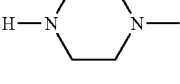 | free | 0.64 |
| 213 | MeO | F | H | 3 | CyprCH₂ | 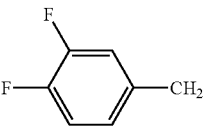 | free | 0.24 |
| 216 | MeO | F | H | 3 | CyprCH₂ | H₂N— | free | 1.14 |
TABLE 2
(1)
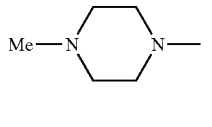
| Example No. | X | Y | Z | n | R¹ | A | IL-1β production inhibiting activity IC50 (μM) |
|---|---|---|---|---|---|---|---|
| 207 | MeO | F | H | 1 | 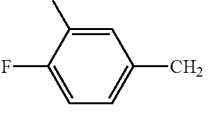 | Me—N⟨piperazine⟩N— | 2.7 |
| 208 | MeO | F | H | 1 | 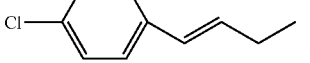 | Me₂N— | 6.1 |
| 209 | MeO | F | H | 1 | 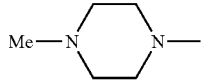 | Me—N⟨piperazine⟩N— | 2.8 |

TABLE 2-continued
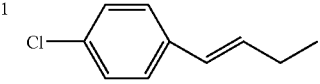
(1)
| Example No. | X | Y | Z | n | R¹ | A | IL-1β production inhibiting activity IC50 (μM) |
|---|---|---|---|---|---|---|---|
| 210 | MeO | F | H | 1 | 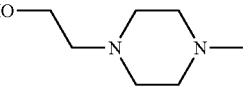 | 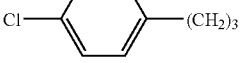 | 3.1 |
| 218 | F | Me | H | 1 | 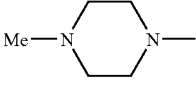 | 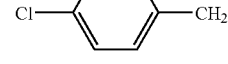 | 6.8 |
| 222 | F | Me | H | 1 | 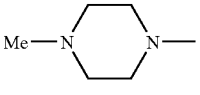 | 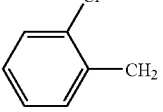 | 5.8 |
| 227 | F | Me | H | 3 | 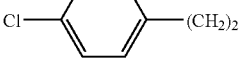 | H₂N— | 5.2 |
| 230 | F | Me | H | 1 | 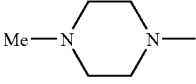 | 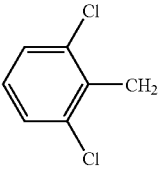 | 4.0 |
| 231 | F | Me | H | 1 | 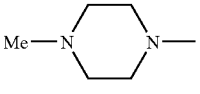 | 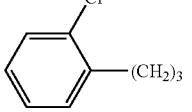 | 5.7 |
| 241 | MeO | F | H | 1 | 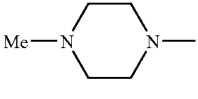 | 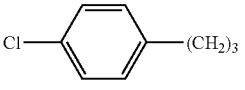 | 6.4 |
| 242 | MeO | F | H | 1 | 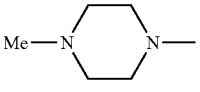 | Me—N⌒N— | 7.7 |

Experiment 2 (Water Solubility Test)

Testing Method

Each sample compound was weighed in the amount shown in Table 3, to which purified water was added in 0.05 mL aliquots. The solubility (%) of the compound was determined based on the amount of water required for its dissolution.

Results

As is shown in Table 3, the compounds of the present invention showed water solubility significantly improved over the comparative compounds.

TABLE 3

| Example No. | Weighed amount (mg) | Amount of added water (mL) | Solubility (%) |
|---|---|---|---|
| 14 | 2.048 | 0.25 | 0.8 |
| 18 | 1.048 | 0.1 | 1 |
| 21 | 10.47 | 0.05 | >20 |
| 23 | 10.82 | 0.1 | 10 |
| 25 | 1.025 | 0.25 | 0.4 |
| 45 | 10.37 | 0.25 | 4 |
| 47 | 10.47 | 0.05 | >20 |
| 89 | 10.57 | 0.05 | >20 |
| 108 | 9.75 | 0.045 | >20 |
| 143 | 5.023 | 0.05 | 10 |
| 149 | 3.09 | 0.03 | >10 |
| 153 | 2.95 | 0.6 | 0.5 |
| 188 | 2.008 | 2.5 | 0.08 |
| 193 | 5.032 | 0.1 | 5 |
| 195 | 5.072 | 2.2 | 0.2 |
| 206 | 2.042 | 3.5 | 0.06 |
| 214 | 5.061 | 0.05 | 10 |
| 217 | 5.061 | 0.05 | 10 |
| 245 | 5.020 | 0.05 | 10 |
| 246 | 4.992 | 0.2 | 2 |
| 247 | 4.999 | 0.05 | 10 |
| 248 | 2.002 | 3.5 | 0.06 |
| 249 | 2.017 | 7.0 | 0.03 |
| Comparative Compound 1 | 0.677 | 100 (insoluble) | <0.001 |
| Comparative Compound 2 | 0.742 | 100 (insoluble) | <0.001 |
| Comparative Compound 3 | 0.740 | 100 (insoluble) | <0.001 |
| Comparative Compound 4 | 0.95 | 100 (insoluble) | <0.001 |

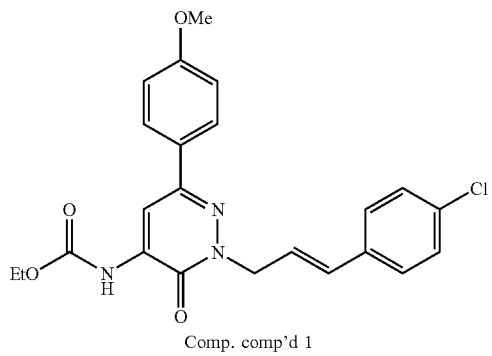

Comp. comp'd 1

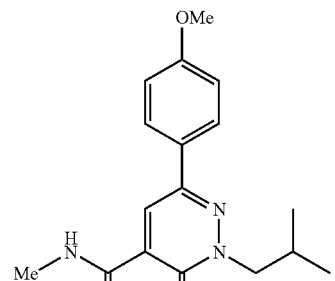

Comp. comp'd 2

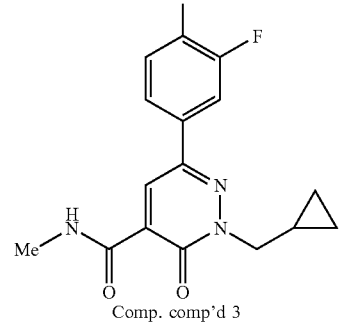

Comp. comp'd 3

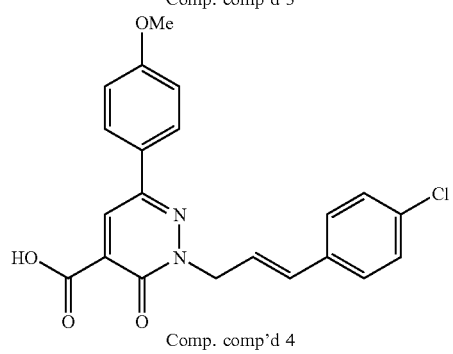

Comp. comp'd 4

Experiment 3 (Oral Absorbability Test on Rats)

The compound of Example 83 and the comparative compound 3 were suspended at 2 mg/mL with a 0.5% MC solution in mortars, respectively, and were orally administered to male SD rats at 10 mg/5 mL/kg. Upon elapsed time of 0.25, 0.5, 1, 2, 4, 6 and 8 hours after the administration, blood samples were collected and then centrifuged to provide plasma samples. The plasma levels of the respective compounds were determined by HPLC. As is shown in FIG. 1, no substantial absorption was observed on the comparative compound 3, but good absorption was observed on the compound of Example 83 equipped with increased water solubility. The compound of Example 83 is, therefore, useful as an orally dosable medicine.

Experiment 4 (Oral Absorbability Test on Rats and/or Mice)

In a similar manner as in Experiment 3, test compounds of Examples 23, 25, 143, 193, 245, 246, 247, 248 and 249 were orally administered to mice and/or rats to test their oral absorbability. As is shown in FIGS. 2 to 6, good absorbability was observed on all the test compounds of Examples 23, 25, 143, 193, 245, 246, 247, 248 and 249 so that they are useful as orally dosable medicines.

What is claimed is:

1. A phenylpyridazine derivative represented by the formula (1):

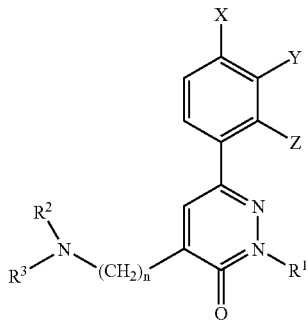

wherein:
R$^1$ is optionally substituted or unsubstituted C$_1$–C$_{12}$ alkyl, or substituted or unsubstituted C$_2$–C$_{12}$ alkenyl; wherein the alkyl can be linear, branched, cyclic or a structure containing a cylic structure therein,
  wherein, if substituted, the substituent on the alkyl or alkenyl represented by R$^1$ is independently a substituted or unsubstituted C$_6$–C$_{14}$ aryl or a 5- or 6-membered heteroaryl having 1 to 3 nitrogen atoms; and said aryl or heteroaryl, wherein if substituted, the aryl or heteroaryl are substituted with 1 to 3 substituents selected from the group consisting of halogen, C$_1$–C$_{12}$ alkyl, C$_1$–C$_{12}$ alkoxy, and combinations thereof;
R$^2$ and R$^3$ each independently represents hydrogen or C$_1$–C$_{12}$ alkyl, hydroxy C$_1$–C$_{12}$ alkyl, dihydroxy C$_1$–C$_{12}$alkyl or C$_3$–C$_{12}$alkynyl, or R$^2$ and R$^3$ are fused together with the adjacent nitrogen atom to form a substituted or unsubstituted, nitrogen-containing, saturated 5- to 7-membered heterocyclic group;
  wherein, if substituted, the 5- to 7-membered heterocyclic group is substituted with at least one of a halogen atom, C$_1$–C$_{12}$ alkyl, C$_1$–C$_{12}$ alkoxycarbonyl or phenyl-C$_1$–C$_7$ alkyl,
X, Y and Z each independently represents hydrogen, halogen, substituted or unsubstituted C$_1$–C$_{12}$ alkyl, C$_1$–C$_{12}$ alkoxy, C$_1$–C$_{12}$ alkylthio, C$_1$–C$_{12}$ alkylsulfinyl, C$_1$–C$_{12}$alkylsulfonyl, or C$_6$–C$_{14}$ aryl;
  wherein the C$_1$–C$_{12}$ alkyl is optionally substituted with at least one of a halogen atom or C$_1$–C$_{12}$ alkoxy, the aryl is optionally substituted with at least one of a halogen, C$_1$–C$_{12}$ alkyl, or C$_1$–C$_{12}$ alkoxy; and
n stands for a number of from 1 to 5;
with the proviso that R$^2$ and R$^3$ are not hydrogens or the same C$_1$–C$_3$ alkyl groups at the same time when R$^1$ is a benzyl group or a C$_1$–C$_3$ alkyl group; or a salt thereof.

2. The compound of claim 1, wherein R$^1$ is a group selected from halogenobenzyl, dihalogenobenzyl, (halogenophenyl)ethyl, (dihalogenophenyl)ethyl, (halogenophenyl)propyl or (dihalogenophenyl)propyl; R$^2$(R$^3$)N— is a group selected from amino, dimethylamino, piperazinyl or N-methylpiperazinyl; X is halogen or methoxy; Y is methyl or halogen; Z is hydrogen; and n stands for 1 or 3.

3. The compound of claim 1, wherein R$^1$ is a group selected from chlorobenzyl, dichlorobenzyl, fluorobenzyl, difluorobenzyl, (chlorophenyl)ethyl, (dichlorophenyl)ethyl, (chlrorophenyl)propyl or (dichlorophenyl)propyl; R$^2$(R$^3$)N— is a group selected from amino, dimethylamino, piperazinyl or N-methylpiperazinyl; X is halogen or methoxy; Y is methyl or halogen; Z is hydrogen; and n stands for 1 or 3.

4. A pharmaceutical composition comprising the compound of claim 1 or a salt thereof and a pharmacologically acceptable carrier.

5. A method of treating osteoporosis or ichorrhemia in an individual comprising, administering the compound of claim 1 or a salt thereof in an amount sufficient to treat osteoporosis or ichorrhemia in the individual.

6. A method of treating rheumatism, arthritis or inflammatory colitis in an individual comprising, administering the compound of claim 1 or a salt thereof in an amount sufficient to treat osteoporosis or ichorrhemia in the individual.

7. A phenylpyridazine derivative represented by the formula (1):

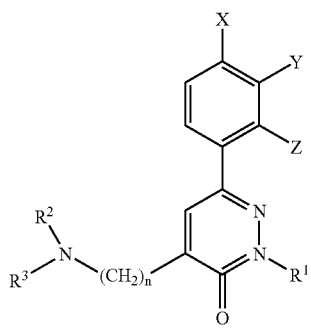

wherein:
R$^1$ is optionally substituted or unsubstituted C$_1$–C$_7$ alkyl, or substituted or unsubstituted C$_2$–C$_7$ alkenyl; wherein the alkyl can be linear, branched, cyclic or a structure containing a cylic structure therein,
  wherein, if substituted, the substituent on the alkyl or alkenyl represented by R$^1$ is phenyl, which is optionally substituted with 1 to 3 substituents selected from the group consisting of halogen, C$_1$–C$_7$ alkyl, C$_1$–C$_7$ alkoxy, and combinations thereof;
R$^2$ and R$^3$ each independently represents hydrogen or C$_1$–C$_7$ alkyl or R$^2$ and R$^3$ are fused together with the adjacent nitrogen atom to form a piperazinyl, wherein the piperazinyl is optionally substituted with one or more of an alkyl or a hydroxyl-C$_1$–C$_7$-alkyl;
X, Y and Z each independently represents hydrogen, halogen, C$_1$–C$_7$ alkyl, or C$_1$–C$_7$ alkoxy; and
n stands for a number of from 1 to 5;
with the proviso that R$^2$ and R$^3$ are not hydrogens or the same C$_1$–C$_3$ alkyl groups at the same time when R$^1$ is a benzyl group or a C$_1$–C$_3$ alkyl group; or a salt thereof.

8. A pharmaceutical composition comprising the compound of claim 7 or a salt thereof and a pharmacologically acceptable carrier.

9. A method of treating osteoporosis, or ichorrhemia in an individual comprising, administering the compound of claim 7 or a salt thereof in an amount sufficient to treat osteoporosis or ichorrhemia in the individual.

10. A method of treating rheumatism, arthritis or inflammatory colitis in an individual comprising, administering the compound of claim 7 or a salt thereof in an amount sufficient to treat osteoporosis or ichorrhemia in the individual.

* * * * *